US012565497B2

(12) United States Patent
Bell et al.

(10) Patent No.: US 12,565,497 B2
(45) Date of Patent: Mar. 3, 2026

(54) SULFONE DERIVATIVES

(71) Applicant: Hoffmann-La Roche Inc., Little Falls, NJ (US)

(72) Inventors: Andrew Simon Bell, Dundee (GB); Jérémy Besnard, Dundee (GB); Anthony Richard Bradley, Dundee (GB); Luke Green, Basel (CH); Wolfgang Haap, Loerrach (DE); Buelent Kocer, Maulburg (DE); Andreas Kuglstatter, Loerrach (DE); Xavier Lucas, Basel (CH); Patrizio Mattei, Riehen (CH); Dmitry Mazunin, Grenzach-Wyhlen (DE); Claus Riemer, Freiburg (DE); Willem Paul Van Hoorn, Dundee (GB)

(73) Assignee: Hoffmann-La Roche Inc., Little Falls, NJ (US)

( * ) Notice: Subject to any disclaimer, the term of this patent is extended or adjusted under 35 U.S.C. 154(b) by 443 days.

(21) Appl. No.: 18/068,360

(22) Filed: Dec. 19, 2022

(65) Prior Publication Data

US 2023/0219953 A1 Jul. 13, 2023

Related U.S. Application Data

(63) Continuation of application No. PCT/EP2021/066767, filed on Jun. 21, 2021.

(30) Foreign Application Priority Data

Jun. 22, 2020 (EP) .................................... 20181363

(51) Int. Cl.
*C07D 471/04* (2006.01)
*C07D 209/08* (2006.01)
*C07D 231/56* (2006.01)

(52) U.S. Cl.
CPC ......... *C07D 471/04* (2013.01); *C07D 209/08* (2013.01); *C07D 231/56* (2013.01)

(58) Field of Classification Search
None
See application file for complete search history.

(56) References Cited

U.S. PATENT DOCUMENTS

| | | | | |
|---|---|---|---|---|
| 10,221,163 | B2 * | 3/2019 | Bennett | A61K 31/4192 |
| 2006/0128729 | A1 | 6/2006 | Pal et al. | |
| 2009/0227575 | A1 | 9/2009 | Venkatesan et al. | |
| 2010/0036123 | A1 | 2/2010 | Kremer et al. | |
| 2011/0237791 | A1 | 9/2011 | Kawaguchi et al. | |
| 2014/0128374 | A1 | 5/2014 | Davoren et al. | |

FOREIGN PATENT DOCUMENTS

| | | | | |
|---|---|---|---|---|
| EP | 1 958 666 | A1 | 8/2008 | |
| JP | 2008-520749 | | 6/2008 | |
| JP | 2022-516882 | A | 3/2022 | |
| WO | 2006/073610 | A2 | 7/2006 | |
| WO | 2010/096338 | A1 | 8/2010 | |
| WO | 2010/106333 | A1 | 9/2010 | |
| WO | 2011/138751 | A2 | 11/2011 | |
| WO | 2011/146335 | A1 | 11/2011 | |
| WO | 2012/138678 | A1 | 10/2012 | |
| WO | 2013/033228 | A1 | 3/2013 | |
| WO | WO-2013130855 | A1 * | 9/2013 | A61K 31/416 |
| WO | 2015/025025 | A1 | 2/2015 | |
| WO | 2016/071293 | A2 | 5/2016 | |
| WO | 2018/011628 | A1 | 1/2018 | |
| WO | 2018/132372 | A1 | 7/2018 | |
| WO | 2018/045071 | A1 | 8/2018 | |
| WO | 2020/139992 | A1 | 2/2020 | |
| WO | 2020/123395 | A1 | 6/2020 | |

OTHER PUBLICATIONS

Belikov Pharmaceutical chemistry 4th edition,: 27-29 ( 2007).
Ansel, H., et al. Ansel's Pharmaceutical Dosage Forms and Drug Delivery Systems Allen, L. & Popovich, N., eds., 8th edition, Baltimore, MD—USA:Lippincott, Williams & Wilkins,:1-6 (Jan. 1, 2005).
Boyer, J. et al., "Difluoromethylbenzoxazole Pyrimidine Thioether Derivatives: A Novel Class of Potent Non-Nucleoside HIV-1 Reverse Transcriptase Inhibitors" ACS J Med Chem 54(23):7974-7985 (Oct. 21, 2011).
International Preliminary Report on Patentability—PCT/EP2021/066767 issued Dec. 13, 2022, pp. 1-10.
International Search Report with Written Opinion—PCT/EP2021/066767 mailed Aug. 17, 2021, pp. 1-15.

(Continued)

*Primary Examiner* — Traviss C McIntosh, III
(74) *Attorney, Agent, or Firm* — Thomas|Horstemeyer, LLP

(57) ABSTRACT

The present invention provides compounds of formula I (I)

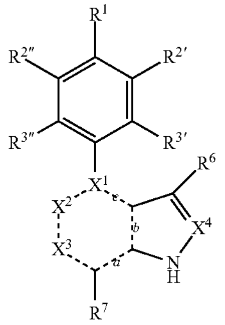

wherein $X^1$, $X^2$, $X^3$, $X^4$, $R^1$, $R^{1a}$, $R^{1b}$, $R^{2'}$, $R^{2''}$, $R^{3'}$, $R^{3''}$, $R^6$ and $R^7$ are as described herein, as well as pharmaceutically acceptable salts thereof. Further the present invention is concerned with the manufacture of the compounds of formula I, pharmaceutical compositions comprising them and their use as medicaments.

36 Claims, No Drawings

(56) References Cited

OTHER PUBLICATIONS

Keaveney, S., et al., "Modular Functionalization of Arenes in a Triply Selective Sequence: Rapid C(sp2) and C(sp3) Coupling of C—Br, C-OTf, and C—Cl Bonds Enabled by a Single Palladium(I) Dimer" Angew Chem Int Ed Engl 57(38):12573-12577 (Sep. 17, 2018).
Kovach, E., et al., "Preparation and Properties of Some New Chelating Agents" Acs J Amer Chem Soc 76(4):1176-1178 (Feb. 1, 1954).
Kress, T., et al., "Synthesis, Stability, and Reactions of 2,6-Dichlorophenyllithium" SYNTHESIS 10:803-805 (Oct. 1, 1988).
Kryukov, G., et al., "MTAP deletion confers enhanced dependency on the PRMT5 arginine methyltransferase in cancer cells" SCIENCE 351(6278):1214-1218 (Mar. 11, 2016).
Lunazzi, L., et al., "Conformational consequences of the dynamic processes in the stereolabile atropisomers of acyl-substituted m-terphenyl derivatives" ACS J Organic Chem 72(7):2501-2507 (Mar. 30, 2007).
Marjon, K, et al., "MTAP Deletions in Cancer Create Vulnerability to Targeting of the MAT2A/PRMT5/RIOK1 Axis" Cell Reps 15(3):574-587 (Apr. 19, 2016).
Mavrakis, K., et al., "Disordered methionine metabolism in MTAP/CDKN2A-deleted cancers leads to dependence on PRMT5" Science 351(6278):1208-1213 (Mar. 11, 2016).
Mehta, V. P. et al., "S-,N-, and Se-Difluoromethylation Using Sodium Chlorodifluoroacetate" Org. Lett. 15(19):5036-5039 ( 2013).
Ozawa, H., et al., "Efficient Ruthenium Sensitizer with a Terpyridine Ligand Having a Hexylthiophene Unit for Dye-Sensitized Solar Cells: Effects of the Substituent Position on the Solar Cell Performance" Eur J Organic Chem 2014(28):4734-4739 (Oct. 1, 2014).
Remington, J., et al. Remington's Pharmaceutical Sciences (Table of Contents, total in 4 pages), OSOL , eds., 16th edition, Easton, PA:Mack Publishing Company, ( 1980).
Rowe, R.C. et al. Handbook of Pharmaceutical Excipients Rowe, R.C., 5th edition, Grayslake, IL—USA:Pharmaceutical Press,:1-6 (Jan. 1, 2005).
Uno, T., et al., "Discovery of 3-Ethyl-4-(3-isopropyl-4-(4-(1-methyl-l H-pyrazol-4-yl)-1 H-imidazol-l-yl)-1 H-pyrazolo[3,4-b]pyridin-l-yl)benzamide (TAS-116) as a Potent, Selective, and Orally Available HSP90 Inhibitor" ACS J MED CHEM 62(2):531-551 (Jan. 24, 2019).

* cited by examiner

SULFONE DERIVATIVES

CROSS-REFERENCE TO RELATED APPLICATIONS

This application is a Continuation of International Application No. PCT/EP2021/066767, filed on Jun. 21, 2021, which claims benefit of priority to European Application No. 20181363.1 filed Jun. 22, 2020, each of which is incorporated herein by reference in its entirety.

The present invention provides compounds which are inhibitors of the Human methionine adenosyltransferase 2A (Mat2A), for use in the treatment, prevention and/or delay of progression of Cancer.

In particular, the present invention relates to compounds of formula I (I)

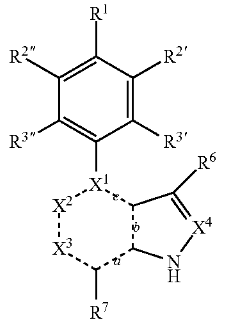

wherein $X^1$ is either N or C $X^2$ is either N or $CR^4$ $X^3$ is either N or $CR^5$ $X^4$ is either N or CH provided that no more than two of $X^1$, $X^2$ and $X^3$ represent N;

the dotted lines represent a single or double bond, to enable the six membered rings to be aromatic with the proviso that when $X^1$ is N and $X^2$ is C═O then the bond between $X^1$ and $X^2$, the bond between $X^2$ and $X^3$, the bonds a and c are single bonds and the bond between $X^3$ and $CR^7$ and b are double bonds; and with the proviso that when $X^1$ is N and $X^2$ is not C═O then the bond between $X^1$ and $X^2$, the bond between $X^3$ and $CR^7$, the bonds b and c are single bonds and the bond between $X^2$ and $X^3$ and the bond a are double bonds;

$R^1$ is —$SO_2R^{1a}$ or —$SOR^{1b}$;

$R^{1a}$ and $R^{1b}$ are independently selected from ($C_1$-$C_6$)alkyl, ($C_3$-$C_6$)cycloalkyl, ($C_3$-$C_6$)cycloalkyl-($C_1$-$C_6$)alkyl, halo($C_1$-$C_6$)alkyl, halo($C_1$-$C_6$)alkoxy, hydroxy($C_1$-$C_6$)alkyl, ($C_1$-$C_6$)alkoxy-($C_1$-$C_6$)alkyl, $NR^{1'a}$, $R^{1'b}$, oxetanyl, furanyl and pyranyl, wherein at least one of $R^{1'a}$ and $R^{1'b}$ is ($C_1$-$C_6$)alkyl and the other is H or ($C_1$-$C_6$)alkyl; or $R^{2'}$ is hydrogen, halogen, —$NH_2$, ($C_1$-$C_6$)alkyl, ($C_1$-$C_6$)alkoxy, halo($C_1$-$C_6$)alkyl or halo($C_1$-$C_6$)alkoxy;

$R^{2''}$ is hydrogen, halogen, —$NH_2$, ($C_1$-$C_6$)alkyl, ($C_1$-$C_6$)alkoxy, halo($C_1$-$C_6$)alkyl or halo($C_1$-$C_6$)alkoxy;

$R^{3'}$ is hydrogen, halogen, —$NH_2$, ($C_1$-$C_6$)alkyl, ($C_1$-$C_6$)alkoxy, halo($C_1$-$C_6$)alkyl or halo($C_1$-$C_6$)alkoxy;

$R^{3''}$ is hydrogen, halogen, —$NH_2$, ($C_1$-$C_6$)alkyl, ($C_1$-$C_6$)alkoxy, halo($C_1$-$C_6$)alkyl or halo($C_1$-$C_6$)alkoxy;

$R^4$ is hydrogen, cyano, oxo, hydroxy, halogen, —$NH_2$, ($C_1$-$C_6$)alkyl, ($C_1$-$C_6$)alkoxy, halo($C_1$-$C_6$)alkyl, halo($C_1$-$C_6$)alkoxy, ($C_1$-$C_6$)alkoxy-($C_1$-$C_6$)alkyl, ($C_3$-$C_6$)cycloalkyl, ($C_3$-$C_6$)cycloalkyl-($C_1$-$C_6$)alkyl, —$CO_2R^{4a}$, —$CONR^{4b}R^{4c}$, —$SO_2R^{4d}$, —$SOR^{4e}$, —$SR^{4f}$, —$SO(NR^{4h})R^{4g}$ or —$SO_2(NR^{4i})R^{4j}$;

$R^{4a}$, $R^{4b}$ and $R^{4c}$ are independently selected from hydrogen, ($C_1$-$C_6$)alkyl, ($C_3$-$C_6$)cycloalkyl, ($C_3$-$C_6$)cycloalkyl-($C_1$-$C_6$)alkyl, halo($C_1$-$C_6$)alkyl and oxetanyl;

$R^{4d}$, $R^{4e}$ and $R^{4f}$ are independently selected from ($C_1$-$C_6$)alkyl, ($C_3$-$C_6$)cycloalkyl, ($C_3$-$C_6$)cycloalkyl-($C_1$-$C_6$)alkyl, halo($C_1$-$C_6$)alkyl and oxetanyl;

$R^{4h}$ and $R^{4g}$ are independently selected from hydrogen, ($C_1$-$C_6$)alkyl, ($C_3$-$C_6$)cycloalkyl, ($C_3$-$C_6$)cycloalkyl-($C_1$-$C_6$)alkyl, halo($C_1$-$C_6$)alkyl and oxetanyl;

$R^{4i}$ and $R^{4j}$ are independently selected from hydrogen, ($C_1$-$C_6$)alkyl, ($C_3$-$C_6$)cycloalkyl, ($C_3$-$C_6$)cycloalkyl-($C_1$-$C_6$)alkyl, halo($C_1$-$C_6$)alkyl and oxetanyl;

$R^5$ is hydrogen, halogen, ($C_1$-$C_6$)alkyl, ($C_3$-$C_6$)cycloalkyl, ($C_1$-$C_6$)alkoxy, halo($C_1$-$C_6$)alkyl or halo($C_1$-$C_6$)alkoxy;

$R^6$ is halogen, ($C_1$-$C_6$)alkyl, ($C_1$-$C_6$)alkoxy, cyano, halo($C_1$-$C_6$)alkyl, halo($C_1$-$C_6$)alkoxy, ($C_3$-$C_6$)cycloalkyl, oxetanyl or thiophenyl or —$SO_2R^{6a}$;

$R^{6a}$ is ($C_1$-$C_6$)alkyl, ($C_3$-$C_6$)cycloalkyl or halo($C_1$-$C_6$)alkyl;

$R^7$ is hydrogen, halogen, hydroxy, ($C_1$-$C_6$)alkyl, ($C_1$-$C_6$)alkoxy, halo-($C_1$-$C_6$)alkyl, halo-($C_1$-$C_6$)alkoxy or $NR^{7'a}R^{7'b}$, wherein one of $R^{7'a}$ and $R^{7'b}$ is hydrogen and the other is hydrogen, ($C_1$-$C_6$)alkyl, ($C_1$-$C_6$)alkoxy, —($C_1$-$C_6$)alkyl-O—($C_1$-$C_6$)alkyl-NHCO—($C_1$-$C_6$)alkyl, —($C_1$-$C_6$)alkyl ($C_1$-$C_6$)alkyl-$NH_2$, —($C_1$-$C_6$)alkyl-NHCO—($C_1$-$C_6$)alkyl or —($C_1$-$C_6$)alkyl-$NH_2$;

and pharmaceutically acceptable salts thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

"halo" or "halogen" means fluoro, chloro, bromo or iodo, particularly chloro or fluoro.

"hydroxy" refers to a —OH group.

"($C_1$-$C_6$)alkyl" refers to a branched or straight hydrocarbon chain of one to six carbon atoms, such as methyl, ethyl, n-propyl, isopropyl, n-butyl, isobutyl, sec-butyl, t-butyl, pentyl and hexyl.

"($C_1$-$C_6$)alkoxy" means a moiety of the formula —$OR^a$, wherein $R^a$ is an ($C_1$-$C_6$)alkyl moiety as defined herein. Examples of ($C_1$-$C_6$)alkoxy moieties include, but are not limited to, methoxy, ethoxy, isopropoxy, and the like.

The term "($C_3$-$C_6$)cycloalkyl" denotes a saturated monovalent saturated monocyclic hydrocarbon group of 3 to 6 ring carbon atoms. Examples for monocyclic ($C_3$-$C_6$)cycloalkyl are cyclopropyl, cyclobutanyl, cyclopentyl or cyclohexyl. One particular example of ($C_3$-$C_6$)cycloalkyl is cyclopropyl.

"($C_3$-$C_6$)cycloalkyl-($C_1$-$C_6$)alkyl" refers to an ($C_1$-$C_6$) alkyl, as defined above, substituted with one or more ($C_3$-$C_6$)cycloalkyl group, particularly with one ($C_3$-$C_6$)cycloalkyl group. More particularly "($C_3$-$C_6$)cycloalkyl-($C_1$-$C_6$) alkyl refers to

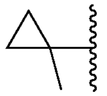 or 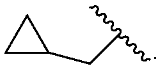.

The term "perhalo($C_1$-$C_3$)alkyl" means an ($C_1$-$C_3$)alkyl group as defined above wherein all hydrogen atoms have been replaced with halogen atoms. More particularly "($C_1$-$C_3$)perhaloalkyl" is ($C_1$-$C_3$)perfluoroalkyl, most preferably trifluoromethyl.

"halo-($C_1$-$C_6$)alkyl" refers to an ($C_1$-$C_6$)alkyl, as defined above, substituted with one or more halogen atoms, particularly with one to three halogen atoms. More particularly halo-($C_1$-$C_6$)alkyl is the chloro- and fluoro-($C_1$-$C_6$)alkyl. In some particular embodiment halo-($C_1$-$C_6$)alkyl refers to perhalo($C_1$-$C_3$)alkyl as defined herein. Most particularly halo-($C_1$-$C_6$)alkyl is trifluoromethyl, difluoromethyl or fluoromethyl.

"halo-($C_1$-$C_6$)alkoxy" refers to an ($C_1$-$C_6$)alkoxy, as defined above, substituted with one or more halogen atoms, particularly with one to three halogen atoms. More particularly halo-($C_1$-$C_6$) alkoxy is the chloro- and fluoro-($C_1$-$C_6$) alkoxy. In some particular embodiment halo-($C_1$-$C_6$) alkoxy refers to perhalo($C_1$-$C_3$) alkoxy, such as trifluoromethoxy or difluoromethoxy.

"hydroxy-($C_1$-$C_6$)alkyl" refers to an ($C_1$-$C_6$)alkyl, as defined above, substituted with one or more hydroxy group, particularly with one hydroxy group. More particularly hydroxy-($C_1$-$C_6$)alkyl refers to methyl-hydroxide or ethyl-hydroxide.

"($C_1$-$C_6$)alkoxy-($C_1$-$C_6$)alkyl" refers to an ($C_1$-$C_6$)alkyl, as defined above, substituted with one or more ($C_1$-$C_6$) alkoxy group as defined herein, particularly with one ($C_1$-$C_6$)alkoxy group. More particularly ($C_1$-$C_6$)alkoxy-($C_1$-$C_6$) alkyl refers to $-CH_2-O-CH_3$ or $-CH_2CH_2-O-CH_3$.

"halo-($C_1$-$C_6$)alkoxy" refers to an alkoxy, as defined above, substituted with one or more halogen atoms, particularly with one to three halogen atoms. More particularly halo-($C_1$-$C_6$)alkoxy are the chloro- and fluoro-($C_1$-$C_6$) alkoxy.

"Heteroaryl" means a monovalent monocyclic or bicyclic moiety of 5 to 12 ring atoms having at least one aromatic ring containing one, two, or three ring heteroatoms selected each independently from N, O, or S (preferably N or O), the remaining ring atoms being C, with the understanding that the attachment point of the heteroaryl moiety will be on an aromatic ring. More specifically the term heteroaryl includes, but is not limited to, pyridinyl, furanyl, thienyl, thiazolyl, isothiazolyl, triazolyl, imidazolyl, isoxazolyl, oxazolyl, pyrrolyl, pyrazolyl, pyrimidinyl, pyrazinyl, pyridazinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof "N-heteroaryl" in particular refers to heteroaryl as previously defined containing at least one nitrogen atom. The point of attachment of the N-heteroaryl to the rest of the molecule can be through the nitrogen or a carbon ring atom. Example of N-heteroaryl are pyridinyl, pyrazinyl, pyridazinyl, pyrimidinyl. The term "heterocycloalkyl" or "heterocyclic" denotes a monovalent saturated or partly unsaturated mono-ring system of 4 to 9 ring atoms, comprising 1, 2, or 3 ring heteroatoms selected independently from N, O and S, the remaining ring atoms being carbon. Examples for heterocycloalkyl are pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, dioxolane, 1,1-dioxo-thiomorpholin-4-yl, azepanyl, diazepanyl, homopiperazinyl, or oxazepanyl. More particularly heterocycloalkyl refers to dihydrofuryl, 1,3-dioxolyl, dihydropyrryl, dihydrothiophyl, dihydropyrazolyl, dihydroisoxazolyl, tetrahydropyridyl, tetrahydropyranyl, tetrahydrothiopyranyl, piperazinyl, 3,4-dihydro-2H-1,4-oxazinyl, 3,4-dihydro-2H-1,4-thiazyl, 1,2,3,4-tetrahydropyrazyl.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

The terms "individual" or "subject" refer to a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The terms "compound(s) of this invention" and "compound(s) of the present invention" refer to compounds as disclosed herein and stereoisomers, tautomers, solvates, and salts (e.g., pharmaceutically acceptable salts) thereof.

When the compounds of the invention are solids, it is understood by those skilled in the art that these compounds, and their solvates and salts, may exist in different solid forms, particularly different crystal forms, all of which are intended to be within the scope of the present invention and specified formulae.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "active pharmaceutical ingredient" (or "API") denotes the compound or molecule in a pharmaceutical composition that has a particular biological activity.

The terms "pharmaceutical composition" and "pharmaceutical formulation" (or "formulation") are used interchangeably and denote a mixture or solution comprising a therapeutically effective amount of an active pharmaceutical ingredient together with pharmaceutically acceptable excipients to be administered to a mammal, e.g., a human in need thereof.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The terms "treating" or "treatment" of a disease state include inhibiting the disease state, i.e., arresting the development of the disease state or its clinical symptoms, or relieving the disease state, i.e., causing temporary or permanent regression of the disease state or its clinical symptoms.

Compounds that have the same molecular formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula I can possess one or more asymmetric centers or axes. Unless indicated otherwise, the description or naming of a particular compound in the specification and claims is intended to include both individual enantiomers, atropisomers and mixtures, racemic or otherwise, thereof, as well as individual epimers, atropisomers and mixtures thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

Certain compounds may exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while in phenols, the enol form predominates. Common prototropic tautomers include keto/enol (—C(=O)—CH—⇔—C(—OH)=CH—), amide/imidic acid (—C(=O)—NH—⇔—C(—OH)=N—) and amidine (—C(=NR)—NH—⇔—C(—NHR)=N—) tautomers. The latter two are particularly common in heteroaryl and heterocyclic rings and the present invention encompasses all tautomeric forms of the compounds.

Now it has been found that the present compounds of formula formula I are inhibitors of Mat2A and as such may be of therapeutic use for the treatment of Cancer disorders including Lung Adenocarcinoma, Melanoma, Pancreatic Adenocarcinoma, Head and Neck Squamous Cell Carcinoma, Lung Squamous Cell Carcinoma, Esophageal Carcinoma, Glioblastmoa Multiforme, and Mesothelioma.

These compounds are potent inhibitors of the Human methionine adenosyltransferase II alpha (MAT2A). MAT2A and MAT1A (methionine adenosyltransferase I alpha) are two genes that encode for methionine adenosyltransferase activity thereby producing S-adenosylmethionine (SAM), the principal methyl donor in the cells. MAT1A is the liver specific SAM producing enzyme, whereas MAT2A is broadly expressed, except in the liver. MAT2A is found in complex with MAT2B (methionine adenosyltransferase II beta), the allosteric regulator of MAT2A, and MAT2B acts like a rheostat for MAT2A enzymatic activity. When MAT2B binds to MAT2A, MAT2A undergoes a conformational change that increases its affinity for methionine and SAM. The net effect is that MAT2A, when bound to MAT2B, is more active under low methionine concentrations, but is inhibited under high methionine concentrations.

Loss-of-function mutations in tumor suppressor genes are critical in the molecular pathogenesis of cancer, however successful targeting of tumor suppressors has been elusive mainly because the mutant proteins cannot be directly inhibited for therapeutic benefit, and restoration of mutant function (such as restoring function of mutant p53), has so far not been possible. The recent clinical success of inhibiting PARP in BRCA1/2 deficient patients has shown that targeting conditional synthetic lethalities (CSLs) that arise from loss-of-function mutations in tumor suppressors is a clinically valid approach for the treatment of cancers. The CSL relationship is not only valid for tumor suppressors but can be extended to genes that reside in the same genetic region of a tumor suppressor and are lost when that region is deleted. Methylthioadenosine phosphorylase (MTAP) is one such gene that is in close proximity to the tumor suppressor CDKN2A, and is deleted in ~15% of all cancers. MTAP is deleted in, but not limited to, ~53% of glioblastoma multiforme (GBM), ~25% of pancreatic adenocarcinoma (PDAC), ~25% of melanoma, ~23% lung squamous cell carcinoma, ~20% head and neck squamous cell carcinoma, and ~15% lung adenocarcinoma. Indeed, this deletion occurs across multiple indications, many of which are areas of high unmet medical need with limited efficacious therapies. In glioblastoma, were the median survival is 14 months, the approval of the most recent therapies has not increased the overall survival (OS) time significantly and the standard of care (SoC) remains the same for over a decade. The same is true for the majority of patients with PDAC where OS is less than 1 year. MTAP deletion is a truncal event that occurs early on in tumor development and would be carried through all evolutions of the tumor including metastasis. Therefore its loss represents an alteration that is not affected by tumor heterogeneity, genetic background, or resistance to any approved agents in the clinic. A CSL relationship identified for MTAP deficiency would represent a true Achilles' heel for multiple tumor indications.

MTAP is located in close proximity to the tumor suppressor CDKN2A on chromosome 9. When CDKN2A is deleted, MTAP is frequently co-deleted. Its loss is thought to be a bystander effect and phenotypically neutral. MTAP is the cornerstone of the adenine and methionine salvage pathways in cells. The methionine salvage pathway feeds into the SAM production pathway, and the levels of SAM are a key regulator of cancer cell growth that needs to be tightly regulated because large changes in SAM concentrations, either increases or decreases, lead to cell cycle arrest. The importance of SAM levels to cancerous growth lies in its central role for protein, DNA, and RNA methylation, acting as a checkpoint for the health of the cell, and can be read out as hypomethylation when SAM is reduced or hypermethylation when SAM is increased. Cells that lack MTAP accumulate methylthioadenosine (MTA) and decarboxylated SAM (dcSAM) without adversely affecting the levels of any salvage metabolites/products including SAM. This accumulation creates a novel stress on the cell where MTA acts as a competitive inhibitor of SAM dependent reactions due to their structural similarity. The loss of MTAP forces the cell to adapt to the new MTA/SAM paradigm without any loss in viability that a MTAP proficient cell would not have to contend with, and this adaptation creates a robust dependence on methionine adenosyltransferase II alpha2 (MAT2A), one of the enzymes that produces SAM, in MTAP deficient cells. This conditional synthetic lethal (CSL) relationship of MTAP loss and MAT2A dependence was identified in three large scale shRNA screens (Marjon Cell Reports 2016, Kryukov Science 2016, and Mavrakis Science 2016).

Targeting MAT2A with a small molecule inhibition would bring benefit to a genetically defined patient population representing many areas of high unmet medical need.

Objects of the present invention are compounds of formula I the use of such compounds for the preparation of medicaments for the treatment, prevention and/or delay of progression of Cancer, in particular Lung Adenocarcinoma, Melanoma, Pancreatic Adenocarcinoma, Head and Neck Squamous Cell Carcinoma, Lung Squamous Cell Carcinoma, Esophageal Carcinoma, Glioblastmoa Multiforme, and Mesothelioma more particularly for the treatment of cancer including Lung Adenocarcinoma, Lung Squamous Carcinoma, Pancreatic Adenocarcinoma, Glioblastoma Multiforme, and Head and Neck Squamous Carcinoma, their manufacture and medicaments based on a compound of formula I in accordance with the invention.

Further objects of the present invention are all forms of optically pure enantiomers, racemates or diastereometric mixtures for compounds of formula I.

In particular, the present invention relates to compounds of formula Ia (Ia)

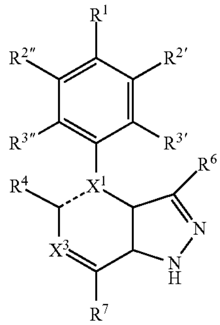

wherein $X^1$ is either N or C;

$X^3$ is either N or $CR^5$ the dotted line represents a double bond to enable the six membered rings to be aromatic with the proviso that when $X^1$ is N and $R^4$ is oxo then the bond is a single bond;

$R^1$ is —$SO_2R^{1a}$ or —$SOR^{1b}$;

$R^{1a}$ and $R^{1b}$ are independently selected from $(C_1\text{-}C_6)$alkyl, $(C_3\text{-}C_6)$cycloalkyl, $(C_3\text{-}C_6)$cycloalkyl-$(C_1\text{-}C_6)$alkyl, halo$(C_1\text{-}C_6)$alkyl, halo$(C_1\text{-}C_6)$alkoxy, hydroxy$(C_1\text{-}C_6)$alkyl, $(C_1\text{-}C_6)$alkoxy-$(C_1\text{-}C_6)$alkyl, $NR^{1'a}$ $R^{1'b}$, oxetanyl, furanyl and pyranyl, wherein at least one of $R^{1'a}$ and $R^{1'b}$ is $(C_1\text{-}C_6)$alkyl and the other is H or $(C_1\text{-}C_6)$alkyl; or $R^{2'}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^{2''}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^{3'}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^{3''}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^4$ is hydrogen, cyano, oxo, hydroxy, halogen, —$NH_2$, $(C_1\text{-}C_6)$alkyl, $(C_1\text{-}C_6)$alkoxy, halo$(C_1\text{-}C_6)$alkyl, halo$(C_1\text{-}C_6)$alkoxy, $(C_1\text{-}C_6)$alkoxy-$(C_1\text{-}C_6)$alkyl, $(C_3\text{-}C_6)$cycloalkyl, $(C_3\text{-}C_6)$cycloalkyl-$(C_1\text{-}C_6)$alkyl, —$CO_2R^{4a}$, —$CONR^{4b}R^{4c}$, —$SO_2R^{4d}$, —$SOR^{4e}$, —$SR^{4f}$, —$SO(NR^{4h})R^{4g}$ or —$SO_2(NR^{4i})R^{4j}$;

$R^{4a}$, $R^{4b}$ and $R^{4c}$ are independently selected from hydrogen, $(C_1\text{-}C_6)$alkyl, $(C_3\text{-}C_6)$cycloalkyl, $(C_3\text{-}C_6)$cycloalkyl-$(C_1\text{-}C_6)$alkyl, halo$(C_1\text{-}C_6)$alkyl and oxetanyl;

$R^{4d}$, $R^{4e}$ and $R^{4f}$ are independently selected from $(C_1\text{-}C_6)$alkyl, $(C_3\text{-}C_6)$cycloalkyl, $(C_3\text{-}C_6)$cycloalkyl-$(C_1\text{-}C_6)$alkyl, halo$(C_1\text{-}C_6)$alkyl and oxetanyl;

$R^{4h}$ and $R^{4g}$ are independently selected from hydrogen, $(C_1\text{-}C_6)$alkyl, $(C_3\text{-}C_6)$cycloalkyl, $(C_3\text{-}C_6)$cycloalkyl-$(C_1\text{-}C_6)$alkyl, halo$(C_1\text{-}C_6)$alkyl and oxetanyl;

$R^{4i}$ and $R^{4j}$ are independently selected from hydrogen, $(C_1\text{-}C_6)$alkyl, $(C_3\text{-}C_6)$cycloalkyl, $(C_3\text{-}C_6)$cycloalkyl-$(C_1\text{-}C_6)$alkyl, halo$(C_1\text{-}C_6)$alkyl and oxetanyl;

$R^5$ is hydrogen, halogen, $(C_1\text{-}C_6)$alkyl, $(C_3\text{-}C_6)$cycloalkyl, $(C_1\text{-}C_6)$alkoxy, halo$(C_1\text{-}C_6)$alkyl or halo$(C_1\text{-}C_6)$alkoxy;

$R^6$ is halogen, $(C_1\text{-}C_6)$alkyl, $(C_1\text{-}C_6)$alkoxy, cyano, halo$(C_1\text{-}C_6)$alkyl, halo$(C_1\text{-}C_6)$alkoxy, $(C_3\text{-}C_6)$cycloalkyl, oxetanyl or thiophenyl or —$SO_2R^{6a}$;

$R^{6a}$ is $(C_1\text{-}C_6)$alkyl, $(C_3\text{-}C_6)$cycloalkyl or halo$(C_1\text{-}C_6)$alkyl;

$R^7$ is hydrogen, halogen, hydroxy, $(C_1\text{-}C_6)$alkyl, $(C_1\text{-}C_6)$alkoxy, halo-$(C_1\text{-}C_6)$alkyl, halo-$(C_1\text{-}C_6)$alkoxy or $NR^{7'a}R^{7'b}$, wherein one of $R^{7'a}$ and $R^{7'b}$ is hydrogen and the other is hydrogen, $(C_1\text{-}C_6)$alkyl, $(C_1\text{-}C_6)$alkoxy, —$(C_1\text{-}C_6)$alkyl-O—$(C_1\text{-}C_6)$alkyl-NHCO—$(C_1\text{-}C_6)$alkyl, —$(C_1\text{-}C_6)$alkyl-O—$(C_1\text{-}C_6)$alkyl-$NH_2$, —$(C_1\text{-}C_6)$alkyl-NHCO—$(C_1\text{-}C_6)$alkyl or —$(C_1\text{-}C_6)$alkyl-$NH_2$;

and pharmaceutically acceptable salts thereof.

In particular, the present invention relates to compounds of formula Ib (Ib)

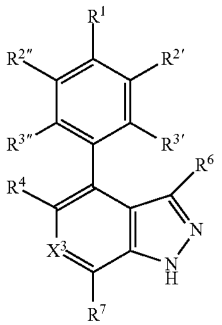

wherein $X^3$ is either N or $CR^5$ $R^1$ is —$SO_2R^{1a}$ or —$SOR^{1b}$;

$R^{1a}$ and $R^{1b}$ are independently selected from $(C_1\text{-}C_6)$alkyl, $(C_3\text{-}C_6)$cycloalkyl, $(C_3\text{-}C_6)$cycloalkyl-$(C_1\text{-}C_6)$alkyl, halo$(C_1\text{-}C_6)$alkyl, halo$(C_1\text{-}C_6)$alkoxy, hydroxy$(C_1\text{-}C_6)$alkyl, $(C_1\text{-}C_6)$alkoxy-$(C_1\text{-}C_6)$alkyl, $NR^{1'a}R^{1'b}$, oxetanyl, furanyl and pyranyl, wherein at least one of $R^{1'a}$ and $R^{1'b}$ is $(C_1\text{-}C_6)$alkyl and the other is H or $(C_1\text{-}C_6)$alkyl; or $R^{2'}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^{2''}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^{3'}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^{3''}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^4$ is hydrogen, cyano, oxo, hydroxy, halogen, —$NH_2$, $(C_1\text{-}C_6)$alkyl, $(C_1\text{-}C_6)$alkoxy, halo$(C_1\text{-}C_6)$alkyl, halo$(C_1\text{-}C_6)$alkoxy, $(C_1\text{-}C_6)$alkoxy-$(C_1\text{-}C_6)$alkyl, $(C_3\text{-}C_6)$cycloalkyl, $(C_3\text{-}C_6)$cycloalkyl-$(C_1\text{-}C_6)$alkyl, —$CO_2R^{4a}$, —$CONR^{4b}R^{4c}$, —$SO_2R^{4d}$, —$SOR^{4e}$, —$SR^{4f}$, —$SO(NR^{4h})R^{4g}$ or —$SO_2(NR^{4i})R^{4j}$;

$R^{4a}$, $R^{4b}$ and $R^{4c}$ are independently selected from hydrogen, $(C_1\text{-}C_6)$alkyl, $(C_3\text{-}C_6)$cycloalkyl, $(C_3\text{-}C_6)$cycloalkyl-$(C_1\text{-}C_6)$alkyl, halo$(C_1\text{-}C_6)$alkyl and oxetanyl;

$R^{4d}$, $R^{4e}$ and $R^{4f}$ are independently selected from $(C_1\text{-}C_6)$alkyl, $(C_3\text{-}C_6)$cycloalkyl, $(C_3\text{-}C_6)$cycloalkyl-$(C_1\text{-}C_6)$alkyl, halo$(C_1\text{-}C_6)$alkyl and oxetanyl;

$R^{4h}$ and $R^{4g}$ are independently selected from hydrogen, $(C_1\text{-}C_6)$alkyl, $(C_3\text{-}C_6)$cycloalkyl, $(C_3\text{-}C_6)$cycloalkyl-$(C_1\text{-}C_6)$alkyl, halo$(C_1\text{-}C_6)$alkyl and oxetanyl;

$R^{4i}$ and $R^{4j}$ are independently selected from hydrogen, $(C_1\text{-}C_6)$alkyl, $(C_3\text{-}C_6)$cycloalkyl, $(C_3\text{-}C_6)$cycloalkyl-$(C_1\text{-}C_6)$alkyl, halo$(C_1\text{-}C_6)$alkyl and oxetanyl;

$R^5$ is hydrogen, halogen, $(C_1\text{-}C_6)$alkyl, $(C_3\text{-}C_6)$cycloalkyl, $(C_1\text{-}C_6)$alkoxy, halo$(C_1\text{-}C_6)$alkyl or halo$(C_1\text{-}C_6)$alkoxy;

$R^6$ is halogen, $(C_1\text{-}C_6)$alkyl, $(C_1\text{-}C_6)$alkoxy, cyano, halo$(C_1\text{-}C_6)$alkyl, halo$(C_1\text{-}C_6)$alkoxy, $(C_3\text{-}C_6)$cycloalkyl, oxetanyl or thiophenyl or —$SO_2R^{6a}$;

$R^{6a}$ is $(C_1\text{-}C_6)$alkyl, $(C_3\text{-}C_6)$cycloalkyl or halo$(C_1\text{-}C_6)$alkyl;

$R^7$ is hydrogen, halogen, hydroxy, $(C_1\text{-}C_6)$alkyl, $(C_1\text{-}C_6)$alkoxy, halo-$(C_1\text{-}C_6)$alkyl, $C_6)$alkoxy or $NR^{7'a}R^{7'b}$, wherein one of $R^{7'a}$ and $R^{7'b}$ is hydrogen and the other is hydrogen, $(C_1\text{-}C_6)$alkyl, $(C_1\text{-}C_6)$alkoxy, —$(C_1\text{-}C_6)$alkyl-O—$(C_1\text{-}C_6)$alkyl-NHCO—$(C_1\text{-}C_6)$alkyl, —$(C_1\text{-}C_6)$alkyl-O—$(C_1\text{-}C_6)$alkyl-$NH_2$, —$(C_1\text{-}C_6)$alkyl-NHCO—$(C_1\text{-}C_6)$alkyl or —$(C_1\text{-}C_6)$alkyl-$NH_2$;

and pharmaceutically acceptable salts thereof.

In another embodiment the present invention relates to compounds of formula Ic (Ic)

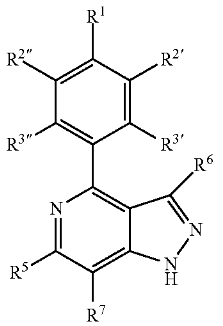

wherein $R^1$ is —$SO_2R^{1a}$ or —$SOR^{1b}$;

$R^{1a}$ and $R^{1b}$ are independently selected from $(C_1\text{-}C_6)$alkyl, $(C_3\text{-}C_6)$cycloalkyl, $(C_3\text{-}C_6)$cycloalkyl-$(C_1\text{-}C_6)$alkyl, halo$(C_1\text{-}C_6)$alkyl, halo$(C_1\text{-}C_6)$alkoxy, hydroxy$(C_1\text{-}C_6)$alkyl, $(C_1\text{-}C_6)$alkoxy-$(C_1\text{-}C_6)$alkyl, $NR^{1'a}R^{1'b}$, oxetanyl, furanyl and pyranyl, wherein at least one of $R^{1'a}$ and $R^{1'b}$ is $(C_1\text{-}C_6)$alkyl and the other is H or $(C_1\text{-}C_6)$alkyl; or $R^{2'}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^{2''}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^{3'}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^{3''}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^5$ is hydrogen, halogen, $(C_1\text{-}C_6)$alkyl, $(C_3\text{-}C_6)$cycloalkyl, $(C_1\text{-}C_6)$alkoxy, halo$(C_1\text{-}C_6)$alkyl or halo$(C_1\text{-}C_6)$alkoxy;

$R^6$ is halogen, $(C_1\text{-}C_6)$alkyl, $(C_1\text{-}C_6)$alkoxy, cyano, halo$(C_1\text{-}C_6)$alkyl, halo$(C_1\text{-}C_6)$alkoxy, $(C_3\text{-}C_6)$cycloalkyl, oxetanyl or thiophenyl or —$SO_2R^{6a}$;

$R^{6a}$ is $(C_1\text{-}C_6)$alkyl, $(C_3\text{-}C_6)$cycloalkyl or halo$(C_1\text{-}C_6)$alkyl;

$R^7$ is hydrogen, halogen, hydroxy, $(C_1\text{-}C_6)$alkyl, $(C_1\text{-}C_6)$alkoxy, halo-$(C_1\text{-}C_6)$alkyl, halo-$(C_1\text{-}C_6)$alkoxy or $NR^{7a}R^{7b}$, wherein one of $R^{7'a}$ and $R^{7'b}$ is hydrogen and the other is hydrogen, $(C_1\text{-}C_6)$alkyl, $(C_1\text{-}C_6)$alkoxy, —$(C_1-C_6)$alkyl-O—$(C_1-C_6)$alkyl-NHCO—$(C_1-C_6)$alkyl, —$(C_1-C_6)$alkyl-O—$(C_1-C_6)$alkyl-$NH_2$, —$(C_1-C_6)$alkyl-NHCO—$(C_1-C_6)$alkyl or —$(C_1-C_6)$alkyl-$NH_2$; and pharmaceutically acceptable salts thereof.

In another embodiment, the present invention provides a compound of formula Id, (Id)

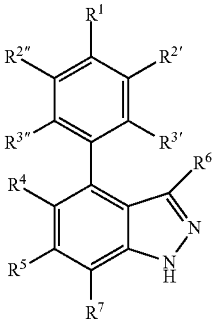

wherein $R^1$ is —$SO_2R^{1a}$ or —$SOR^{1b}$;

$R^{1a}$ and $R^{1b}$ are independently selected from $(C_1-C_6)$alkyl, $(C_3-C_6)$cycloalkyl, $(C_3-C_6)$cycloalkyl-$(C_1-C_6)$alkyl, halo$(C_1-C_6)$alkyl, halo$(C_1-C_6)$alkoxy, hydroxy$(C_1-C_6)$alkyl, $(C_1-C_6)$alkoxy-$(C_1-C_6)$alkyl, $NR^{1'a}$ $R^{1'b}$, oxetanyl, furanyl and pyranyl, wherein at least one of $R^{1'a}$ and $R^{1'b}$ is $(C_1-C_6)$alkyl and the other is H or $(C_1-C_6)$alkyl; or $R^{2'}$ is hydrogen, halogen, —$NH_2$, $(C_1-C_6)$alkyl, $(C_1-C_6)$alkoxy, halo$(C_1-C_6)$alkyl or halo$(C_1-C_6)$alkoxy;

$R^{2''}$ is hydrogen, halogen, —$NH_2$, $(C_1-C_6)$alkyl, $(C_1-C_6)$alkoxy, halo$(C_1-C_6)$alkyl or halo$(C_1-C_6)$alkoxy;

$R^{3'}$ is hydrogen, halogen, —$NH_2$, $(C_1-C_6)$alkyl, $(C_1-C_6)$alkoxy, halo$(C_1-C_6)$alkyl or halo$(C_1-C_6)$alkoxy;

$R^{3''}$ is hydrogen, halogen, —$NH_2$, $(C_1-C_6)$alkyl, $(C_1-C_6)$alkoxy, halo$(C_1-C_6)$alkyl or halo$(C_1-C_6)$alkoxy;

$R^4$ is hydrogen, cyano, oxo, hydroxy, halogen, —$NH_2$, $(C_1-C_6)$alkyl, $(C_1-C_6)$alkoxy, halo$(C_1-C_6)$alkyl, halo$(C_1-C_6)$alkoxy, $(C_1-C_6)$alkoxy-$(C_1-C_6)$alkyl, $(C_3-C_6)$cycloalkyl, $(C_3-C_6)$cycloalkyl-$(C_1-C_6)$alkyl, —$CO_2R^{4a}$, —$CONR^{4b}R^{4c}$, —$SO_2R^{4d}$, —$SOR^{4e}$, —$SR^{4f}$, —$SO(NR^{4h})R^{4g}$ or —$SO_2(NR^{4i})R^{4j}$;

$R^{4a}$, $R^{4b}$ and $R^{4c}$ are independently selected from hydrogen, $(C_1-C_6)$alkyl, $(C_3-C_6)$cycloalkyl, $(C_3-C_6)$cycloalkyl-$(C_1-C_6)$alkyl, halo$(C_1-C_6)$alkyl and oxetanyl;

$R^{4d}$, $R^{4e}$ and $R^{4f}$ are independently selected from $(C_1-C_6)$alkyl, $(C_3-C_6)$cycloalkyl, $(C_3-C_6)$cycloalkyl-$(C_1-C_6)$alkyl, halo$(C_1-C_6)$alkyl and oxetanyl;

$R^{4h}$ and $R^{4g}$ are independently selected from hydrogen, $(C_1-C_6)$alkyl, $(C_3-C_6)$cycloalkyl, $(C_3-C_6)$cycloalkyl-$(C_1-C_6)$alkyl, halo$(C_1-C_6)$alkyl and oxetanyl;

$R^{4i}$ and $R^{4j}$ are independently selected from hydrogen, $(C_1-C_6)$alkyl, $(C_3-C_6)$cycloalkyl, $(C_3-C_6)$cycloalkyl-$(C_1-C_6)$alkyl, halo$(C_1-C_6)$alkyl and oxetanyl;

$R^5$ is hydrogen, halogen, $(C_1-C_6)$alkyl, $(C_3-C_6)$cycloalkyl, $(C_1-C_6)$alkoxy, halo$(C_1-C_6)$alkyl or halo$(C_1-C_6)$alkoxy;

$R^6$ is halogen, $(C_1-C_6)$alkyl, $(C_1-C_6)$alkoxy, cyano, halo$(C_1-C_6)$alkyl, halo$(C_1-C_6)$alkoxy, $(C_3-C_6)$cycloalkyl, oxetanyl or thiophenyl or —$SO_2R^{6a}$;

$R^{6a}$ is $(C_1-C_6)$alkyl, $(C_3-C_6)$cycloalkyl or halo$(C_1-C_6)$alkyl;

$R^7$ is hydrogen, halogen, hydroxy, $(C_1-C_6)$alkyl, $(C_1-C_6)$alkoxy, halo-$(C_1-C_6)$alkyl, halo-$(C_1-C_6)$alkoxy or $NR^{7'a}R^{7'b}$, wherein one of $R^{7'a}$ and $R^{7'b}$ is hydrogen and the other is hydrogen, $(C_1-C_6)$alkyl, $(C_1-C_6)$alkoxy, —$(C_1-C_6)$alkyl-O—$(C_1-C_6)$alkyl-NHCO—$(C_1-C_6)$alkyl, —$(C_1-C_6)$alkyl-O—$(C_1-C_6)$alkyl-$NH_2$, —$(C_1-C_6)$alkyl-NHCO—$(C_1-C_6)$alkyl or —$(C_1-C_6)$alkyl-$NH_2$; and pharmaceutically acceptable salts thereof.

In another embodiment the present invention relates to compounds of formula Ie (Ie)

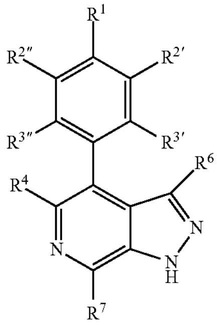

wherein $R^1$ is —$SO_2R^{1a}$ or —$SOR^{1b}$;

$R^{1a}$ and $R^{1b}$ are independently selected from $(C_1-C_6)$alkyl, $(C_3-C_6)$cycloalkyl, $(C_3-C_6)$cycloalkyl-$(C_1-C_6)$alkyl, halo$(C_1-C_6)$alkyl, halo$(C_1-C_6)$alkoxy, hydroxy$(C_1-C_6)$alkyl, $(C_1-C_6)$alkoxy-$(C_1-C_6)$alkyl, $NR^{1'a}$ $R^{1'b}$), oxetanyl, furanyl and pyranyl, wherein at least one of $R^{1'a}$ and $R^{1'b}$ is $(C_1-C_6)$alkyl and the other is H or $(C_1-C_6)$alkyl; or $R^{2'}$ is hydrogen, halogen, —$NH_2$, $(C_1-C_6)$alkyl, $(C_1-C_6)$alkoxy, halo$(C_1-C_6)$alkyl or halo$(C_1-C_6)$alkoxy;

$R^{2''}$ is hydrogen, halogen, —$NH_2$, $(C_1-C_6)$alkyl, $(C_1-C_6)$alkoxy, halo$(C_1-C_6)$alkyl or halo$(C_1-C_6)$alkoxy;

$R^{3'}$ is hydrogen, halogen, —$NH_2$, $(C_1-C_6)$alkyl, $(C_1-C_6)$alkoxy, halo$(C_1-C_6)$alkyl or halo$(C_1-C_6)$alkoxy;

$R^{3''}$ is hydrogen, halogen, —$NH_2$, $(C_1-C_6)$alkyl, $(C_1-C_6)$alkoxy, halo$(C_1-C_6)$alkyl or halo$(C_1-C_6)$alkoxy;

$R^4$ is hydrogen, cyano, oxo, hydroxy, halogen, —$NH_2$, $(C_1-C_6)$alkyl, $(C_1-C_6)$alkoxy, halo$(C_1-C_6)$alkyl, halo$(C_1-C_6)$alkoxy, $(C_1-C_6)$alkoxy-$(C_1-C_6)$alkyl, $(C_3-C_6)$cycloalkyl, $(C_3-C_6)$cycloalkyl-$(C_1-C_6)$alkyl, —$CO_2R^{4a}$, —$CONR^{4b}R^{4c}$, —$SO_2R^{4d}$, —$SR^{4f}$, —$SO(NR^{4h})R^{4g}$ or —$SO_2(NR^{4i})R^{4j}$;

$R^{4a}$, $R^{4b}$ and $R^{4c}$ are independently selected from hydrogen, $(C_1-C_6)$alkyl, $(C_3-C_6)$cycloalkyl, $(C_3-C_6)$cycloalkyl-$(C_1-C_6)$alkyl, halo$(C_1-C_6)$alkyl and oxetanyl;

$R^{4d}$, $R^{4e}$ and $R^{4f}$ are independently selected from $(C_1-C_6)$alkyl, $(C_3-C_6)$cycloalkyl, $(C_3-C_6)$cycloalkyl-$(C_1-C_6)$alkyl, halo$(C_1-C_6)$alkyl and oxetanyl;

$R^{4h}$ and $R^{4g}$ are independently selected from hydrogen, $(C_1-C_6)$alkyl, $(C_3-C_6)$cycloalkyl, $(C_3-C_6)$cycloalkyl-$(C_1-C_6)$alkyl, halo$(C_1-C_6)$alkyl and oxetanyl;

$R^{4i}$ and $R^{4j}$ are independently selected from hydrogen, $(C_1-C_6)$alkyl, $(C_3-C_6)$cycloalkyl, $(C_3-C_6)$cycloalkyl-$(C_1-C_6)$alkyl, halo$(C_1-C_6)$alkyl and oxetanyl;

$R^6$ is halogen, $(C_1-C_6)$alkyl, $(C_1-C_6)$alkoxy, cyano, halo$(C_1-C_6)$alkyl, halo$(C_1-C_6)$alkoxy, $(C_3-C_6)$cycloalkyl, oxetanyl or thiophenyl or —$SO_2R^{6a}$;

$R^{6a}$ is $(C_1-C_6)$alkyl, $(C_3-C_6)$cycloalkyl or halo$(C_1-C_6)$alkyl;

$R^7$ is hydrogen, halogen, hydroxy, $(C_1-C_6)$alkyl, $(C_1-C_6)$alkoxy, halo-$(C_1-C_6)$alkyl, halo-$(C_1-C_6)$alkoxy or $NR^{7'a}R^{7'b}$, wherein one of $R^{7'a}$ and $R^{7'b}$ is hydrogen and the other is hydrogen, $(C_1-C_6)$alkyl, $(C_1-C_6)$alkoxy, —$(C_1-C_6)$alkyl-O—$(C_1-C_6)$alkyl-NHCO—$(C_1-C_6)$alkyl, —$(C_1-C_6)$alkyl-O—$(C_1-C_6)$alkyl-$NH_2$, —$(C_1-C_6)$alkyl-NHCO—$(C_1-C_6)$alkyl or —$(C_1-C_6)$alkyl-$NH_2$, and pharmaceutically acceptable salts thereof.

Further, it is to be understood that every embodiment relating to a specific $X^1$, $X^2$, $X^3$, $X^4$, $R^1$, $R^{1a}$, $R^{1b}$, $R^{1'a}$, $R^{1'b}$, $R^{2'}$, $R^{2''}$, $R^{3'}$, $R^{3''}$, $R^4$, $R^{4a}$, $R^{4b}$, $R^{4c}$, $R^{4d}$, $R^{4e}$, $R^{4f}$, $R^{4h}$, $R^{4g}$, $R^{4i}$, $R^{4j}$, $R^5$, $R^6$, $R^{6a}$, $R^7$, $R^{7'a}$ and $R^{7'b}$ as disclosed herein may be combined with any other embodiment relating to another $X^1$, $X^2$, $X^3$, $R^1$, $R^{1a}$, $R^{1b}$, $R^{1'a}$, $R^{1'jjb}$, $R^{2'}$, $R^{2''}$, $R^{3'}$, $R^{3''}$, $R^4$, $R^{4a}$, $R^{4b}$, $R^{4c}$, $R^{4d}$, $R^{4e}$, $R^{4f}$, $R^{4h}$, $R^{4g}$, $R^{4i}$, $R^{4j}$, $R^5$, $R^6$, $R^{6a}$; $R^7$, $R^{7'a}$ and $R^{7'b}$ as disclosed herein.

A particular embodiment of the present invention relates to a compound of formula I, wherein $X^4$ is N.

A particular embodiment of the present invention relates to a compound of formula I, wherein wherein $X^1$ is N or C, $X^2$ is N or $CR^4$ and $X^3$ is N or $CR^5$.

A particular embodiment of the present invention relates to a compound of formula I, wherein wherein $X^1$ is C.

A particular embodiment of the present invention relates to a compound of formula I, wherein wherein $X^2$ is $CR^4$.

A particular embodiment of the present invention relates to a compound of formula I, wherein wherein $X^3$ is N.

A particular embodiment of the present invention relates to a compound of formula I, Ia, Ib, Ic, Id or Ie wherein $R^1$ is —$SO_2R^{1a}$.

A particular embodiment of the present invention relates to a compound of formula I, Ia, Ib, Ic, Id or Ie wherein $R^{1a}$ and $R^{1b}$ are independently selected from $(C_1-C_6)$alkyl, $(C_3-C_6)$cycloalkyl, $(C_3-C_6)$cycloalkyl-$(C_1-C_6)$alkyl, halo$(C_1-C_6)$alkyl, halo$(C_1-C_6)$alkoxy, hydroxy$(C_1-C_6)$alkyl, $(C_1-C_6)$alkoxy-$(C_1-C_6)$alkyl, $NR^{1'a}R^{1'b}$, oxetanyl, furanyl and pyranyl, wherein at least one of $R^{1'a}$ and $R^{1'b}$ is $(C_1-C_6)$alkyl and the other is H or $(C_1-C_6)$alkyl, particularly wherein $R^{1a}$ is selected from $(C_1-C_3)$alkyl, $(C_3-C_4)$cycloalkyl, $(C_3-C_4)$cycloalkyl-$(C_1-C_3)$alkyl, halo$(C_1-C_3)$alkyl, hydroxy$(C_1-C_3)$alkyl, $(C_1-C_3)$alkoxy-$(C_1-C_3)$alkyl, $NR^{1'a}R^{1'b}$ and oxetanyl, wherein at least one of $R^{1'a}$ and $R^{1'b}$ is $(C_1-C_3)$alkyl and the other is H or $(C_1-C_3)$alkyl, more particularly wherein $R^{1a}$ is selected from methyl, ethyl, propyl, i-propyl, i-butyl, cyclopropyl,

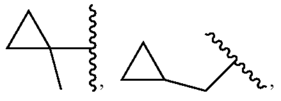

fluoromethyl, difluoromethyl, fluoro-ethanyl, difluoro-ethanyl, 1,2 difluoroethanyl, 1,1,2-trifluoroethanyl, 1,2,2-trifluoroethanyl, Hydroxymethyl, hydroxyethyl, metoxymethyl, methylaminyl (—$NHCH_3$), dimethylaminyl (—$N(CH_3)_2$) and oxetanyl, even more particularly wherein $R^{1a}$ is selected from ethyl, propyl, i-propyl, i-butyl, cyclopropyl, fluoromethyl, difluoromethyl, fluoro-ethanyl, difluoro-ethanyl, 1,2 difluoroethanyl, 1,1,2-trifluoroethanyl and 1,2,2-trifluoroethanyl, most particularly wherein $R^{1a}$ is selected from methyl, ethyl, cyclopropyl and difluoromethyl.

A particular embodiment of the present invention relates to a compound of formula I, Ia, Ib, Ic, Id or Ie wherein $R^{1b}$ is $(C_1-C_6)$alkyl, more particularly is $(C_1-C_3)$alkyl, most particularly methyl.

A particular embodiment of the present invention relates to a compound of formula I, Ia, Ib, Ic, Id or Ie if $R^{2'}$ is other than hydrogen as defined herein, then $R^{3'}$ is hydrogen, $R^{2''}$ is hydrogen and $R^{3''}$ is as defined herein and conversely if $R^{2''}$ is other than hydrogen than $R^{3''}$ is hydrogen, $R^{2'}$ is hydrogen and $R^{3'}$ is as defined herein.

A particular embodiment of the present invention relates to a compound of formula I, Ia, Ib, Ic, Id or Ie wherein one of $R^{2'}$ and $R^{2''}$ is hydrogen, halogen, —$NH_2$, $(C_1-C_2)$alkyl, $(C_1-C_2)$alkoxy or halo$(C_1-C_2)$alkyl, while the other one is hydrogen, particularly wherein $R^{2'}$ is hydrogen, halogen, —$NH_2$, methyl, ethyl, methoxy fluoromethyl, difluoromethyl, fluoro-ethanyl, difluoro-ethanyl or 1,2 difluoroethanyl, and $R^{2''}$ is hydrogen, more particularly $R^{2'}$ is methyl, ethyl, fluoromethyl, difluoromethyl, fluoro-ethanyl, difluoro-ethanyl, 1,2 difluoroethanyl, and $R^{2''}$ is hydrogen, most particularly $R^{2'}$ is methyl or difluoromethyl and $R^{2''}$ is hydrogen.

A particular embodiment of the present invention relates to a compound of formula I, Ia, Ib, Ic, Id or Ie wherein one of $R^{3'}$ and $R^{3''}$ is hydrogen, halogen, —$NH_2$, $(C_1-C_3)$alkyl, $(C_1-C_3)$alkoxy or halo$(C_1-C_3)$alkyl, while the other one is hydrogen, more particularly $R^{3''}$ is hydrogen, halogen or $(C_1-C_3)$alkyl and $R^{3'}$ is hydrogen, even more particularly $R^{3''}$ is hydrogen or fluorine and $R^{3'}$ is hydrogen, most particularly both $R^{3'}$ and $R^{3''}$ are hydrogen.

A particular embodiment of the present invention relates to a compound of formula I, Ia, Ib, Id or Ie wherein $R^4$ is cyano, oxo, hydroxy, $(C_1-C_3)$alkyl, $(C_1-C_3)$alkoxy, halo$(C_1-C_3)$alkyl, halo$(C_1-C_6)$alkoxy, $(C_1-C_3)$alkoxy-$(C_1-C_3)$alkyl, $(C_3-C_4)$cycloalkyl, —$CO_2R^{4a}$, —$CONR^{4b}R^{4c}$, —$SO_2R^{4d}$, —$SOR^{4e}$, —$SR^{4f}$, —$SO(NR^{4h})R^{4g}$ or —$SO_2(NR^{4i})R^{4j}$, particularly wherein $R^4$ is cyano, oxo, hydroxy, $(C_1-C_2)$alkoxy, halo$(C_1-C_2)$alkyl, halo$(C_1-C_2)$alkoxy, $(C_1-C_2)$alkoxy-$(C_1-C_2)$alkyl, cyclopropyl, —$CO_2H$, —$CONR^{4b}R^{4c}$, —$SO_2R^{4d}$, —$SOR^{4e}$, —$SR^{4f}$, or —$SO(NH)CH_3$ particularly wherein $R^4$ is cyano, oxo, hydrorxy, methoxy, —$CF_3$, —$OCF_3$, -methyl-methoxy, cyclopropyl, —$CO_2H$, —$CONR^{4b}R^{4c}$, —$SO_2R^{4d}$, —$SOR^{4e}$ or —$SR^{4f}$, most particularly $R^4$ is cyano, oxo, —$CONHR^{4c}$ or —$SO_2R^{4d}$.

A particular embodiment of the present invention relates to a compound of formula I, Ia, Ib, Id or Ie wherein $R^{4a}$, $R^{4b}$ and $R^{4c}$, are independently selected from hydrogen, $(C_1-C_3)$alkyl, $(C_3-C_4)$cycloalkyl, and oxetanyl, particularly wherein $R^{4a}$, $R^{4b}$ and $R^{4c}$ are independently selected from hydrogen, $(C_1-C_3)$alkyl, cyclopropyl, and oxetanyl, more particularly $R^{4a}$, $R^{4b}$ and $R^{4c}$ are independently selected from hydrogen, $(C_1-C_3)$alkyl and cyclopropyl, most particularly $R^{4a}$ and $R^{4b}$ are hydrogen, $R^{4c}$ is hydrogen or methyl.

A particular embodiment of the present invention relates to a compound of formula I, Ia, Ib, Id or Ie wherein $R^{4d}$, $R^{4e}$ and $R^{4f}$ are independently selected from $(C_1-C_3)$alkyl, $(C_3-C_4)$cycloalkyl, and oxetanyl, particularly wherein $R^{4d}$, $R^{4e}$ and $R^{4f}$ are independently selected from $(C_1-C_3)$alkyl, cyclopropyl, and oxetanyl, more particularly $R^{4d}$, $R^{4e}$ and $R^{4f}$ are independently selected from $(C_1-C_3)$alkyl and cyclopropyl, most particularly $R^{4d}$ is methyl or cyclopropyl.

A particular embodiment of the present invention relates to a compound of formula I, Ia, Ib, Id or Ie wherein $R^{4h}$ and $R^{4g}$ are independently selected from hydrogen and $(C_1-C_6)$alkyl, particularly hydrogen and $(C_1-C_3)$alkyl, more particularly wherein $R^{4h}$ is hydrogen and $R^{4g}$ is $(C_1-C_3)$alkyl, most particularly wherein $R^{4h}$ is hydrogen and $R^{4g}$ is methyl.

A particular embodiment of the present invention relates to a compound of formula I, Ia, Ib, Id or Ie wherein $R^{4i}$ and $R^{4j}$ are independently selected from hydrogen and $(C_1-C_6)$alkyl, particularly from hydrogen and $(C_1-C_3)$alkyl, more particularly wherein $R^{4i}$ is hydrogen and $R^{4j}$ is $(C_1-C_3)$alkyl, most particularly wherein $R^{4i}$ is hydrogen and $R^{4j}$ is methyl.

A particular embodiment of the present invention relates to a compound of formula I, Ia, Ib, Ic or Id wherein $R^5$ is hydrogen, halogen, $(C_1-C_6)$alkyl, $(C_1-C_6)$alkoxy or $(C_3-C_6)$cycloalkyl, particularly $R^5$ is hydrogen, halogen, $(C_1-C_2)$alkyl, $(C_1-C_2)$alkoxy or $(C_3-C_4)$cycloalkyl, more particularly $R^5$ is hydrogen, fluoro, chloro, cylclopropyl, methyl or methoxy, most particularly $R^5$ is hydrogen.

A particular embodiment of the present invention relates a compound of formula I, Ia, Ib, Ic, Id or Ie wherein $R^6$ is halogen, $(C_1-C_6)$alkyl, $(C_1-C_6)$alkoxy, cyano, halo$(C_1-C_6)$alkyl, halo$(C_1-C_6)$alkoxy, $(C_3-C_6)$cycloalkyl, thiophenyl, oxetanyl or —$SO_2R^{6a}$, wherin $R^{6a}$ is $(C_1-C_6)$alkyl, particularly $R^6$ is bromo, $(C_1-C_3)$alkyl, $(C_1-C_3)$alkoxy, cyano, halo$(C_1-C_3)$alkyl, halo$(C_1-C_3)$alkoxy, $(C_3-C_4)$cycloalkyl, thiophenyl, oxetanyl or —$SO_2R^{6a}$, wherin $R^{6a}$ is $(C_1-C_6)$alkyl, particularly $R^6$ is halo$(C_1-C_3)$alkyl, halo$(C_1-C_3)$alkoxy or $(C_3-C_4)$cycloalkyl, more particularly $R^6$ is trifluoromethyl, trifluoromethoxy, difluoromethoxy or cyclopropyl.

A particular embodiment of the present invention relates a compound of formula I, Ia, Ib, Ic, Id or Ie wherein $R^{6a}$ is $(C_1-C_6)$alkyl, more particularly $R^{6a}$ is methyl.

A particular embodiment of the present invention relates a compound of formula I, Ia, Ib, Ic, Id or Ie wherein $R^7$ is hydrogen, halogen, hydroxy or $(C_1-C_6)$alkyl, particularly $R^7$ is hydrogen, halogen or hydroxy, more particularly $R^7$ is hydrogen.

A particular embodiment of the present invention relates a compound of formula I, Ia, Ib, Ic, Id or Ie wherein one of $R^{7'a}$ and $R^{7'b}$ is hydrogen and the other is hydrogen, $(C_1-C_6)$alkyl, $(C_1-C_6)$alkoxy, —$(C_1-C_3)$alkyl-O—$(C_1-C_3)$alkyl-NHCO—$(C_1-C_3)$alkyl, —$(C_1-C_3)$alkyl-O—$(C_1-C_3)$alkyl-$NH_2$, —$(C_1-C_3)$alkyl-NHCO—$(C_1-C_3)$alkyl or —$(C_1-C_3)$alkyl-$NH_2$, in particular wherein one of $R^{7'a}$ and $R^{7'b}$ is hydrogen and the other is hydrogen, $(C_1-C_6)$alkyl, or $(C_1-C_6)$alkoxy, more particularly wherein one of $R^{7'a}$ and $R^{7'b}$ is hydrogen and the other is hydrogen, $(C_1-C_3)$alkyl, or $(C_1-C_3)$alkoxy.

Particular compounds of formula I of the present invention are those selected from the group consisting of:

3-cyclopropyl-4-(3-methyl-4-(methylsulfonyl)phenyl)-1H-pyrazolo[4,3-c]pyridine;

3-cyclopropyl-4-(3-methoxy-4-(methylsulfonyl)phenyl)-1H-pyrazolo[4,3-c]pyridine;

4-(3-chloro-4-(methylsulfonyl)phenyl)-3-cyclopropyl-1H-pyrazolo[4,3-c]pyridine;

3-cyclopropyl-4-(4-(methylsulfonyl)-3-(trifluoromethyl)phenyl)-1H-pyrazolo[4,3-c]pyridine;

4-(3-cyclopropyl-1H-pyrazolo[4,3-c]pyridin-4-yl)-N,N,2-trimethylbenzenesulfonamide;

3-cyclopropyl-5-methoxy-4-(4-methylsulfonylphenyl)-1H-pyrazolo[3,4-c]pyridine;

3-cyclopropyl-4-(4-(cyclopropylsulfonyl)-3-methylphenyl)-1H-pyrazolo[4,3-c]pyridine;

4-(3-chloro-4-(cyclopropylsulfonyl)phenyl)-3-cyclopropyl-1H-pyrazolo[4,3-c]pyridine;

2-chloro-4-(3-cyclopropyl-1H-pyrazolo[4,3-c]pyridin-4-yl)-N,N-dimethylbenzenesulfonamide;

4-(3-methyl-4-(methylsulfonyl)phenyl)-3-(trifluoromethyl)-1H-pyrazolo[3,4-b]pyridine;

4-(4-(methylsulfonyl)phenyl)-3-(trifluoromethyl)-1H-pyrazolo[4,3-c]pyridine;

3-cyclopropyl-4-(3-(difluoromethyl)-4-(methylsulfonyl)phenyl)-1H-pyrazolo[4,3-c]pyridine;

3-cyclopropyl-4-(3-(fluoromethyl)-4-(methylsulfonyl)phenyl)-1H-pyrazolo[4,3-c]pyridine;

3-bromo-4-(3-methyl-4-(methylsulfonyl)phenyl)-1H-pyrazolo[4,3-c]pyridine;

3-cyclopropyl-4-(3-methyl-4-(methylsulfonyl)phenyl)-1H-pyrrolo[3,2-c]pyridine;

3-cyclopropyl-4-(3-methyl-4-(oxetan-3-ylsulfonyl)phenyl)-1H-pyrazolo[4,3-c]pyridine;

3-(difluoromethoxy)-4-(3-methyl-4-(methylsulfonyl)phenyl)-1H-pyrazolo[4,3-c]pyridine;

3-methoxy-4-(3-methyl-4-(methylsulfonyl)phenyl)-1H-pyrazolo[4,3-c]pyridine;

5-(3-cyclopropyl-1H-pyrazolo[4,3-c]pyridin-4-yl)-2-(methylsulfonyl)aniline;

4-(3-methyl-4-(methylsulfonyl)phenyl)-3-(methylsulfonyl)-1H-pyrazolo[4,3-c]pyridine;

3-cyclopropyl-4-(3-methyl-4-(methylsulfonyl)phenyl)-1H-pyrazolo[3,4-c]pyridine-5-carbonitrile;

3-(1,1-difluoroethyl)-4-(3-methyl-4-(methylsulfonyl)phenyl)-1H-pyrazolo[4,3-c]pyridine;

4-(3-methyl-4-(methylsulfonyl)phenyl)-1H-pyrazolo[4,3-c]pyridine-3-carbonitrile;

3-(difluoromethyl)-4-(3-methyl-4-methylsulfonylphenyl)-1H-pyrazolo[4,3-c]pyridine;

3-isopropyl-4-(3-methyl-4-(methylsulfonyl)phenyl)-1H-pyrazolo[4,3-c]pyridine;

3-cyclopropyl-4-(4-ethylsulfonyl-3-methyl-phenyl)-1H-pyrazolo[4,3-c]pyridine;

3-cyclopropyl-4-(2-fluoro-5-methyl-4-methylsulfonyl-phenyl)-1H-pyrazolo[4,3-c]pyridine;

3-cyclopropyl-4-(2,5-dimethyl-4-methylsulfonyl-phenyl)-1H-pyrazolo[4,3-c]pyridine hydrochloride;

3-cyclopropyl-4-(3-methyl-4-(methylsulfonyl)phenyl)-1H-pyrazolo[3,4-c]pyridine-5-carboxylic acid 3-cyclopropyl-4-(3-methyl-4-methylsulfonylphenyl)-1H-indazole-5-carbonitrile;

3-cyclopropyl-4-(3-methyl-4-methylsulfinyl-phenyl)-1H-pyrazolo[4,3-c]pyridine hydrochloride 3-cyclopropyl-4-(3-methyl-4-methylsulfonyl-phenyl)-1H-pyrazolo[4,3-c]pyridin-7-ol 4-(3-methyl-4-(methylsulfonyl)phenyl)-3-(thiophen-3-yl)-1H-pyrazolo[4,3-c]pyridine;

3-cyclopropyl-5-methoxy-4-(3-methyl-4-(methylsulfonyl)phenyl)-1H-pyrazolo[3,4-c]pyridine;

3-ethoxy-4-(3-methyl-4-methylsulfonyl-phenyl)-1H-pyrazolo[4,3-c]pyridine;

3-(difluoromethoxy)-4-[4-(difluoromethylsulfonyl)-3-methyl-phenyl]-1H-pyrazolo[4,3-c]pyridine;

4-(4-cyclopropylsulfonyl-3-methyl-phenyl)-3-(difluoromethoxy)-1H-pyrazolo[4,3-c]pyridine;

3-cyclopropyl-7-fluoro-4-(3-methyl-4-methylsulfonyl-phenyl)-1H-pyrazolo[4,3-c]pyridine;

3-(difluoromethoxy)-4-(4-ethylsulfonyl-3-methyl-phenyl)-1H-pyrazolo[4,3-c]pyridine;

4-(3-methyl-4-methylsulfonyl-phenyl)-3-(oxetan-3-yl)-1H-pyrazolo[4,3-c]pyridine;

4-[4-(cyclopropylmethylsulfonyl)-3-methyl-phenyl]-3-(difluoromethoxy)-1H-pyrazolo[4,3-c]pyridine;

3-(difluoromethoxy)-4-(3-methyl-4-propylsulfonyl-phenyl)-1H-pyrazolo[4,3-c]pyridine;

3-(difluoromethoxy)-4-[3-(difluoromethyl)-4-methylsulfonyl-phenyl]-1H-pyrazolo[4,3-c]pyridine;

3-(difluoromethoxy)-4-(4-isopropylsulfonyl-3-methyl-phenyl)-1H-pyrazolo[4,3-c]pyridine;

4-[3-(difluoromethoxy)-1H-pyrazolo[4,3-c]pyridin-4-yl]-N,2-dimethyl-benzenesulfonamide;

3-methoxy-4-(3-methyl-4-(methylsulfonyl)phenyl)-1H-indazole-5-carbonitrile;

3-(difluoromethoxy)-4-(3-methyl-4-(methylsulfonyl)phenyl)-1H-indazole-5-carbonitrile;

6-chloro-3-cyclopropyl-4-(3-methyl-4-methylsulfonylphenyl)-1H-pyrazolo[4,3-c]pyridine;

3-(difluoromethoxy)-4-[3-methyl-4-(oxetan-3-ylsulfonyl)phenyl]-1H-pyrazolo[4,3-c]pyridine;

2-[4-[3-(difluoromethoxy)-1H-pyrazolo[4,3-c]pyridin-4-yl]-2-methyl-phenyl]sulfonylethanol 3-cyclopropyl-6-methoxy-4-(3-methyl-4-methylsulfonylphenyl)-1H-pyrazolo[4,3-c]pyridine 2,2,2-trifluoroacetic acid;

3-(difluoromethoxy)-4-[3-methyl-4-(1-methylcyclopropyl)sulfonyl-phenyl]-1H-pyrazolo[4,3-c]pyridine;

4-(3-methyl-4-(methylsulfonyl)phenyl)-3-(trifluoromethoxy)-1H-pyrazolo[4,3-c]pyridine;

3-cyclopropyl-4-(3-methyl-4-(methylsulfonyl)phenyl)-1H-pyrazolo[3,4-c]pyridine-5-carboxamide;

3-cyclopropyl-N-methyl-4-(3-methyl-4-(methylsulfonyl)phenyl)-1H-pyrazolo[3,4-c]pyridine-5-carboxamide;

3-cyclopropyl-4-(3-methyl-4-(methylsulfonyl)phenyl)-1H-pyrazolo[3,4-d]pyridazine;

3-cyclopropyl-4-(3-methyl-4-(methylsulfonyl)phenyl)-5-(methylthio)-1H-indazole;

3-cyclopropyl-4-(3-methyl-4-(methylsulfonyl)phenyl)-5-(methylsulfinyl)-1H-indazole;

3-cyclopropyl-4-(3-methyl-4-(methylsulfonyl)phenyl)-5-(methylsulfonyl)-1H-indazole;

3-(difluoromethoxy)-4-[4-(methoxymethylsulfonyl)-3-methyl-phenyl]-1H-pyrazolo[4,3-c]pyridine formic acid;

5-methoxy-4-(3-methyl-4-(methylsulfonyl)phenyl)-3-(trifluoromethyl)-1H-pyrazolo[3,4-c]pyridine;

4-(3-methyl-4-(methylsulfonyl)phenyl)-3-(trifluoromethyl)-1H-pyrrolo[3,2-c]pyridine;

3-(difluoromethoxy)-4-(3-methyl-4-methylsulfonyl-phenyl)-1H-pyrazolo[4,3-b]pyridin-5-one 3-cyclopropyl-4-(3-methyl-4-methylsulfonylphenyl)-5-(trifluoromethyl)-1H-pyrazolo[3,4-c]pyridine;

3-cyclopropyl-6-methyl-4-(3-methyl-4-methylsulfonyl-phenyl)-1H-pyrazolo[4,3-b]pyridin-5-one;

3,6-dicyclopropyl-4-(3-methyl-4-methylsulfonyl-phenyl)-1H-pyrazolo[4,3-b]pyridin-5-one;

3-cyclopropyl-5-(difluoromethoxy)-4-(3-methyl-4-(methylsulfonyl)phenyl)-1H-pyrazolo[3,4-c]pyridine;

3-cyclopropyl-N,N-dimethyl-4-(3-methyl-4-(methylsulfonyl)phenyl)-1H-pyrazolo[3,4-c]pyridine-5-carboxamide;

3-cyclopropyl-5-(methoxymethyl)-4-(3-methyl-4-(methylsulfonyl)phenyl)-1H-pyrazolo[3,4-c]pyridine;

3-cyclopropyl-4-(3-methyl-4-(methylsulfonyl)phenyl)-N-(oxetan-3-yl)-1H-pyrazolo[3,4-c]pyridine-5-carboxamide;

3,5-dicyclopropyl-4-(3-methyl-4-methylsulfonylphenyl)-1H-pyrazolo[3,4-c]pyridine;

N,3-dicyclopropyl-4-(3-methyl-4-(methylsulfonyl)phenyl)-1H-pyrazolo[3,4-c]pyridine-5-carboxamide;

3-cyclopropyl-6-fluoro-4-(3-methyl-4-(methylsulfonyl)phenyl)-1H-indazole-5-carbonitrile;

3-cyclopropyl-4-(4-ethylsulfonyl-3-methyl-phenyl)-1H-pyrazolo[3,4-c]pyridine-5-carbonitrile;

3-cyclopropyl-4-(4-cyclopropylsulfonyl-3-methyl-phenyl)-1H-pyrazolo[3,4-c]pyridine-5-carbonitrile;

4-(3-methyl-4-(methylsulfonyl)phenyl)-5-(methylsulfonyl)-3-(trifluoromethyl)-1H-indazole 3-cyclopropyl-4-(3-methyl-4-methylsulfonylphenyl)-1H-indole-5-carbonitrile;

3-cyclopropyl-4-(4-cyclopropylsulfonyl-3-methyl-phenyl)-N-methyl-1H-pyrazolo[3,4-c]pyridine-5-carboxamide;

3-cyclopropyl-6-fluoro-N-methyl-4-(3-methyl-4-(methylsulfonyl)phenyl)-1H-indazole-5-carboxamide;

3-cyclopropyl-6-fluoro-4-(3-methyl-4-(methylsulfonyl)phenyl)-1H-indazole-5-carboxamide;

6-chloro-3-cyclopropyl-4-(3-methyl-4-methylsulfonylphenyl)-1#H!-indazole-5-carbonitrile;

3-cyclopropyl-4-(2-fluoro-5-methyl-4-methylsulfonyl-phenyl)-1H-pyrazolo[3,4-c]pyridine-5-carbonitrile;

4-(3-methyl-4-methylsulfonyl-phenyl)-3-(trifluoromethoxy)-1H-pyrazolo[4,3-b]pyridin-5-one;

3-cyclopropyl-4-(3-methyl-4-methylsulfonyl-phenyl)-1H-pyrrolo[3,2-b]pyridin-5-one;

4-[3-(difluoromethoxy)-1H-pyrazolo[4,3-c]pyridin-4-yl]-2-(difluoromethyl)-N,N-dimethyl-benzenesulfonamide;

3-(difluoromethoxy)-4-(3-methyl-4-(methylsulfonyl)phenyl)-5-(methylsulfonyl)-1H-indazole;

3-cyclopropyl-4-[4-(difluoromethylsulfonyl)-3-methyl-phenyl]-1H-pyrazolo[3,4-c]pyridine-5-carbonitrile;

4-(3-methyl-4-(methylsulfonyl)phenyl)-5-(methylsulfonyl)-3-(trifluoromethoxy)-1H-indazole;

3-cyclopropyl-4-[3-(difluoromethyl)-4-methylsulfonyl-phenyl]-N-methyl-1H-pyrazolo[3,4-c]pyridine-5-carboxamide;

3-(difluoromethoxy)-4-(3-methyl-4-methylsulfonyl-phenyl)-1H-pyrazolo[3,4-c]pyridine-5-carbonitrile;

3-(difluoromethoxy)-4-[5-(difluoromethyl)-2-methyl-4-methylsulfinyl-phenyl]-1H-pyrazolo[3,4-c]pyridine-5-carbonitrile;

4-[3-(difluoromethyl)-4-methylsulfonyl-phenyl]-5-methoxy-3-(trifluoromethyl)-1H-pyrazolo[3,4-c]pyridine;

3-cyclopropyl-4-(3-(difluoromethyl)-4-(methylsulfonyl)phenyl)-5-(methylsulfonyl)-1H-indazole;

3-(difluoromethoxy)-N-methyl-4-(3-methyl-4-methylsulfonyl-phenyl)-1H-pyrazolo[3,4-c]pyridine-5-carboxamide;

3-cyclopropyl-4-(4-cyclopropylsulfonyl-2-fluoro-5-methylphenyl)-N-methyl-1H-pyrazolo[3,4-c]pyridine-5-carboxamide;

4-(4-cyclopropylsulfonyl-3-methyl-phenyl)-3-(difluoromethoxy)-5-methylsulfonyl-1H-indazole;

3-cyclopropyl-4-(2-fluoro-5-methyl-4-methylsulfonyl-phenyl)-N-methyl-1H-pyrazolo[3,4-c]pyridine-5-carboxamide;

3-(difluoromethoxy)-4-(3-methyl-4-methylsulfonyl-phenyl)-1H-pyrazolo[3,4-c]pyridine-5-carboxamide;

3-(difluoromethoxy)-4-(4-((difluoromethyl)sulfonyl)-3-methylphenyl)-1H-pyrazolo[3,4-c]pyridine-5-carbonitrile;

3-(difluoromethoxy)-4-[4-(difluoromethylsulfonyl)-3-methyl-phenyl]-1H-pyrazolo[3,4-c]pyridine-5-carboxamide;

3-(difluoromethoxy)-4-[4-(difluoromethylsulfonyl)-3-methyl-phenyl]-N-(oxetan-3-yl)-1H-pyrazolo[3,4-c]pyridine-5-carboxamide;

3-(difluoromethoxy)-4-[4-(difluoromethylsulfonyl)-3-methyl-phenyl]-N-methyl-1H-pyrazolo[3,4-c]pyridine-5-carboxamide;

3-(difluoromethoxy)-4-[4-(difluoromethylsulfonyl)-3-methyl-phenyl]-N-(2-methoxyethyl)-1H-pyrazolo[3,4-c]pyridine-5-carboxamide;

3-(difluoromethoxy)-N-methyl-4-(3-methyl-4-methylsulfonyl-phenyl)-1H-pyrazolo[3,4-c]pyridine-5-carboxamide;

3-(difluoromethoxy)-4-(3-methyl-4-methylsulfonyl-phenyl)-5-(oxetan-3-ylsulfonyl)-1H-indazole;

[3-cyclopropyl-4-(3-methyl-4-methylsulfonylphenyl)-1H-indazol-5-yl]-imino-methyl-oxo-sulfane;

[3-cyclopropyl-4-(3-methyl-4-methylsulfonyl-phenyl)-1H-indazol-5-yl]-methyl-methylimino-oxo-$\lambda^6$-sulfane;

3-cyclopropyl-N,N-dimethyl-4-(3-methyl-4-methylsulfonyl-phenyl)-1H-indazole-5-sulfonamide;

3-cyclopropyl-N-methyl-4-(3-methyl-4-methylsulfonyl-phenyl)-1H-indazole-5-sulfonamide;

4-(4-cyclopropylsulfonyl-3-methyl-phenyl)-3-(difluoromethoxy)-1H-pyrazolo[3,4-c]pyridine-5-carboxamide;

3-(difluoromethoxy)-4-(4-((difluoromethyl)sulfonyl)-3-methylphenyl)-5-(methylsulfonyl)-1H-indazole;

5-cyclopropylsulfonyl-3-(difluoromethoxy)-4-(3-methyl-4-methylsulfonyl-phenyl)-1H-indazole;

3-(difluoromethoxy)-4-(2-fluoro-5-methyl-4-methylsulfonyl-phenyl)-5-methylsulfonyl-1H-indazole;

or 4-(4-cyclopropylsulfonyl-3-methyl-phenyl)-3-(difluoromethoxy)-N-methyl-1H-pyrazolo[3,4-c]pyridine-5-carboxamide and pharmaceutically acceptable salts thereof.

Particular compounds of formula I of the present invention are those selected from the group consisting of:

3-(difluoromethoxy)-4-(3-methyl-4-(methylsulfonyl)phenyl)-1H-indazole-5-carbonitrile;

3-(difluoromethoxy)-4-(3-methyl-4-methylsulfonyl-phenyl)-1H-pyrazolo[4,3-b]pyridin-5-one;

3-cyclopropyl-4-(4-ethylsulfonyl-3-methyl-phenyl)-1H-pyrazolo[3,4-c]pyridine-5-carbonitrile;

4-(3-methyl-4-(methylsulfonyl)phenyl)-5-(methylsulfonyl)-3-(trifluoromethyl)-1H-indazole;

3-(difluoromethoxy)-4-(3-methyl-4-(methylsulfonyl)phenyl)-5-(methylsulfonyl)-1H-indazole;

3-cyclopropyl-4-[4-(difluoromethylsulfonyl)-3-methyl-phenyl]-1H-pyrazolo[3,4-c]pyridine-5-carbonitrile;

4-(3-methyl-4-(methylsulfonyl)phenyl)-5-(methylsulfonyl)-3-(trifluoromethoxy)-1H-indazole;

3-cyclopropyl-4-[3-(difluoromethyl)-4-methylsulfonyl-phenyl]-N-methyl-1H-pyrazolo[3,4-c]pyridine-5-carboxamide;

3-(difluoromethoxy)-4-(3-methyl-4-methylsulfonyl-phenyl)-1H-pyrazolo[3,4-c]pyridine-5-carbonitrile;

3-(difluoromethoxy)-N-methyl-4-(3-methyl-4-methylsulfonyl-phenyl)-1H-pyrazolo[3,4-c]pyridine-5-carboxamide;

3-(difluoromethoxy)-4-(3-methyl-4-methylsulfonyl-phenyl)-1H-pyrazolo[3,4-c]pyridine-5-carboxamide;

or 3-(difluoromethoxy)-4-[4-(difluoromethylsulfonyl)-3-methyl-phenyl]-1H-pyrazolo[3,4-c]pyridine-5-carboxamide and pharmaceutically acceptable salts thereof.

In another embodiment, the present invention provides a compound according to formula I, Ia, Ib, Ic, Id or Ie as described herein for use as a therapeutically active substance.

In yet another embodiment, the present invention provides a compound according to formula I, Ia, Ib, Ic, Id or Ie as described herein for the treatment, prevention and/or delay of progression of, more particularly for the treatment of Cancer in particular Lung Adenocarcinoma, Melanoma, Pancreatic Adenocarcinoma, Head and Neck Squamous Cell Carcinoma, Lung Squamous Cell Carcinoma, Esophageal Carcinoma, Glioblastmoa Multiforme, and Mesothelioma, more particularly Lung Adenocarcinoma, Lung Squamous Carcinoma, Pancreatic Adenocarcinoma, Glioblastoma Multiforme, and Head and Neck Squamous Carcinoma.

In another embodiment, the present invention provides the use of a compound according to formula I, Ia, Ib, Ic, Id or Ie as described herein for the preparation of a medicament for the treatment, prevention and/or delay of progression of, more particularly for the treatment of, Cancer in particular Lung Adenocarcinoma, Melanoma, Pancreatic Adenocarcinoma, Head and Neck Squamous Cell Carcinoma, Lung Squamous Cell Carcinoma, Esophageal Carcinoma, Glioblastmoa Multiforme, and Mesothelioma, more particularly Lung Adenocarcinoma, Lung Squamous Carcinoma, Pancreatic Adenocarcinoma, Glioblastoma Multiforme, and Head and Neck Squamous Carcinoma.

In one aspect, the application provides a method of treating a Mat2A disorder in a subject having Mat2A related disorders, said method comprising administering to a subject in need thereof a therapeutically effective amount of any of the above compounds.

In another embodiment, the present invention provides a method of the treatment, prevention and/or delay of progression of, more particularly of the treatment of, Cancer in particular Lung Adenocarcinoma, Melanoma, Pancreatic Adenocarcinoma, Head and Neck Squamous Cell Carcinoma, Lung Squamous Cell Carcinoma, Esophageal Carcinoma, Glioblastmoa Multiforme, and Mesothelioma, more particularly Lung Adenocarcinoma, Lung Squamous Carcinoma, Pancreatic Adenocarcinoma, Glioblastoma Multiforme, and Head and Neck Squamous Carcinoma which comprises administering an effective amount of a compound according to formula I, Ia, Ib, Ic, Id or Ie as described herein.

In particular embodiment, the present invention provides a method of treatment, prevention and/or delay of progression of, more particularly of the treatment of, Cancer in particular Lung Adenocarcinoma, Melanoma, Pancreatic Adenocarcinoma, Head and Neck Squamous Cell Carcinoma, Lung Squamous Cell Carcinoma, Esophageal Carcinoma, Glioblastmoa Multiforme, and Mesothelioma, more particularly Lung Adenocarcinoma, Lung Squamous Carcinoma, Pancreatic Adenocarcinoma, Glioblastoma Multiforme, and Head and Neck Squamous Carcinoma which comprises administering an effective amount of a compound according to formula I, Ia, Ib, Ic, Id or Ie as described herein.

In particular, Mat2A disorders or Mat2A related diseases are Cancer in particular Lung Adenocarcinoma, Melanoma, Pancreatic Adenocarcinoma, Head and Neck Squamous Cell Carcinoma, Lung Squamous Cell Carcinoma, Esophageal Carcinoma, Glioblastmoa Multiforme, and Mesothelioma, more particularly Lung Adenocarcinoma, Lung Squamous Carcinoma, Pancreatic Adenocarcinoma, Glioblastoma Multiforme, and Head and Neck Squamous Carcinoma.

In one aspect, the application provides a pharmaceutical composition comprising the compound of any one of the above embodiments, admixed with at least one pharmaceutically acceptable carrier, such as excipient or diluent.

In another embodiment, the present invention provides a use of a compound of formula I, Ia, Ib, Ic, Id or Ie in the preparation of a medicament for the treatment, prevention and/or delay of progression of, more particularly for the treatment of, diseases associated with Mat2A.

In yet another embodiment, the present invention provides a medicaments containing a compound of formula I, Ia, Ib, Ic, Id or Ie as defined herein or a pharmaceutically acceptable salt thereof and a therapeutically inert carrier are also an object of the present invention, as is a process for their production, which comprises bringing one or more compounds of formula I, Ia, Ib, Ic, Id or Ie and/or pharmaceutically acceptable acid addition salts and, if desired, one or more other therapeutically valuable substances into a galenical administration form together with one or more therapeutically inert carriers.

Another embodiment provides pharmaceutical compositions or medicaments comprising the compounds of the invention and a therapeutically inert carrier, diluent or pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. For example, such amount may be below the amount that is toxic to normal cells, or the mammal as a whole.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, coated tablets, dragees, powders, capsules (hard and soft gelatine capsules), solutions (i.e. injection solutions), dispersions, suspensions, syrups, sprays, suppositories, gels, emulsions, patches, eye drops, ear drops etc. Such compositions may contain components conventional in pharmaceutical preparations, e.g., diluents, carriers, pH modifiers, sweeteners, bulking agents, and further active agents.

A typical formulation is prepared by mixing a compound of the present invention and pharmaceutically acceptable carrier or excipient. Suitable pharmaceutically acceptable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxy¬methyl¬cellulose, a low melting wax, cocoa butter, and the like.

The dosage at which compounds of the invention can be administered can vary within wide limits and will, of course, be fitted to the individual requirements in each particular case. In general, in the case of oral administration a daily dosage of about 0.01 to 1000 mg per person of a compound formula I, Ia, Ib, Ic, Id or Ie should be appropriate, although the above upper limit can also be exceeded when necessary.

An example of a suitable oral dosage form is a tablet comprising about 100 mg to 500 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution may be filtered, e.g., using a 0.2 μm filter, to remove impurities and contaminants.

An embodiment, therefore, includes a pharmaceutical composition comprising a compound according to the invention herein described, or a stereoisomer thereof. In a further embodiment includes a pharmaceutical composition comprising a compound according to the invention herein described, or a stereoisomer thereof, together with a pharmaceutically acceptable carrier or excipient.

The compounds of the present invention can be used, either alone or in combination with other drugs, for the treatment, prevention and/or delay of progression of Mat2A related diseases, in particular Cancer in particular Lung Adenocarcinoma, Melanoma, Pancreatic Adenocarcinoma, Head and Neck Squamous Cell Carcinoma, Lung Squamous Cell Carcinoma, Esophageal Carcinoma, Glioblastmoa Multiforme, and Mesothelioma, more particularly Lung Adenocarcinoma, Lung Squamous Carcinoma, Pancreatic Adenocarcinoma, Glioblastoma Multiforme, and Head and Neck Squamous Carcinoma.

A particular embodiment of the present invention relates to pharmaceutical compositions comprising compounds of formula I, Ia, Ib, Ic, Id or Ie or their pharmaceutically acceptable salts as defined above and one or more pharmaceutically acceptable excipients for use in the treatment, prevention and/or delay of progression of cognitive impairments associated with Cancer in particular Lung Adenocarcinoma, Melanoma, Pancreatic Adenocarcinoma, Head and Neck Squamous Cell Carcinoma, Lung Squamous Cell Carcinoma, Esophageal Carcinoma, Glioblastmoa Multiforme, and Mesothelioma, more particularly Lung Adenocarcinoma, Lung Squamous Carcinoma, Pancreatic Adenocarcinoma, Glioblastoma Multiforme, and Head and Neck Squamous Carcinoma.

Another embodiment includes a pharmaceutical composition comprising a compound according to the invention herein described for use in the the treatment, prevention and/or delay of progression of, more particularly in the treatment of a Mat2A related diseases. Another embodiment includes a pharmaceutical composition comprising a compound according to the invention herein described for use in the treatment, prevention and/or delay of progression of, more particularly in the treatment of Mat2A related diseases.

In another embodiment the present invention provides the manufacture of compounds of formula I, Ia, Ib, Ic, Id or Ie as described herein.

The preparation of compounds of formula I, Ia, Ib, Ic, Id or Ie of the present invention may be carried out in sequential or convergent synthetic routes. Syntheses of the invention are shown in the following general scheme. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization.

Furthermore the compounds of the present invention can be prepared from commercially available starting materials or by the use of general synthetic techniques and procedures that are known to those skilled in the art. Outlined below are reaction schemes suitable for the preparation of such compounds. The substituents and indices used in the following description of the processes have the significance given herein. Further exemplification can be found in the specific examples detailed below.

General Synthesis

In more detail, compounds of formula I, Ia, Ib, Ic, Id or Ie and their intermediates may be prepared by schemes 1 to 2 and by the description of the specific examples.

A subgroup of compounds of formula I, Ia, Ib, Ic, Id or Ie, wherein X is halo, $X^1$ is C, $X^4$ is CH, $R^{2''}$ and $R^{3'}$ are H, and $R^7$ is H and $X^2$, $X^3$, $R^{1a}$, $R^{2'}$, $R^{3''}$, $R^4$, $R^5$ and $R^6$ are as defined previously, can be prepared as outlined in schemes 1-2 below.

Scheme 1

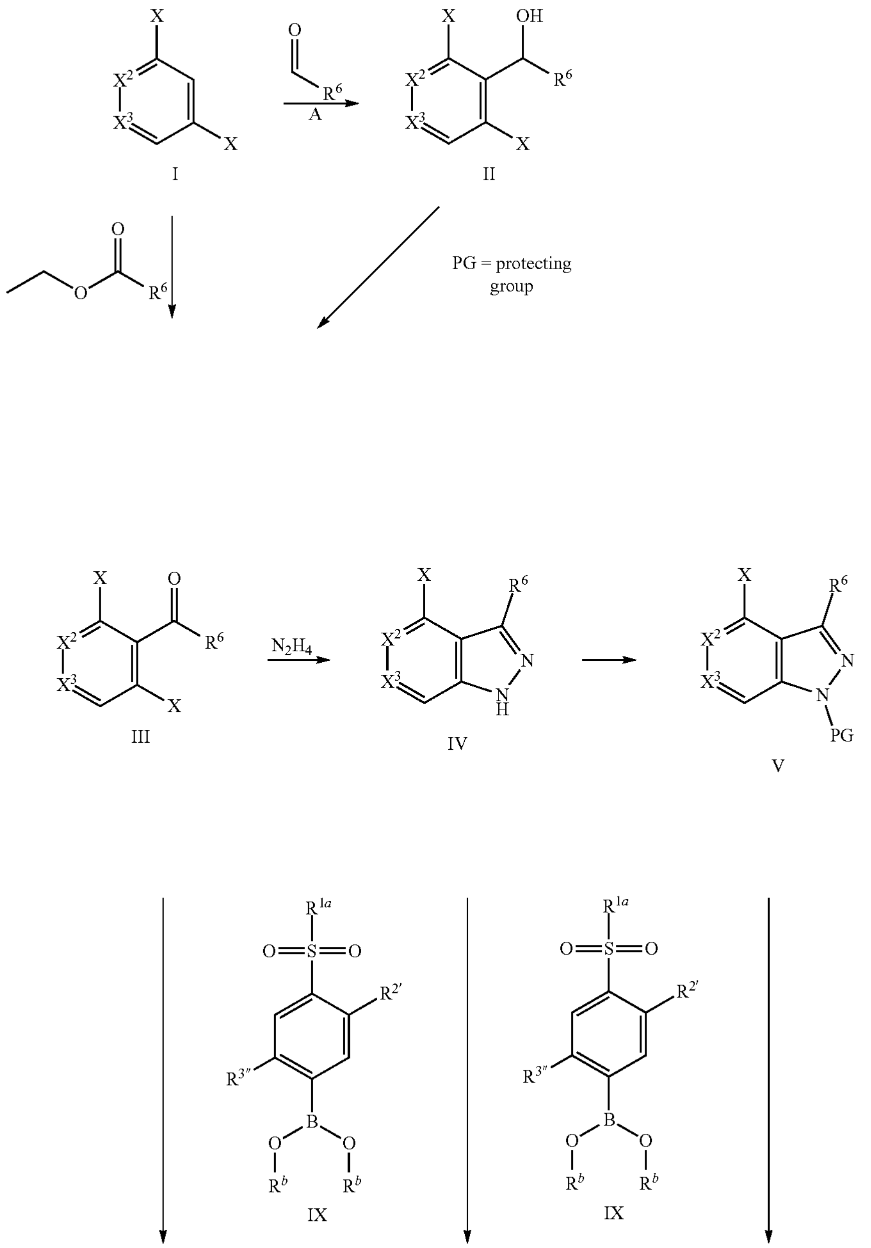

-continued

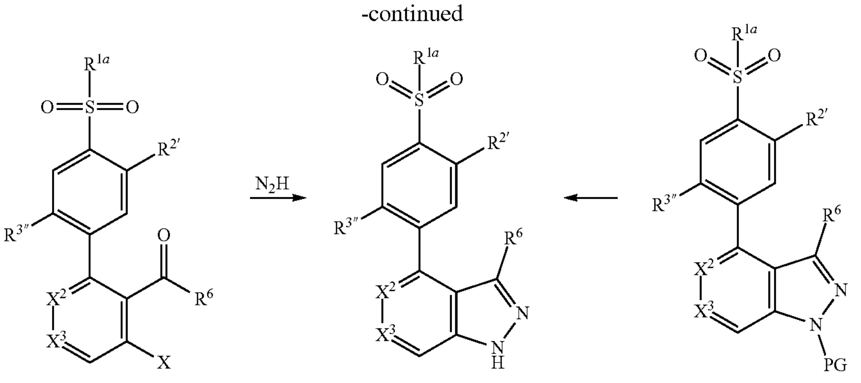

VII VIII VI wherein X is halo, $R^b$ is H or cylised to the pinacol ester and $X^2$, $X^3$ and $R^6$ are as defined previously.

Dihalide A is deprotonated with strong bases (e.g. n-BuLi, LDA, LiHDMS, TMPMgCl·LiCl) at reduced temperature (−78° C.) in THF and subsequently reacted with either aldehydes to afford alcohol II (as described in Synthesis, 1988, p. 803-805), or the appropriate esters to afford directly ketone III (as described in Journal of Organic Chemistry, 2007 p. 2501-2507). Alternatively alcohol II can be oxidised to ketone III using common oxidising agents (e.g. $MnO_2$, Dess-Martin periodinane, TEMPO/PhI$(OAc)_2$) in dichloroethane. Ketone III can be subsequently reacted with hydrazine (aqueous or monohydrate) at ambient or reduced temperatures in THF, dioxane or ethanol to afford pyrazoles IV (as described in Journal of Medicinal Chemistry, 2019 p. 531-551). Alternatively, ketone III can be coupled with bomic ester or acids X in a Suzuki-Miyura coupling in dioxane/water mixtures at elevated temperatures (e.g. 80° C.-120° C.) under palladium catalysis (e.g. Pd(dppf)) in the presence of carbonate bases (e.g. $K_2CO_3$, $Cs_2CO_3$) to afford ketone VII which is likewise cyclised to pyrazole VIII with hydrazine. Alternatively, pyrazole IV can be N-protected (e.g. SEM, THP or Trityl) under standard conditions, reacted similarly with boronic acid or esters X, and subsequently deprotected with strong acids (e.g. 4N HCl in dioxane or TFA) to afford pyrazole VIII.

Scheme 2

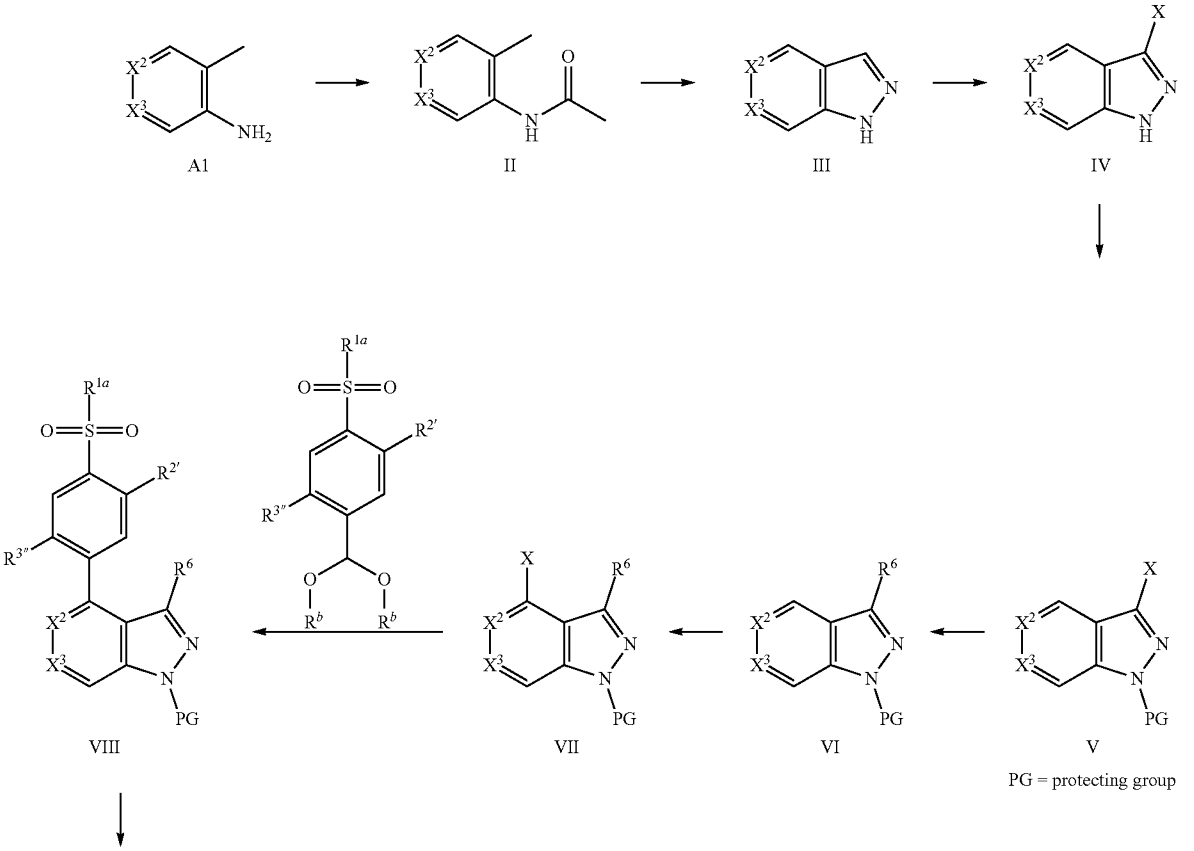

A1 II III IV

VIII VII VI V

PG = protecting group

-continued

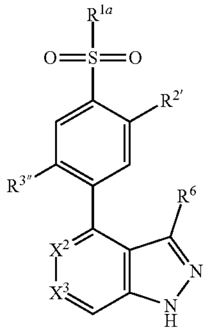

IX wherein X is halo, $R^b$ is H or cyclised to the pinacol ester.

Alternatively, the pyrazole core III can be constructed from anilines A1 as described in Journal of the American Chemical Society, 1954, 1176. Subsequent halogenation with halo-succinimides in polar solvents (e.g. DMF) affords halo-pyrazole IV. N-Protection of pyrazole IV (e.g. SEM, THP or Trityl) under standard conditions then allows for subsequent reaction of the halogen (e.g. Suzuki coupling) to afford pyrazole VI. Halogenation of VI can be effected using halo-succinimides as before to afford pyrazole VII which is then coupled with boronic esters or acids and deprotected as described in Scheme 1.

A subgroup of compounds of formula I or Ia, wherein X is halo, $X^1$ is N, $X^2$ is C═O, $X^3$ is CH, $R^{2"}$ and $R^{3'}$ are H, and $R^7$ is H and $X^4$, $R^{1a}$, $R^{2'}$, $R^{3"}$, $R^4$, $R^5$ and $R^6$ are as defined previously, can be prepared as outlined in scheme 3 below Scheme 3

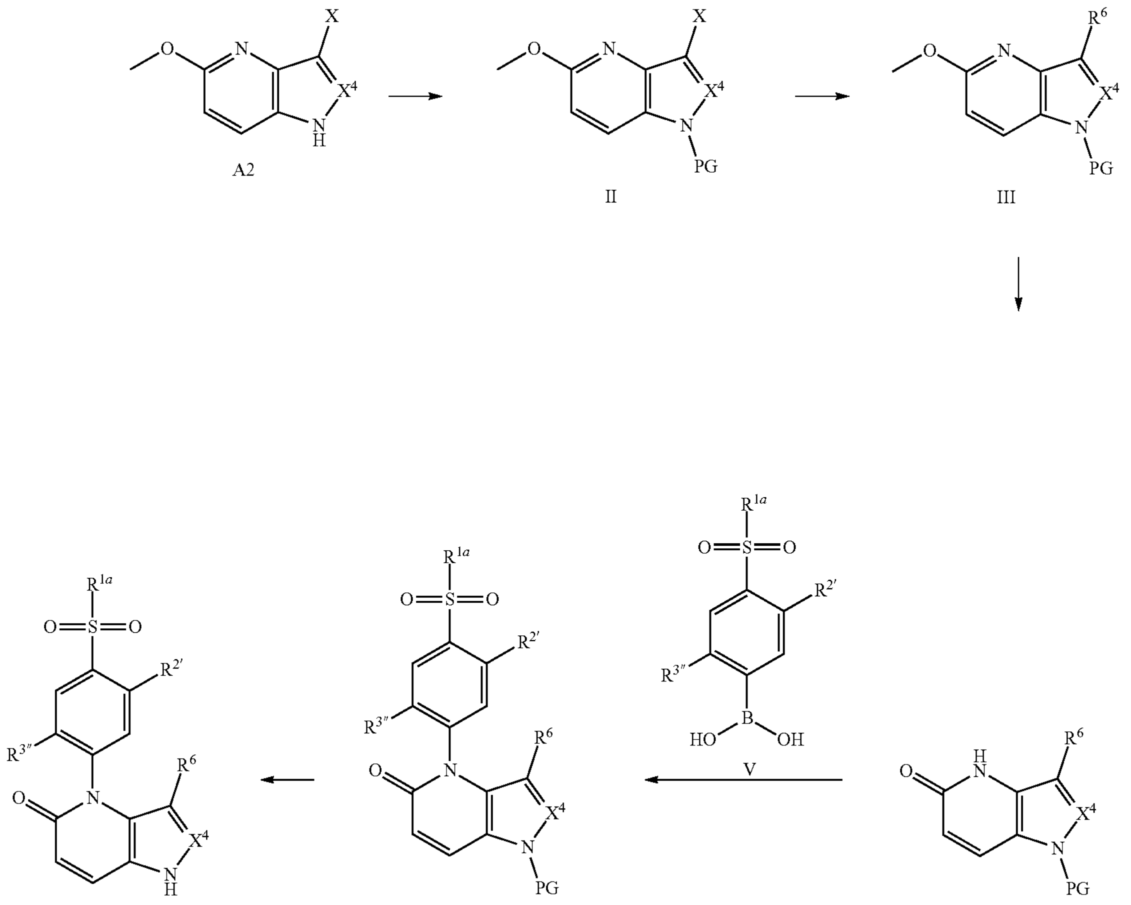

A2 II III IV V VI VII

PG = protecting group

The pyridone structures are prepared by first protecting the pyrazole or pyrrole nitrogens of A2 with suitable protecting groups e.g. (THP, SEM, Trityl) under standard conditions to afford II. Derivitisation of the halogen X (e.g. by Suzuki coupling) affords III which can converted to the pyridone by treatment with strongly acidic conditions (e.g. hydrochloric acid in dioxane) which in some cases causes the protecting group (PG) to be removed necessitating its reinstallment to afford IV. Chan-Lam coupling of boronic acids V under copper (II) acetate catalysis with a mixture of pyridine and triethylamine affords derivative VI which after standard removal of the protecting group (e.g. 4N HCl in dioxane, TFA) affords the final compounds VII.

General Procedures

Scheme 4

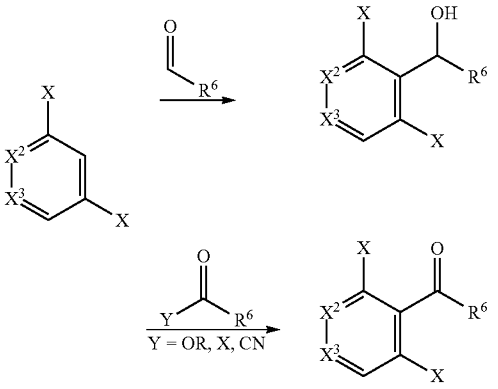

wherein X is halo and $X^2$, $X^3$ and $R^6$ are as defined previously.

General Procedure A: Aryl/Heteroaryl Functionalisation

To a −78° C. cooled solution of aryl or heteroaryldihalide (Eq: 1) in anhydrous THF (0.1 M) under Ar is added dropwise lithium diisopropylamine or nBuLi (Eq: 1.1-1.5). After stirring for the appropriate period of time (10 minutes to 1 h), the requisite electrophile (aldehyde, ester or chloroformate Eq: 1.5-2) is added and the reaction stirred for a further time period (10 minutes to 1 h) at the same temperature. After which time the reaction is quenched at −78° C. by addition of aqueous saturated ammonium chloride, the reaction brought to room temperature, diluted with ethyl acetate, the organic washed with water, brine, dried ($Na_2SO_4$) and concentrated. The crude products can be used directly in the next step or purified by flash column chromatography.

Scheme 5

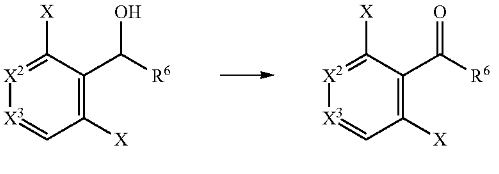

wherein X is halo and $X^2$, $X^3$, and $R^6$ are as defined previously.

General Procedure B1: Benzylic Alcohol Oxidation with Dess-Martin Periodinane

To a solution of benzylic alcohol (Eq: 1) in dichloromethane (0.1 M) is added Dess-Martin periodinane (Eq: 1.3) and the reaction stirred until reaction is complete (1 h). The reaction is diluted with dichloromethane, washed with saturated aqueous $NaHCO_3$, dried ($Na_2SO_4$) and concentrated. The residue is purified by flash column chromatography.

General Procedure B2: Benzylic Alcohol Oxidation with TEMPO

To a solution of benzylic alcohol (Eq: 1) in dichloromethane (0.1 M) is added TEMPO (Eq: 0.1) followed by (diacetoxyiodo)benzene (Eq: 1.1) and the reaction stirred until reaction is complete (3 h). The reaction is diluted with dichloromethane, washed with saturated aqueous $NaHCO_3$, dried ($Na_2SO_4$) and concentrated. The residue is purified by flash column chromatography.

Scheme 6

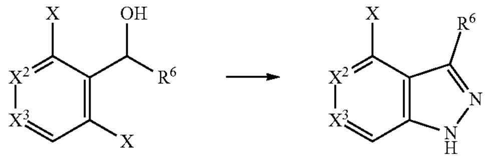

wherein X is halo and $X^2$, $X^3$ and $R^6$ are as defined previously.

General Procedure C: Pyrazole Cyclisation

To a solution of ketone or ester (Eq: 1) dissolved in THF, dioxane or ethanol (0.1 M) at ambient temperature or with cooling is added hydrazine (Eq:2-5) in the presence/absence of additional base ($Et_3N$ Eq. 1.5) and the reaction stirred until reaction is complete (1 h). The reaction is diluted with ethylacetate, washed with water, dried ($Na_2SO_4$) and concentrated. The residue is purified by flash column chromatography.

General Procedure D: Suzuki Coupling

To a solution of halide (Eq: 1) dissolved in dioxane:water (0.1 M, 4:1-10:1) is added potassium carbonate (Eq: 3-6), the required boronic acid or ester (Eq: 1-6) and the mixture degassed by sonicating while bubbling Ar through the mixture. 1,1'-Bis(diphenylphosphino)ferrocene-palladium (II)dichloride dichloromethane adduct is added (Eq: typically 0.05, and for difficult cases 0.5) is added and the mixture heated under Ar atmosphere to 100-120° C. until starting material is consumed (0.5 h-16 h). The reaction is diluted with ethyl acetate, washed with water, dried ($Na_2SO_4$) and concentrated. Alternatively the reaction mixture can be absorbed directly onto silica gel and concentrated. The residue is purified by flash column chromatography.

General Procedure E1: SEM Protection

To a solution of pyrazole (Eq: 1) dissolved in anhydrous DMF or THF (0.1 M) under Ar was added sodium hydride (60% dispersion in mineral oil, Eq: 2), the reaction stirred for 15 minutes before addition of SEM-Cl (Eq: 1.8) and the reaction stirred until complete consumption of starting material (1 h). The reaction was then diluted with ethyl acetate, extracted with water, dried ($Na_2SO_4$) and concentrated. The residue is purified by flash column chromatography.

General Procedure E2: SEM Protection

To a solution of pyrazole (Eq: 1) dissolved in dichloromethane (0.1 M) under Ar was added DIPEA (Eq: 1.2) and SEM-Cl (Eq: 1.2) and the reaction stirred until complete consumption of starting material (1 h). The reaction was then concentrated and the residue is purified by flash column chromatography.

Scheme 7

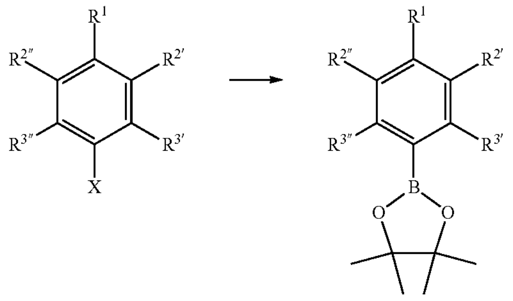

wherein X is halo and $R^1$ $R^{2'}$, $R^{2''}$, $R^{3'}$ and $R^{3''}$ are as defined previously.

General Procedure F: Conversion of Aryl Halides to Boronates

To a solution of aryl halide (Eq: 1) dissolved in dioxane (0.1 M) is added bis (pinacolato)diboron (Eq: 1.1), potassium acetate (Eq: 3) and the mixture degassed by sparging with Ar under sonication. [1,1'-bis(diphenylphosphino)ferrocene]dichloropalladium(II) dichloromethane adduct (Eq: 0.1) was added and the reaction heated (80° C.-100° C.) until complete conversion. The reaction is then diluted with ethyl acetate, washed with brine, dried ($Na_2SO_4$) and concentrated. The residue is purified by flash column chromatography.

General Procedure G: Oxidation of Sulfides

To an ice cold solution of sulfide (Eq: 1) in dichloromethane (0.1 M) is added m-chloroperbenzoic acid (Eq: 1-2.5, depending on whether sulfoxide or sulfone is required), the ice bath removed and the reaction allowed to come to room temperature. Stirring is continued until complete conversion after which time the reaction is diluted with dichloromethane, washed with 1N NaOH, dried ($Na_2SO_4$) and concentrated. The residue is purified by flash column chromatography.

General Procedure H: Trityl Deprotection

Trityl-protected compound (Eq: 1) is dissolved in trifluoroacetic acid (0.1 M) and triethylsilane added (Eq: 1.5) and the reaction stirred at ambient temperature until complete. The mixture is then cautiously poured onto saturated aqueous sodium hydrogen carbonate, extracted with dichloromethane, the combined organic extracts washed with brine, dried ($Na_2SO_4$) and concentrated. The residue is purified by flash column chromatography or reversed phase preparative HPLC.

General Procedure I1: THP Deprotection

THP-protected compound (Eq: 1) is dissolved in dichloromethane (0.1 M), trifluoroacetic acid (Eq: 10) is added and the reaction stirred at ambient temperature until complete. The mixture is then diluted with dichloromethane, washed with saturated aqueous sodium hydrogen carbonate, dried ($Na_2SO_4$) and concentrated. The residue is purified by flash column chromatography or reversed phase preparative HPLC.

General Procedure I2: THP Deprotection

THP-protected compound (Eq: 1) is dissolved in 4 N HCl in dioxane (0.1 M) and the reaction stirred at ambient temperature until complete. The mixture is then diluted with ethyl acetate, washed with saturated aqueous sodium hydrogen carbonate, dried ($Na_2SO_4$) and concentrated. The residue is purified by flash column chromatography or reversed phase preparative HPLC.

General Procedure J: SEM/MOM Deprotection

SEM/MOM-protected compound (Eq: 1) is dissolved in trifluoroacetic acid (0.1 M) and the reaction stirred at ambient temperature until complete. Evaporation of the trifluoroacetic acid followed by redissolution of reaction in dichloromethane or dioxane (0.1 M) and addition of ethylenediamine (Eq: 10) completed the deprotection. The mixture is then concentrated and purified by flash column chromatography or reversed phase preparative HPLC.

General procedure J2: SEM Deprotection

SEM-protected compound (Eq: 1) is dissolved in 1 M TBAF solution in THF (Eq: 10) and the reaction heated to 50° C. until complete. The reaction was diluted with ethyl acetate, washed with saturated aqueous sodium hydrogen carbonate, brine, dried ($Na_2SO_4$) and concentrated. The residue is purified by flash column chromatography or reversed phase preparative HPLC.

A particular embodiment of the invention relates to a process for the preparation of compounds of formula (I) and pharmaceutically acceptable salts thereof as defined in accordance with the present invention, comprising a deprotection a compound of formula (Ia) wherein $X^1$, $X^2$, $X^3$, $X^4$, $R^1$, $R^{2'}$, $R^{2''}$, $R^{3'}$, $R^{3''}$, $R^4$, $R^5$, $R^6$ and $R^7$ are as defined herein, in particular in the presence of organic acid (e.g. TFA) or inorganic acid (e.g. aqueous HCl), in as shown in scheme 8.

Scheme 8

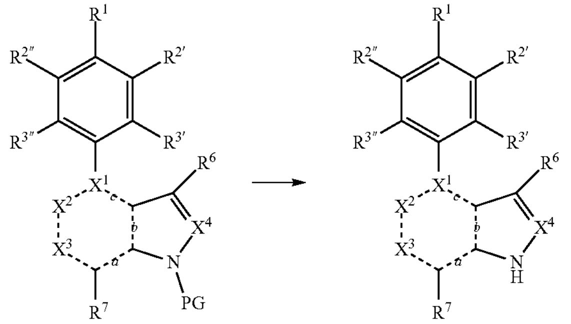

(Ia) (I)

The compounds were investigated in accordance with the test given hereinafter.

Determination of Mat2A Activity

Measurement of Mat2A inhibition is performed in 384 well format absorbance-based assay. Recombinant human Mat2a (12.5 nM) and serial diluted compounds in DMSO (range of concentrations from 10 μM to 508 pM) or controls (DMSO) are incubated for 15 minutes at room temperature (RT) in assay buffer containing 50 mM HEPES pH 7.5, 50 mM KCl, 50 mM $MgCl_2$, 0.01%Tween 20 and 10 mM DTT. The reaction is initiated by the addition of the combined substrates ATP and Methionine, each at a final concentration of 100 μM. Final assay condition are 12.5 nM Mat2A, 100 μM ATP and Methionine Substrates and 2% DMSO. After 120 minutes of incubation at RT, the reaction is stopped by the addition of Biomol Green. The absorbance signal is measured at λ=635 nm with a multiplate reader (BMG Pherastar reader or equivalent) after 30 min of equilibration at RT.

The table below shows the data for selected compounds:

| Example number | MAT2A_LEC IC50 (uM) (Num) |
|---|---|
| 1 | 0.048 |
| 2 | 0.37 |
| 3 | 0.15 |
| 4 | 0.24 |
| 5 | 0.17 |
| 6 | 0.17 |
| 7 | 0.046 |
| 8 | 0.37 |
| 9 | 0.24 |
| 10 | <0.013 |
| 11 | 0.28 |
| 12 | 0.22 |
| 13 | 0.11 |
| 14 | 0.099 |
| 15 | 0.27 |
| 16 | <0.013 |
| 17 | <0.013 |
| 18 | 0.095 |
| 19 | 0.042 |
| 20 | 0.015 |
| 21 | 0.056 |
| 22 | 0.15 |
| 23 | 0.083 |
| 24 | <0.013 |
| 25 | 0.013 |
| 26 | <0.013 |
| 27 | <0.013 |
| 28 | 0.51 |
| 29 | 0.29 |
| 30 | 0.057 |
| 31 | 0.033 |
| 32 | <0.013 |
| 33 | 0.029 |
| 34 | <0.013 |
| 35 | 0.12 |
| 36 | 0.051 |
| 37 | 0.10 |
| 38 | 0.021 |
| 39 | <0.013 |
| 40 | 0.029 |
| 41 | 0.14 |
| 42 | <0.013 |
| 43 | <0.013 |
| 44 | 0.017 |
| 45 | 0.02 |
| 46 | <0.013 |
| 47 | 0.017 |
| 48 | 0.13 |
| 49 | <0.013 |
| 50 | <0.013 |
| 51 | <0.013 |
| 52 | <0.013 |
| 53 | 0.062 |
| 54 | 0.015 |
| 55 | <0.013 |
| 56 | 0.19 |
| 57 | <0.013 |
| 58 | 0.24 |
| 59 | 0.26 |
| 60 | 0.29 |
| 61 | 0.25 |
| 62 | <0.013 |
| 63 | <0.013 |
| 64 | 0.2 |
| 65 | 0.52 |
| 66 | 0.13 |
| 67 | 0.025 |
| 68 | <0.013 |
| 69 | <0.013 |
| 70 | 0.061 |
| 71 | <0.013 |
| 72 | <0.013 |
| 73 | <0.013 |
| 74 | 0.11 |
| 75 | 0.013 |
| 76 | 0.26 |
| 77 | 0.013 |
| 78 | <0.013 |
| 79 | <0.013 |
| 80 | 0.031 |
| 81 | 0.079 |
| 82 | <0.013 |
| 83 | 0.5 |
| 84 | <0.013 |
| 85 | 0.02 |
| 86 | <0.013 |
| 87 | <0.013 |
| 88 | <0.013 |
| 89 | 0.035 |
| 90 | <0.013 |
| 91 | <0.013 |
| 92 | 0.029 |
| 93 | <0.013 |
| 94 | 0.05 |
| 95 | <0.013 |
| 96 | <0.013 |
| 97 | <0.013 |
| 98 | <0.013 |
| 99 | 0.07 |
| 100 | 0.03 |
| 101 | 0.14 |
| 102 | 0.06 |
| 103 | 0.04 |
| 104 | 0.04 |
| 105 | <0.013 |
| 106 | <0.013 |
| 107 | 0.013 |
| 108 | 0.015 |
| 109 | <0.013 |
| 110 | <0.013 |
| 111 | <0.013 |
| 112 | 0.09 |
| 113 | 0.31 |
| 114 | 0.03 |
| 115 | 0.03 |
| 116 | <0.013 |
| 117 | <0.013 |
| 118 | <0.013 |
| 119 | 0.02 |
| 120 | <0.013 |

Experimental Part

The following examples are provided for illustration of the invention. They should not be considered as limiting the scope of the invention, but merely as being representative thereof.

General

Analytical Methods

HPLC (method LCMS_fastgradient)

Column: Agilent Zorbax Eclipse Plus C18, Rapid Resolution HT, 2.1×30 mm, 1.8 μm, Part.no. 959731-902

Solvent A: Water 0.01% Formic Acid; Solvent B: acetonitrile (MeCN) Gradients:

| Time [min] | Flow Rate [ml/min] | % A | % B |
|---|---|---|---|
| Initial | 0.8 | 97 | 3 |
| 0.2 | 1.0 | 97 | 3 |
| 1.7 | 1.0 | 3 | 97 |
| 2.0 | 1.0 | 3 | 97 |
| 2.1 | 1.0 | 97 | 3 |

Abbreviations

The Following Abbreviations were Used in the Experimental Part:

Ar=argon; nBuLi=n-butyl lithium; DCM=dichloromethane; DIPEA=diisopropylethylamine; DMSO=dimethylsufoxide; DMF=dimethylformamide; EtOH=ethanol; Ex. No.=Example number; HCl=hydrochloric acid; HPLC=high performance liquid chromatography; LDA=lithium diisopropylamide;

LiHMDS=lithium bis (trimethylsilyl)amide; mCPBA=metachloroperbenzoic acid; Mol=Molecular; MOM=methoxymethyl; NMP=N-methyl-2-pyrolidone; Prep.=Preparation; SEM=[2-(trimethylsilyl)ethoxy)methyl] acetal; TBTU=2-(1H-Benzotriazole-1-yl)-1,1,3,3-tetramethylaminium tetrafluoroborate; THF=tetrahydrofuran; TEMPO=2,2,6,6-tetramethylpiperidinyloxyl; TBAF=tetra-n-butyl ammonium fluoride; TLC=thin layer chromatography;

Starting Materials

Basic chemicals and solvents were purchased and used as is without further purification. Some intermediates are commercially available, or they can be synthesized using methods known in the art.

Intermediates

Intermediate 1: 4-chloro-3-cyclopropyl-1H-pyrazolo[4,3-c]pyridine

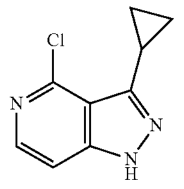 [SMILES: Clc1nccc2[nH]nc(C3CC3)c12]

The title compound ([M+H, Cl]$^+$194.1) was prepared as described in WO2010/106333 A1.

Intermediate 2: 4-bromo-3-cyclopropyl-5-methoxy-1-((2-(trimethylsilyl)ethoxy)methyl)-1H-pyrazolo[3,4-c]pyridine

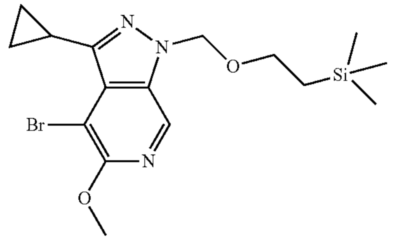 [SMILES: COc1ncc2c(c(C3CC3)nn2COCC[Si](C)(C)C)c1Br]

Step 1: 3-iodo-5-methoxy-1-((2-(trimethylsilyl)ethoxy)methyl)-1H-pyrazolo[3,4-c]pyridine 3-iodo-5-methoxy-1H-pyrazolo[3,4-c]pyridine (76006-07-0: WO2015/25025 A1) was converted to the title compound ([M+H]$^+$406.2) using General Procedure E1 (accompanied by 20% of the regioisomer).

Step 2: 3-cyclopropyl-5-methoxy-1-((2-(trimethylsilyl)ethoxy)methyl)-1H-pyrazolo[3,4-c]pyridine 3-iodo-5-methoxy-1-((2-(trimethylsilyl)ethoxy)methyl)-1H-pyrazolo[3,4-c]pyridine (step 1) is reacted with cyclopropyl boronic acid (6 eq), potassium carbonate (3 eq) under, 1'bis(diphenylphosphino)ferrocene-palladium(II)dichloride dichloromethane adduct (0.1 eq) catalysis for 4 h in accordance with the General procedure D to afford the title compound ([M+H]$^+$320.3).

Step 3: 4-bromo-3-cyclopropyl-5-methoxy-1-((2-(trimethylsilyl)ethoxy)methyl)-1H-pyrazolo[3,4-c]pyridine To a solution of 3-cyclopropyl-5-methoxy-1-((2-(trimethylsilyl)ethoxy)methyl)-1H-pyrazolo[3,4-c]pyridine (Step 2, 20 mg, 63 μmol) in DCM (1 ml) was added N-bromosuccinimide (12 mg, 70 μmol) and the reaction stirred for 4 h. The reaction was then absorbed on silica gel and concentrated. Flash column chromatography (Ethyl acetate: n-Heptane 4:1) afforded the title compound (18 mg, 65%) as a brown oil ([M+H, Br]$^+$400.2)

Intermediate 3: 4-chloro-3-(trifluoromethyl)-1-((2-(trimethylsilyl)ethoxy)methyl)-1H-pyrazolo[4,3-c]pyridine

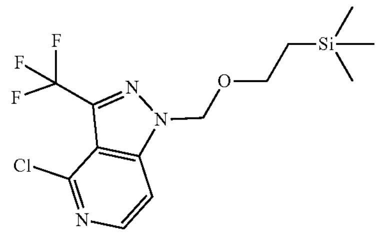 [SMILES: C[Si](C)(C)CCOCn1nc(C(F)(F)F)c2c(Cl)nccc21]

Step 1: 4-chloro-3-(trifluoromethyl)-1H-pyrazolo[4,3-c]pyridine 2,4-dichloropyridine was deprotonated with nBuLi (1.3 eq) for 30 minutes and reacted with ethyl 2,2,2-trifluoroacetate (2 eq) in accordance with General procedure A to afford 1-(2,4-dichloropyridin-3-yl)-2,2,2-trifluoroethan-1-one which was reacted directly with hydrazine hydrate (5 eq) in THF initially at −40° C. and raising to ambient temperature for 16 h in accordance with General procedure C to afford the title compound ([M+H, Cl]$^+$220.0).

Step 2: 4-chloro-3-(trifluoromethyl)-1-((2-(trimethylsilyl)ethoxy)methyl)-1H-pyrazolo[4,3-c]pyridine The title compound ([M+H, Cl]$^+$352.2). was prepared from 4-chloro-3-(trifluoromethyl)-1H-pyrazolo[4,3-c]pyridine (Step 1) using General procedure E2.

Intermediate 4: 4-chloro-3-cyclopropyl-1-((2-(trimethylsilyl)ethoxy)methyl)-1H-pyrrolo[3,2-c]pyridine

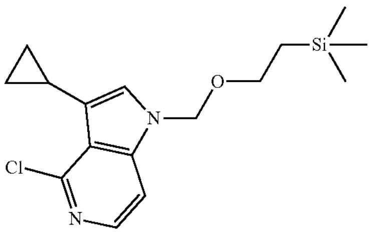 [SMILES: C[Si](C)(C)CCOCn1cc(C2CC2)c2c(Cl)nccc21]

Step 1: 3-bromo-4-chloro-1-((2-(trimethylsilyl)ethoxy)methyl)-1H-pyrrolo[3,2-c]pyridine 3-Bromo-4-chloro-1H-pyrrolo[3,2-c]pyridine was was converted to the title compound ([M+H, Br, Cl]$^+$361.1) using General Procedure E1.

Step 2: 4-chloro-3-cyclopropyl-1-((2-(trimethylsilypethoxy)methyl)-1H-pyrrolo[3,2-c]pyridine 3-Bromo-4-chloro-1-((2-(trimethylsilypethoxy)methyl)-1H-pyrrolo[3,2-c]pyridine(step 1) is reacted with cyclopropyl boronic acid (6 eq), potassium carbonate (6 eq), under l'bis(diphenylphosphino)ferrocene-palladium(II)dichloride dichloromethane adduct (0.15 eq) catalysis for 1 h at 100° C. in accordance with the General procedure D to afford the title compound ([M+H, Cl]$^+$323.2).

Intermediate 5: 4-bromo-3-cyclopropyl-1H-pyrazolo[3,4-c]pyridine-5-carbonitrile

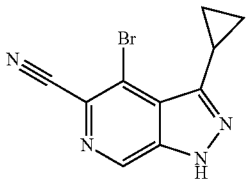 [SMILES: N#Cc1ncc2[nH]nc(C3CC3)c2c1Br]

Step 1: 3-bromo-4-(cyclopropanecarbonyl)-5-fluoropicolinonitrile 3-bromo-5-fluoropicolinonitrile is treated with with LDA (2 eq) for 10 minutes before addition of cyclopropanecarbaldehyde in accordance with General procedure A to afford crude 3-bromo-4-(cyclopropyl(hydroxy)methyl)-5-fluoropicolinonitrile which was then oxidised to the title compound ([M−H, Br]$^-$265.3) using General procedure E2.

Step 3: 4-bromo-3-cyclopropyl-1H-pyrazolo[3,4-c]pyridine-5-carbonitrile 3-bromo-4-(cyclopropanecarbonyl)-5-fluoropicolinonitrile (step 2) is reacted with hydrazine hydrate (2 eq) in EtOH initially at 0° C. and raising to ambient temperature for 1 h in accordance with General procedure C to afford the title compound ([M+H, Br]$^+$263.1).

Intermediate 6: 4-chloro-3-(1,1-difluoroethyl)-1H-pyrazolo[4,3-c]pyridine

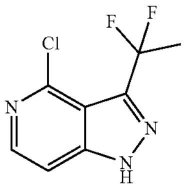

Step 1: 1-(2-chloro-4-fluoropyridin-3-yl)-2,2-difluoropropan-1-one

2-Chloro-4-fluoropyridine was deprotonated with nBuLi (1.3 eq) for 1 h and reacted with ethyl 2,2-difluoropropanoate (1.3 eq) in accordance with General procedure A to afford the title compound ([M+H, Cl]$^+$224.1.

Step 2: 4-chloro-3-(1,1-difluoroethyl)-1H-pyrazolo[4,3-c]pyridine 1-(2-chloro-4-fluoropyridin-3-yl)-2,2-difluoropropan-1-one (Step 1) was reacted with hydrazine hydrate (5 eq) in THF at ambient temperature for 15 minutes in accordance with General procedure C to afford the title compound ([M+H, Cl]$^+$218.1).

Intermediate 7: 2-[[4-chloro-3-(difluoromethyl)pyrazolo[4,3-c]pyridin-1-yl]methoxy]ethyl-trimethylsilane

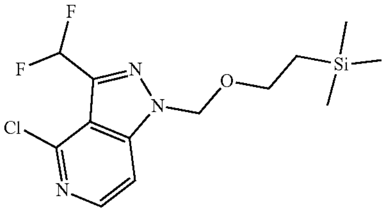 [SMILES: C[Si](C)(C)CCOCn1nc(C(F)F)c2c(Cl)nccc21]

Step 1: 1-(2-chloro-4-fluoropyridin-3-yl)-2,2-difluoroethan-1-one 2-chloro-4-fluoropyridine was deprotonated with LDA (2 eq) for 3h and reacted with ethyl 2,2-difluoroacetate (1.3 eq) for 3h in accordance with General procedure A to afford the title compound ([M−H, Cl]$^-$206.1.

Step 2: 4-chloro-3-(difluoromethyl)-1H-pyrazolo[4,3-c]pyridine 1-(2-chloro-4-fluoropyridin-3-yl)-2,2-difluoroethan-1-one (Step 1) was reacted with hydrazine hydrate (5 eq) in THF at −40° C. for 1 h in accordance with General procedure C to afford the title compound ([M+H, Cl]$^+$204.0).

Step 3: 4-chloro-3-(1,1-difluoroethyl)-1H-pyrazolo[4,3-c]pyridine 4-chloro-3-(difluoromethyl)-1H-pyrazolo[4,3-c]pyridine (step 2) was was converted to the title compound ([M+H, Cl]$^+$324.1) using General Procedure E2 accompanied by its regioisomer.

Intermediate 8: 4-chloro-3-(difluoromethoxy)-1-trityl-pyrazolo[4,3-c]pyridine

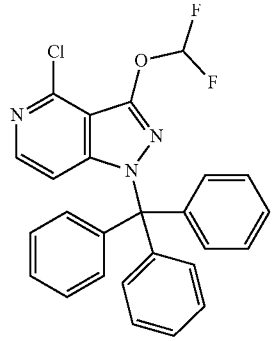 [SMILES: FC(F)Oc1nn(C(c2ccccc2)(c2ccccc2)c2ccccc2)c2ccnc(Cl)c12]

Step 1: 4-chloro-1H-pyrazolo[4,3-c]pyridin-3-ol

To a solution of methyl 2-chloro-4-fluoro-pyridine-3-carboxylate (950 mg, 5.0 mmol) in dioxane (9.5 ml) was added hydrazine monohydrate (325 mg, 6.5 mmol) and triethylamine (1.4 ml, 10.0 mmol) and the mixture heated to 70° C. for 16 h. The reaction was diluted with 2-methoxy methylpropane (5 ml) and the precipitate isolated by filtration to afford the title compound (900 mg, 95%) as a yellow solid. 1H NMR (400 MHz, DMSO-d6) δ=11.36-9.59 (m, 2H), 8.01-7.85 (m, 1H), 7.38-7.03 (m, 1H).

Step 2: 4-Chloro-1-trityl-pyrazolo[4,3-c]pyridin-3-ol

To a solution of 4-chloro-1H-pyrazolo[4,3-c]pyridin-3-ol (step 1) (700 mg, 3.7 mmol), triphenylmethyl chloride (1035 mg, 3.7 mmol) in DMF (100 ml) under Ar was added triethylamine (1.55 mL, 11.5 mmol) and the reaction stirred at 30° C. for 4 h after which time it was diluted with water and extracted repeatedly with ethyl acetate. The combined organic layers were dried ($Na_2SO_4$) and concentrated. Flash column chromatography (Ethyl acetate: n-Heptane 1:6-3:1) afforded the title compound (620 mg, 41%) as a yellow solid 1H NMR (400 MHz, CHLOROFORM-d) δ=7.77 (d, J=6.1 Hz, 1H), 7.33-7.27 (s, 15H), 6.13 (d, J=6.1 Hz, 1H).

Step 3: 4-Chloro-3-(difluoromethoxy)-1-trityl-pyrazolo[4,3-c]pyridine

A suspension of 4-chloro-1-trityl-pyrazolo[4,3-c]pyridin-3-ol (Step 2) (100 mg, 0.2 mmol), cesium carbonate (158 mg, 0.5 mmol) and 2-chloro-2,2-difluoro-acetyl)oxysodium (74 mg, 0.45 mmol) in acetonitrile was heated to 80° C. for 2 h. The reaction mixture was filtered and concentrated in vacuo to afford the title compound (100 mg, 89%) as a yellow solid, used without further purification. $^1$H NMR (400 MHz, CHLOROFORM-d) δ=7.79-7.74 (d, 1H), 7.33-7.28 (m, 9H), 7.22-6.85 (m, 6H), 7.28-6.85 (t, 1H), 5.99-5.94 (m, 1H)

Intermediate 9: 4-chloro-3-(oxetan-3-yl)-1-tetrahydropyran-2-yl-pyrazolo[4,3-c]pyridine

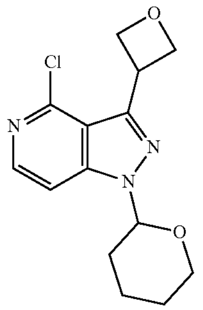 [SMILES: Clc1nccc2c1c(C1COC1)nn2C1CCCCO1]

Step 1: (2,4-dichloro-3-pyridyl)-(oxetan-3-yl)methanol 2,4-dichloropyridine was deprotonated with LDA (1.2 eq) for 0.5 h and reacted with oxetane carbaldehyde (1.5 eq) for 1 h in accordance with General procedure A to afford the title compound ([M+H, Cl]$^+$233.8.

Step 2: (2,4-dichloro-3-pyridyl)-(oxetan-3-yl)methanone (2,4-dichloro-3-pyridyl)-(oxetan-3-yl)methanol (step 1) was oxidised using General procedure B1 to afford the title compound. ([M+H, Cl]$^+$231.7.

Step 3: 4-chloro-3-(oxetan-3-yl)-1H-pyrazolo[4,3-c]pyridine (2,4-dichloro-3-pyridyl)-(oxetan-3-yl)methanone (step 2) was reacted with hydrazine monohydrate (1.5 eq) and triethylamine (1.5 eq) in dioxane at 60° C. for 1 h in accordance with General procedure C to afford the title compound ([M+H, Cl]$^+$209.8).

Step 4: 4-chloro-3-(oxetan-3-yl)-1-tetrahydropyran-2-yl-pyrazolo[4,3-c]pyridine

A solution of 4-chloro-3-(oxetan-3-yl)-1H-pyrazolo[4,3-c]pyridine (step 3) (200.0 mg, 0.95 mmol), p-toluene sulfonic acid monohydrate (18.2 mg, 0.1 mmol) and 3,4-dihydro-2H-pyran (0.44 ml, 4.77 mmol) in THF (20 ml) was heated to 60° C. for 16 h. The reaction was neutralised by addition of triethylamine (0.2 ml) and the concentrated to dryness. Purification by preparative TLC (nHeptane: Ethyl acetate 1:1) afforded the title compound (150 mg, 53%) as a light yellow solid. $^1$H NMR (400 MHz, CHLOROFORM-d) δ=8.08 (d, J=6.0 Hz, 1H), 7.35 (d, J=5.9 Hz, 1H), 5.63 (dd, J=2.7, 9.0 Hz, 1H), 5.16-5.10 (m, 1H), 5.09-4.98 (m, 3H), 4.89-4.77 (m, 1H), 3.94 (m, 1H), 3.72-3.63 (m, 1H), 2.54-2.39 (m, 1H), 2.17-1.98 (m, 2H), 1.83-1.63 (m, 3H).

Intermediate 10: 4,6-dichloro-3-cyclopropyl-1H-pyrazolo[4,3-c]pyridine

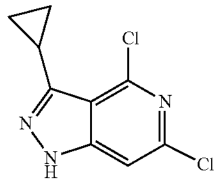 [SMILES: Clc1cc2[nH]nc(C3CC3)c2c(Cl)n1]

Step 1: Cyclopropyl(2,4,6-trichloropyridin-3-yl)methanone 2,4,6-trichloropyridine (300 mg, 1.64 mmol, Eq: 1) was deprotonated with LDA (0.9 eq) for 1 h and reacted with cyclopropanecarbaldehyde (1.5 eq) for 1.5 h in accordance with General procedure A to afford crude cyclopropyl(2,4,6-trichloropyridin-3-yl)methanol which was directly oxidised using General procedure B1 to afford the title compound. ([M+H, 2Cl]$^+$250.1.

Step 2: 4,6-dichloro-3-cyclopropyl-1H-pyrazolo[4,3-c]pyridine

Cyclopropyl(2,4,6-trichloropyridin-3-yl)methanone (step 2) was reacted with hydrazine monohydrate (5 eq) in THF at 0° C. for 2 h and then 2 h at ambient temperature in accordance with General procedure C to afford the title compound ([M+H, 2Cl]$^+$228.1).

Intermediate 11: 4-bromo-5-methoxy-3-(trifluoromethyl)-2-((2-(trimethylsilyl)ethoxy)methyl)-2H-pyrazolo[3,4-c]pyridine

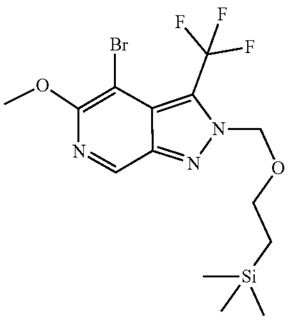 [SMILES: COc1ncc2nn(COCC[Si](C)(C)C)c(C(F)(F)F)c2c1Br]

Step 1: 3-iodo-5-methoxy-2-((2-(trimethylsilyl)ethoxy)methyl)-2H-pyrazolo[3,4-c]pyridine 3-Iodo-5-methoxy-1H-pyrazolo[3,4-c]pyridine (WO2015/25025 A1) was was converted to the title compound ([M+H]$^+$406.2) using General Procedure E1 accompanied by its regioisomer.

Step 2: 5-methoxy-3-(trifluoromethyl)-2-((2-(trimethylsilyl)ethoxy)methyl)-2H-pyrazolo[3,4-c]pyridine To a suspension of 3-iodo-5-methoxy-2-((2-(trimethylsilypethoxy)methyl)-2H-pyrazolo[3,4-c]pyridine (step 1) (70 mg, 0.17 mmol), copper (I) iodide (164 mg, 0.86 mmol) and potassium fluoride (50 mg, 0.17 mmol) in NMP (1 ml) was added (trifluromethyl)trimethylsilane (0.13 mL, 0.86 mmol) and the mixture heated under Ar to 50° C. for 1 h. The reaction was then diluted with water, filtered through Celite®, extracted with ethyl acetate and the organic dried ($Na_2SO_4$) and concentrated. Flash column chromatography (Ethyl acetate: n-Heptane 1:4) afforded the title compound (32 mg, 53%) as a yellow viscous oil ([M+H]$^+$348.3)

Step 3: 4-bromo-5-methoxy-3-(trifluoromethyl)-2-((2-(trimethylsilyl)ethoxy)methyl)-2H-pyrazolo[3,4-c]pyridine 5-Methoxy-3-(trifluoromethyl)-2-((2-(trimethylsilyl)ethoxy)methyl)-2H-pyrazolo[3,4-c]pyridine (step 2) (32 mg, 0.9 mmol) was dissolved in 1,2-dichroethane (0.5 ml), N-bromosuccinamide (18 mg, 1.0 mmol) added and the mixture heated to 70° C. for 2h. The reaction was concentrated and purified by flash column chromatography (Ethyl acetate: n-Heptane 1:4) to afford the title compound (20 mg, 51%) as a yellow solid ([M+H, Br]$^+$428.3)

Intermediate 12: 4-chloro-3-(trifluoromethyl)-1-((2-(trimethylsilyl)ethoxy)methyl)-1H-pyrrolo[3,2-c]pyridine

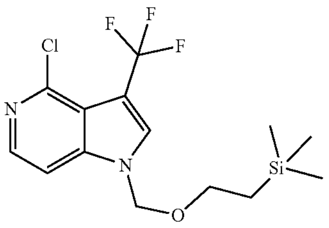 [SMILES: C[Si](C)(C)CCOCn1cc(C(F)(F)F)c2c(Cl)nccc21]

Step 1: 4-chloro-3-(trifluoromethyl)-1H-pyrrolo[3,2-c]pyridine 4-chloro-3-iodo-1H-pyrrolo[3,2-c]pyridine (CAS: 1190313-39-3) (100 mg, 0.4 mmol) and diphenyl(trifluormethyl)sulfoniumtrifulormethanesufonate (436 mg, 1.1 mmol) were dissolved in DMF (2 ml) and copper (138 mg, 2.2 mmol) was added and the mixture stirred in a sealed tube under Ar for 6 h at 60° C. The reaction was diluted with ethyl acetate, the organic washed with water, brine, dried ($Na_2SO_4$) and concentrated. Flash column chromatography (Ethyl acetate: n-Heptane 0:1-6:1) afforded the title compound (18 mg, 22%) as a white solid ([M+H, Cl]$^+$221.0)

Step 2: 4-chloro-3-(trifluoromethyl)-1-((2-(trimethylsilyl)ethoxy)methyl)-1H-pyrrolo[3,2-c]pyridine 4-chloro-3-(trifluoromethyl)-1H-pyrrolo[3,2-c]pyridine was converted to the title compound ([M+H,Cl]$^+$351.2) using General Procedure E1.

Intermediate 13: 4-bromo-3-cyclopropyl-5-(methoxymethyl)-1-(tetrahydro-2H-pyran-2-yl)-1H-pyrazolo[3,4-c]pyridine

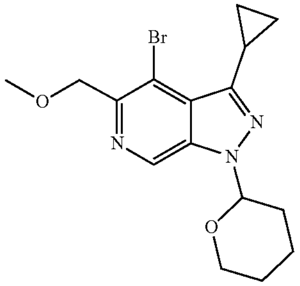 [SMILES: COCc1ncc2c(c(C3CC3)nn2C2CCCCO2)c1Br]

Step 1: 4-Bromo-3-cyclopropyl-1-(tetrahydro-2H-pyran-2-yl)-1H-pyrazolo[3,4-c]pyridine-5-carboxylic acid 4-Bromo-3-cyclopropyl-1H-pyrazolo[3,4-c]pyridine-5-carbonitrile (Intermediate 5) (500 mg, 1.9 mmol) was suspended in water (15 ml) and sodium hydroxide (380 mg, 9.5 mmol) was added and the reaction heated to 100° C. for 15 h. The reaction was then acidified with conc. HCl and the resulting solid isolated by filtration affording the title compound (435 mg, 77%) as a light brown solid ([M+H, Br]$^+$282.1)

Step 2: Methyl 4-bromo-3-cyclopropyl-1-(tetrahydro-2H-pyran-2-yl)-1H-pyrazolo[3,4-c]pyridine-5-carboxylate 4-Bromo-3-cyclopropyl-1H-pyrazolo[3,4-c]pyridine-5-carboxylic acid (step 1) (300 mg, 1.1 mmol) was suspended in dichloromethane (2 ml) and 3,4-dihydro-2H-pyran (0.5 ml, 5.3 mol) and p-toluenesulfonic acid monohydrate (20 mg, 0.1 mmol) was added. The reaction was stirred for 4 h after which time it was diluted with ethyl acetate, washed with 1 N HCl, dried ($Na_2SO_4$) and concentrated. The crude 4-bromo-3-cyclopropyl-1-(tetrahydro-2H-pyran-2-yl)-1H-pyrazolo[3,4-c]pyridine-5-carboxylic acid (389 mg, 1.1 mmol) was dissolved in a mixture of DCM/MeOH (6 ml/3 ml) and trimethylsilyldiazomethane (5.3 ml, 2M in hexanes, 10.6 mmol) was added. The reaction was stirred for 15 h after which time it was concentrated to dryness. Flash column chromatography (Ethyl acetate: n-Heptane 4:6) afforded the title compound (320 mg, 90%) as a colourless gum ([M+H, Br]$^+$380.2)

Step 3: (4-bromo-3-cyclopropyl-1-(tetrahydro-2H-pyran-2-yl)-1H-pyrazolo[3,4-c]pyridin-5-yl)methanol Methyl 4-bromo-3-cyclopropyl-1-(tetrahydro-2H-pyran-2-yl)-1H-pyrazolo[3,4-c]pyridine carboxylate (Step 2) (320 mg, 0.8 mmol) was dissolved in THF (10 ml) and cooled to −78° C. before addition of di-isobutylaluminium hydride (3.37 ml, 1 M in THF, 3.4 mmol) and the reaction stirred for 90 minutes before a second portion of di-isobutylaluminium hydride (3.37 ml, 1 M in THF, 3.4 mmol) was added and the mixture stirred for a further 3 h. The reaction was quenched by addition of a few drops of water, acidified by addition of 1N HCl, extracted with ethyl acetate, dried ($Na_2SO_4$) and concentrated. Flash column chromatography (Ethyl acetate: n-Heptane 3:7) afforded the title compound (60 mg, 19%) as a light grey solid ([M+H, Br]$^+$354.2)

Step 4: 4-bromo-3-cyclopropyl-5-(methoxymethyl)-1-(tetrahydro-2H-pyran-2-yl)-1H-pyrazolo[3,4-c]pyridine (4-bromo-3-cyclopropyl-1-(tetrahydro-2H-pyran-2-yl)-1H-pyrazolo[3,4-c]pyridin-5-yl)methanol (step 3) (60 mg, 0.17 mmol) was dissolved in dichloromethane (2 ml), triethylamine (49 µl, 0.3 mmol) was added followed by methanesulfonyl chloride (16 µL, 0.2 mmol) and the reaction stirred for 30 min. A second portion of triethylamine (49 µl, 0.3 mmol) was added followed by methanesulfonyl chloride (16 µL, 0.2 mmol) was added and the reaction stirred for a further 3 h. The reaction was concentrated to dryness, redissolved in DCM (1 ml) and sodium methoxide (2.0 g, 9.3 mmol) was added. After 1 h, the reaction was diluted with saturated aqueous sodium hydrogen carbonate, extracted with DCM and the combined organic dried ($Na_2SO_4$) and concentrated. Flash column chromatography (Ethyl acetate: n-Heptane 1:1) afforded the title compound (40 mg, 64%) as a colourless solid ([M+H, Br]$^+$368.2)

Intermediate 14: 4-bromo-5-(methylsulfonyl)-3-(trifluoromethyl)-1-((2-(trimethylsilyl)ethoxy)methyl)-1H-indazole

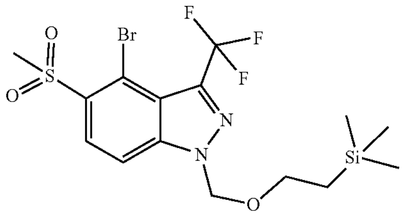 [SMILES: C[Si](C)(C)CCOCn1nc(C(F)(F)F)c2c(Br)c(S(C)(=O)=O)ccc21]

Step 1: 1-(2-bromo-6-fluoro-3-(methylsulfonyl)phenyl)-2,2,2-trifluoroethan-1-one (2-Bromo-4-fluorophenyl)(methyl)sulfane was deprotonated with LDA (1.3 eq) for 30 minutes and reacted with ethyl 2,2,2-trifluoroacetate (2 eq) in accordance with General procedure A to afford crude 1-(2-bromo-6-fluoro-3-(methylthio)phenyl)-2,2,2-trifluoroethan-1-one used directly.

Crude 1-(2-bromo-6-fluoro-3-(methylthio)phenyl)-2,2,2-trifluoroethan-1-one (1.8 g, 5.1 mmol) was dissolved in dichloromethane (25 ml) and cooled to 0° C. mCPBA (3.5 g, 11.2 mmol) was added the mixture brought to ambient temperature and stirred for 3 h. The reaction was diluted with dichloromethane, washed repeatedly with 1 N NaOH, dried ($Na_2SO_4$) and concentrated. Flash column chromatography (Ethyl acetate: n-Heptane 7:3) afforded the title compound (1.0 g, 56%) as a yellow oil.

Step 32 4-bromo-5-(methylsulfonyl)-3-(trifluoromethyl)-1H-indazole 1-(2-bromo-6-fluoro-3-(methylsulfonyl)phenyl)-2,2,2-trifluoroethan-1-one (Step 1) was reacted with hydrazine monohydrate (5 eq) in THF for 1 h at ambient temperature in accordance with General procedure C to afford the title compound ([M+H, Br]$^+$343.1).

Step 3: 4-bromo-5-(methylsulfonyl)-3-(trifluoromethyl)-1-((2-(trimethylsilyl)ethoxy)methyl)-1H-indazole 4-bromo-5-(methylsulfonyl)-3-(trifluoromethyl)-1H-indazole (Step 3) was converted to the title compound ([M+H,Cl]$^+$351.2) using General Procedure E2. $^1$H NMR (CHLOROFORM-d, 300 MHz) δ 8.37 (d, 1H, J=9.1 Hz), 7.83 (d, 1H, J=9.1 Hz), 5.85 (s, 2H), 3.5-3.7 (m, 2H), 3.41 (s, 3H), 0.8-1.0 (m, 2H), 0.00 (s, 8H).

Intermediate 15: 4-bromo-3-cyclopropyl-N-methyl-1H-pyrazolo[3,4-c]pyridine-5-carboxamide

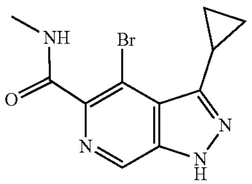 [SMILES: CNC(=O)c1ncc2[nH]nc(C3CC3)c2c1Br]

To a solution of 4-bromo-3-cyclopropyl-1-(tetrahydro-2H-pyran-2-yl)-1H-pyrazolo[3,4-c]pyridine-5-carboxylic acid (Intermediate 13, step 1) (3000 mg, 10.6 mmol), methylamine hydrochloride (1070 mg, 15.8 mmol) and diisopropylethylamine (4 ml, 42.2 mmol) in DMF (60 ml) was added TBTU (4068 mg, 12.7 mmol) and the mixture stirred for 16 h. The reaction was then diluted with ethyl acetate and washed with water, dried ($Na_2SO_4$) and concentrated. Reversed phase preparative HPLC afforded the title compound (1.6 g, 51%) as a white solid ([M+H, Br]$^+$296.0).

Intermediate 16: 4-bromo-3-(difluoromethoxy)-5-(methylsulfonyl)-1-trityl-1H-indazole

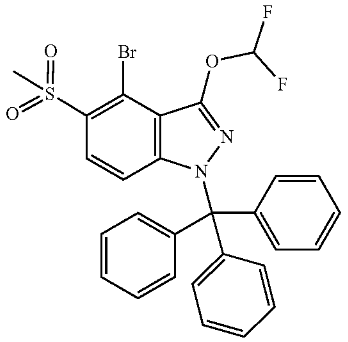 [SMILES: CS(=O)(=O)c1ccc2c(c(OC(F)F)nn2C(c2ccccc2)(c2ccccc2)c2ccccc2)c1Br]

Step 1: ethyl 2-bromo-6-fluoro-3-(methylthio)benzoate (2-Bromo-4-fluorophenyl)(methyl)sulfane was deprotonated with LDA (1.1 eq) for 30 minutes and reacted with ethyl chloroformate (1.2 eq) in accordance with General procedure A to afford the title compound. ([M+H,Br]$^+$ 292.3).

Step 2: ethyl 2-bromo-6-fluoro-3-(methylsulfonyl)benzoate

To a solution of ethyl 2-bromo-6-fluoro-3-(methylthio) benzoate (step 1) (100 mg, 0.3 mmol) in dichloromethane (3 ml) was added mCPBA (153 mg, 0.7 mmol) and the reaction stirred at ambient temperature for 16 h. The reaction was then diluted with DCM, washed with 1 N NaOH, dried ($Na_2SO_4$) and concentrated to afford the title compound (111 mg, quant.) as a light yellow oil. ([M+H, Br]$^+$325.0).

Step 3: 4-bromo-5-(methylsulfonyl)-1,2-dihydro-3H-indazol-3-one

To an ice-cold solution of ethyl 2-bromo-6-fluoro-3-(methylsulfonyl)benzoate (step 2) (1050 mg, 3.2 mmol) in ethanol (13 ml) was added hydrazine monohydrate (157 μL, 3.2 mmol) followed by triethylamine (0.45 ml, 0.8 mmol) and the reaction brought to ambient temperature. It was then heated to 80° C. for 2 h after which time on cooling to ambient temperature, the desired product precipitated out and was isolated by filtration. The title compound (192 mg, 70%) was obtained as a light yellow solid. ([M+H, Br]$^+$ 290.9).

Step 4: 4-bromo-5-(methylsulfonyl)-1-trityl-1H-indazol-3-ol

To an ice cold solution of 4-bromo-5-(methylsulfonyl)-1,2-dihydro-3H-indazol-3-one (step 3) (540 mg, 1.9 mmol) in DMF (20 ml) was added trityl chloride (517 mg, 1.9 mmol) followed by sodium hydride (89 mg, 60% dispersion in mineral oil, 2.2 mmol), the cooling bath was removed and the reaction stirred at ambient temperature for 2 h. The reaction was then diluted with ethyl acetate, washed with water, dried ($Na_2SO_4$) and concentrated. Flash column chromatography (Ethyl acetate: n-Heptane 1:9-1:0) afforded the title compound (460 mg, 43%) as a colourless solid. ([M−H, Br]$^-$533.3).

Step 5: 4-Bromo-3-(difluoromethoxy)-5-(methylsulfonyl)-1-trityl-1H-indazole

To a solution of 4-bromo-5-(methylsulfonyl)-1-trityl-1H-indazol-3-ol (step 4) (250 mg, 0.5 mmol) in DMF (7.5 ml) was added sodium chlorodifluoroacetate (143 mg, 0.9 mmol) and potassium carbonate (194 mg, 1.4 mmol)and the mixture heated to 80° C. for 30 minutes. The reaction was then diluted with ethyl acetate, washed with water, dried ($Na_2SO_4$) and concentrated. Flash column chromatography (Ethyl acetate: n-Heptane 5:95-1:0) afforded the title compound (192 mg, 70%) as a light yellow solid. ([M+H−Tr, Br]$^+$339.1).

Intermediate 17: 4-bromo-3-(difluoromethoxy)-1-trityl-pyrazolo[3,4-c]pyridine-5-carbonitrile

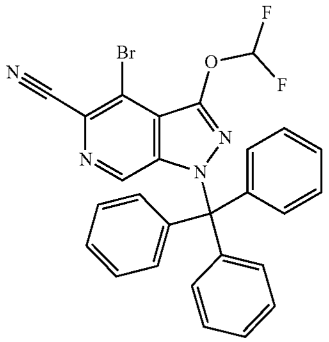 [SMILES: N#Cc1ncc2c(c(OC(F)F)nn2C(c2ccccc2)(c2ccccc2)c2ccccc2)c1Br]

Step 1: ethyl 3-bromo-2-cyano-5-fluoro-pyridine-4-carboxylate

3-Bromo-5-fluoropicolinonitrile is deprotonated with 2,2,6,6-tetramethylpiperidinylmagnesium chloride lithium chloride complex solution (2.5 eq) in THF at −78° C. for 1 h and then reacted with ethyl cyanoformate in accordance with General procedure A to afford the title compound. 1H NMR (400 MHz, CHLOROFORM-d) δ=8.6 (s, 1H), 4.60-4.44 (m, 2H), 1.43 (t, J=7.2 Hz, 3H).

Step 2: 4-bromo-3-oxo-1,2-dihydropyrazolo[3,4-c]pyridine-5-carbonitrile

To a solution of ethyl 3-bromo-2-cyano-5-fluoro-pyridine-4-carboxylate (Step 1) (5.0 g, 18.3 mmol) in ethanol (50 ml) was added hydrazine monohydrate (1.9 ml, 36.6 mmol) and the reaction heated to 70° C. for 2 h. The reaction was concentrated to dryness and the residue purified by reversed phase HPLC to afford the title compound (3.5 g, 80%) as a yellow solid. 1H NMR (400 MHz, DMSO-d6) δ=13.15 (s, 1H), 11.74 (s, 1H), 8.88 (s, 1H).

Step 3: 4-bromo-3-hydroxy-1-trityl-pyrazolo[3,4-c]pyridine-5-carbonitrile

To a solution of 4-bromo-3-oxo-1,2-dihydropyrazolo[3,4-c]pyridine-5-carbonitrile (step 2) (3500 mg, 14.6 mmol) in DMF (200 ml) was added triphenylmethyl chloride (4286 mg, 15.4 mmol) and triethylamine (6.1 mL, 43.9 mmol) and the mixture stirred for 12 h. The reaction was concentrated to dryness and the residue purified by flash column chromatography (Ethyl acetate: n-Heptane 1:9-1:3) afforded the title compound (400 mg, 6%) as a yellow solid. ($[M-H,Br]^-$ 533.3). $^1$H NMR (400 MHz, DMSO-d6) δ=7.48 (s, 1H), 7.44 (t, 1H), 7.39-7.35 (m, 9H), 7.21-7.17 (m, 6H).

Step 4: 4-bromo-3-(difluoromethoxy)-1-trityl-pyrazolo[3,4-c]pyridine-5-carbonitrile To a solution of 4-bromo-3-hydroxy-1-trityl-pyrazolo[3,4-c]pyridine-5-carbonitrile (step 3) (50 mg, 0.1 mmol) in acetonitrile (1.5 ml) was added (2-chloro-2,2-difluoro-acetyl)oxysodium (32 mg, 0.2 mmol) and cesium carbonate (68 mg, 0.2 mmol) and the mixture heated to 80° C. for 2 h. The reaction was diluted with ethyl acetate, filtered and concentrated to afford the title compound (50 mg, 91%) as a yellow solid. 1H NMR (400 MHz, DMSO-d6) δ=7.49 (s, 1H), 7.45-7.16 (m, 16H).

Intermediate 18: 2-(4-(cyclopropylsulfonyl)-3-methylphenyl)-4,4,5,5-tetramethyl-1,3,2-dioxaborolane

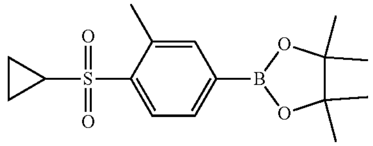 [SMILES: Cc1cc(B2OC(C)(C)C(C)(C)O2)ccc1S(=O)(=O)C1CC1]

Step 1: (4-bromo-2-methylphenyl)(cyclopropyl)sulfane 4-bromo-2-methylbenzenethiol (600 mg, 3.0 mmol) was dissolved in DMF (12 ml), the solution was sparged with Ar under sonication before the addition of potassium tert-butoxide (398 mg, 3.6 mmol) and cyclopropylbromide (0.5 ml, 5.9 mmol) and the mixture heated to 100° C. for 26 h. The reaction was diluted with ethyl acetate, washed repeatedly with water, dried ($Na_2SO_4$) and concentrated to afford the title compound (737 mg, 59%) as a light brown oil. 1H NMR (CHLOROFORM-d, 300 MHz) δ 7.4-7.4 (m, 1H), 7.3-7.3 (m, 1H), 7.2-7.3 (m, 1H), 2.2-2.2 (m, 3H), 2.0-2.1 (m, 1H), 1.1-1.1 (m, 2H), 0.6-0.7 (m, 2H)

Step 2: 4-bromo-1-(cyclopropylsulfonyl)-2-methylbenzene (4-Bromo-2-methylphenyl)(cyclopropyl)sulfane (step 1) is converted to the title compound using General procedure G. 1H NMR (CHLOROFORM-d, 300 MHz) δ 7.7-7.8 (m, 1H), 7.5-7.5 (m, 2H), 2.7-2.7 (m, 3H), 2.5-2.6 (m, 1H), 1.3-1.4 (m, 2H), 1.0-1.1 (m, 2H).

Step 3: 2-(4-(cyclopropylsulfonyl)-3-methylphenyl)-4,4,5,5-tetramethyl-1,3,2-dioxaborolane 4-bromo-1-(cyclopropylsulfonyl)-2-methylbenzene (step 2) is converted to the title compound employing General procedure F. ($[M+H]^+$323.2).

Intermediate 19: 2-(4-(cyclopropylsulfonyl)-3-chlorophenyl)-4,4,5,5-tetramethyl-1,3,2-dioxaborolane

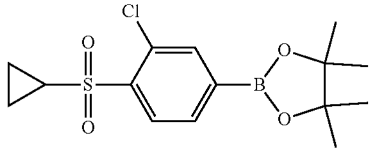 [SMILES: CC1(C)OB(c2ccc(S(=O)(=O)C3CC3)c(Cl)c2)OC1(C)C]

4-Bromo-1-(cyclopropylsulfonyl)-2-methylbenzene (CAS: 1310947-51-3, US2011/237791 A1) is converted to the title compound employing General procedure F. ($[M+H]^+$343.2).

Intermediate 20: 2-chloro-N,N-dimethyl-4-(4,4,5,5-tetramethyl-1,3,2-dioxaborolan-2-yl)benzenesulfonamide

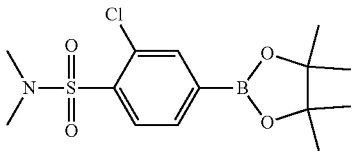

Step 1: 4-bromo-2-chloro-N,N-dimethyl-benzenesulfonamide

To a solution of dimethylamine hydrochloride (2.1 g, 25.9 mmol) and diispropylethylamine (6.5 ml, 17.2 mmol) in dichloromethane (40 ml) was added 4-bromo-2-chlorobenzenesulfonyl chloride (5.0 g, 17.2 mmol) and the mixture stirred at ambient temperature for 2 h. The reaction was then washed with water, brine, dried ($Na_2SO_4$) and concentrated to afford the title compound (4.3 g, 84%) as a light brown solid. ([M+H, Br, Cl]$^+$299.9).

Step 2: 2-chloro-N,N-dimethyl-4-(4,4,5,5-tetramethyl-1,3,2-dioxaborolan-2-yl)benzenesulfonamide 4-bromo-2-chloro-N,N-dimethyl-benzenesulfonamide (step 1) is converted to the title compound employing General procedure F. ([M+H]$^+$346.1).

Intermediate 21: 2-(3-(difluoromethyl)-4-(methylsulfonyl)phenyl)-4,4,5,5-tetramethyl-1,3,2-dioxaborolane

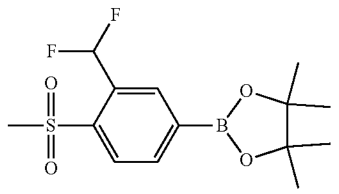

Step 1: (2-(difluoromethyl)phenyl)(methyl)sulfane

To a degassed solution of bromo-2-(difluoromethyl)benzene (400 mg, 1.9 mmol) in DMF(6 ml) was added sodium thiomethoxide (271 mg, 3.9 mmol) and the mixture heated to 100° C. for 3 h. It was then diluted with ethyl acetate, washed with water, brine, dried ($Na_2SO_4$) and concentrated to afford the title compound (0.22 g, 44%) as a yellow oil. 1H NMR (CHLOROFORM-d, 300 MHz) δ 8.0-8.0 (m, 1H), 7.61 (s, 1H), 7.4-7.5 (m, 2H), 7.3-7.3 (m, 1H), 7.02 (s, 1H), 2.5-2.5 (m, 3H)

Step 2: 4-bromo-2-(difluoromethyl)phenyl)(methyl)sulfane

To an ice-cold solution of 2-(difluoromethyl)phenyl) (methyl)sulfane (step 1, 224 mg, 1.3 mmol) in DCM (4.5 ml) was added bromine (93 μL, 1.8 mmol) and the reaction warmed to ambient temperature and stirred for 4 days. The reaction was diluted with DCM, washed with aqueous sodium thiosulfate, brine, dried ($Na_2SO_4$) and concentrated to afford the title compound (0.29 g, 67%) as a yellow oil. 1H NMR (CHLOROFORM-d, 300 MHz) δ 7.74 (br d, 1H, J=2.2 Hz), 7.55 (tdd, 1H, J=1.0, 2.2, 8.5 Hz), 7.2-7.3 (m, 2H), 6.95 (t, 1H, J=1.0 Hz), 2.48 (s, 3H)

Step 3: 4-bromo-2-(difluoromethyl)-1-(methylsulfonyl)benzene 4-bromo-2-(difluoromethyl)phenyl)(methyl)sulfane (step 2) is converted to the title compound using General procedure G. 1H NMR (CHLOROFORM-d, 300 MHz) δ 8.0-8.1 (m, 1H), 8.0-8.0 (m, 1H), 7.8-7.9 (m, 1H), 7.4-7.8 (m, 1H), 3.1-3.1 (m, 3H)

Step 4: 2-(3-(difluoromethyl)-4-(methylsulfonyl) phenyl)-4,4,5,5-tetramethyl-1,3,2-dioxaborolane 4-bromo-2-(difluoromethyl)-1-(methylsulfonyl)benzene (Step 3) is converted to the title compound employing General procedure F. ([M+H−$C_6H_{12}$]$^+$500.2).

Intermediate 22: 2-(3-(difluoromethyl)-4-(methylsulfonyl)phenyl)-4,4,5,5-tetramethyl-1,3,2-dioxaborolane

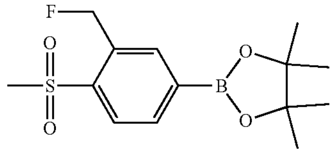

Step 1: 4-bromo-2-(fluoromethyl)-1-(methylsulfonyl)benzene

To a solution (5-bromo-2-(methylsulfonyl)phenyl)methanol (CAS: 773134-43-3, WO2011/138751 A2) (780 mg, 2.9 mmol) cooled to −78° C. is added diethylaminosulfurtrifluoride (0.5 ml, 3.5 mmol) and the reaction stirred for 1 h before raising the temperature to 0° C. for 2 h. The reaction was then washed with saturated aqueous sodium hydrogen carbonate, dried ($Na_2SO_4$) and concentrated. Flash column chromatography (Ethyl acetate: n-Heptane 3:7) afforded the title compound (400 mg, 6%) as a yellow solid. ([M−H, Br]$^-$533.3). to afford the title compound (0.62 g, 75%) as a white solid. 1H NMR (DMSO-d6, 300 MHz) δ 7.9-8.0 (m, 1H), 7.7-7.8 (m, 2H), 5.64 (s, 1H), 4.9-4.9 (m, 2H), 3.25 (s, 3H)

Step 2: 2-(3-(difluoromethyl)-4-(methylsulfonyl) phenyl)-4,4,5,5-tetramethyl-1,3,2-dioxaborolane 4-bromo-2-(fluoromethyl)-1-(methylsulfonyl)benzene (Step 1) is converted to the title compound employing General procedure F. 1H NMR (CHLOROFORM-d, 300 MHz) δ 7.90-8.10 (m, 3H), 5.70-6.00 (m, 2H), 3.14 (s, 3H), 1.37 (s, 12H)

Intermediate 23: 4,4,5,5-tetramethyl-2-(3-methyl-4-(oxetan-3-ylsulfonyl)phenyl)-1,3,2-dioxaborolane

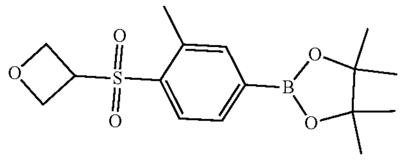 [SMILES: Cc1cc(B2OC(C)(C)C(C)(C)O2)ccc1S(=O)(=O)C1COC1]

Step 1: 3-((4-bromo-2-methylphenyl)thio)oxetane

A degassed solution of 4-bromo-2-methylbenzenethiol (200 mg, 0.9 mmol) and oxetan-3-yl 4-methylbenzenesulfonate (CAS: 26272-83-3, WO2012/138678 A1) (275 mg, 1.1 mmol) was heated to 85° C. for 1 h. The reaction was then diluted with ethyl acetate, washed with water, brine, dried ($Na_2SO_4$) and concentrated. Flash column chromatography (Ethyl acetate: n-Heptane 3:7) afforded the title compound (185 mg, 71%) as a colourless oil. ([M+H, Br]$^+$261.0).

Step 2: 3-((4-bromo-2-methylphenyl)sulfonyl)oxetane 3-((4-bromo-2-methylphenyl)thio)oxetane (step 2) is converted to the title compound using General procedure G. ([M+H+MeCN, Br]$^+$334.1).

Step 4: 4,4,5,5-tetramethyl-2-(3-methyl-4-(oxetan-3-ylsulfonyl)phenyl)-1,3,2-dioxaborolane 3-((4-bromo-2-methylphenyl)sulfonyl)oxetane is converted to the title compound employing General procedure F. ([M+H+MeCN]$^+$380.3).

Intermediate 24: 2-(4-ethylsulfonyl-3-methyl-phenyl)-4,4,5,5-tetramethyl-1,3,2-dioxaborolane

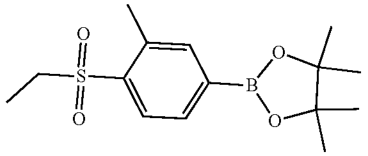 [SMILES: CCS(=O)(=O)c1ccc(B2OC(C)(C)C(C)(C)O2)cc1C]

Step 1: 4-bromo-1-ethylsulfanyl-2-methyl-benzene

To a solution of 1-ethylsulfanyl-2-methyl-benzene (CAS: 3695-36-1) (30.0 g, 197.0 mmol) in dichloromethane (300 ml) at 0° C. was added bromine (40.0 g, 256.0 mmol) and the reaction subsequently stirred at ambient temperature for 1 h. The reaction was concentrated to afford the title compound (40.0 g, 87%) as a yellow oil. 1H NMR (400 MHz, DMSO-d6) δ ppm 1.23 (t, J=7.34 Hz, 3 H) 2.23 (s, 3 H) 2.93 (q, J=7.34 Hz, 2 H) 7.18 (d, J=8.31 Hz, 1 H) 7.31-7.41 (m, 2H)

Step 2: 4-bromo-1-ethylsulfonyl-2-methyl-benzene

4-Bromo-1-ethylsulfanyl-2-methyl-benzene (step 1) is converted to the title compound using General procedure G.

1H NMR (400 MHz, CHLOROFORM-d) δ=7.89-7.82 (m, 1H), 7.55-7.50 (m, 2H), 3.17-3.11 (m, 2H), 2.67 (s, 3H), 1.27 (t, 3H) Step 3: 2-(4-ethylsulfonyl-3-methyl-phenyl)-4,4,5,5-tetramethyl-1,3,2-dioxaborolane 4-bromo-1-ethylsulfonyl-2-methyl-benzene (Step 2) is converted to the title compound employing General procedure F. ([M+H]$^+$229.1)

Intermediate 25: 2-(2-fluoro-5-methyl-4-methylsulfonyl-phenyl)-4,4,5,5-tetramethyl-1,3,2-dioxaborolane

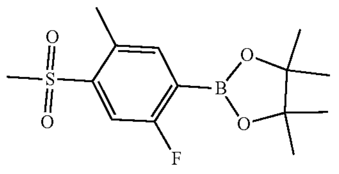

Step 1: 1-bromo-2-fluoro-5-methyl-4-methylsulfonyl-benzene 1-bromo-2-fluoro-5-methyl-4-methylsulfanyl-benzene (CAS: 1351167-83-3, WO2011/146335 A1) is converted to the title compound using General procedure G. ([M+H+MeCN, Br]$^+$267.0).

Step 2: 2-(2-fluoro-5-methyl-4-methylsulfonyl-phenyl)-4,4,5,5-tetramethyl-1,3,2-dioxaborolane 1-bromo-2-fluoro-5-methyl-4-methylsulfonyl-benzene (Step 1) is converted to the title compound employing General procedure F at 70° C. ([M+H−$C_6H_{12}$]$^+$233.1).

Intermediate 26: 2-(2,5-dimethyl-4-methylsulfonyl-phenyl)-4,4,5,5-tetramethyl-1,3,2-dioxaborolane

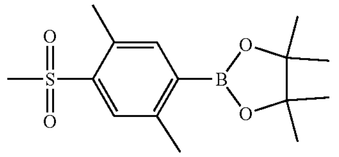

Step 1: 1-bromo-2,5-dimethyl-4-methylsulfonyl-benzene

To a mixture of 1,4-dibromo-2,5-dimethylbenzene (2.0 g, 7.6 mmol), L-proline (0.7 g, 6.1 mmol) and copper(1) iodide (1.2 g, 6.1 mmol) in DMSO (20 mL) was added sodium hydroxide (0.2 g, 6.1 mmol) and sodium methanesulfinate (1.0 g, 9.9 mmol). The mixture was stirred 120° C. for 20 h under a nitrogen atmosphere after which time it was diluted with water and repeatedly extracted with ethyl acetate. The combined organic was washed with brine, dried ($Na_2SO_4$) and concentrated. Flash column chromatography (Ethyl acetate: n-Heptane 1:4) afforded the title compound (627 mg, 13%) as a yellow solid. ([M+H, Br]$^+$263.0).

Step 2: 2-(2,5-dimethyl-4-methylsulfonyl-phenyl)-4,4,5,5-tetramethyl-1,3,2-dioxaborolane 1-Bromo-2,5-dimethyl-4-methylsulfonyl-benzene (Step 1) is converted to the title compound employing General procedure F at 95° C. ($[M+H]^+$311.2).

Intermediate 27: 2-[4-(difluoromethylsulfonyl)-3-methyl-phenyl]-4,4,5,5-tetramethyl-1,3,2-dioxaborolane

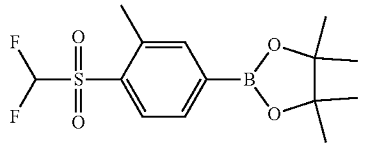 [SMILES: Cc1cc(B2OC(C)(C)C(C)(C)O2)ccc1S(=O)(=O)C(F)F]

Step 1: 4-bromo-1-(difluoromethylsulfanyl)-2-methyl-benzene

To a solution of 1-(difluoromethylsulfanyl)-2-methyl-benzene (CAS: 1450743-54-0, Organic Letters, 2013, 5036-5039) (15.0 g, 86.1 mmol) in heptane (162 ml) was added bromine (15.1 g, 94.7 mmol) and the mixture stirred at ambient temperature for 12 h after which time the reaction was diluted with ethylaceate, washed with saturated sodium bisulfate, dried ($Na_2SO_4$) and concentrated to afford the title compound (15.0 g, 69%) as a yellow liquid. 1H NMR (400 MHz, CHLOROFORM-d) δ=7.50 (d, J=1.9 Hz, 1H), 7.51-7.48 (m, 1H), 7.40-7.31 (m, 2H), 6.97-6.61 (m, 1H), 2.50 (s, 3H)

Step 2: 4-bromo-1-(difluoromethylsulfonyl)-2-methyl-benzene

4-Bromo-1-(difluoromethylsulfanyl)-2-methyl-benzene (step 1) is converted to the title compound using General procedure G. 1H NMR (400 MHz, CHLOROFORM-d) δ=7.89 (d, J=9.0 Hz, 1H), 7.64-7.58 (m, 2H), 6.37-6.05 (m, 1H), 2.71 (s, 3H)

Step 3: 2-[4-(difluoromethylsulfonyl)-3-methyl-phenyl]-4,4,5,5-tetramethyl-1,3,2-dioxaborolane 4-bromo-1-(difluoromethylsulfonyl)-2-methyl-benzene (Step 1) is converted to the title compound employing General procedure F at 80° C. 1H NMR (400 MHz, CHLOROFORM-d) δ=7.99 (d, J=7.8 Hz, 1H), 7.86-7.79 (m, 2H), 6.38-5.97 (m, 1H), 2.71 (s, 3H), 1.36 (s, 12H)

Intermediate 28: 2-[4-(cyclopropylmethylsulfonyl)-3-methyl-phenyl]-4,4,5,5-tetramethyl-1,3,2-dioxaborolane

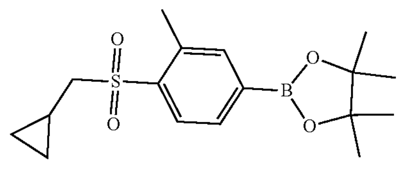 [SMILES: Cc1cc(B2OC(C)(C)C(C)(C)O2)ccc1S(=O)(=O)CC1CC1]

Step 1: 1-(cyclopropylmethylsulfanyl)-2-methyl-benzene

To solution of o-thiocresol (2.0 g, 16.1 mmol) in acetonitrile (20 mL) was added potassium carbonate (4.4 g, 32.2 mmol) and (bromomethyl)cyclopropane (1.6 mL, 16.1 mmol). The mixture was stirred at 50° C. for 12 h. The reaction was then diluted with ethyl acetate, filtered and concentrated to afford title compound (3.0 g, quant) as a yellow liquid. $^1$H NMR (400 MHz, CHLOROFORM-d) δ ppm 0.24-0.30 (m, 2 H) 0.56-0.63 (m, 2 H) 1.01-1.15 (m, 1 H) 2.40 (s, 3H) 2.84 (d, J=7.00 Hz, 2 H) 7.05-7.12 (m, 1H) 7.12-7.20 (m, 2H) 7.27-7.33 (m, 1H)

Step 2: 4-bromo-1-(cyclopropylmethylsulfanyl)-2-methyl-benzene

To a solution of 1-(cyclopropylmethylsulfanyl)-2-methyl-benzene (step 1) (3.0 g, 16.8 mmol) in hexane (35 ml) was added bromine (2.7 g, 16.9 mmol) and the mixture stirred at ambient temperature for 3 h after which time the reaction was diluted with ethyl acetate, washed with saturated sodium bisulfate, dried ($Na_2SO_4$) and concentrated to afford the title compound (3.7 g, 86%) as a yellow liquid. $^1$H NMR (400 MHz, CHLOROFORM-d) δ ppm 0.01-0.07 (m, 2 H) 0.34-0.42 (m, 2 H) 0.76-0.90 (m, 1 H) 2.14 (s, 3 H) 2.16-2.19 (m, 1 H) 2.17-2.18 (m, 1 H) 2.59 (d, J=7.00 Hz, 2 H) 2.62 (d, J=7.00 Hz, 1 H) 6.93 (d, J=8.25 Hz, 1 H) 6.91-6.94 (m, 1 H) 7.03-7.06 (m, 1 H) 7.08-7.10 (m, 1 H) 7.09 (d, J=2.25 Hz, 1 H)

Step 3: 4-bromo-1-(cyclopropylmethylsulfonyl)-2-methyl-benzene

4-Bromo-1-(cyclopropylmethylsulfanyl)-2-methyl-benzene (step 2) is converted to the title compound using General procedure G. $^1$H NMR (400 MHz, CHLOROFORM-d) δ ppm 0.13-0.18 (m, 2 H) 0.53-0.58 (m, 2 H) 0.90-1.03 (m, 1 H) 2.65 (s, 3 H) 3.04 (d, J=7.25 Hz, 2 H) 7.49-7.54 (m, 2 H) 7.88 (d, J=8.25 Hz, 1 H)

Step 4: 2-[4-(cyclopropylmethylsulfonyl)-3-methyl-phenyl]-4,4,5,5-tetramethyl-1,3,2-dioxaborolane 4-bromo-1-(cyclopropylmethylsulfonyl)-2-methyl-benzene (step 3) is converted to the title compound employing General procedure F at 70° C. $^1$H NMR (400 MHz, CHLOROFORM-d) δ ppm 0.12 (q, J=5.13 Hz, 2 H) 0.47-0.56 (m, 2 H) 0.95 (quint, J=7.65, 7.65, 7.65, 7.65, 4.85, 4.85 Hz, 1 H) 1.36 (s, 12 H) 2.68 (s, 3 H) 3.05 (d, J=7.13 Hz, 2 H) 7.74 (s, 1 H) 7.77 (d, J=7.88 Hz, 1 H) 8.01 (d, J=7.88 Hz, 1 H)

Intermediate 29: 4,4,5,5-tetramethyl-2-(3-methyl-4-propylsulfonyl-phenyl)-1,3,2-dioxaborolane

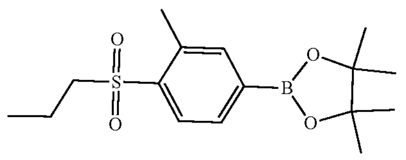 [SMILES: CCCS(=O)(=O)c1ccc(B2OC(C)(C)C(C)(C)O2)cc1C]

Step 1: 1-methyl-2-propylsulfanyl-benzene

To solution of o-thiocresol (2.0 g, 16.1 mmol) in acetonitrile (20 mL) was added potassium carbonate (4.4 g, 32.2 mmol) and 1-iodopropane (4.3 mL, 29.0 mmol). The mixture was stirred at 60° C. for 12 h. The reaction was then diluted with ethyl acetate, filtered and concentrated to afford title compound (2.5 g, 94%) as a yellow liquid. $^1$H NMR (400 MHz, CHLOROFORM-d) δ=7.30-7.26 (m, 1H), 7.19-7.14 (m, 2H), 7.12-7.07 (m, 1H), 2.90 (t, J=7.3 Hz, 2H), 2.39 (s, 3H), 1.71 (m, 2H), 1.06 (t, J=7.4 Hz, 3H)

Step 2: 4-bromo-2-methyl-1-propylsulfanyl-benzene

To a solution of 1-methyl-2-propylsulfanyl-benzene (step 1) (2.5 g, 15.0 mmol) in dichloromethane (25 ml) was added bromine (2.6 g, 16.5 mmol) and the mixture stirred at ambient temperature for 3 h after which time the reaction was diluted with dichloromethane, washed with saturated sodium bisulfite, dried ($Na_2SO_4$) and concentrated to afford the title compound (3.6 g, 98%) as a yellow liquid. $^1$H NMR (400 MHz, CHLOROFORM-d) δ ppm 0.01-0.07 (m, 2 H) 0.34-0.42 (m, 2 H) 0.76-0.90 (m, 1 H) 2.14 (s, 3 H) 2.16-2.19 (m, 1 H) 2.17-2.18 (m, 1 H) 2.59 (d, J=7.00 Hz, 2 H) 2.62 (d, J=7.00 Hz, 1 H) 6.93 (d, J=8.25 Hz, 1 H) 6.91-6.94 (m, 1 H) 7.03-7.06 (m, 1 H) 7.08-7.10 (m, 1 H) 7.09 (d, J=2.25 Hz, 1 H)

Step 3: 4-bromo-2-methyl-1-propylsulfonyl-benzene4-bromo-2-methyl-1-propylsulfanyl-benzene (step 2) is converted to the title compound using General procedure G. $^1$H NMR (400 MHz, CHLOROFORM-d) δ=7.87-7.83 (m, 1H), 7.54-7.50 (m, 2H), 3.11-3.07 (m, 2H), 2.67 (s, 3H), 1.77-1.69 (m, 2H), 1.01 (t, J=7.5 Hz, 3H)

Step 4: 4,4,5,5-tetramethyl-2-(3-methyl-4-propylsulfonyl-phenyl)-1,3,2-dioxaborolane4-bromo-1-(cyclopropylmethylsulfonyl)-2-methyl-benzene (step 3) is converted to the title compound employing General procedure F at 90° C. ([M+H]$^+$311.2).

Intermediate 30: 2-(4-isopropylsulfonyl-3-methyl-phenyl)-4,4,5,5-tetramethyl-1,3,2-dioxaborolane

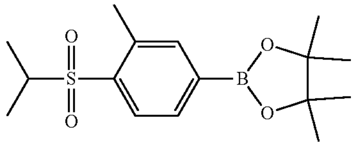 [SMILES: Cc1cc(B2OC(C)(C)C(C)(C)O2)ccc1S(=O)(=O)C(C)C]

Step 1: 1-isopropylsulfanyl-2-methyl-benzene

To solution of o-thiocresol (2.0 g, 16.1 mmol) in acetonitrile (20 mL) was added potassium carbonate (4.4 g, 32.2 mmol) and 2-bromopropane (3.1 mL, 29.0 mmol). The mixture was stirred at 60° C. for 2 h. The reaction was then diluted with ethyl acetate, filtered and concentrated to afford title compound (2.5 g, 94%) as a yellow liquid. $^1$H NMR (400 MHz, CHLOROFORM-d) δ=7.40-7.36 (m, 1H), 7.22-7.19 (m, 1H), 7.19-7.18 (m, 1H), 7.18-7.12 (m, 2H), 3.38 (td, J=6.7, 13.3 Hz, 1H), 2.42 (s, 3H), 1.33 (s, 3H), 1.31 (s, 3H)

Step 2: 4-bromo-2-methyl-1-propylsulfanyl-benzeneTo a solution of 1-isopropylsulfanyl-2-methyl-benzene (step 1) (2.5 g, 15.0 mmol) in dichloromethane (25 ml) was added bromine (2.6 g, 16.5 mmol) and the mixture stirred at ambient temperature for 3 h after which time the reaction was diluted with dichloromethane, washed with saturated sodium bisulfate, dried ($Na_2SO_4$) and concentrated to afford the title compound (3.6 g, 98%) as a yellow liquid. $^1$H NMR (400 MHz, CHLOROFORM-d) δ=7.35 (d, J=2.0 Hz, 1H), 7.30-7.26 (m, 1H), 7.24-7.20 (m, 1H), 3.33 (td, J=6.7, 13.3 Hz, 1H), 2.38 (s, 3H), 1.31 (s, 3H), 1.29 (s, 3H)

Step 3: 4-bromo-1-isopropylsulfonyl-2-methyl-benzene 4-bromo-2-methyl-1-propylsulfanyl-benzene (step 2) is converted to the title compound using General procedure G. $^1$H NMR (400 MHz, CHLOROFORM-d) δ=7.83 (d, J=8.9 Hz, 1H), 7.54-7.49 (m, 2H), 3.24 (d, J=6.8 Hz, 1H), 2.66 (s, 3H), 1.31 (s, 3H), 1.29 (s, 3H)

Step 4: 2-(4-isopropylsulfonyl-3-methyl-phenyl)-4,4,5,5-tetramethyl-1,3,2-dioxaborolane4-bromo-1-(cyclopropylmethylsulfonyl)-2-methyl-benzene (step 3) is converted to the title compound employing General procedure F at 90° C. ([M+H]$^+$325.1).

Intermediate 31: N,2-dimethyl-4-(4,4,5,5-tetramethyl-1,3,2-dioxaborolan yl)benzenesulfonamide

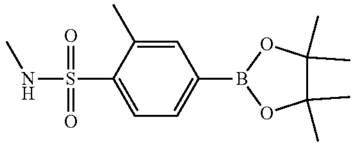

Step 1: 4-bromo-N,2-dimethyl-benzenesulfonamide

To a solution of methylamine hydrochloride (0.6 g, 8.9 mmol) in dichloromethane (30 mL) was added triethylamine (2.5 mL, 17.8 mmol) and 4-bromo-2-methylbenzene-1-sulfonyl chloride (2.0 g, 7.4 mmol) and the reaction stirred for 1 h at ambient temperature. The reaction was diluted with dichloromethane, washed with brine, dried ($Na_2SO_4$) and concentrated to afford the title compound (1.9 g, 92%) as a white solid. $^1$H NMR (400 MHz, CHLOROFORM-d) δ=7.82 (d, J=8.3 Hz, 1H), 7.51-7.45 (m, 2H), 4.68 (br s, 1H), 2.64 (s, 3H), 2.61 (s, 3H)

Step 2: N,2-dimethyl-4-(4,4,5,5-tetramethyl-1,3,2-dioxaborolan-2-yl)benzenesulfonamide4-Bromo-N,2-dimethyl-benzenesulfonamide (step 2) is converted to the title compound employing General procedure F at 90° C. ([M+H]$^+$ 312.1).

Intermediate 32: tert-butyl-dimethyl-[2-[2-methyl-4-(4,4,5,5-tetramethyl-1,3,2-dioxaborolan-2-yl)phenyl]sulfonylethoxy]silane

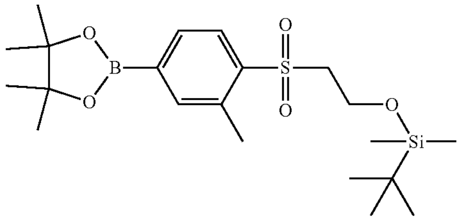

Step 1: tert-butyl-dimethyl-[2-(o-tolylsulfanyl) ethoxy]silane

To solution of o-thiocresol (2.0 g, 16.1 mmol) in acetonitrile (30 mL) was added potassium carbonate (4.4 g, 32.2 mmol) and (2-bromoethoxy)-tert-butyldimethylsilane (6.0 mL, 29.0 mmol). The mixture was stirred at 60° C. for 2 h. The reaction was then diluted with ethyl acetate, filtered and concentrated to afford title compound (7.5 g, 82%) as a colourless liquid. $^1$H NMR (400 MHz, CHLOROFORM-d) δ=7.32 (d, J=7.6 Hz, 1H), 7.18-7.14 (m, 2H), 7.12-7.07 (m, 1H), 3.81 (t, J=7.2 Hz, 2H), 3.06 (t, J=7.2 Hz, 2H), 2.39 (s, 3H), 0.90 (s, 9H), 0.06 (s, 6H)

Step 2: 2-(4-bromo-2-methyl-phenyl)sulfanylethoxy-tert-butyl-dimethyl-silane To a solution of tert-butyl-dimethyl-[2-(o-tolylsulfanyl)ethoxy]silane (step 1) (7.5 g, 13.3 mmol) in dichloromethane (50 ml) was added bromine (2.3 g, 14.6 mmol) and the mixture stirred at ambient temperature for 3 h after which time the reaction was diluted with dichlomethane, washed with saturated sodium bisulfate, dried ($Na_2SO_4$) and concentrated to afford the title compound (9.0 g, 65%) as a yellow liquid used directly in the next step.

Step 3: 2-(4-bromo-2-methyl-phenyl)sulfonylethoxy-tert-butyl-dimethyl-silane 2-(4-bromo-2-methyl-phenyl)sulfanylethoxy-tert-butyl-dimethyl-silane (step 2) is converted to the title compound using General procedure G. ([M+H]$^+$393.0).

Step 4: tert-butyl-dimethyl-[2-[2-methyl-4-(4,4,5,5-tetramethyl-1,3,2-dioxaborolan-2-yl)phenyl]sulfonylethoxy]silane 2-(4-bromo-2-methyl-phenyl)sulfonylethoxy-tert-butyl-dimethyl-silane (step 3) is converted to the title compound employing General procedure F at 90° C. ([M−H]$^+$441.1).

Intermediate 33: 4,4,5,5-tetramethyl-2-[3-methyl-4-(1-methylcyclopropyl)sulfonyl-phenyl]-1,3,2-dioxaborolane

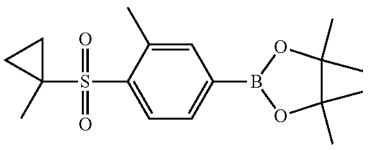 [SMILES: Cc1cc(B2OC(C)(C)C(C)(C)O2)ccc1S(=O)(=O)C1(C)CC1]

Step 1: 4-bromo-2-methyl-1-(1-methylcyclopropyl) sulfonyl-benzene

To a solution of 4-bromo-1-cyclopropylsulfonyl-2-methyl-benzene (Intermediate 18, step 2) (500 mg, 1.8 mmol) in THF (23 mL) under nitrogen at −78° C. was added LiHMDS (2.18 mL, 1 M in THF, 2.18 mmol) and the mixture was stirred for 1 h before the addition of iodomethane (515 mg, 3.6 mmol) and the mixture was warmed to 20° C. and stirred for another 15 h. The mixture was diluted with ethyl acetate, washed with water dried ($Na_2SO_4$) and concentrated. Purification by prep.TLC (petroleum ether: ethyl acetate 5:1) to afford the title compound (0.45 g, 86%) as colourless gum. $^1$H NMR (400 MHz, CHLOROFORM-d) δ=7.84-7.80 (m, 1H), 7.51-7.47 (m, 2H), 3.48 (s, 1H), 2.66 (s, 3H), 1.63-1.60 (m, 2H), 1.29 (s, 3H), 0.88-0.84 (m, 2H)

Step 2: 4,4,5,5-tetramethyl-2-[3-methyl-4-(1-methylcyclopropyl)sulfonyl-phenyl]-1,3,2-dioxaborolane 4-Bromo-2-methyl-1-(1-methylcyclopropyl)sulfonyl-benzene (step 2) is converted to the title compound employing General procedure F at 80° C. $^1$H NMR (400 MHz, CHLOROFORM-d) δ=7.98 (d, J=7.7 Hz, 1H), 7.81-7.76 (m, 2H), 2.72 (s, 3H), 1.66 (br d, J=2.0 Hz, 2H), 1.42-1.37 (m, 15H), 0.89-0.84 (m, 2H)

Intermediate 34: 2-[4-(methoxymethylsulfonyl)-3-methyl-phenyl]-4,4,5,5-tetramethyl-1,3,2-dioxaborolane

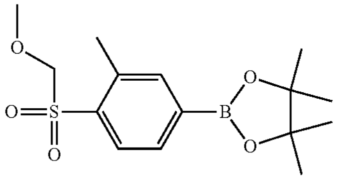 [SMILES: COCS(=O)(=O)c1ccc(B2OC(C)(C)C(C)(C)O2)cc1C]

Step 1: 4-bromo-1-(methoxymethylsulfanyl)-2-methyl-benzene

To solution of chloromethyl methyl ether (0.28 mL, 3.7 mmol) in acetonitrile (3 mL) was added potassium carbonate (680 mg, 4.9 mmol) and 4-bromo-2-methyl-benzenethiol (500 mg, 2.5 mmol). The mixture was stirred at 50° C. for 12 h. The reaction was then diluted with ethyl acetate, washed with water, dried ($Na_2SO_4$) and concentrated. Flash column chromatography (n-Heptane) afforded the title compound (220 mg, 36%) as a light yellow oil. $^1$H NMR (400 MHz, CHLOROFORM-d) δ=7.34-7.30 (m, 1H), 7.25 (d, J=1.9 Hz, 1H), 7.22-7.18 (m, 1H), 4.87-4.83 (m, 2H), 3.35 (s, 3H), 2.29 (s, 3H)

Step 2: 4-bromo-1-(methoxymethylsulfonyl)-2-methyl-benzene 4-bromo-1-(methoxymethylsulfanyl)-2-methyl-benzene (step 2) is converted to the title compound using General procedure G. $^1$H NMR (400 MHz, CHLOROFORM-d) δ=7.86 (d, J=8.3 Hz, 1H), 7.56-7.49 (m, 2H), 4.54 (s, 2H), 3.64 (s, 3H), 2.67 (s, 3H)

Step 3: 2-[4-(methoxymethylsulfonyl)-3-methyl-phenyl]-4,4,5,5-tetramethyl-1,3,2-dioxaborolane 4-bromo-1-(methoxymethylsulfonyl)-2-methyl-benzene (step 3) is converted to the title compound employing General procedure F at 70° C. and used crude in the next step.

Intermediate 35: 2-[5-(difluoromethyl)-2-methyl-4-methylsulfinyl-phenyl]-4,4,5,5-tetramethyl-1,3,2-dioxaborolane

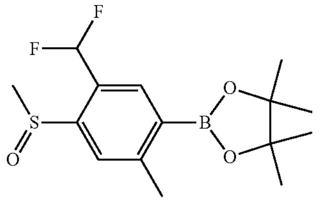

Step 1: 2-bromo-1-(difluoromethyl)-4-methyl-benzene

To a solution of 2-bromo-4-methylbenzaldehyde (5.0 g, 25.1 mmol) in dichloromethane (75 mL) was slowly added diethylaminosulfur trifluoride (6.1 g, 37.7 mmol) over 0.5 h and the reaction stirred for 16 h. The reaction was diluted with dichloromethane, cautiously washed with saturated aqueous sodium hydrogen carbonate and concentrated. Flash column chromatography (n-Heptane) afforded the title compound (3.6 g, 65%) as a yellow liquid. $^1$H NMR (400 MHz, CHLOROFORM-d) δ=7.53 (d, J=7.9 Hz, 1H), 7.43 (s, 1H), 7.21 (d, J=7.9 Hz, 1H), 7.04-6.72 (m, 1H), 2.47-2.29 (m, 3H)

Step 2: 1-(difluoromethyl)-4-methyl-2-methylsulfanyl-benzene

To a cooled (−78° C.) solution of 2-bromo-1-(difluoromethyl)-4-methyl-benzene (step 1) (3.6 g, 16.3 mmol) in THF (67 mL) under nitrogen was added n-butyl lithium (7.2 mL, 2.5 M in hexanes, 18 mmol) and the mixture stirred for 0.5 h before (methyldisulfanyl)methane (2.0 g, 21.5 mmol) was added and the mixture stirred for a further 1 h. Saturated ammonium chloride was then added and the reaction brought to ambient temperature and extracted repeatedly with ethyl acetate. The combined organic was concentrated to afford the title compound (2.5 g, 82%) as a yellow liquid. $^1$H NMR (400 MHz, CHLOROFORM-d) δ=7.50 (d, J=7.8 Hz, 1H), 7.21 (s, 1H), 7.16-6.84 (m, 2H), 2.48 (s, 3H), 2.38 (s, 3H)

Step 3: 1-bromo-5-(difluoromethyl)-2-methyl-4-methylsulfanyl-benzene

To a solution 1-(difluoromethyl)-4-methyl-2-methylsulfanyl-benzene (step 2) (100 mg, 0.5 mmol) in n-heptane (1 mL) was added bromine (93 mg, 0.6 mmol) and the mixture was stirred at ambient temperature for 12 h after which time the reaction was diluted with dichloromethane, washed with saturated sodium bisulfite, dried ($Na_2SO_4$) and concentrated to afford the title compound (90 mg, 63%) as a yellow liquid. $^1$H NMR (400 MHz, CHLOROFORM-d) δ=7.75 (s, 1H), 7.25 (s, 1H), 7.11-6.77 (m, 1H), 2.47 (s, 3H), 2.42 (s, 3H)

Step 4: 1-bromo-5-(difluoromethyl)-2-methyl-4-methylsulfinyl-benzene

To a solution of 1-bromo-5-(difluoromethyl)-2-methyl-4-methylsulfanyl-benzene (step 3) (1.0 g, 3.7 mmol) in dichloromethane (20 mL) cooled to 0° C. was added 3-chlorobenzenecarboperoxoic acid (0.6 g, 3.0 mmol) and the mixture stirred at 0° C. for 0.5 h after which time the reaction was diluted with dichloromethane, washed with saturated sodium bisulfite, saturated aqueous sodium hydrogen carbonate, brine, dried ($Na_2SO_4$) and concentrated. Flash column chromatography (Ethyl acetate: n-Heptane 3:7) afforded the title compound (800 mg, 57%) as a white solid. ([M+H, Br]$^+$282.0).

Step 5: 2-[5-(difluoromethyl)-2-methyl-4-methylsulfinyl-phenyl]-4,4,5,5-tetramethyl-1,3,2-dioxaborolane 1-bromo-5-(difluoromethyl)-2-methyl-4-methylsulfinylbenzene (step 4) is converted to the title compound employing General procedure F at 80° C. ([M+H]$^+$331.2).

Intermediate 36: 4-bromo-3-(difluoromethoxy)-5-methylsulfonyl-1-trityl-indazole

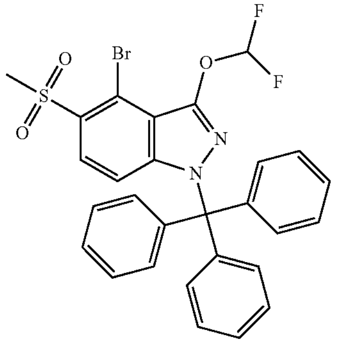 [SMILES: CS(=O)(=O)c1ccc2c(c(OC(F)F)nn2C(c2ccccc2)(c2ccccc2)c2ccccc2)c1Br]

Step 1: ethyl 2-bromo-6-fluoro-3-methylsulfanyl-benzoate

2-Bromo-4-fluoro-1-methylsulfanyl-benzene was deprotonated with LDA (1.2 eq) for 0.5 h and reacted with ethyl chloroformate (1.5 eq) for 1 h in accordance with General procedure A to afford the title compound. $^1$H NMR (400 MHz, CHLOROFORM-d) δ=7.21-7.17 (m, 1H), 7.14-7.08 (m, 1H), 4.46 (q, J=7.1 Hz, 2H), 2.48 (s, 3H), 1.41 (t, J=7.2 Hz, 3H)

Step 2: ethyl 2-bromo-6-fluoro-3-methylsulfonyl-benzoate

Ethyl 2-bromo-6-fluoro-3-methylsulfanyl-benzoate is converted to the title compound using General procedure G. ([M+H, Br]$^+$326.9).

Step 3: 4-bromo-5-methylsulfonyl-1,2-dihydroindazol-3-one

To a solution of ethyl 2-bromo-6-fluoro-3-methylsulfonyl-benzoate (step 2) (10.8 g, 33.2 mmol) in ethanol (120 mL) was added hydrazine hydrate (2.2 g, 44.4 mmol,) and triethylamine (4.6 mL, 33.2 mmol) at 0° C. and the reaction was then heated to 80° C. for 4 h. After cooling to ambient temperature, the title compound was isolated by filtration (5.0 g mg, 52%) as an off-white solid. ([M+Na, Br]$^+$314.8).

Step 4:
4-bromo-5-methylsulfonyl-1-trityl-indazol-3-ol

To a solution of 4-bromo-5-methylsulfonyl-1,2-dihydroindazol-3-one (step 3) (200 mg, 0.7 mmol) in DMF (5 mL) was added sodium hydride (41 mg, 60% dispersion in mineral oil, 1.0 mmol) and triphenylmethyl chloride (211 mg, 0.8 mmol) at 0° C. under nitrogen atmosphere. The cooling bath was removed and the reaction stirred for 2 h on reaching ambient temperature. The reaction was quenched by addition of saturated aqueous ammonium chloride, repeatedly extracted with ethyl acetate and the combined organic extracts washed with brine and concentrated. Flash column chromatography (Ethyl acetate: n-Heptane 1:1) afforded the title compound (150 mg, 41%) as a white solid. ([M+Na, Br]$^+$556.9).

Step 5: 4-bromo-3-(difluoromethoxy)-5-methylsulfonyl-1-trityl-indazole

To a solution of 4-bromo-5-methylsulfonyl-1-trityl-indazol-3-ol (step 4) (1.0 g, 1.9 mmol) in DMF (30 mL) was added sodium chlorodifluoroacetate (0.6 g, 3.8 mmol) and potassium carbonate (0.8 g, 5.6 mmol) and the reaction heated to 80° C. for 30 min. The reaction was filtered and concentrated. Flash column chromatography (Ethyl acetate: n-Heptane 1:3) afforded the title compound (0.9 g, 71%) as a white solid. ([M+Na, Br]$^+$605.0

Intermediate 37: 4-chloro-3-cyclopropyl-2-trimethylsilyl-1-(2-trimethylsilylethoxymethyl)indole-5-carbonitrile

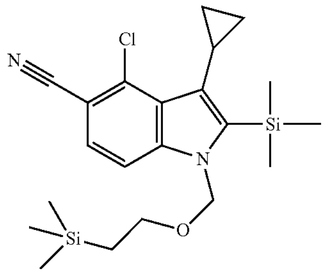 [SMILES: C[Si](C)(C)CCOCn1c([Si](C)(C)C)c(C2CC2)c2c(Cl)c(C#N)ccc21]

Step 1: 4-bromo-3-chloro-2-iodoaniline was prepared as described in WO2013/33228 A1

Step 2: 5-bromo-4-chloro-3-cyclopropyl-2-(trimethylsilyl)-1H-indole

A mixture of 4-bromo-3-chloro-2-iodoaniline (step 1) (441 mg, 1.3 mmol), (cyclopropylethynyl)trimethylsilane (159 µl, 1.5 mmol), lithium chloride (56 mg, 1.33 mmol) and sodium carbonate (281 mg, 2.7 mmol) in DMF (5 ml) was sparged with argon, then [1,1'-1,1'-bis(diphenylphosphino) ferrocene-palladium(II)dichloride dichloromethane adduct (49 mg, 66 µmol) was added. The reaction was heated in a sealed tube to 100° C. for 16 h, after which time the reaction was diluted with ethyl acetate washed with aqueous sodium thiosulphate, brine, dried ($Na_2SO_4$) and concentrated. Flash column chromatography (Ethyl acetate: n-Heptane 4:1) afforded the title compound (185 mg, 39%) as a yellow solid. ([M+H, Cl, Br]$^+$342.2).

Step 3: 5-bromo-4-chloro-3-cyclopropyl-2-(trimethylsilyl)-1-((2-(trimethylsilyl)ethoxy)methyl)-1H-indole 5-bromo-4-chloro-3-cyclopropyl-2-(trimethylsilyl)-1H-indole was converted to the title compound using General Procedure E1 in THF. $^1$H NMR (CHLOROFORM-d, 300 MHz) δ 7.44 (d, 1H, J=8.7 Hz), 7.22 (d, 1H, J=8.9 Hz), 5.4-5.5 (m, 2H), 3.7-3.8 (m, 1H), 3.6-3.8 (m, 1H), 3.3-3.5 (m, 2H), 2.12 (tt, 1H, J=5.2, 8.3 Hz),1.1-1.2 (m, 2H), 0.7-0.8 (m, 2H), 0.5-0.6 (m, 9H), 0.1-0.1 (m, 9H)

Step 4: 4-chloro-3-cyclopropyl-2-trimethylsilyl-1-(2-trimethylsilylethoxymethyl)indole-5-carbonitrile 5-bromo-4-chloro-3-cyclopropyl-2-(trimethylsilyl)-1-((2-(trimethylsilyl)ethoxy)methyl)-1H-indole (step 3) (170 mg, 0.3 mmol) and zinc cyanide (34 mg, 0.3 mmol) were suspended in DMF (3 ml). The reaction mixture was sparged with argon and the reaction heated in a the microwave at 150° C. for 30 min. The reaction was diluted with water and repeatedly extracted times with ethyl acetate. The combined organic layers were washed with water, brine, dried ($Na_2SO_4$) and concentrated. Flash column chromatography (Ethyl acetate: n-Heptane 4:1) afforded the title compound (57 mg, 46%) as a yellow solid. ([M+H, Cl]$^+$301.2).

Intermediate 38: 2-(difluoromethyl)-N,N-dimethyl-4-(4,4,5,5-tetramethyl-1,3,2-dioxaborolan-2-yl)benzenesulfonamide

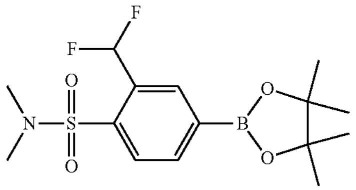

Step 1:
1-benzylsulfanyl-4-bromo-2-(difluoromethyl)benzene

To an ice cold solution of benzyl mercaptan (2.4 g, 19.4 mmol) in DMF (20 mL) was added sodium hydride (0.8 g, 60% dispersion in mineral oil, 20 mmol), after 0.5 h 4-bromo-2-(difluoromethyl)-1-fluoro-benzene (3.0 g, 13.3 mmol) was added and the reaction stirred for a further 0.5 h. The reaction was diluted with ethyl acetate, washed with saturated aqueous ammonium chloride, brine and concentrated. Flash column chromatography (Ethyl acetate: Heptane 0:1-5:95) afforded the title compound (3.8 g, 83%) as a colourless oil. 1H NMR (400 MHz, CHLOROFORM-d) δ=7.77 (d, J=2.1 Hz, 1H), 7.49 (td, J=1.1, 8.3 Hz, 1H), 7.32-7.27 (m, 2H), 7.27-7.22 (m, 2H), 7.18-7.15 (m, 2H), 7.07-6.75 (m, 1H), 4.03 (s, 2H)

Step 2: 4-bromo-2-(difluoromethyl)benzenesulfonyl chloride

To an ice cold solution of 1-benzylsulfanyl-4-bromo-2-(difluoromethyl)benzene (200 mg, 0.6 mmol) in acetonitrile (5 mL) is added acetic acid (182 mg, 3.0 mmol) and water (0.05 mL, 3. mmol) was added N-chlorosuccinimide (243 mg, 1.8 mmol) and the mixture stirred for 1 h. The reaction was diluted with ethyl acetate, washed with water, brine and concentrated. Flash column chromatography (Ethyl acetate: Heptane 1:10) afforded the title compound (150 mg, 65%) as a colourless oil. 1H NMR (400 MHz, CHLOROFORM-d) δ=8.16-8.12 (m, 1H), 8.03 (d, J=8.6 Hz, 1H), 7.93-7.86 (m, 1H), 7.67-7.38 (m, 1H)

Step 3: 4-bromo-2-(difluoromethyl)-N,N-dimethyl-benzenesulfonamide

To an ice cold solution of 4-bromo-2-(difluoromethyl) benzenesulfonyl chloride (step 2) (2.6 g, 6.8 mmol) in acetonitrile (20 mL) was added dimethylamine hydrochloride (1.7 g, 20.4 mmol) followed by pyridine (1.65 mL, 20.4 mmol) and the mixture stirred for 0.5 h. The reaction was diluted with ethyl acetate, washed with 1N HCl, brine and concentrated. Flash column chromatography (Ethyl acetate: n-Heptane 1:5) afforded the title compound (1.6 g, 71%) as a white solid. ([M+H, Br]$^+$315.9).

Step 4: 2-(difluoromethyl)-N,N-dimethyl-4-(4,4,5,5-tetramethyl-1,3,2-dioxaborolan-2-yl)benzenesulfonamide 4-bromo-2-(difluoromethyl)-N,N-dimethyl-benzenesulfonamide (step 3) is converted to the title compound employing General procedure F at 80° C. ([M+H]$^+$362.2).

EXAMPLES

| Ex. No. | Structure | Product Name | Mol. weight found | From Intermediates | Prep. |
|---|---|---|---|---|---|
| 1 | 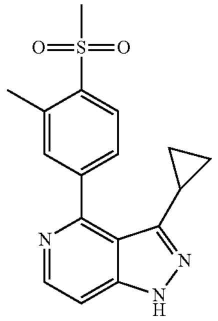 [SMILES: Cc1cc(-c2nccc3[nH]nc(C4CC4)c23)ccc1S(C)(=O)=O] | 3-cyclopropyl-4-(3-methyl-4-(methylsulfonyl) phenyl)-1H-pyrazolo[4,3-c]pyridine | [M + H]$^+$ 328.1 | 4-chloro-3-cyclopropyl-1H-pyrazolo[4,3-c]pyridine (Intermediate 1) and (3-methyl-4-(methylsulfonyl) phenyl)boronic acid | D |
| 2 | 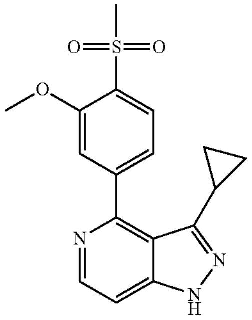 [SMILES: COc1cc(-c2nccc3[nH]nc(C4CC4)c23)ccc1S(C)(=O)=O] | 3-cyclopropyl-4-(3-methoxy-4-(methylsulfonyl) phenyl)-1H-pyrazolo[4,3-c]pyridine | [M + H]$^+$ 344.1 | 4-chloro-3-cyclopropyl-1H-pyrazolo[4,3-c]pyridine (Intermediate 1) and (4-Methanesulfonyl-3-methoxyphenyl) boronic acid | D |
| 3 | 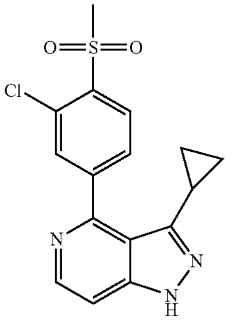 [SMILES: CS(=O)(=O)c1ccc(-c2nccc3[nH]nc(C4CC4)c23)cc1Cl] | 4-(3-chloro-4-(methylsulfonyl) phenyl)-3-cyclopropyl-1H-pyrazolo[4,3-c]pyridine | [M + H, Cl]$^+$ 348.1 | 4-chloro-3-cyclopropyl-1H-pyrazolo[4,3-c]pyridine (Intermediate 1) and (3-Chloro-4-methanesulfonyl-phenyl)boronic acid | D |

-continued

| Ex. No. | Structure | Product Name | Mol. weight found | From Intermediates | Prep. |
|---|---|---|---|---|---|
| 4 | 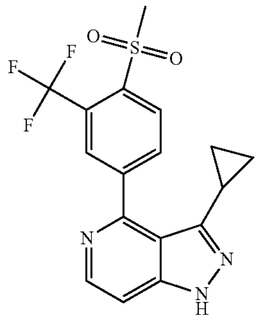 [SMILES: CS(=O)(=O)c1ccc(-c2nccc3[nH]nc(C4CC4)c23)cc1C(F)(F)F] | 3-cyclopropyl-4-(4-(methylsulfonyl)-3-(trifluoromethyl) phenyl)-1H-pyrazolo[4,3-c]pyridine | $[M + H]^+$ 382.1 | 4-chloro-3-cyclopropyl-1H-pyrazolo[4,3-c]pyridine (Intermediate 1) and [4-Methanesulfonyl-3-(trifluoromethyl) phenyl]boronic acid | D |
| 5 | 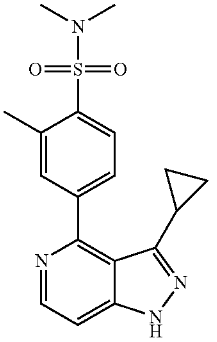 [SMILES: Cc1cc(-c2nccc3[nH]nc(C4CC4)c23)ccc1S(=O)(=O)N(C)C] | 4-(3-cyclopropyl-1H-pyrazolo[4,3-c]pyridin-4-yl)-N,N,2-trimethylbenzene-sulfonamide | $[M + H]^+$ 357.1 | 4-chloro-3-cyclopropyl-1H-pyrazolo[4,3-c]pyridine (Intermediate 1) and N,N,2-trimethyl-4-(4,4,5,5-tetramethyl-1,3,2-dioxoborolan-2-yl)benzensulfona-mide | D |
| 6 | 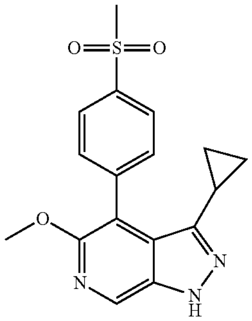 [SMILES: COc1ncc2[nH]nc(C3CC3)c2c1-c1ccc(S(C)(=O)=O)cc1] | 3-cyclopropyl-5-methoxy-4-(4-methylsulfonyl-phenyl)-1H-pyrazolo[3,4-c]pyridine | $[M + H]^+$ 344.1 | 4-bromo-3-cyclopropyl-5-methoxy-1-((2-(trimethylsilyl) ethoxy)methyl)-1H-pyrazolo[3,4-c]pyridine (Intermediate 2) and 4-(methanesulfonyl) phenyl boronic acid | D, J |
| 7 | 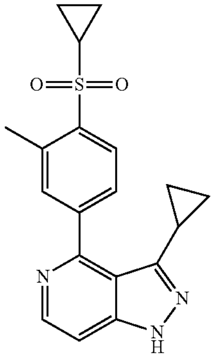 [SMILES: Cc1cc(-c2nccc3[nH]nc(C4CC4)c23)ccc1S(=O)(=O)C1CC1] | 3-cyclopropyl-4-(4-(cyclopropylsulfonyl)-3-methylphenyl)-1H-pyrazolo[4,3-c]pyridine | $[M + H]^+$ 354.1 | 4-chloro-3-cyclopropyl-1H-pyrazolo[4,3-c]pyridine (Intermediate 1) and 2-(4-(cyclopropyl-sulfonyl)-3-methylphenyl)-4,4,5,5-tetramethyl-1,3,2-dioxaborolane (Intermediate 18) | D |

-continued

| Ex. No. | Structure | Product Name | Mol. weight found | From Intermediates | Prep. |
|---|---|---|---|---|---|
| 8 | 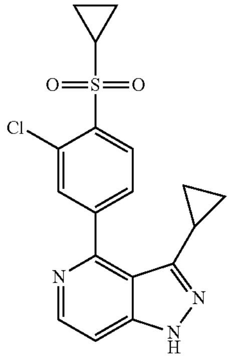 [SMILES: O=S(=O)(c1ccc(-c2nccc3[nH]nc(C4CC4)c23)cc1Cl)C1CC1] | 4-(3-chloro-4-(cyclopropylsulfonyl) phenyl)-3-cyclopropyl-1H-pyrazolo[4,3-c]pyridine | $[M + H]^+$ 374.1 | 4-chloro-3-cyclopropyl-1H-pyrazolo[4,3-c]pyridine (Intermediate 1) and 2-(4-(cyclopropyl-sulfonyl)-3-chlorophenyl)-4,4,5,5-tetramethyl-1,3,2-dioxaborolane (Intermediate 19) | D |
| 9 | 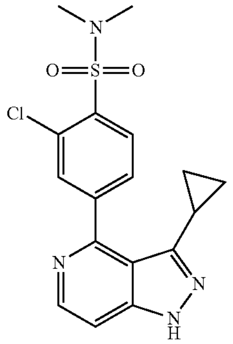 [SMILES: CN(C)S(=O)(=O)c1ccc(-c2nccc3[nH]nc(C4CC4)c23)cc1Cl] | 2-chloro-4-(3-cyclopropyl-1H-pyrazolo[4,3-c]pyridin-4-yl)-N,N-dimethylbenzene-sulfonamide | $[M + H]^+$ 377.1 | 4-chloro-3-cyclopropyl-1H-pyrazolo[4,3-c]pyridine (Intermediate 1) and 2-chloro-N,N-dimethyl-4-(4,4,5,5-tetramethyl-1,3,2-dioxaborolan-2-yl)benzenesul-fonamide (Intermediate 20) | D |
| 10 | 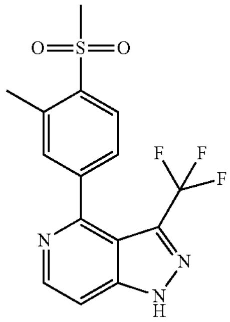 [SMILES: Cc1cc(-c2nccc3[nH]nc(C(F)(F)F)c23)ccc1S(C)(=O)=O] | 4-(3-methyl-4-(methylsulfonyl) phenyl)-3-(trifluoromethyl)-1H-pyrazolo[3,4-b]pyridine | $[M + H]^+$ 356.1 | 4-chloro-3-(trifluoromethyl)-1-((2-(trimethylsilyl) ethoxy)methyl)-1H-pyrazolo[4,3-c]pyridine (Intermediate 3) and (3-methyl-4-(methylsulfonyl) phenyl)boronic acid | D, J |
| 11 | 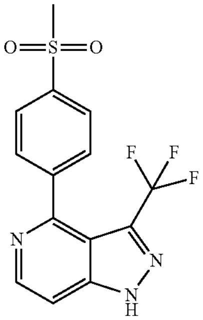 [SMILES: CS(=O)(=O)c1ccc(-c2nccc3[nH]nc(C(F)(F)F)c23)cc1] | 4-(4-(methylsulfonyl) phenyl)-3-(trifluoromethyl)-1H-pyrazolo[4,3-c]pyridine | $[M + H]^+$ 342.0 | 4-chloro-3-(trifluoromethyl)-1-((2-(trimethylsilyl) ethoxy)methyl)-1H-pyrazolo[4,3-c]pyridine (Intermediate 3) and 4-(methanesulfonyl) phenyl boronic acid | D, J |

-continued

| Ex. No. | Structure | Product Name | Mol. weight found | From Intermediates | Prep. |
|---|---|---|---|---|---|
| 12 | 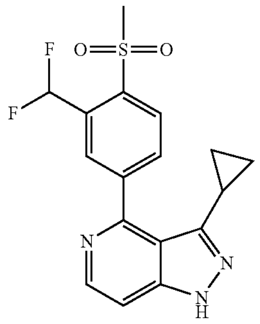 [SMILES: CS(=O)(=O)c1ccc(-c2nccc3[nH]nc(C4CC4)c23)cc1C(F)F] | 3-cyclopropyl-4-(3-(difluoromethyl)-4-(methylsulfonyl)phenyl)-1H-pyrazolo[4,3-c]pyridine | $[M + H]^+$ 364.1 | 4-chloro-3-cyclopropyl-1H-pyrazolo[4,3-c]pyridine (Intermediate 1) and 2-(3-(difluoromethyl)-4-(methylsulfonyl)phenyl)-4,4,5,5-tetramethyl-1,3,2-dioxaborolane (Intermediate 21) | D |
| 13 | 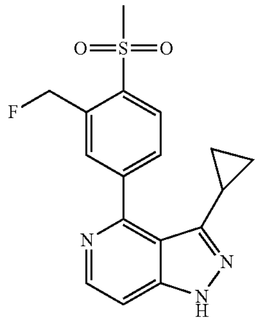 [SMILES: CS(=O)(=O)c1ccc(-c2nccc3[nH]nc(C4CC4)c23)cc1CF] | 3-cyclopropyl-4-(3-(fluoromethyl)-4-(methylsulfonyl)phenyl)-1H-pyrazolo[4,3-c]pyridine | $[M + H]^+$ 346.1 | 4-chloro-3-cyclopropyl-1H-pyrazolo[4,3-c]pyridine (Intermediate 1) and 2-(3-(difluoromethyl)-4-(methylsulfonyl)phenyl)-4,4,5,5-tetramethyl-1,3,2-dioxaborolane (Intermediate 22) | D |
| 14 | 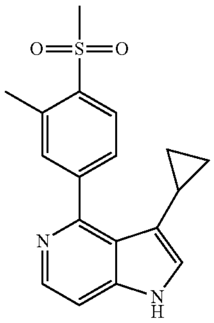 [SMILES: Cc1cc(-c2nccc3[nH]cc(C4CC4)c23)ccc1S(C)(=O)=O] | 3-cyclopropyl-4-(3-methyl-4-(methylsulfonyl)phenyl)-1H-pyrrolo[3,2-c]pyridine | $[M + H]^+$ 327.2 | 4-chloro-3-cyclopropyl-1-((2-(trimethylsilyl)ethoxy)methyl)-1H-pyrrolo[3,2-c]pyridine (Intermediate 4) and (3-methyl-4-(methylsulfonyl)phenyl)boronic acid | D, J |
| 15 | 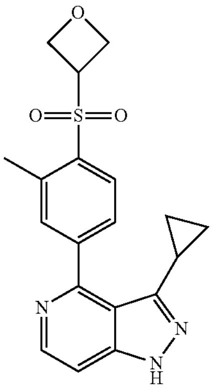 [SMILES: Cc1cc(-c2nccc3[nH]nc(C4CC4)c23)ccc1S(=O)(=O)C1COC1] | 3-cyclopropyl-4-(3-methyl-4-(oxetan-3-ylsulfonyl)phenyl)-1H-pyrazolo[4,3-c]pyridine | $[M + H]^+$ 370.2 | 4-chloro-3-cyclopropyl-1H-pyrazolo[4,3-c]pyridine (Intermediate 1) and 4,4,5,5-tetramethyl-2-(3-methyl-4-(oxetan-3-ylsulfonyl)phenyl)-1,3,2-dioxaborolane (Intermediate 23) | D |

-continued

| Ex. No. | Structure | Product Name | Mol. weight found | From Intermediates | Prep. |
|---|---|---|---|---|---|
| 16 | 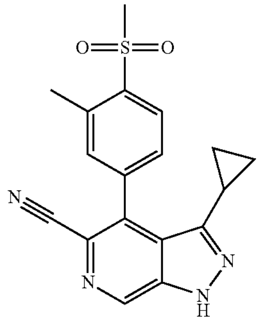 [SMILES: Cc1cc(-c2c(C#N)ncc3[nH]nc(C4CC4)c23)ccc1S(C)(=O)=O] | 3-cyclopropyl-4-(3-methyl-4-(methylsulfonyl) phenyl)-1H-pyrazolo[3,4-c]pyridine-5-carbonitrile | $[M + H]^+$ 353.1 | 4-bromo-3-cyclopropyl-1H-pyrazolo[3,4-c]pyridine-5-carbonitrile (Intermediate 5) and (3-methyl-4-(methylsulfonyl) phenyl)boronic acid | D |
| 17 | 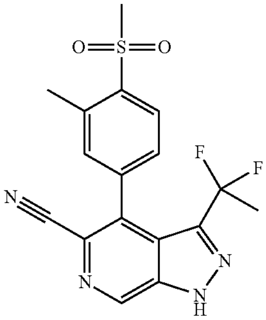 | 3-(1,1-difluoroethyl)-4-(3-methyl-4-(methylsulfonyl) phenyl)-1H-pyrazolo[4,3-c]pyridine | $[M + H]^+$ 352.2 | 4-chloro-3-(1,1-difluoroethyl)-1H-pyrazolo[4,3-c]pyridine (Intermediate 6) and (3-methyl-4-(methylsulfonyl) phenyl)boronic acid | D |
| 18 | 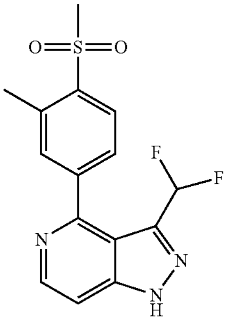 [SMILES: Cc1cc(-c2nccc3[nH]nc(C(F)F)c23)ccc1S(C)(=O)=O] | 3-(difluoromethyl)-4-(3-methyl-4-methylsulfonyl-phenyl)-1H-pyraxolo[4,3-c]pyridine | $[M + H]^+$ 338.1 | 2-[[4-chloro-3-(difluoromethyl) pyrazolo[4,3-c]pyridin-1-yl]methoxy]ethyl-trimethylsilane (Intermediate 7) and (3-methyl-4-(methylsulfonyl) phenyl)boronic acid | D, J |
| 19 | 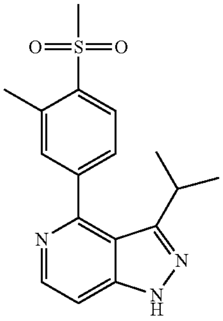 [SMILES: Cc1cc(-c2nccc3[nH]nc(C(C)C)c23)ccc1S(C)(=O)=O] | 3-isopropyl-4-(3-methyl-4-(methylsulfonyl) phenyl)-1H-pyrazolo[4,3-c]pyridine | $[M + H]^+$ 330.1 | 4-chloro-3-isopropyl-1H-pyrazolo[4,3-c]pyridine and (3-methyl-4-(methylsulfonyl) phenyl)boronic acid | D |

-continued

| Ex. No. | Structure | Product Name | Mol. weight found | From Intermediates | Prep. |
|---|---|---|---|---|---|
| 20 | 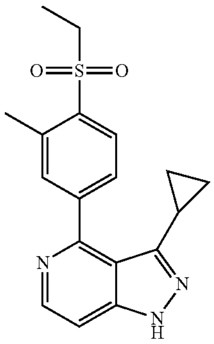 | 3-cyclopropyl-4-(4-ethylsulfonyl-3-methyl-phenyl)-1H-pyrazolo[4,3-c]pyridine | $[M + H]^+$ 314.9 | 4-chloro-3-cyclopropyl-1H-pyrazolo[4,3-c]pyridine (Intermediate 1) and 2-(4-ethylsulfonyl-3-methyl-phenyl)-4,4,5,5-tetramethyl-1,3,2-dioxaborolane (Intermediate 24) | D |
| 21 | 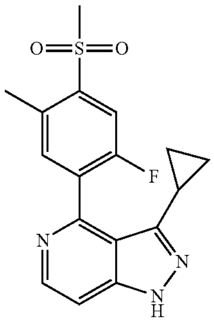 [SMILES: Cc1cc(-c2nccc3[nH]nc(C4CC4)c23)c(F)cc1S(C)(=O)=O] | 3-cyclopropyl-4-(2-fluoro-5-methyl-4-methylsulfonyl-phenyl)-1H-pyrazolo[4,3-c]pyridine | $[M + H]^+$ 346.1 | 4-chloro-3-cyclopropyl-1H-pyrazolo[4,3-c]pyridine (Intermediate 1) and 2-(2-fluoro-5-methyl-4-methylsulfonyl-phenyl)-4,4,5,5-tetramethyl-1,3,2-dioxaborolane (Intermediate 25) | D |
| 22 | 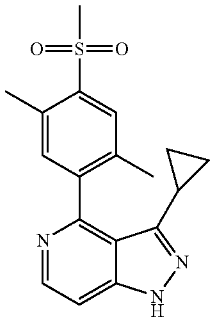 [SMILES: Cc1cc(S(C)(=O)=O)c(C)cc1-c1nccc2[nH]nc(C3CC3)c12] | 3-cyclopropyl-4-(2,5-dimethyl-4-methylsulfonyl-phenyl)-1H-pyrazolo[4,3-c]pyridine hydrochloride | $[M + H]^+$ 342.1 | 4-chloro-3-cyclopropyl-1H-pyrazolo[4,3-c]pyridine (Intermediate 1) and 2-(2,5-dimethyl-4-methylsulfonyl-phenyl)-4,4,5,5-tetramethyl-1,3,2-dioxaborolane (Intermediate 26) | D |
| 23 | 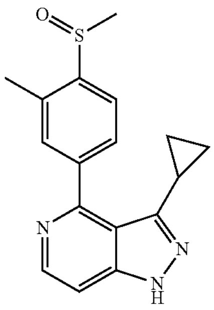 [SMILES: Cc1cc(-c2nccc3[nH]nc(C4CC4)c23)ccc1S(C)=O] | 3-cyclopropyl-4-(3-methyl-4-methylsulfinyl-phenyl)-1H-pyrazolo[4,3-c]pyridine hydrochloride | $[M + H]^+$ 312.2 | 4-chloro-3-cyclopropyl-1H-pyrazolo[4,3-c]pyridine (Intermediate 1) and 3-Methyl-4-(methylthio) phenylboronic acid | D, G (1 eq) |

-continued

| Ex. No. | Structure | Product Name | Mol. weight found | From Intermediates | Prep. |
|---|---|---|---|---|---|
| 24 | 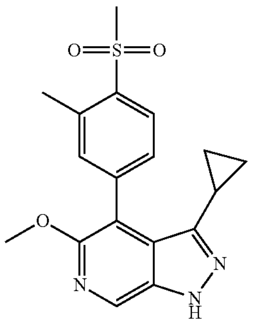 [SMILES: COc1ncc2[nH]nc(C3CC3)c2c1-c1ccc(S(C)(=O)=O)c(C)c1] | 3-cyclopropyl-5-methoxy-4-(3-methyl-4-(methylsulfonyl) phenyl)-1H-pyrazolo[3,4-c]pyridine | [M + H]+ 358.3 | 4-bromo-3-cyclopropyl-5-methoxy-1-((2-(trimethylsilyl) ethoxy)methyl)-1H-pyrazolo[3,4-c]pyridine (Intermediate 2) and (3-methyl-4-(methylsulfonyl) phenyl)boronic acid | D, J |
| 25 | 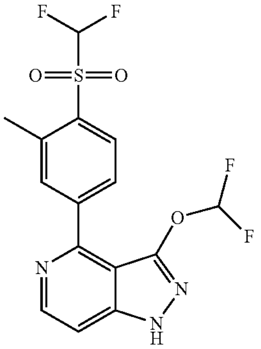 [SMILES: Cc1cc(-c2nccc3[nH]nc(OC(F)F)c23)ccc1S(=O)(=O)C(F)F] | 3-(difluoromethoxy)-4-[4-(difluoromethyl-sulfonyl)-3-methyl-phenyl]-1H-pyrazolo[4,3-c]pyridine | [M + H]+ 390.1 | 4-chloro-3-(difluoromethoxy)-1-trityl-pyrazolo[4,3-c]pyridine (Intermediate 8) and 2-[4-(difluoromethyl-sulfonyl)-3-methyl-phenyl]-4,4,5,5-tetramethyl-1,3,2-dioxaborolane (Intermediate 27) | D, H |
| 26 | 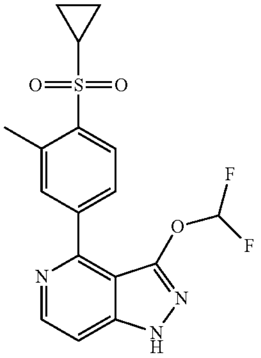 [SMILES: Cc1cc(-c2nccc3[nH]nc(OC(F)F)c23)ccc1S(=O)(=O)C1CC1] | 4-(4-cyclopropylsulfonyl-3-methyl-phenyl)-3-(difluoromethoxy)-1H-pyrazolo[4,3-c]pyridine | [M + H]+ 380.1 | 4-chloro-3-(difluoromethoxy)-1-trityl-pyrazolo[4,3-c]pyridine (Intermediate 8) and 2-(4-(cyclopropyl-sulfonyl)-3-methylphenyl)-4,4,5,5-tetramethyl-1,3,2-dioxaborolane (Intermediate 18) | D, H |
| 27 | 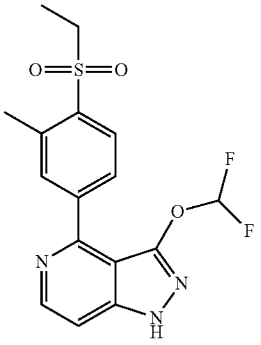 [SMILES: CCS(=O)(=O)c1ccc(-c2nccc3[nH]nc(OC(F)F)c23)cc1C] | 3-(difluoromethoxy)-4-(4-ethylsulfonyl-3-methyl-phenyl)-1H-pyrazolo[4,3-c]pyridine | [M + H]+ 368.0 | 4-chloro-3-(difluoromethoxy)-1-trityl-pyrazolo[4,3-c]pyridine (Intermediate 8) and 2-(4-ethylsulfonyl-3-methyl-phenyl)-4,4,5,5-tetramethyl-1,3,2-dioxaborolane (Intermediate 24) | D, H |

-continued

| Ex. No. | Structure | Product Name | Mol. weight found | From Intermediates | Prep. |
|---|---|---|---|---|---|
| 28 | 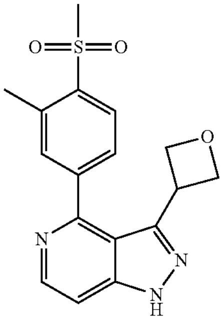 [SMILES: Cc1cc(-c2nccc3[nH]nc(C4COC4)c23)ccc1S(C)(=O)=O] | 4-(3-methyl-4-methylsulfonyl-phenyl)-3-(oxetan-3-yl)-1H-pyrazolo[4,3-c]pyridine | $[M + H]^+$ 344.0 | 4-chloro-3-(oxetan-3-yl)-1-tetrahydropyran-2-yl-pyrazolo[4,3-c]pyridine (Intermediate 9) and (3-methyl-4-(methylsulfonyl) phenyl)boronic acid | D, I1 |
| 29 | 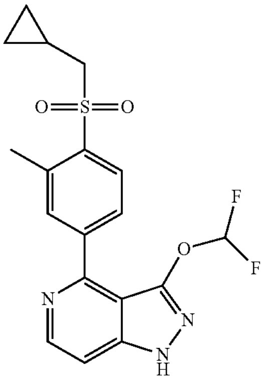 [SMILES: Cc1cc(-c2nccc3[nH]nc(OC(F)F)c23)ccc1S(=O)(=O)CC1CC1] | 4-[4-(cyclopropylmethyl-sulfonyl)-3-methyl-phenyl]-3-(difluoromethoxy)-1H-pyrazolo[4,3-c]pyridine | $[M + H]^+$ 394.1 | 4-chloro-3-(difluoromethoxy)-1-trityl-pyrazolo[4,3-c]pyridine (Intermediate 8) and 2-[4-(cyclopropyl-methylsulfonyl)-3-methyl-phenyl]-4,4,5,5-tetramethyl-1,3,2-dioxaborolane (Intermediate 28) | D, H |
| 30 | 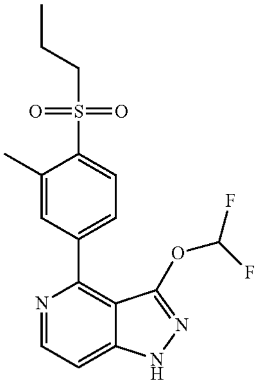 [SMILES: CCCS(=O)(=O)c1ccc(-c2nccc3[nH]nc(OC(F)F)c23)cc1C] | 3-(difluoromethoxy)-4-[3-(difluoromethyl)-4-methylsulfonyl-phenyl]-1H-pyrazolo[4,3-c]pyridine | $[M + H]^+$ 382.2 | 4-chloro-3-(difluoromethoxy)-1-trityl-pyrazolo[4,3-c]pyridine (Intermediate 8) and 4,4,5,5-tetramethyl-2-(3-methyl-4-propylsulfonyl-phenyl)-1,3,2-dioxaborolane (Intermediate 29) | D, H |
| 31 | 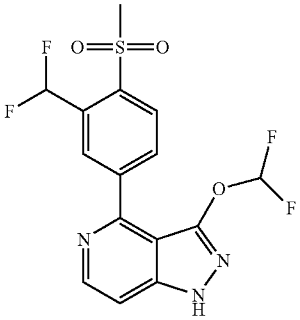 [SMILES: CS(=O)(=O)c1ccc(-c2nccc3[nH]nc(OC(F)F)c23)cc1C(F)F] | 3-(difluoromethoxy)-4-(4-isopropylsulfonyl-3-methyl-phenyl)-1H-pyrazolo[4,3-c]pyridine | $[M + H]^+$ 390.1 | 4-chloro-3-(difluoromethoxy)-1-trityl-pyrazolo[4,3-c]pyridine (Intermediate 8) and 2-(3-(difluoromethyl)-4-(methylsulfonyl) phenyl)-4,4,5,5-tetramethyl-1,3,2-dioxaborolane (Intermediate 21) | D, H |

-continued

| Ex. No. | Structure | Product Name | Mol. weight found | From Intermediates | Prep. |
|---|---|---|---|---|---|
| 32 | 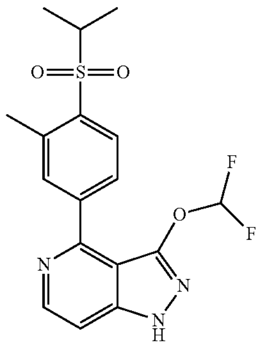 [SMILES: Cc1cc(-c2nccc3[nH]nc(OC(F)F)c23)ccc1S(=O)(=O)C(C)C] | 4-(3-methyl-4-methylsulfonyl-phenyl)-3-(oxetan-3-yl)-1H-pyrazolo[4,3-c]pyridine | $[M + H]^+$ 382.0 | 4-chloro-3-(difluoromethoxy)-1-trityl-pyrazolo[4,3-c]pyridine (Intermediate 8) and 2-(4-isopropylsulfonyl-3-methyl-phenyl)-4,4,5,5-tetramethyl-1,3,2-dioxaborolane (Intermediate 30) | D, H |
| 33 | 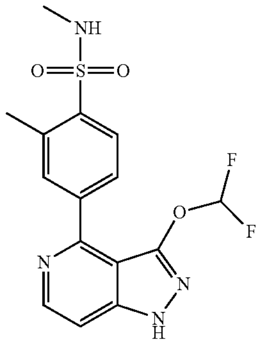 [SMILES: CNS(=O)(=O)c1ccc(-c2nccc3[nH]nc(OC(F)F)c23)cc1C] | 4-[3-(difluoromethoxy)-1H-pyrazolo[4,3-c]pyridin-4-yl]-N,2-dimethyl-benzenesulfonamide | $[M + H]^+$ 369.0 | 4-chloro-3-(difluoromethoxy)-1-trityl-pyrazolo[4,3-c]pyridine (Intermediate 8) and N,2-dimethyl-4-(4,4,5,5-tetramethyl-1,3,2-dioxaborolan-2-yl)benzenesulfonamide (Intermediate 30) | D, H |
| 34 | 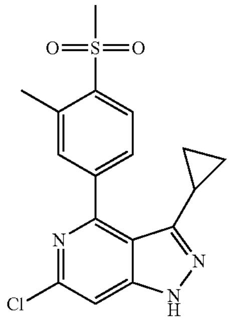 [SMILES: Cc1cc(-c2nc(Cl)cc3[nH]nc(C4CC4)c23)ccc1S(C)(=O)=O] | 6-chloro-3-cyclopropyl-4-(3-methyl-4-methylsulfonylphenyl)-1H-pyrazolo[4,3-c]pyridine | $[M + H]^+$ 362.3 | 4,6-dichloro-3-cyclopropyl-1H-pyrazolo[4,3-c]pyridine (Intermediate 10) and (3-methyl-4-(methylsulfonyl) phenyl)boronic acid | D |
| 35 | 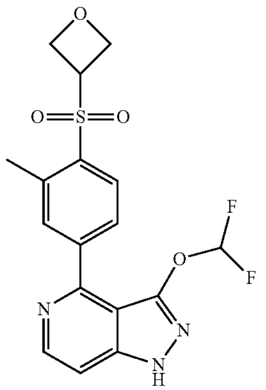 [SMILES: Cc1cc(-c2nccc3[nH]nc(OC(F)F)c23)ccc1S(=O)(=O)C1COC1] | 3-(difluoromethoxy)-4-[3-methyl-4-(oxetan-3-ylsulfonyl)phenyl]-1H-pyrazolo[4,3-c]pyridine | $[M + H]^+$ 396.1 | 4-chloro-3-(difluoromethoxy)-1-trityl-pyrazolo[4,3-c]pyridine (Intermediate 8) and 4,4,5,5-tetramethyl-2-(3-methyl-4-(oxetan-3-ylsulfonyl)phenyl)-1,3,2-dioxaborolane (Intermediate 23) | D, H |

-continued

| Ex. No. | Structure | Product Name | Mol. weight found | From Intermediates | Prep. |
|---|---|---|---|---|---|
| 36 | 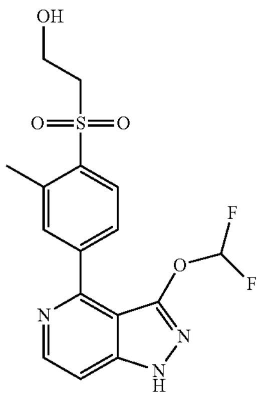 [SMILES: Cc1cc(-c2nccc3[nH]nc(OC(F)F)c23)ccc1S(=O)(=O)CCO] | 2-[4-[3-(difluoromethoxy)-1H-pyrazolo[4,3-c]pyridin-4-yl]-2-methyl-phenyl]sulfonylethanol | [M + H]+ 384.1 | 4-chloro-3-(difluoromethoxy)-1-trityl-pyrazolo[4,3-c]pyridine (Intermediate 8) and tert-butyl-dimethyl-[2-[2-methyl-4-(4,4,5,5-tetramethyl-1,3,2-dioxaborolan-2-yl)phenyl]sulfonyl-ethoxy]silane (Intermediate 32) | D, H |
| 37 | 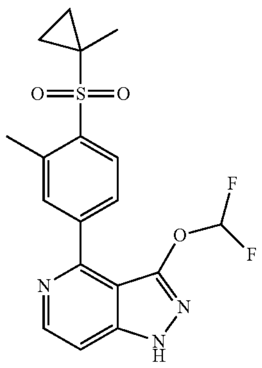 [SMILES: Cc1cc(-c2nccc3[nH]nc(OC(F)F)c23)ccc1S(=O)(=O)C1(C)CC1] | 3-(difluoromethoxy)-4-[3-methyl-4-(1-methylcyclopropyl)sulfonyl-phenyl]-1H-pyrazolo[4,3-c]pyridine | [M + H]+ 394.1 | 4-chloro-3-(difluoromethoxy)-1-trityl-pyrazolo[4,3-c]pyridine (Intermediate 8) and 4,4,5,5-tetramethyl-2-[3-methyl-4-(1-methylcyclopropyl)sulfonyl-phenyl]-1,3,2-dioxaborolane (Intermediate 33) | D, H |
| 38 | 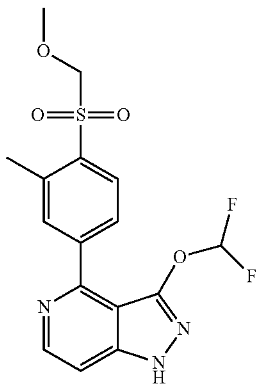 [SMILES: COCS(=O)(=O)c1ccc(-c2nccc3[nH]nc(OC(F)F)c23)cc1C] | 3-(difluoromethoxy)-4-[4-(methoxymethyl-sulfonyl)-3-methyl-phenyl]-1H-pyrazolo[4,3-c]pyridine | [M + H]+ 384.1 | 4-chloro-3-(difluoromethoxy)-1-trityl-pyrazolo[4,3-c]pyridine (Intermediate 8) and 2-[4-(methoxymethyl-sulfonyl)-3-methyl-phenyl]-4,4,5,5-tetramethyl-1,3,2-dioxaborolane (Intermediate 34) | D, H |
| 39 | 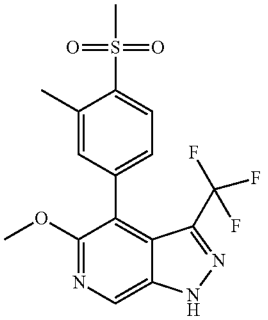 [SMILES: COc1ncc2[nH]nc(C(F)(F)F)c2c1-c1ccc(S(C)(=O)=O)c(C)c1] | 5-methoxy-4-(3-methyl-4-(methylsulfonyl)phenyl)-3-(trifluoromethyl)-1H-pyrazolo[3,4-c]pyridine | [M + H]+ 386.3 | 4-bromo-5-methoxy-3-(trifluoromethyl)-2-((2-(trimethylsilyl)ethoxy)methyl)-2H-pyrazolo[3,4-c]pyridine (Intermediate 11) and (3-methyl-4-(methylsulfonyl)phenyl)boronic acid | D, J |

-continued

| Ex. No. | Structure | Product Name | Mol. weight found | From Intermediates | Prep. |
|---|---|---|---|---|---|
| 40 | 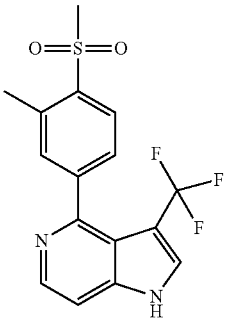 [SMILES: Cc1cc(-c2nccc3[nH]cc(C(F)(F)F)c23)ccc1S(C)(=O)=O] | 4-(3-methyl-4-(methylsulfonyl) phenyl)-3-(trifluoromethyl)-1H-pyrrolo[3,2-c]pyridine | $[M + H]^+$ 355.2 | 4-chloro-3-(trifluoromethyl)-1-((2-(trimethylsilyl) ethoxy)methyl)-1H-pyrrolo[3,2-c]pyridine (Intermediate 12) and (3-methyl-4-(methylsulfonyl) phenyl)boronic acid | D, J |
| 41 | 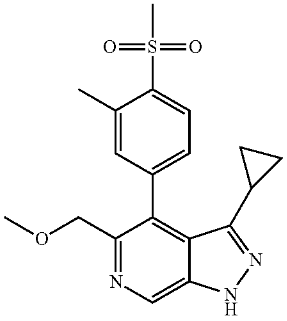 [SMILES: COCc1ncc2[nH]nc(C3CC3)c2c1-c1ccc(S(C)(=O)=O)c(C)c1] | 3-cyclopropyl-5-(methoxymethyl)-4-(3-methyl-4-(methylsulfonyl) phenyl)-1H-pyrazolo[3,4-c]pyridine | $[M + H]^+$ 372.2 | 4-bromo-3-cyclopropyl-5-(methoxymethyl)-1-(tetrahydro-2H-pyran-2-yl)-1H-pyrazolo[3,4-c]pyridine (Intermediate 13) and (3-methyl-4-(methylsulfonyl) phenyl)boronic acid | D, I1 |
| 42 | 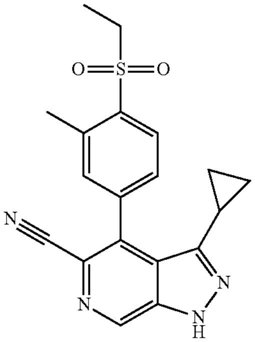 [SMILES: CCS(=O)(=O)c1ccc(-c2c(C#N)ncc3[nH]nc(C4CC4)c23)cc1C] | 3-cyclopropyl-4-(4-ethylsulfonyl-3-methyl-phenyl)-1H-pyrazolo[3,4-c]pyridine-5-carbonitrile | $[M + H]^+$ 367.0 | 4-bromo-3-cyclopropyl-1H-pyrazolo[3,4-c]pyridine-5-carbonitrile (Intermediate 5) and -(4-ethylsulfonyl-3-methyl-phenyl)-4,4,5,5-tetramethyl-1,3,2-dioxaborolane (Intermediate 24) | D |
| 43 | 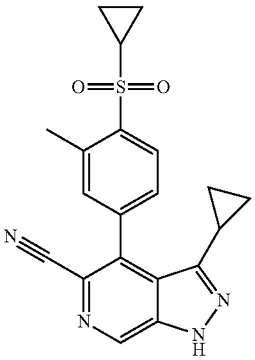 [SMILES: Cc1cc(-c2c(C#N)ncc3[nH]nc(C4CC4)c23)ccc1S(=O)(=O)C1CC1] | 3-cyclopropvl-4-(4-cyclopropylsulfonyl-3-methyl-phenyl)-1H-pyrazolo[3,4-c]pyridine-5-carbonitrile | $[M + H]^+$ 379.0 | 4-bromo-3-cyclopropyl-1H-pyrazolo[3,4-c]pyridine-5-carbonitrile (Intermediate 5) and 2-(4-(cyclopropyl-sulfonyl)-3-methylphenyl)-4,4,5,5-tetramethyl-1,3,2-dioxaborolane (Intermediate 18) | D |

-continued

| Ex. No. | Structure | Product Name | Mol. weight found | From Intermediates | Prep. |
|---|---|---|---|---|---|
| 44 | 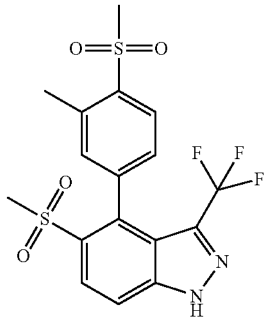 [SMILES: Cc1cc(-c2c(S(C)(=O)=O)ccc3[nH]nc(C(F)(F)F)c23)ccc1S(C)(=O)=O] | 4-(3-methyl-4-(methylsulfonyl)phenyl)-5-(methylsulfonyl)-3-(trifluoromethyl)-1H-indazole | $[M + H]^+$ 433.2 | 4-bromo-5-(methylsulfonyl)-3-(trifluoromethyl)-1-((2-(trimethylsilyl)ethoxy)methyl)-1H-indazole (Intermediate 14) and (3-methyl-4-(methylsulfonyl)phenyl)boronic acid | D, J |
| 45 | 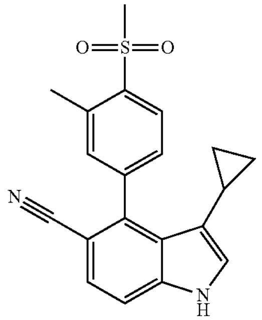 [SMILES: Cc1cc(-c2c(C#N)ccc3[nH]cc(C4CC4)c23)ccc1S(C)(=O)=O] | 3-cyclopropyl-4-(3-methyl-4-methylsulfonylphenyl)-1H-indole-5-carbonitrile | $[M + H]^+$ 351.2 | 3-cyclopropyl-4-(3-methyl-4-(methylsulfonyl)phenyl)-2-(trimethylsilyl)-1-((2-(trimethylsilyl)ethoxy)methyl)-1H-indole-5-carbonitrile (Intermediate 37) and (3-methyl-4-(methylsulfonyl)phenyl)boronic acid | D, J2 |
| 46 | 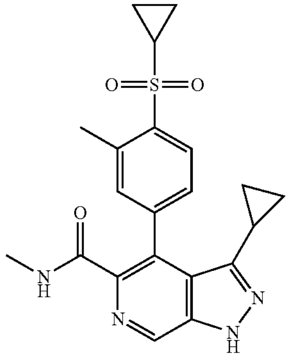 [SMILES: CNC(=O)c1ncc2[nH]nc(C3CC3)c2c1-c1ccc(S(=O)(=O)C2CC2)c(C)c1] | 3-cyclopropyl-4-(4-cyclopropylsulfonyl-3-methyl-phenyl)-N-methyl-1H-pyrazolo[3,4-c]pyridine-5-carboxamide | $[M + H]^+$ 411.2 | 4-bromo-3-cyclopropyl-N-methyl-1H-pyrazolo[3,4-c]pyridine-5-carboxamide (Intermediate 15) and 2-(4-(cyclopropylsulfonyl)-3-methylphenyl)-4,4,5,5-tetramethyl-1,3,2-dioxaborolane (Intermediate 18) | D |
| 47 | 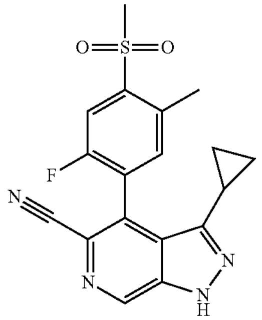 [SMILES: Cc1cc(-c2c(C#N)ncc3[nH]nc(C4CC4)c23)c(F)cc1S(C)(=O)=O] | 3-cyclopropyl-4-(2-fluoro-5-methyl-4-methylsulfonyl-phenyl)-1H-pyrazolo[3,4-c]pyridine-5-carbonitrile | $[M + H]^+$ 371.0 | 4-bromo-3-cyclopropyl-1H-pyrazolo[3,4-c]pyridine-5-carbonitrile (Intermediate 5) and 2-(2-fluoro-5-methyl-4-methylsulfonyl-phenyl)-4,4,5,5-tetramethyl-1,3,2-dioxaborolane (Intermediate 25) | D |

-continued

| Ex. No. | Structure | Product Name | Mol. weight found | From Intermediates | Prep. |
|---|---|---|---|---|---|
| 48 | 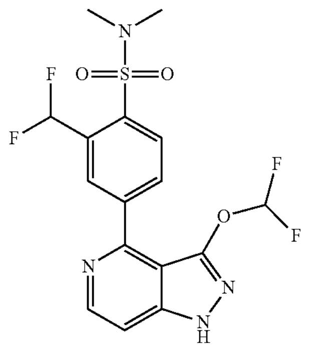 [SMILES: CN(C)S(=O)(=O)c1ccc(-c2nccc3[nH]nc(OC(F)F)c23)cc1C(F)F] | 4-[3-(difluoromethoxy)-1H-pyrazolo[4,3-c]pyridin-4-yl]-2-(difluoromethvl)-N,N-dimethyl-benzenesulfonamide | $[M + H]^+$ 419.1 | 4-chloro-3-(difluoromethoxy)-1-trityl-pyrazolo[4,3-c]pyridine (Intermediate 8) and 2-(difluoromethyl)-N,N-dimethyl-4-(4,4,5,5-tetramethyl-1,3,2-dioxaborolan-2-yl)benzenesulfonamide(Intermediate 38) | D, H |
| 49 | 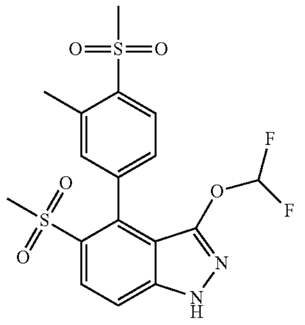 [SMILES: Cc1cc(-c2c(S(C)(=O)=O)ccc3[nH]nc(OC(F)F)c23)ccc1S(C)(=O)=O] | 3-(difluoromethoxy)-4-(3-methyl-4-(methylsulfonyl) phenyl)-5-(methylsulfonyl)-1H-indazole | $[M + H]^+$ 430.1 | 4-bromo-3-(difluoromethoxy)-5-(methylsulfonyl)-1-trityl-1H-indazole (Intermediate 16) and (3-methyl-4-(methylsulfonyl) phenyl)boronic acid | D, H |
| 50 | 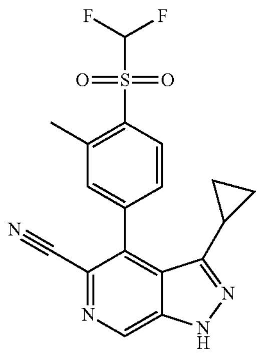 [SMILES: Cc1cc(-c2c(C#N)ncc3[nH]nc(C4CC4)c23)ccc1S(=O)(=O)C(F)F] | 3-cyclopropyl-4-[4-(difluoromethyl-sulfonyl)-3-methyl-phenyl]-1H-pyrazolo[3,4-c]pyridine-5-carbonitrile | $[M + H]^+$ 389.0 | 4-bromo-3-cyclopropyl-1H-pyrazolo[3,4-c]pyridine-5-carbonitrile (Intermediate 5) and -[4-(difluoromethyl-sulfonyl)-3-methyl-phenyl]-4,4,5,5-tetramethyl-1,3,2-dioxaborolane (Intermediate 27) | D |
| 51 | 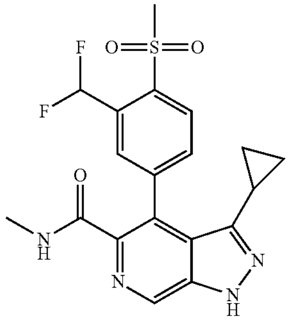 [SMILES: CNC(=O)c1ncc2[nH]nc(C3CC3)c2c1-c1ccc(S(C)(=O)=O)c(C(F)F)c1] | 3-cyclopropyl-4-[3-(difluoromethyl)-4-methylsulfonyl-phenyl]-N-methyl-1H-pyrazolo[3,4-c]pyridine-5-carboxamide | $[M + H]^+$ 421.2 | 4-bromo-3-cyclopropyl-N-methyl-1H-pyrazolo[3,4-c]pyridine-5-carboxamide (Intermediate 15) and 2-(3-(difluoromethyl)-4-(methylsulfonyl) phenyl)-4,4,5,5-tetramethyl-1,3,2-dioxaborolane (Intermediate 21) | D |

-continued

| Ex. No. | Structure | Product Name | Mol. weight found | From Intermediates | Prep. |
|---|---|---|---|---|---|
| 52 | 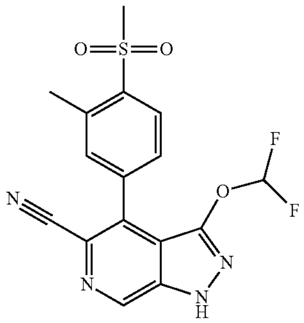 [SMILES: Cc1cc(-c2c(C#N)ncc3[nH]nc(OC(F)F)c23)ccc1S(C)(=O)=O] | 3-(difluoromethoxy)-4-(3-methyl-4-methylsulfonyl-phenyl)-1H-pyrazolo[3,4-c]pyridine-5-carbonitrile | $[M + H]^+$ 379.1 | 4-bromo-3-(difluoromethoxy)-1-trityl-pyrazolo[3,4-c]pyridine-5-carbonitrile (Intermediate 17) and (3-methyl-4-(methylsulfonyl) phenyl)boronic acid | D, H |
| 53 | 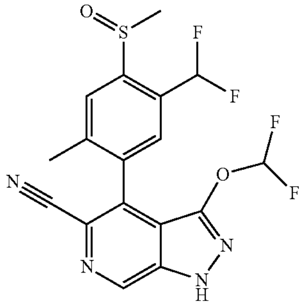 [SMILES: Cc1cc(S(C)=O)c(C(F)F)cc1-c1c(C#N)ncc2[nH]nc(OC(F)F)c12] | 3-(difluoromethoxy)-4-[5-(difluoromethyl)-2-methyl-4-methylsulfinyl-phenyl]-1H-pyrazolo[3,4-c]pyridine-5-carbonitrile | $[M + H]^+$ 413.1 | 4-bromo-3-(difluoromethoxy)-1-trityl-pyrazolo[3,4-c]pyridine-5-carbonitrile (Intermediate 17) and 4-bromo-3-(difluoromethoxy)-1-trityl-pyrazolo[3,4-c]pyridine-5-carbonitrile (Intermediate 35) | D, H |
| 54 | 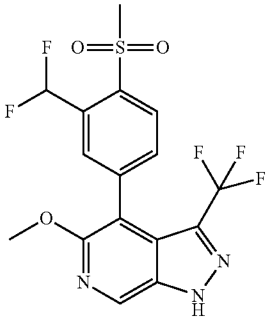 [SMILES: COc1ncc2[nH]nc(C(F)(F)F)c2c1-c1ccc(S(C)(=O)=O)c(C(F)F)c1] | 4-[3-(difluoromethyl)-4-methylsulfonyl-phenyl]-5-methoxy-3-(trifluoromethyl)-1H-pyrazolo[3,4-c]pyridine | $[M + H]^+$ 422.2 | 4-bromo-5-methoxy-3-(trifluoromethyl)-2-((2-(trimethylsilyl) ethoxy)methyl)-2H-pyrazolo[3,4-c]pyridine (Intermediate 11) 2-(3-(difluoromethyl)-4-(methylsulfonyl) phenyl)-4,4,5,5-tetramethyl-1,3,2-dioxaborolane (Intermediate 21) | D, J |
| 55 | 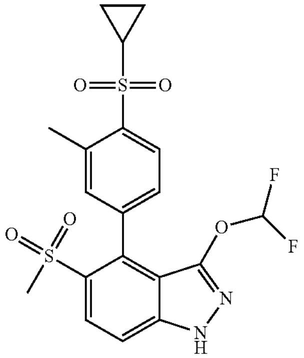 [SMILES: Cc1cc(-c2c(S(C)(=O)=O)ccc3[nH]nc(OC(F)F)c23)ccc1S(=O)(=O)C1CC1] | 4-(4-cyclopropylsulfonyl-3-methyl-phenyl)-3-(difluoromethoxy)-5-methylsulfonyl-1H-indazole | $[M + H]^+$ 457.1 | 4-bromo-3-(difluoromethoxy)-5-methylsulfonyl-1-trityl-indazole (Intermediate 36) and 2-(4-(cyclopropyl-sulfonyl)-3-methylphenyl)-4,4,5,5-tetramethyl-1,3,2-dioxaborolane (Intermediate 18) | D, J |

Example 56: 3-bromo-4-(3-methyl-4-(methylsulfonyl)phenyl)-1H-pyrazolo[4,3-c]pyridine

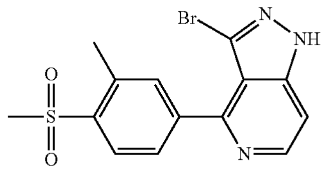 [SMILES: Cc1cc(-c2nccc3[nH]nc(Br)c23)ccc1S(C)(=O)=O]

Step 1: 4-(3-methyl-4-(methylsulfonyl)phenyl)-1-(tetrahydro-2H-pyran-2-yl)-1H-pyrazolo[4,3-c]pyridine 4-chloro-1-(tetrahydro-2H-pyran-2-yl)-1H-pyrazolo[4,3-c]pyridine (CAS: 1416713-66-0, US2014/128374 A1) is reacted with (3-methyl-4-(methylsulfonyl)phenyl)boronic acid (1.1 eq) at 100° C. using General procedure D. ([M+H]$^+$372.2).

Step 2: 4-(3-methyl-4-(methylsulfonyl)phenyl)-1H-pyrazolo[4,3-c]pyridine 4-(3-Methyl-4-(methylsulfonyl)phenyl)-1-(tetrahydro-2H-pyran-2-yl)-1H-pyrazolo[4,3-c]pyridine (step 1) (40 mg, 0.1 mmol) was dissolved in dioxane/DCM (2.0/0.5 ml) and HCl (50 µL, 4 N in dioxane, 0.2 mmol) was added. The reaction was stirred for 16 h after which time it was washed with saturated aqueous sodium hydrogen carbonate, water, brine, dried ($Na_2SO_4$) and concentrated to afford the title compound (23 mg, 67%) as an off-white solid. ([M+H]$^+$288.1).

Step 3: 3-bromo-4-(3-methyl-4-(methylsulfonyl)phenyl)-1H-pyrazolo[4,3-c]pyridine 4-(3-methyl-4-(methylsulfonyl)phenyl)-1H-pyrazolo[4,3-c]pyridine (step 2) (23 mg, 0.1 mmol) was suspended in DCM (1.5 ml) and N-bromosuccinimide (14 mg, 0.1 mmol) was added. The reaction was stirred for 2 h after which time it was concentrated to dryness. Flash column chromatography (Ethyl acetate: n-Heptane 4:6-1:0) afforded the title compound (185 mg, 71%) as a white solid. ([M+H, Br]$^+$366.1).

Example 57 & 58: 3-(difluoromethoxy)-4-(3-methyl-4-(methylsulfonyl)phenyl)-1H-pyrazolo[4,3-c]pyridinepyridine & 3-methoxy-4-(3-methyl-4-(methylsulfonyl)phenyl)-1H-pyrazolo[4,3-c]pyridine

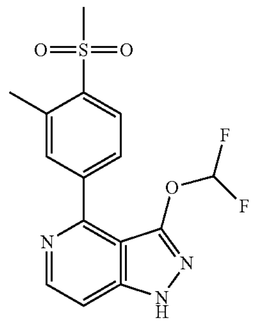

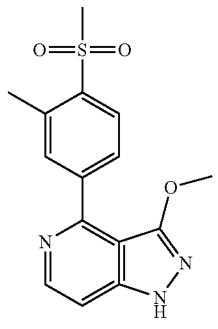

Step 1: 4-chloro-1,2-dihydro-3H-pyrazolo[4,3-c]pyridin-3-one

Ethyl 2-chloro-4-fluoronicotinate was reacted with hydrazine hydrate (1 eq) and triethylamine (1 eq) in ethanol at 80° C. in accordance with General procedure C to afford the title compound. ([M+H,Cl]$^+$170.0).

Step 2: 4-chloro-1-trityl-1H-pyrazolo[4,3-c]pyridin-3-ol 4-chloro-1,2-dihydro-3H-pyrazolo[4,3-c]pyridin-3-one (20 mg, 0.1 mmol) in DMF (1 mL) was added sodium hydride (6 mg, 60% dispersion in mineral oil, 0.1 mmol) and triphenylmethyl chloride (33 mg, 0.1 mmol) at 0° C. under nitrogen atmosphere. The cooling bath was removed and the reaction stirred for 2 h on reaching ambient temperature. The reaction was quenched by addition of saturated aqueous ammonium chloride, repeatedly extracted with ethyl acetate and the combined organic extracts washed with brine and concentrated. Flash column chromatography (Ethyl acetate: n-Heptane 1:1) afforded the title compound (19 mg, 37%) as a light yellow solid. ([M+H]$^+$412.3).

Step 3: 4-(3-methyl-4-(methylsulfonyl)phenyl)-1-trityl-1H-pyrazolo[4,3-c]pyridin-3-ol The title compound ([M+H]$^+$546.2) was prepared from Suzuki coupling of 4-chloro-1-trityl-1H-pyrazolo[4,3-c]pyridin-3-ol (step 2) and (3-methyl-4-(methylsulfonyl)phenyl)boronic acid with potassium carbonate at 100° C. in accordance with General procedure D.

Step 4: 3-(difluoromethoxy)-4-(3-methyl-4-(methylsulfonyl)phenyl)-1-trityl-1H-pyrazolo[4,3-c]pyridine & 3-methoxy)-4-(3-methyl-4-(methylsulfonyl)phenyl)-1-trityl-1H-pyrazolo[4,3-c]pyridine To a mixture of 4-(3-methyl-4-(methylsulfonyl)phenyl)-1-trityl-1H-pyrazolo[4,3-c]pyridin-3-ol (step 3) (51 mg, 0.1 mmol) and potassium carbonate (39 mg, 0.3 mmol) in DMF (1.5 mL) was added methyl 2-chloro-2,2-difluoroacetate (20 µL, 0.2 mmol). The reaction was stirred in a sealed tube at 80° C. for 30 min. The reaction was diluted with ethyl acetate washed with water, brine, dried ($Na_2SO_4$) and concentrated. Flash column chromatography (Ethyl acetate: n-Heptane 0:1-1:4) afforded the titled compounds as a mixture (4:1) (27 mg, 35%) as a white solid. ([M+H]$^+$596.3 & 560.3).

Step 5: 3-(difluoromethoxy)-4-(3-methyl-4-(methylsulfonyl)phenyl)-1H-pyrazolo[4,3-c]pyridinepyridine & 3-methoxy-4-(3-methyl-4-(methylsulfonyl)phenyl)-1H-pyrazolo[4,3-c]pyridine The mixture of 3-(difluoromethoxy)-4-(3-methyl-4-(methylsulfonyl)phenyl)-1-trityl-1H-pyrazolo[4,3-c]pyridine and 3-methoxy-4-(3-methyl-4-(methylsulfonyl)phenyl)-1-trityl-1H-pyrazolo[4,3-c]pyridine (step 4) is deprotected using General procedure H to afford the titled compounds, separate by preparative reversed phase HPLC. ([M+H]$^+$354.1 & 318.2).

Example 59: 5-(3-cyclopropyl-1H-pyrazolo[4,3-c]pyridin-4-yl)-2-(methylsulfonyl)aniline

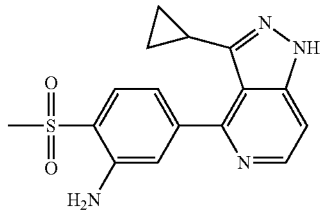 [SMILES: CS(=O)(=O)c1ccc(-c2nccc3[nH]nc(C4CC4)c23)cc1N]

Step 1: 3-cyclopropyl-4-(3-fluoro-4-(methylsulfonyl)phenyl)-1H-pyrazolo[4,3-c]pyridine The title compound ([M+H]$^+$332.1) was prepared from Suzuki coupling of 4-chloro-3-cyclopropyl-1H-pyrazolo[4,3-c]pyridine (Intermediate 1) and (3-methyl-4-(methylsulfonyl)phenyl)boronic acid with cesium carbonate at 100° C. in accordance with General procedure D.

Step 2: 5-(3-cyclopropyl-1H-pyrazolo[4,3-c]pyridin-4-yl)-2-(methylsulfonyl)aniline In a pressure tube was added 3-cyclopropyl-4-(3-fluoro-4-(methylsulfonyl)phenyl)-1H-pyrazolo[4,3-c]pyridine (step 1) (30 mg, 0.1 mmol) was condensed ammonia (approx 3 mL) at −78° C. Then the tube was tightly closed and then allowed to warm up to ambient temperature and stirred for 8 days. Evaporation of the ammonia and flash column chromatography (Ethyl acetate: n-Heptane 1:1-1:0) afforded the titled compound (6 mg, 21%) as a white solid. ([M+H]$^+$ 329.1).

Example 60: 4-(3-methyl-4-(methylsulfonyl)phenyl)-3-(methylsulfonyl)-1H-pyrazolo[4,3-c]pyridine

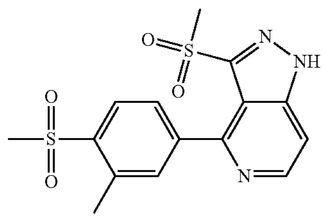 [SMILES: Cc1cc(-c2nccc3[nH]nc(S(C)(=O)=O)c23)ccc1S(C)(=O)=O]

Step 1: 3-bromo-4-(3-methyl-4-(methylsulfonyl)phenyl)-1-(tetrahydro-2H-pyran-2-yl)-1H-pyrazolo[4,3-c]pyridine To a mixture of 3-bromo-4-(3-methyl-4-(methylsulfonyl)phenyl)-1H-pyrazolo[4,3-c]pyridine (Product 56) (648 mg, 1.8 mmol) in THF (20 ml) was added 3,4-dihydro-2H-pyran (1.6 ml, 17.7 mmol) and p-toluenesulfonic acid monohydrate (34 mg, 0.2 mmol) and the reaction mixture was stirred at 70° C. for 36 h. after which time it was concentrated in vacuo. The residue was redissolved with ethyl acetate and washed with water, dried ($Na_2SO_4$) and concentrated. Flash column chromatography (DCM: MeOH 1:0-9:1) afforded the titled compound (689 mg, 78%) as a yellow solid. ([M+H]$^+$452.1).

Step 2: 4-(3-methyl-4-(methylsulfonyl)phenyl)-3-(methylthio)-1-(tetrahydro-2H-pyran-2-yl)-1H-pyrazolo[4,3-c]pyridine 3-bromo-4-(3-methyl-4-(methylsulfonyl)phenyl)-1-(tetrahydro-2H-pyran-2-yl)-1H-pyrazolo[4,3-c]pyridine (step 1) (102 mg, 0.2 mmol) was dissolved in DMSO (2.5 ml). 2-methyl-2 thiopsuedourea sulfate (63 mg, 0.2 mmol) and cesium carbonate (295 mg, 0.9 mmol) were added. The reaction mixture was heated to 100° C. for 15 h. The reaction mixture was allowed to cool down to RT, then silica gel was added. The suspension was concentrated in high vacuo. The crude mixture was purified by flash column chromatography (Ethyl acetate: n-Heptane 0:1-1:0) to afford the title compound (40 mg, 42% yield) as a light yellow gum. ([M+H]$^+$ 418.1).

Step 3: 4-(3-methyl-4-(methylsulfonyl)phenyl)-3-(methylthio)-1-(tetrahydro-2H-pyran-2-yl)-1H-pyrazolo[4,3-c]pyridine 4-(3-methyl-4-(methylsulfonyl)phenyl)-3-(methylthio)-1-(tetrahydro-2H-pyran-2-yl)-1H-pyrazolo[4,3-c]pyridine (step 2) was oxidised to the title compound using General procedure G. ([M+H]$^+$450.2).

Step 4: 4-(3-methyl-4-(methylsulfonyl)phenyl)-3-(methylsulfonyl)-1H-pyrazolo[4,3-c]pyridine 4-(3-Methyl-4-(methylsulfonyl)phenyl)-3-(methylthio)-1-(tetrahydro-2H-pyran-2-yl)-1H-pyrazolo[4,3-c]pyridine (Step 3) was deprotected using General procedure I to afford the title compound. ([M+H]$^+$366.0).

Example 61: 4-(3-methyl-4-(methylsulfonyl)phenyl)-1H-pyrazolo[4,3-c]pyridine-3-carbonitrile

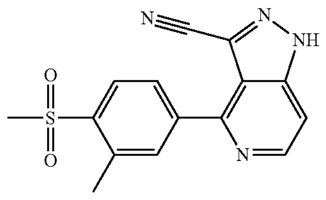 [SMILES: Cc1cc(-c2nccc3[nH]nc(C#N)c23)ccc1S(C)(=O)=O]

Step 1: 4-(3-methyl-4-(methylsulfonyl)phenyl)-1-(tetrahydro-2H-pyran-2-yl)-1H-pyrazolo[4,3-c]pyridine-3-carbonitrile 3-Bromo-4-(3-methyl-4-(methylsulfonyl)phenyl)-1-(tetrahydro-2H-pyran-2-yl)-1H-pyrazolo[4,3-c]pyridine (Intermediate 60, step 1) (40 mg, 0.1 mmol), zinc cyanide (10 mg, 0.1 mmol) and tetrakistriphenylphosphine palladium (15 mg, 0.01 mmol) were suspended in DMF (1 ml) at ambient temperature. The reaction mixture was heated to 150° C. for 0.5 h in a microwave reactor. Silica gel was added to the reaction mixture and concentrated. The crude mixture was purified by flash column chromatography (Ethyl acetate: n-Heptane 0:1-1:0) to afford the title compound (16 mg, 44% yield) as a yellow solid. ([M+H]$^+$397.2).

Step 2: 4-(3-methyl-4-(methylsulfonyl)phenyl)-1H-pyrazolo[4,3-c]pyridine-3-carbonitrile 4-(3-methyl-4-(methylsulfonyl)phenyl)-1-(tetrahydro-2H-pyran-2-yl)-1H-pyrazolo[4,3-c]pyridine-3-carbonitrile (step 1) was deprotected using General procedure I to afford the title compound. ([M+H]$^+$313.1).

Example 62: 3-cyclopropyl-4-(3-methyl-4-(methylsulfonyl)phenyl)-1H-pyrazolo[3,4-c]pyridine-5-carboxylic acid

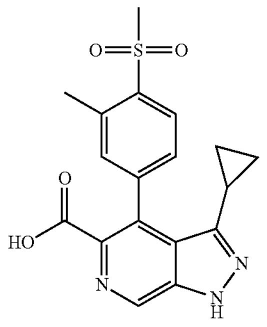 [SMILES: Cc1cc(-c2c(C(=O)O)ncc3[nH]nc(C4CC4)c23)ccc1S(C)(=O)=O]

3-Cyclopropyl-4-(3-methyl-4-(methylsulfonyl)phenyl)-1H-pyrazolo[3,4-c]pyridine-5-carbonitrile (Example 16) (20 mg, 0.1 mmol) was suspended in aqueous sodium hydroxide solution (0.5 ml, 6 M, 3.0 mmol) an the mixture was heated to 100° C. for 16 h. The reaction was cooled to ambient temperature, acidified with 37% HCl and concentrated. Purification by reversed phase preparative HPLC afforded the title compound (8 mg, 36% yield) as a white solid. ([M+H]+372.2).

Example 63: 3-cyclopropyl-4-(3-methyl-4-methylsulfonylphenyl)-1H-indazole-5-carbonitrile

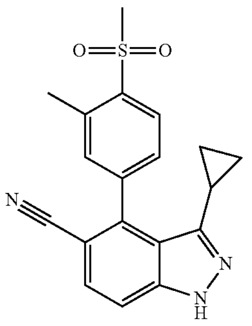 [SMILES: Cc1cc(-c2c(C#N)ccc3[nH]nc(C4CC4)c23)ccc1S(C)(=O)=O]

Step 1: 2-bromo-3-(cyclopropyl(hydroxy)methyl)-4-fluorobenzonitrile 2-bromo-4-fluorobenzonitrile is treated with with LDA (1.3 eq) for 10 minutes before addition of cyclopropanecarbaldehyde (1.4 eq) in accordance with General procedure A. $^1$H NMR (CHLOROFORM-d, 300 MHz) δ 7.62 (dd, 1H, J=5.2, 8.7 Hz), 7.1-7.2 (m, 1H), 4.4-4.6 (m, 1H), 2.4-2.6 (m, 1H), 1.5-1.6 (m, 1H), 0.7-0.8 (m, 1H), 0.5-0.6 (m, 3H)

Step 2: 2-bromo-3-(cyclopropanecarbonyl)-4-fluorobenzonitrile

2-Bromo-3-(cyclopropyl(hydroxy)methyl)-4-fluorobenzonitrile was oxidised using General procedure B1 to afford the title compound. 1H NMR (CHLOROFORM-d, 300 MHz) δ 7.7-7.8 (m, 1H), 7.2-7.3 (m, 1H), 2.24 (dtt, 1H, J=1.0, 4.5, 7.8 Hz), 1.4-1.5 (m, 2H), 1.2-1.3 (m, 2H)

Step 3: 3-(cyclopropanecarbonyl)-4-fluoro-2-(3-methyl-4-methylsulfonylphenyl)benzonitrile The title compound ([M+H]$^+$358.2) was prepared from Suzuki coupling of 2-bromo-3-(cyclopropanecarbonyl)-4-fluorobenzonitrile (Step 2) and (3-methyl-4-(methylsulfonyl)phenyl)boronic acid with potassium carbonate at 90° C. in accordance with General procedure D.

Step 4: 3-cyclopropyl-4-(3-methyl-4-methylsulfonylphenyl)-1H-indazole-5-carbonitrile 3-(cyclopropanecarbonyl)-4-fluoro-2-(3-methyl-4-methylsulfonylphenyl)benzonitrile (step 3) was reacted with hydrazine hydrate (5 eq) in THF at ambient temperature in accordance with General procedure C to afford the title compound. ([M+H]$^+$352.3).

Example 64: 3-cyclopropyl-4-(3-methyl-4-methylsulfonyl-phenyl)-1H-pyrazolo[4,3-c]pyridin-7-ol

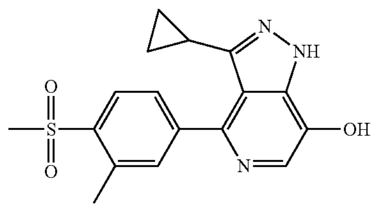 [SMILES: Cc1cc(-c2ncc(O)c3[nH]nc(C4CC4)c23)ccc1S(C)(=O)=O]

Step 1: 7-bromo-3-cyclopropyl-4-(3-methyl-4-methylsulfonyl-phenyl)-1H-pyrazolo[4,3-c]pyridine A mixture of N-bromosuccinimide (109 mg, 0.6 mmol), 3-cyclopropyl-4-(3-methyl-4-methylsulfonyl-phenyl)-1H-pyrazolo[4,3-c]pyridine (Example 1) (100 mg, 0.3 mmol) in DMF (2 mL) was stirred at 80° C. for 24 h. The reaction was directly purified by preparative reversed phase HPLC afforded the title compound (30 mg, 24%) as a green solid. ([M+H, Br]$^+$405.8).

Step 2: 3-cyclopropyl-4-(3-methyl-4-methylsulfonyl-phenyl)-1H-pyrazolo[4,3-c]pyridin-7-ol To a mixture of 7-bromo-3-cyclopropyl-4-(3-methyl-4-methylsulfonyl-phenyl)-1H-pyrazolo [4,3-c]pyridine (step 3) (60 mg, 0.2 mmol), potassium hydroxide (33 mg, 0.6 mmol), $Pd_2$(dba)2 (5 mg, 0.03 mmol,), tBuXPhos (4 mg, 0.01 mmol, 0.060 eq) in dioxane (1.5 mL) and water (1 mL) and the mixture stirred at 90° C. for 1 h under nitrogen atmosphere. The reaction mixture was filtered and concentrated. Purification by preparative reversed phase HPLC afforded the title compound (6 mg, 10%) as a yellow solid. ([M+H]$^+$343.9)

Example 65: 4-(3-methyl-4-(methylsulfonyl)phenyl)-3-(thiophen-3-yl)-1H-pyrazolo[4,3-c]pyridine

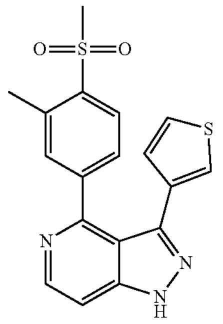 [SMILES: Cc1cc(-c2nccc3[nH]nc(-c4ccsc4)c23)ccc1S(C)(=O)=O]

Step 1: 4-(3-methyl-4-(methylsulfonyl)phenyl)-1-(tetrahydro-2H-pyran-2-yl)-3-(thiophen-3-yl)-1H-pyrazolo[4,3-c]pyridine 3-bromo-4-(3-methyl-4-(methylsulfonyl)phenyl)-1-(tetrahydro-2H-pyran-2-yl)-1H-pyrazolo[4,3-c]pyridine (Intermediate 60, step 1) is reacted with thiophene-3-boronic acid using potassium carbonate as base at 90° C. in accordance with General procedure D. ([M+H]$^+$454.2).

Step 2: 4-(3-methyl-4-(methylsulfonyl)phenyl)-3-(thiophen-3-yl)-1H-pyrazolo[4,3-c]pyridine 4-(3-methyl-4-(methylsulfonyl)phenyl)-1-(tetrahydro-2H-pyran-2-yl)-3-(thiophen-3-yl)-1H-pyrazolo[4,3-c]pyridine (step 1) was deprotected using General procedure I2 to afford the title compound. ([M+H]$^+$370.2).

Example 66: 3-ethoxy-4-(3-methyl-4-methylsulfonyl-phenyl)-1H-pyrazolo[4,3-c]pyridine

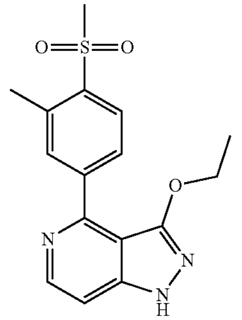 [SMILES: CCOc1n[nH]c2ccnc(-c3ccc(S(C)(=O)=O)c(C)c3)c12]

Step 1: 3-ethoxy-4-(3-methyl-4-methylsulfonyl-phenyl)-1-trityl-pyrazolo[4,3-c]pyridine To a solution of 4-(3-methyl-4-methylsulfonyl-phenyl)-1-trityl-pyrazolo[4,3-c]pyridin-3-ol (Example 57, step 3) (100 mg, 0.2 mmol) in acetonitrile (2 mL) was added cesium carbonate (120 mg, 0.4 mmol) and iodoethane (0.04 mL, 0.6 mmol) and the reaction mixture was stirred at 80° C. for 2 h. The reaction was filtered and concentrated. Purification by preparative-TLC (heptane: ethyl acetate 3:1) to afford the title compound (60 mg, 54%) as a white solid. ([M+H]$^+$ 574.3).

Step 2: 3-ethoxy-4-(3-methyl-4-methylsulfonyl-phenyl)-1H-pyrazolo[4,3-c]pyridine 3-Ethoxy-4-(3-methyl-4-methylsulfonyl-phenyl)-1-trityl-pyrazolo[4,3-c]pyridine is deprotected using General procedure H to afford the titled compound. ([M+H]$^+$332.1).

Example 67: 3-cyclopropyl-7-fluoro-4-(3-methyl-4-methylsulfonyl-phenyl)-1H-pyrazolo[4,3-c]pyridine

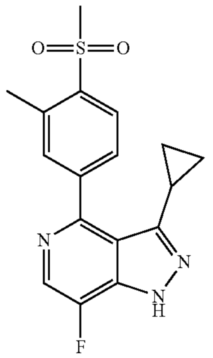 [SMILES: Cc1cc(-c2ncc(F)c3[nH]nc(C4CC4)c23)ccc1S(C)(=O)=O]

Step 1: 2-bromo-4-chloro-5-fluoro-3-pyridyl)-cyclopropyl-methanol 2-bromo-4-chloro-5-fluoro-pyridine was reacted with LDA (1.2 eq) for 30 minutes before addition of cyclopropanecarbaldehyde (1.4 eq) in accordance with General procedure A. ([M+H, Br]$^+$280.0)

Step 2: 2-bromo-4-chloro-5-fluoro-3-pyridyl)-cyclopropyl-methanone 2-bromo-4-chloro-5-fluoro-3-pyridyl)-cyclopropyl-methanol was oxidised using General procedure B1 to afford the title compound. ([M+H, Br]$^+$278.0)

Step 3: [4-chloro-5-fluoro-2-(3-methyl-4-methylsulfonyl-phenyl)-3-pyridyl]-cyclopropyl-methanone The title compound ([M+H]$^+$368.1) was prepared from Suzuki coupling 2-bromo-4-chloro-5-fluoro-3-pyridyl)-cyclopropyl-methanone (step 2) and (3-methyl-4-(methylsulfonyl)phenyl)boronic acid with potassium carbonate at 100° C. in accordance with General procedure D.

Step 4: 3-cyclopropyl-7-fluoro-4-(3-methyl-4-methylsulfonyl-phenyl)-1H-pyrazolo[4,3-c]pyridine 4-chloro-5-fluoro-2-(3-methyl-4-methylsulfonyl-phenyl)-3-pyridyl]-cyclopropyl-methanone (step 3) was reacted with hydrazine hydrate (5 eq) in dioxane at 60° C. in accordance with General procedure C to afford the title compound. ([M+H]$^+$346.1).

Example 68 & 69: 3-methoxy-4-(3-methyl-4-(methylsulfonyl)phenyl)-1H-indazole-5-carbonitrile & 3-(difluoromethoxy)-4-(3-methyl-4-(methylsulfonyl)phenyl)-1H-indazole-5-carbonitrile

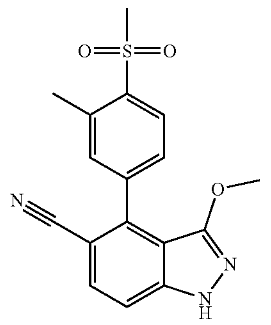

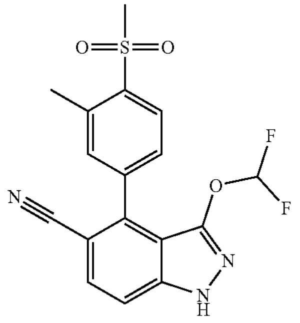

Step 1: ethyl 2-bromo-3-cyano-6-fluorobenzoate

2-Bromo-4-fluorobenzonitrile was deprotonated with LDA (1.2 eq) for 0.5 h and reacted with ethyl chloroformate (1.2 eq) for 0.5 h in accordance with General procedure A to afford the title compound. 1H NMR (300 MHz, DMSO-d6) δ ppm 8.21 (dd, J=8.86, 5.64 Hz, 1 H) 7.70 (t, J=8.76 Hz, 1 H) 4.44 (q, J=7.05 Hz, 2 H) 1.34 (t, J=7.05 Hz, 3 H).

Step 2: 4-bromo-3-oxo-2,3-dihydro-1H-indazole-5-carbonitrile

Ethyl 2-bromo-3-cyano-6-fluorobenzoate (Step 1) was reacted with hydrazine hydrate (1 eq) and triethylamine (1 eq) in ethanol at 80° C. in accordance with General procedure C to afford the title compound. ([M+H, Br]$^+$240.0).

Step 3: 4-bromo-3-hydroxy-1-trityl-1H-indazole-5-carbonitrile 4-bromo-3-oxo-2,3-dihydro-1H-indazole-5-carbonitrile (step 2) (180 mg, 0.8 mmol) in DMF (5 mL) was added sodium hydride (36 mg, 60% dispersion in mineral oil, 0.9 mmol) and triphenylmethyl chloride (232 mg, 0.8 mmol) at 0° C. under nitrogen atmosphere. The cooling bath was removed and the reaction stirred for 2 h on reaching ambient temperature. The reaction was diluted with ethyl acetate, washed with saturated aqueous ammonium chloride, brine, dried ($Na_2SO_4$) and concentrated. Flash column chromatography (Ethyl acetate: n-Heptane 0:1-1:1) afforded the title compound (136 mg, 36%) as a white solid. ([M+Na]$^+$502.1).

Step 4: 3-hydroxy-4-(3-methyl-4-(methylsulfonyl)phenyl)-1-trityl-1H-indazole-5-carbonitrile The title compound ([M−H]$^-$568.4) was prepared from Suzuki coupling of 4-bromo-3-hydroxy-1-trityl-1H-indazole-5-carbonitrile (step 3) and (3-methyl-4-(methylsulfonyl)phenyl)boronic acid with cesium carbonate at 100° C. in accordance with General procedure D. Step 5: 3-methoxy-4-(3-methyl-4-(methylsulfonyl)phenyl)-1H-indazole-5-carbonitrile & 3-(difluoromethoxy)-4-(3-methyl-4-(methylsulfonyl)phenyl)-1H-indazole-5-carbonitrile To a mixture of 3-hydroxy-4-(3-methyl-4-(methylsulfonyl)phenyl)-1-trityl-1H-indazole-5-carbonitrile (step 3) (49 mg, 0.1 mmol) and potassium carbonate (48 mg, 0.3 mmol) in DMF (1 mL) was added methyl 2-chloro-2,2-difluoroacetate (20 μL, 0.2 mmol). The reaction was stirred in a sealed tube at 80° C. for 50 min. The reaction was diluted with ethyl acerate washed with water, brine, dried ($Na_2SO_4$) and concentrated to afford the 3-(difluoromethoxy)-4-(3-methyl-4-(methylsulfonyl)phenyl)-1-trityl-1H-indazole-5-carbonitrile & 3-methoxy-4-(3-methyl-4-(methylsulfonyl)phenyl)-1-trityl-1H-indazole-5-carbonitrile as a crude mixture used directly.

The mixture of 3-(difluoromethoxy)-4-(3-methyl-4-(methylsulfonyl)phenyl)-1-trityl-1H-indazole-5-carbonitrile & 3-methoxy-4-(3-methyl-4-(methylsulfonyl)phenyl)-1-trityl-1H-indazole-5-carbonitrile (step 4) is deprotected using General procedure H to afford the titled compounds, separated by preparative reversed phase HPLC. ([M+H]$^+$342.2 & 378.2).

Example 70: 3-cyclopropyl-6-methoxy-4-(3-methyl-4-methylsulfonylphenyl)-1H-pyrazolo[4,3-c]pyridine

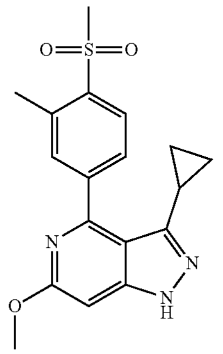 [SMILES: COc1cc2[nH]nc(C3CC3)c2c(-c2ccc(S(C)(=O)=O)c(C)c2)n1]

Step 1: cyclopropyl(2,4,6-trichloropyridin-3-yl)methanone 2,4,6-Trichloropyridine was deprotonated with LDA (0.9 eq) for 1 h and reacted with cyclopropanecarbaldehyde (1.2 eq) for 1.5 h in accordance with General procedure A to afford crude cyclopropyl(2,4,6-trichloropyridin-3-yl)methanol which was directly oxidised was oxidised using General procedure B1 to afford the title compound. ([M+H, Cl]$^+$ 250.1)

Step 2: 4,6-dichloro-3-cyclopropyl-1H-pyrazolo[4,3-c]pyridine

Cyclopropyl(2,4,6-trichloropyridin-3-yl)methanone (step 1) was reacted with hydrazine hydrate (5 eq) in ethanol at ambient temperature in accordance with General procedure C to afford the title compound. ([M+H, Cl]$^+$228.1).

Step 3: 3-cyclopropyl-6-methoxy-4-(3-methyl-4-methylsulfonylphenyl)-1H-pyrazolo[4,3-c]pyridine The title compound ([M+H, Cl]$^+$362.3) was prepared from Suzuki coupling of 4,6-dichloro-3-cyclopropyl-1H-pyrazolo[4,3-c]pyridine (step 2) and (3-methyl-4-(methylsulfonyl)phenyl)boronic acid with potassium carbonate at 100° C. in accordance with General procedure D.

Step 4: 6-chloro-3-cyclopropyl-4-(3-methyl-4-(methylsulfonyl)phenyl)-1H-pyrazolo[4,3-c]pyridine 6-chloro-3-cyclopropyl-4-(3-methyl-4-(methylsulfonyl) phenyl)-1H-pyrazolo[4,3-c]pyridine (step 3) (50 mg, 0.1 mmol) was SEM-protected using General procedure E2. The crude product was dissolved in 2 M sodium methoxide in MeOH (2 mL) and the reaction heated in a microwave to 130° C. for 30 minutes. The reaction mixture was concentrated, redissolved in trifluoroacetic acid (1 mL), ethylenediamine (0.1 ml, 1.4 mmol) was added and the mixture stirred for 1 h. The reaction was concentrated, the residue purified by reversed phase chromatography to afford the title compound (3 mg, 5%) as a white solid. ([M+H]$^+$358.2).

Example 71: 4-(3-methyl-4-(methylsulfonyl)phenyl)-3-(trifluoromethoxy)-1H-pyrazolo[4,3-c]pyridine

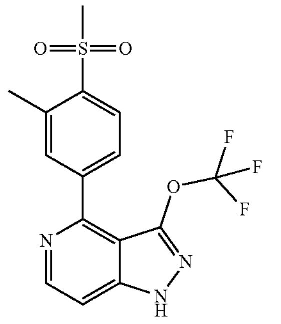 [SMILES: Cc1cc(-c2nccc3[nH]nc(OC(F)(F)F)c23)ccc1S(C)(=O)=O]

Step 1: 4-(3-methyl-4-(methylsulfonyl)phenyl)-3-(trifluoromethoxy)-1-trityl-1H-pyrazolo[4,3-c]pyridine To a mixture of 4-(3-methyl-4-(methylsulfonyl)phenyl)-1-trityl-1H-pyrazolo[4,3-c]pyridin-3-ol (Example 57, step 3) (45 mg, 0.1 mmol) and potassium carbonate (35 mg, 0.3 mmol) in DMF (0.8 mL) was added 1-(trifluoromethyl)-113-benzo[d][1,2]iodaoxol-3(1H)-one (40 mg, 0.3 mmol). The reaction at ambient temperature for 16 h after which time a second portion of potassium carbonate (35 mg, 0.3 mmol) and 1-(trifluoromethyl)-113-benzo[d][1,2]iodaoxol-3(1H)-one (40 mg, 0.3 mmol) was added and the mixture stirred for a further 16 h. The reaction was diluted with ethyl acetate, washed with water, brine, dried ($Na_2SO_4$) and concentrated. Flash column chromatography (Ethyl acetate: n-Heptane 0:1-1:4) afforded the titled compound (12 mg, 22%) as a colourless gum. ([M+H]$^+$614.4).

Step 2: 4-(3-methyl-4-(methylsulfonyl)phenyl)-3-(trifluoromethoxy)-1H-pyrazolo[4,3-c]pyridine 4-(3-methyl-4-(methylsulfonyl)phenyl)-3-(trifluoromethoxy)-1-trityl-1H-pyrazolo[4,3-c]pyridine (step 1) is deprotected using General procedure H to afford the title compound. ([M+H]$^+$372.2).

Example 72: 3-cyclopropyl-4-(3-methyl-4-(methylsulfonyl)phenyl)-1H-pyrazolo[3,4-c]pyridine-5-carboxamide

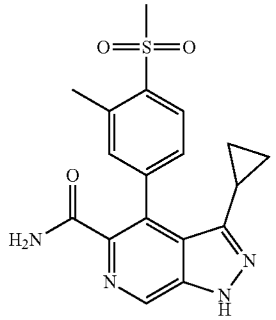 [SMILES: Cc1cc(-c2c(C(N)=O)ncc3[nH]nc(C4CC4)c23)ccc1S(C)(=O)=O]

Step 1: 3-cyclopropyl-4-(3-methyl-4-(methylsulfonyl)phenyl)-1-(tetrahydro-2H-pyran-2-yl)-1H-pyrazolo[3,4-c]pyridine-5-carboxylic acid To a solution of 3-cyclopropyl-4-(3-methyl-4-(methylsulfonyl)phenyl)-1H-pyrazolo[3,4-c]pyridine-5-carboxylic acid (Example 62) (147 mg, 0.4 mmol) in dichloromethane (4 ml) was added 3,4-dihydro-2H-pyran (73 μl, 0.8 mmol) and p-toluenesulfonic acid monohydrate (15 mg, 0.1 mmol) and the reaction stirred for 7 h. Concentration of the reaction afforded the crude title compound (181 mg, quant) as a brown foam. ([M+H]$^+$456.3).

Step 2: 3-cyclopropyl-4-(3-methyl-4-(methylsulfonyl)phenyl)-1H-pyrazolo[3,4-c]pyridine-5-carboxamide To 3-cyclopropyl-4-(3-methyl-4-(methylsulfonyl)phenyl)-1-(tetrahydro-2H-pyran-2-yl)-1H-pyrazolo[3,4-c]pyridine-5-carboxylic acid (45 mg, 0.1 mmol) in DMF (1 ml) was added TBTU (48 mg, 0.2 mmol) followed by triethylamine (41 μL, 0.3 mmol). After 0.5 h ammonium hydroxide (39 μL, 1 mmol) was added and the mixture stirred for 30 min. The reaction was concentrated, redissolved in HCl (0.5 ml, 4 N in dioxane, 2 mmol) and the reaction stirred for 6 h at 50° C. after which time the reaction was again concentrated to dryness. Purification by reversed phase HPLC afforded the title compound (3 mg, 8%) as an off-white solid. ([M+H]$^+$371.3).

Example 73: 3-cyclopropyl-4-(3-methyl-4-(methylsulfonyl)phenyl)-1H-pyrazolo[3,4-c]pyridine-5-carboxamide

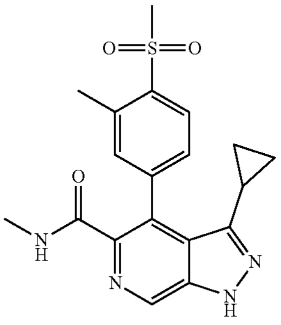 [SMILES: CNC(=O)c1ncc2[nH]nc(C3CC3)c2c1-c1ccc(S(C)(=O)=O)c(C)c1]

The title compound ([M+H]$^+$385.3) was prepared in analogy to Example 72 from 3-cyclopropyl-4-(3-methyl-4-(methylsulfonyl)phenyl)-1-(tetrahydro-2H-pyran-2-yl)-1H-pyrazolo[3,4-c]pyridine-5-carboxylic acid (Example 72, step 1) and methylamine hydrochloride.

Example 74: 3-cyclopropyl-4-(3-methyl-4-(methylsulfonyl)phenyl)-1H-pyrazolo[3,4-d]pyridazine

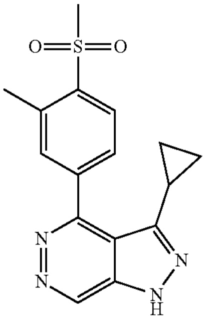 [SMILES: Cc1cc(-c2nncc3[nH]nc(C4CC4)c23)ccc1S(C)(=O)=O]

Step 1: methyl 3-cyclopropyl-1-(tetrahydro-2H-pyran-2-yl)-1H-pyrazole-5-carboxylate To a solution of methyl 3-cyclopropyl-1H-pyrazole-5-carboxylate (300 mg, 1.8 mmol) in dichloromethane (5 ml) was added 3,4-dihydro-2H-pyran (197 μl, 2.2 mmol) and p-toluenesulfonic acid monohydrate (35 mg, 0.2 mmol) and the reaction stirred for 1 h.

Concentration of the reaction and flash column chromatography (Heptane: ethyl acetate 3:7) afforded the title compound (374 mg, 82%) as a colourless oil. ([M+H]$^+$ 251.1).

Step 2: (3-cyclopropyl-1-(tetrahydro-2H-pyran-2-yl)-1H-pyrazol-5-yl)methanol

To a solution of methyl 3-cyclopropyl-1-(tetrahydro-2H-pyran-2-yl)-1H-pyrazole-5-carboxylate (step 1) (1.1 g, 4.6 mmol) in THF (34 ml) cooled to −78° C. under argon was added diisobutylaluminium hydride (9.11 ml, 1 M in THF, 9.1 mmol) and the mixture was stirred at this temperature for 30 min before coming to ambient temperature. The reaction was cooled again to −78° C. and water (0.3 ml) was added and the reaction again returned to ambient temperature, addition of $Na_2SO_4$ followed by filtration and concentrate afforded the title compound (670 mg, 63%) as a white solid. ([M+H]$^+$223.2).

Step 3: 3-cyclopropyl-1-(tetrahydro-2H-pyran-2-yl)-5-(((tetrahydro-2H-pyran-2-yl)oxy)methyl)-1H-pyrazole To a solution of (3-cyclopropyl-1-(tetrahydro-2H-pyran-2-yl)-1H-pyrazol-5-yl)methanol (step 2) (300 mg, 1.4 mmol) in DCM (5 ml) was added 3,4-dihydro-2H-pyran (136 μl, 1.6 mmol) and p-toluenesulfonic acid monohydrate (26 mg, 0.1 mmol) and the reaction stirred for 16 h. Addition of a few drops of triethylamine, concentration of the reaction and flash column chromatography (Heptane:ethyl acetate 1:1) afforded the title compound (354 mg, 66%) as a light yellow oil. ([M+H]$^+$307.1).

Step 4: 3-cyclopropyl-4-iodo-1-(tetrahydro-2H-pyran-2-yl)-5-(((tetrahydro-2H-pyran-2-yl)oxy)methyl)-1H-pyrazole To a solution of 3-cyclopropyl-1-(tetrahydro-2H-pyran-2-yl)-5-(((tetrahydro-2H-pyran-2-yl)oxy)methyl)-1H-pyrazole (step 3) (402 mg, 1.3 mmol) in dichloromethane (2.5 ml) was added N-iodosuccinimide (413 mg, 1.8 mmol) and the reaction was stirred at ambient temperature for 20 h. The reaction was diluted with dichloromethane, washed with 10% aqueous sodium thiosulfate, water, brine, dried ($Na_2SO_4$) and concentrated. Flash column chromatography (Ethyl acetate: n-Heptane 1:3) afforded the titled compound (400 mg, 68%) as a light yellow oil. ([M+H]$^+$433.1).

Step 5: (3-cyclopropyl-1-(tetrahydro-2H-pyran-2-yl)-5-(((tetrahydro-2H-pyran-2-yl)oxy)methyl)-1H-pyrazol-4-yl)(3-methyl-4-(methylsulfonyl)phenyl)methanol To an ice cold solution of 3-cyclopropyl-4-iodo-1-(tetrahydro-2H-pyran-2-yl)-5-(((tetrahydro-2H-pyran-2-yl)oxy)methyl)-1H-pyrazole (step 4) (50 mg, 0.1 mmol) in THF (0.2 ml) under argon atmosphere was added isopropylmagnesium chloride-lithium chloride complex (98 μl, 1.3 M in THF, 0.1 mmol. The reaction was warmed to ambient temperature for 5 min and then cooled back down to 0° C. before quenching with a solution of 3-methyl (methylsulfonyl)benzaldehyde (28 mg, 0.1 mmol) dissolved in THF (0.1 ml) and the reaction subsequently stirred at ambient temperature for 30 minutes. The reaction was diluted with ethyl acetate, washed with saturated ammonium chloride, water, brine, dried ($Na_2SO_4$) and concentrated. Flash column chromatography (Ethyl acetate: n-Heptane 1:9-4:1) afforded the titled compound (40 mg, 62%) as an off-white solid. ([M+H]$^+$505.4).

Step 6: (3-cyclopropyl-5-(hydroxymethyl)-1H-pyrazol-4-yl)(3-methyl-4-(methylsulfonyl)phenyl)methanol (3-cyclopropyl-1-(tetrahydro-2H-pyran-2-yl)-5-(((tetrahydro-2H-pyran-2-yl)oxy)methyl)-1H-pyrazol-4-yl)(3-methyl-4-(methylsulfonyl)phenyl)methanol (step 5) (41 mg, 0.1 mmol) was dissolved in HCl (1.0 ml, 4 N in dioxane, 4.1 mmol) and water (15 μl, 0.1 mmol) added. The reaction mixture was subsequently stirred at 45° C. for 5 min after which time it was concentrated to afford the crude title compound (40 mg, quant) as a light yellow gum. ([M+H]$^+$ 337.2).

Step 7: 3-cyclopropyl-4-(3-methyl-4-(methylsulfonyl)phenyl)-1H-pyrazolo[3,4-d]pyridazine To a solution of (3-cyclopropyl-5-(hydroxymethyl)-1H-pyrazol-4-yl)(3-methyl-4-(methylsulfonyl)phenyl)methanol (step 6) (30 mg, 0.1 mmol) in dichloromethane (0.4 ml) was added Dess-Martin periodinane (76 mg, 0.2 mmol) and the mixture was stirred at ambient temperature for 10 min. Hydrazine monohydrate (48 μl, 0.5 mmol) was then added and the reaction stirred for a further 16 h. The reaction mixture was diluted with dichloromethane and washed with saturated aqueous sodium hydrogen carbonate, water, dried ($Na_2SO_4$) and concentrated. Flash column chromatography (DCM: MeOH 1:0-1:9) afforded the title compound (3 mg, 9%) as a light yellow solid. ([M+H]$^+$329.2).

Example 75: 3-cyclopropyl-4-(3-methyl-4-(methylsulfonyl)phenyl)-5-(methylthio)-1H-indazole

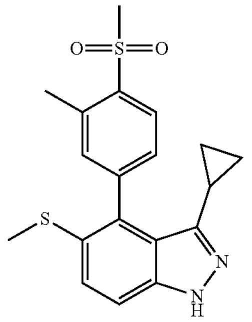 [SMILES: CSc1ccc2[nH]nc(C3CC3)c2c1-c1ccc(S(C)(=O)=O)c(C)c1]

Step 1: (2-bromo-6-fluoro-3-(methylthio)phenyl)(cyclopropyl)methanol (2-bromo-4-fluorophenyl)(methyl)sulfane was reacted with LDA (1.1 eq) for 1 h before addition of cyclopropanecarbaldehyde (1.2 eq) in accordance with General procedure A. 1H NMR (300 MHz, DMSO-d6) δ ppm 6.98-7.11 (m, 1 H) 6.91-6.98 (m, 1 H) 5.25 (d, J=4.63 Hz, 1 H) 4.15 (ddd, J=8.66, 4.53, 1.31 Hz, 1 H) 2.24 (s, 3 H) 1.16-1.35 (m, 1 H), 0.11-0.49 (m, 4 H)

Step 2: (2-bromo-6-fluoro-3-(methylthio)phenyl)(cyclopropyl)methanone (2-bromo-6-fluoro-3-(methylthio)phenyl)(cyclopropyl)methanol (step 1) was oxidised using General procedure B1 to afford the title compound. ([M+H, Br]$^+$291.0)

Step 3: cyclopropyl(3-fluoro-3'-methyl-4'-(methylsulfonyl)-6-(methylthio)-[1,1'-biphenyl]-2-yl)methanone The title compound ([M+H]$^+$379.2) was prepared from Suzuki coupling of 4,6-dichloro-3-cyclopropyl-1H-pyrazolo[4,3-c]pyridine (step 2) and (3-methyl-4-(methylsulfonyl)phenyl)boronic acid with cesium carbonate at 100° C. in accordance with General procedure D.

Step 4: 3-cyclopropyl-4-(3-methyl-4-(methylsulfonyl)phenyl)-5-(methylthio)-1H-indazole Cyclopropyl(3-fluoro-3'-methyl-4'-(methylsulfonyl)-6-(methylthio)-[1,1'-biphenyl]-2-yl)methanone (step 2) was reacted with hydrazine hydrate (15 eq) in ethanol at150° C. (microwave) in accordance with General procedure C to afford the title compound. ([M+H]$^+$373.2).

Example 76: 3-cyclopropyl-4-(3-methyl-4-(methylsulfonyl)phenyl)-5-(methylsulfinyl)-1H-indazole

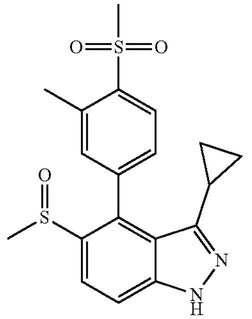 [SMILES: Cc1cc(-c2c(S(C)=O)ccc3[nH]nc(C4CC4)c23)ccc1S(C)(=O)=O]

To an ice-cold solution of 3-cyclopropyl-4-(3-methyl-4-(methylsulfonyl)phenyl)-5-(methylthio)-1H-indazole (Example 74) (23 mg, 0.1 mmol) in DCM (1 ml) was added a solution of m-chloroperbenzoic acid (124 μl, 0.5 M in DCM, 0.1 mmol) and the mixture was stirred at ambient temperature for 1 h. The reaction mixture was diluted with DCM and washed with saturated aqueous sodium hydrogen carbonate, water, dried ($Na_2SO_4$) and concentrated. Flash column chromatography (DCM: MeOH 1:0-1:9) afforded the title compound (15 mg, 59%) as a white solid. ([M+H]$^+$389.2).

Example 77: 3-cyclopropyl-4-(3-methyl-4-(methylsulfonyl)phenyl)-5-(methylsulfonyl)-1H-indazole

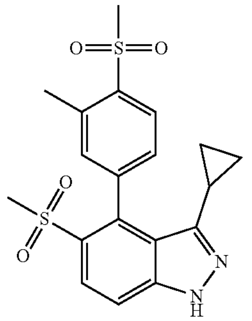 [SMILES: Cc1cc(-c2c(S(C)(=O)=O)ccc3[nH]nc(C4CC4)c23)ccc1S(C)(=O)=O]

To an ice-cold solution of 3-cyclopropyl-4-(3-methyl-4-(methylsulfonyl)phenyl)-5-(methylthio)-1H-indazole (Example 74) (26 mg, 0.1 mmol) in DCM (1 ml) was added a solution of m-chlorperbenzoic acid (263 μl, 0.5 M in DCM, 0.1 mmol) and the mixture was stirred at ambient temperature for 1 h. The reaction mixture was diluted with DCM and washed with saturated aqueous sodium hydrogen carbonate, water, dried ($Na_2SO_4$) and concentrated. Flash column chromatography (DCM: MeOH 1:0-1:9) afforded the title compound (18 mg, 61%) as a white solid. ([M+H]$^+$405.2).

Example 78: 3-(difluoromethoxy)-4-(3-methyl-4-methylsulfonyl-phenyl)-1H-pyrazolo[4,3-b]pyridin-5-one

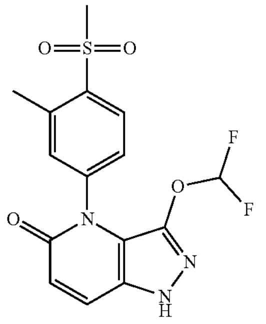 [SMILES: Cc1cc(-n2c(=O)ccc3[nH]nc(OC(F)F)c32)ccc1S(C)(=O)=O]

Step 1: 3-iodo-5-methoxy-1-trityl-pyrazolo[4,3-b]pyridine

To an ice cold solution of 3-iodo-5-methoxy-1H-pyrazolo[4,3-b]pyridine (WO2018/11628 A1) (1.0 g, 3.6 mmol) in DMF (20 mL) under argon atmosphere was added triphenylmethyl chloride (12.2 g, 4.4 mmol) and sodium hydride (175 mg, 60% dispersion in mineral oil, 4.4 mmol) and the reaction mixture was warmed to ambient temperature and stirred for 3 h. The reaction was diluted with ethyl acetate, washed with saturated aqueous ammonium chloride, brine, dried ($Na_2SO_4$) and concentrated. Flash column chromatography (Ethyl acetate: n-Heptane 1:10) afforded the title compound (0.9 g, 46%) as a white solid. ($[M+Na]^+$518.0).

Step 2: 5-methoxy-1-trityl-pyrazolo[4,3-b]pyridin-3-ol

A mixture of 3-iodo-5-methoxy-1-trityl-pyrazolo[4,3-b]pyridine (step 1) (50 mg, 0.1 mmol), potassium hydroxide (16 mg, 0.3 mmol), t-BuBrettPhos (8 mg, 0.02 mmol,), t-BuBrettPhos Pd G3 (10 mg, 0.02 mmol) in dioxane (2 mL) and water (0.5 mL) was stirred at 80° C. for 18 h under nitrogen atmosphere. The reaction mixture was filtered and concentrated. Purification by reversed phase preparative HPLC afforded the title compound (20 mg, 51%) as a white solid. ($[M+Na]^+$408.1)

Step 3: 3-(difluoromethoxy)-5-methoxy-1-trityl-pyrazolo[4,3-b]pyridine

A suspension of 5-methoxy-1-trityl-pyrazolo[4,3-b]pyridin-3-ol (step 2) (400 mg, 1.0 mmol), sodium 2-chloro-2,2-difluoroacetate (224 mg, 1.5 mmol), cesium carbonate (640 mg, 2.0 mmol) in acetonitrile (20 mL) was stirred at 50° C. for 2 h. The reaction mixture was filtered and concentrated.

Purification by reversed phase preparative HPLC afforded the title compound (400 mg, 89%) as a yellow solid. ($[M+H]^+$458.1)

Step 4: 3-(difluoromethoxy)-1,3a,4,7a-tetrahydropyrazolo[4,3-b]pyridin-5-one 3-(difluoromethoxy)-5-methoxy-1-trityl-pyrazolo[4,3-b]pyridine (step 3) (300 mg, 0.7 mmol) was dissolved HCl (15 mL, 4N in dioxane, 60 mmol) and stirred at 80° C. for 3 h. The reaction mixture was concentrated to dryness and purified by reversed phase preparative HPLC to afford the title compound (100 mg, 75%) as a grey solid. ($[M+H]^+$ 202.1)

Step 5: 3-(difluoromethoxy)-1-tetrahydropyran-2-yl-4H-pyrazolo[4,3-b]pyridin-5-one A mixture of 3-(difluoromethoxy)-1,4-dihydropyrazolo[4,3-b]pyridin-5-one (200 mg, 1.0 mmol), 3,4-dihydro-2H-pyran (0.14 mL, 1.5 mmol), p-toluenesulfonic acid monohydrate (86 mg, 0.5 mmol) in THF (5 mL) was stirred at 60° C. for 12 h after which time the reaction was concentrated. Purification by reversed phase preparative HPLC to afford the title compound (150 mg, 52%) as a white solid. ($[M+H]^+$286.0)

Step 6: 3-(difluoromethoxy)-4-(3-methyl-4-methylsulfonyl-phenyl)-1-tetrahydropyran-2-yl-pyrazolo[4,3-b]pyridin-5-one To a solution of 3-(difluoromethoxy)-1-tetrahydropyran-2-yl-4H-pyrazolo[4,3-b]pyridin-5-one (step 5) (100 mg, 0.4 mmol) in dichloromethane (3 mL) was added (3-methyl-4-methylsulfonyl-phenyl)boronic acid (150 mg, 0.7 mmol), pyridine (0.06 mL, 0.7 mmol), triethylamine (0.1 mL, 0.7 mmol) and copper (II) acetate (128 mg, 0.7 mmol) and the reaction was stirred at ambient temperature under air. After 12 h a further portion of (3-methyl-4-methylsulfonyl-phenyl)boronic acid (150 mg, 0.7 mmol) and triethylamine (0.1 mL, 0.7 mmol) was added and the mixture stirred for a further 16 h before the reaction was diluted with ethyl acetate, washed with water, brine, dried ($Na_2SO_4$) and concentrated. Preparative reversed phase HPLC afforded the title compound (70 mg, 44%) as a brown solid. ($[M+H]^+$ 454.1).

Step 5: 3-(difluoromethoxy)-4-(3-methyl-4-methylsulfonyl-phenyl)-1H-pyrazolo[4,3-b]pyridin-5-one 3-(difluoromethoxy)-4-(3-methyl-4-methylsulfonyl-phenyl)-1-tetrahydropyran-2-yl-pyrazolo[4,3-b]pyridin-5-one (step 4) was deprotected using General procedure I1 to afford the title compound. ($[M+H]^+$370.1).

Example 79: 3-cyclopropyl-4-(3-methyl-4-methylsulfonylphenyl)-5-(trifluoromethyl)-1H-pyrazolo[3,4-c]pyridine

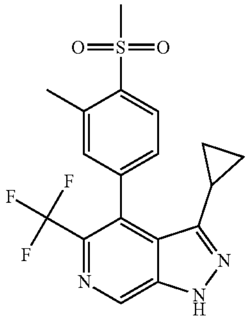 [SMILES: Cc1cc(-c2c(C(F)(F)F)ncc3[nH]nc(C4CC4)c23)ccc1S(C)(=O)=O]

Step 1: (3-bromo-5-fluoro-2-(trifluoromethyl)pyridin-4-yl)(cyclopropyl)methanone 3-bromo-5-fluoro-2-(trifluoromethyl)pyridine was reacted with LDA (1.1 eq) for 1 h before addition of cyclopropanecarbaldehyde (1.2 eq) in accordance with General procedure A to afford crude (3-bromo-5-fluoro-2-(trifluoromethyl)pyridin-4-yl)(cyclopropyl)methanol which was directly oxidised using General procedure B1 to afford the title compound. ([M+H, Br]$^+$312.1)

Step 2: cyclopropyl(5-fluoro-3-(3-methyl-4-(methylsulfonyl)phenyl)-2-(trifluoromethyl)pyridin-4-yl)methanone The title compound ([M+H]$^+$402.2) was prepared from Suzuki coupling of (3-bromo-5-fluoro-2-(trifluoromethyl)pyridin-4-yl)(cyclopropyl)methanone (step 1) and (3-methyl-4-(methylsulfonyl)phenyl)boronic acid with potassium carbonate at 100° C. in accordance with General procedure D.

Step 3: 3-cyclopropyl-4-(3-methyl-4-methylsulfonylphenyl)-5-(trifluoromethyl)-1H-pyrazolo[3,4-c]pyridine 3 cyclopropyl(5-fluoro-3-(3-methyl-4-(methylsulfonyl)phenyl)-2-(trifluoromethyl)pyridin-4-yl)methanone (step 2) was reacted with hydrazine hydrate (5 eq) in THF at ambient temperature in accordance with General procedure C to afford the title compound. ([M+H]$^+$396.2).

Example 80: 3-cyclopropyl-6-methyl-4-(3-methyl-4-methylsulfonyl-phenyl)-1H-pyrazolo[4,3-b]pyridin-5-one

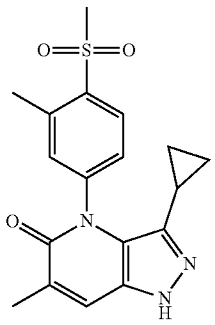 [SMILES: Cc1cc(-n2c(=O)c(C)cc3[nH]nc(C4CC4)c32)ccc1S(C)(=O)=O]

Step 1: 3-iodo-5-methoxy-1-tetrahydropyran-2-yl-pyrazolo[4,3-b]pyridine

To solution of 3-iodo-5-methoxy-1H-pyrazolo[4,3-b]pyridine (WO2018/11628 A1) (1.6 g, 5.8 mmol) in dichloromethane (40 mL) was added 3,4-dihydro-2H-pyran (3.0 g, 35.6 mmol) and p-toluenesulfonic acid monohydrate (100.0 mg, 0.6 mmol) and the mixture was stirred at ambient temperature for 15 h. The reaction was diluted with DCM, washed with saturated aqueous sodium hydrogen carbonate, dried ($Na_2SO_4$) and concentrated. Flash column chromatography (heptane: ethyl acetate 7:3) afforded the title compound (1.8 g, 82%) as a brown viscous oil. ([M+H]$^+$359.9).

Step 2: 3-cyclopropyl-5-methoxy-1-tetrahydropyran-2-yl-pyrazolo[4,3-b]pyridine

The title compound ([M+H]$^+$274.0) was prepared from Suzuki coupling of 3-iodo-5-methoxy-1-tetrahydropyran-2-yl-pyrazolo[4,3-b]pyridine (step 1) and cyclopropylboronic acid (8 eq) with potassium carbonate (4 eq) at 100° C. in accordance with General procedure D.

Step 3: 3-cyclopropyl-1-tetrahydropyran-2-yl-4H-pyrazolo[4,3-b]pyridin-5-one

To 3-cyclopropyl-5-methoxy-1-tetrahydropyran-2-yl-pyrazolo[4,3-b]pyridine (step 2) (270 mg, 1.0 mmol) was dissolved in HCl (30 mL, 4N in dioxane, 120 mmol) and heated to 100° C. for 15 h. The mixture was concentrated and the residue redissolved in in DCM (9 mL) and DMF (3 mL). 4-dihydro-2H-pyran (80 mg, 1.0 mmol) and p-toluenesulfonic acid monohydrate (50 mg, 0.3 mmol) and the reaction stirred for 16 h. A second portion of 4-dihydro-2H-pyran (80 mg, 1.0 mmol) was added and the reaction stirred for a further 12 h. The reaction was diluted with DCM, washed with saturated aqueous sodium hydrogen carbonate, dried ($Na_2SO_4$) and concentrated. Flash column chromatography (Ethyl acetate) afforded the title compound (170 mg, 62%) as a colourless viscous oil. ([M+H]$^+$260.3).

Step 4: 13-cyclopropyl-4-(3-methyl-4-methylsulfonyl-phenyl)-1-tetrahydropyran-2-yl-pyrazolo[4,3-b]pyridin-5-one To a solution of 3-(difluoromethoxy)-1-tetrahydropyran-2-yl-4H-pyrazolo[4,3-b]pyridin-5-one (step 3) (100 mg, 0.4 mmol) in DCM (3 mL) was added (3-methyl-4-methylsulfonyl-phenyl)boronic acid (150 mg, 0.7 mmol), pyridine (0.06 mL, 0.7 mmol), triethylamine (0.1 mL, 0.7 mmol) and copper (II) acetate (128 mg, 0.7 mmol) and the reaction was stirred at ambient temperature under air. After 12 h a further portion of (3-methyl-4-methylsulfonyl-phenyl)boronic acid (150 mg, 0.7 mmol) and triethylamine (0.1 mL, 0.7 mmol) was added and the mixture stirred for a further 16 h before a further portion of (3-methyl-4-methylsulfonyl-phenyl)boronic acid (150 mg, 0.7 mmol) and triethylamine (0.1 mL, 0.7 mmol) was added and the mixture stirred for a further 16 h the reaction was diluted with ethyl acetate, washed with water, brine, dried ($Na_2SO_4$) and concentrated. Purification by preparative TLC (ethyl acetate) afforded the title compound (90 mg, 50%) as a brown gum. ([M+H]$^+$428.1).

Step 5: 6-bromo-3-cyclopropyl-4-(3-methyl-4-methylsulfonyl-phenyl)-1-tetrahydropyran-2-yl-pyrazolo[4,3-b]pyridin-5-one To a solution of 3-cyclopropyl-4-(3-methyl-4-methylsulfonyl-phenyl)-1-tetrahydropyran-2-yl-pyrazolo[4,3-b]pyridin-5-one (50 mg, 0.09 mmol) (step 4) in DMF (2.5 mL) was added N-bromosuccinimide (33 mg, 0.2 mmol). The reaction was stirred for 24 h after which time it was reaction was diluted with ethyl acetate, washed with water, brine, dried ($Na_2SO_4$) and concentrated. Purification by preparative TLC (heptane: ethyl acetate 1:1) afforded the title compound (40 mg, 68%) as a white solid. ([M+H, Br]$^+$ 506.0).

Step 6: 3-cyclopropyl-6-methyl-4-(3-methyl-4-methylsulfonyl-phenyl)-1-tetrahydropyran-2-yl-pyrazolo[4,3-b]pyridin-5-one The title compound ([M+H]+422.1) was prepared from Suzuki coupling of 6-bromo-3-cyclopropyl-4-(3-methyl-4- methylsulfonyl-phenyl)-1-tetrahydropyran-2-yl-pyrazolo[4,3-b]pyridin-5-one (step 5) and trimethylboroxine with potassium carbonate at 100° C. in accordance with General procedure D.

Step 7: 3-cyclopropyl-6-methyl-4-(3-methyl-4-methylsulfonyl-phenyl)-1H-pyrazolo[4,3-b]pyridin-5-one 3-cyclopropyl-6-methyl-4-(3-methyl-4-methylsulfonyl-phenyl)-1-tetrahydropyran-2-yl-pyrazolo[4,3-b]pyridin-5-one (Step 6) was deprotected using General procedure I1 to afford the title compound. ([M+H]$^+$358.1).

Example 81: 3,6-dicyclopropyl-4-(3-methyl-4-methylsulfonyl-phenyl)-1H-pyrazolo[4,3-b]pyridin-5-one

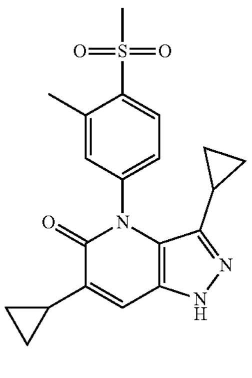 [SMILES: Cc1cc(-n2c(=O)c(C3CC3)cc3[nH]nc(C4CC4)c32)ccc1S(C)(=O)=O]

Step 1: 3,6-dicyclopropyl-4-(3-methyl-4-methylsulfonyl-phenyl)-1-tetrahydropyran-2-yl-pyrazolo[4,3-b]pyridin-5-one The title compound ([M+H]$^+$468.1) was prepared from Suzuki coupling of 6-bromo-3-cyclopropyl-4-(3-methyl-4-methylsulfonyl-phenyl)-1-tetrahydropyran-2-yl-pyrazolo[4,3-b]pyridin-5-one (Example 81, step 5) and cyclopropylboronic acid (10eq) with potassium carbonate (4 eq) at 100° C. in accordance with General procedure D.

Step 2: 3-cyclopropyl-5-(difluoromethoxy)-4-(3-methyl-4-(methylsulfonyl)phenyl)-1H-pyrazolo[3,4-c]pyridine 3,6-Dicyclopropyl-4-(3-methyl-4-methylsulfonyl-phenyl)-1-tetrahydropyran-2-yl-pyrazolo[4,3-b]pyridin-5-one was deprotected using General procedure I1 to afford the title compound. ([M+H]$^+$384.2).

Example 82: 3-cyclopropyl-5-(difluoromethoxy)-4-(3-methyl-4-(methylsulfonyl)phenyl)-1H-pyrazolo[3,4-c]pyridine

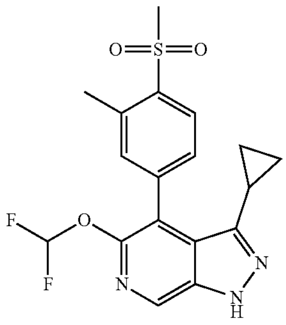 [SMILES: Cc1cc(-c2c(OC(F)F)ncc3[nH]nc(C4CC4)c23)ccc1S(C)(=O)=O]

Step 1: (3-bromo-2-(difluoromethoxy)-5-fluoropyridin-4-yl)(cyclopropyl)methanol 3-bromo-2-(difluoromethoxy)-5-fluoropyridine was reacted with LDA (1.2 eq) for 1 h before addition of cyclopropanecarbaldehyde (3 eq) in accordance with General procedure A to afford the title compound. ([M+H, Br]$^+$312.1).

Step 2: (3-bromo-2-(difluoromethoxy)-5-fluoropyridin-4-yl)(cyclopropyl)methanone (3-bromo-2-(difluoromethoxy)-5-fluoropyridin-4-yl)(cyclopropyl)methanol (step 1) was directly oxidised using General procedure B1 to afford the title compound. 1H NMR (CHLOROFORM-d, 300 MHz) δ 8.06 (s, 1H), 7.61 (s, 0.25 H), 7.37 (s, 0.5 H), 7.13 (s, 0.25 H), 2.23 (tt, 1H, J=4.2, 7.9 Hz), 1.4-1.5 (m, 2H), 1.24 (qd, 2H, J=3.8, 7.7 Hz)

Step 3: cyclopropyl(2-(difluoromethoxy)-5-fluoro-3-(3-methyl-4-(methylsulfonyl)phenyl)pyridin-4-yl)methanone The title compound ([M+H]$^+$400.3) was prepared from Suzuki coupling of (3-bromo-2-(difluoromethoxy)-5-fluoropyridin-4-yl)(cyclopropyl)methanone (step 2) and (3-methyl-4-(methylsulfonyl)phenyl)boronic acid with potassium carbonate at 90° C. in accordance with General procedure D.

Step 4: 3-cyclopropyl-5-(difluoromethoxy)-4-(3-methyl-4-(methylsulfonyl)phenyl)-1H-pyrazolo[3,4-c]pyridine Cyclopropyl(2-(difluoromethoxy)-5-fluoro-3-(3-methyl-4-(methylsulfonyl)phenyl)pyridin-4-yl)methanone (step 3) was reacted with hydrazine hydrate (5 eq) in THF at ambient temperature in accordance with General procedure C to afford the title compound. ([M+H]$^+$394.4).

Example 83: 3-cyclopropyl-N,N-dimethyl-4-(3-methyl-4-(methylsulfonyl)phenyl)-1H-pyrazolo[3,4-c]pyridine-5-carboxamide

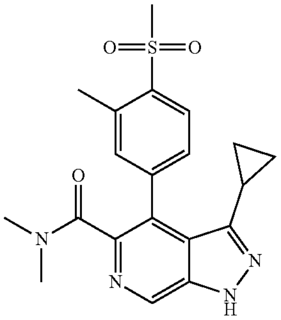 [SMILES: Cc1cc(-c2c(C(=O)N(C)C)ncc3[nH]nc(C4CC4)c23)ccc1S(C)(=O)=O]

The title compound ([M+H]$^+$399.3) was prepared in analogy to Example 72 from 3-cyclopropyl-4-(3-methyl-4-(methylsulfonyl)phenyl)-1-(tetrahydro-2H-pyran-2-yl)-1H-pyrazolo[3,4-c]pyridine-5-carboxylic acid (Example 72, step 1) and dimethylamine hydrochloride.

Example 84: 3-cyclopropyl-4-(3-methyl-4-(methylsulfonyl)phenyl)-N-(oxetan-3-yl)-1H-pyrazolo[3,4-c]pyridine-5-carboxamide

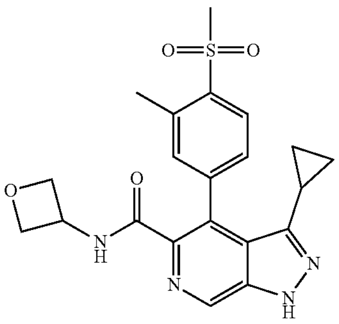 [SMILES: Cc1cc(-c2c(C(=O)NC3COC3)ncc3[nH]nc(C4CC4)c23)ccc1S(C)(=O)=O]

The title compound ([M+H]$^+$425.4) was prepared in analogy to Example 72 from3-cyclopropyl-4-(3-methyl-4-(methylsulfonyl)phenyl)-1-(tetrahydro-2H-pyran-2-yl)-1H-pyrazolo[3,4-c]pyridine-5-carboxylic acid (Example 72, step 1) and 3-oxetanamine.

Example 85: 3-cyclopropyl-4-(3-methyl-4-(methylsulfonyl)phenyl)-N-(oxetan-3-yl)-1H-pyrazolo[3,4-c]pyridine-5-carboxamide

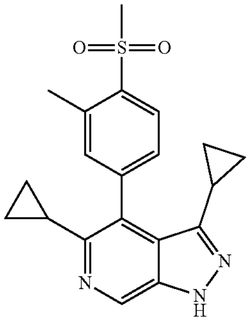 [SMILES: Cc1cc(-c2c(C3CC3)ncc3[nH]nc(C4CC4)c23)ccc1S(C)(=O)=O]

Step 1: 3-chloro-2-cyclopropyl-5-fluoropyridine 2-bromo-3-chloro-5-fluoropyridine (300 mg, 1.4 mmol), potassium cyclopropyltrifluoroborate (232 mg, 1.6 mmol), palladium (II) acetate (6 mg, 29 μmol,) and butyldi-1-adamantylphosphine (31 mg, 86 μmol) and cesium carbonate (1.4 g, 4.3 mmol) in a mixture of toluene (10 ml) and water (1.5 ml) was evacuated and sparged with argon. The reaction mixture was stirred for 2 h at 80° C. The reaction mixture was directly filtered over Dicalite®, washed with ethyl acetate and concentrated. Flash column chromatography (Ethyl acetate: n-Heptane 1:9) afforded the title compound (81 mg, 31%) as a colourless oil. ([M+H]$^+$172.0).

Step 2: (3-chloro-2-cyclopropyl-5-fluoropyridin-4-yl)(cyclopropyl)methanone 3-chloro-2-cyclopropyl-5-fluoropyridine was reacted with LDA (1.1 eq) for 1 h before addition of cyclopropanecarbaldehyde (1.2 eq) in accordance with General procedure A to afford crude (3-bromo-5-fluoro-2-(trifluoromethyl)pyridin-4-yl)(cyclopropyl)methanol which was directly oxidised using General procedure B1 to afford the title compound. ([M+H, Cl]$^+$240.1)

Step 3: cyclopropyl(2-cyclopropyl-5-fluoro-3-(3-methyl-4-(methylsulfonyl)phenyl)pyridin-4-yl)methanone The title compound ([M+H]$^+$374.2) was prepared from Suzuki coupling of (3-bromo-2 (3-chloro-2-cyclopropyl-5-fluoropyridin-4-yl)(cyclopropyl)methanone (step 2) and (3-methyl-4-(methylsulfonyl)phenyl)boronic acid with potassium carbonate at 120° C. in accordance with General procedure D.

Step 4: 3-cyclopropyl-4-(3-methyl-4-(methylsulfonyl)phenyl)-N-(oxetan-3-yl)-1H-pyrazolo[3,4-c]pyridine-5-carboxamide Cyclopropyl(2-cyclopropyl-5-fluoro-3-(3-methyl-4-(methylsulfonyl)phenyl)pyridin-4-yl)methanone (step 3) was reacted with hydrazine hydrate (100 eq) in THF at 170° C. (microwave) in accordance with General procedure C to afford the title compound. ([M+H]$^+$368.2).

Example 86: N,3-dicyclopropyl-4-(3-methyl-4-(methylsulfonyl)phenyl)-1H-pyrazolo[3,4-c]pyridine-5-carboxamide

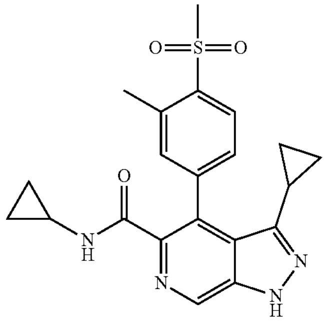 [SMILES: Cc1cc(-c2c(C(=O)NC3CC3)ncc3[nH]nc(C4CC4)c23)ccc1S(C)(=O)=O]

The title compound ([M+H]$^+$425.4) was prepared in analogy to Example 72 from3-cyclopropyl-4-(3-methyl-4-(methylsulfonyl)phenyl)-1-(tetrahydro-2H-pyran-2-yl)-1H-pyrazolo[3,4-c]pyridine-5-carboxylic acid (Example 72, step 1) and cyclopropylamine.

Example 87: 3-cyclopropyl-6-fluoro-4-(3-methyl-4-(methylsulfonyl)phenyl)-1H-indazole-5-carboxamide

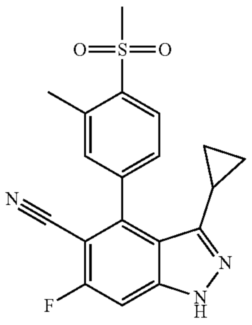

Step 1: 6-chloro-2,4-difluoro-3-(triethylsilyl)benzonitrile

To a solution of 2-chloro-4,6-difluorobenzonitrile (100 mg, 0.6 mmol) dissolved in THF (2 ml) under Ar and cooled to −78° C. was added LDA (0.3 ml, 0.7 mmol) and the mixture stirred for 5 min after which time chlorotrimethylsilane (0.1 ml, 0.6 mmol) was added and the reaction stirred for a further 30 min. The reaction was quenched by addition of saturated aqueous ammonium chloride, allowed to reach ambient temperature, extracted with ethyl acetate, dried ($Na_2SO_4$) and concentrated. Flash column chromatography (heptane) afforded the title compound (127 mg, 73%) as a colourless oil. 1H NMR (CHLOROFORM-d, 300 MHz) δ 7.03 (dd, 1H, J=1.4, 8.1 Hz), 0.9-1.0 (m, 15H)

Step 2: 2-chloro-3-(cyclopropyl(hydroxy)methyl)-4,6-difluoro-5-(triethylsilyl)benzonitrile 6-chloro-2,4-difluoro-3-(triethylsilyl)benzonitrile (step 1) was reacted with LDA (1.2 eq) for 0.25 h before addition of cyclopropanecarbaldehyde (1.3 eq) in accordance with General procedure A to afford the title compound. ([M+H, Cl]$^+$381.2).

Step 3: 2-chloro-3-(cyclopropanecarbonyl)-4,6-difluoro-5-(triethylsilyl)benzonitrile 2-Chloro-3-(cyclopropyl(hydroxy)methyl)-4,6-difluoro-5-(triethylsilyl)benzonitrile (step 2) was oxidised using General procedure B1 to afford the title compound. 1H NMR (CHLOROFORM-d, 300 MHz) δ 2.22 (dtt, 1H, J=1.3, 4.5, 7.8 Hz), 1.37 (t, 2H, J=3.9 Hz), 1.1-1.2 (m, 2H), 0.9-1.0 (m, 15H)

Step 4: 6-(cyclopropanecarbonyl)-3,5-difluoro-3'-methyl-4'-(methylsulfonyl)-[1,1'-biphenyl]-2-carbonitrile The title compound ([M+H]$^+$376.4) was prepared from Suzuki coupling of 2-chloro-3-(cyclopropanecarbonyl)-4,6-difluoro-5-(triethylsilyl)benzonitrile (step 3) and (3-methyl-4-(methylsulfonyl)phenyl)boronic acid with potassium carbonate at 120° C. in accordance with General procedure D.

Step 5: 3-cyclopropyl-6-fluoro-4-(3-methyl-4-(methylsulfonyl)phenyl)-1H-indazole-5-carboxamide 6-(cyclopropanecarbonyl)-3,5-difluoro-3'-methyl-4'-(methylsulfonyl)-[1,1'-biphenyl]-2-carbonitrile (step 4) was reacted with hydrazine hydrate (2 eq) in THF at ambient temperature in accordance with General procedure C to afford the title compound. ([M+H]$^+$370.2).

Example 88 & 89: 3-cyclopropyl-6-fluoro-N-methyl-4-(3-methyl-4-(methylsulfonyl)phenyl)-1H-indazole-5-carboxamide & 3-cyclopropyl-4-(4-cyclopropylsulfonyl-3-methyl-phenyl)-N-methyl-1H-pyrazolo[3,4-c]pyridine-5-carboxamide

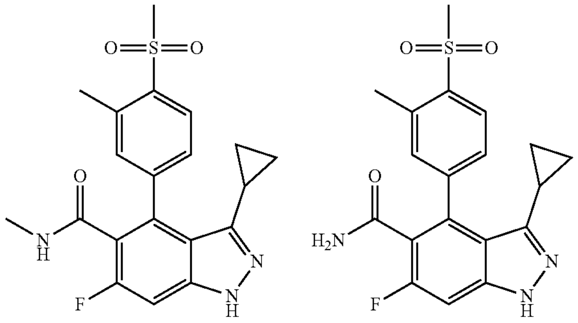 [SMILES: CNC(=O)c1c(F)cc2[nH]nc(C3CC3)c2c1-c1ccc(S(C)(=O)=O)c(C)c1 ; Cc1cc(-c2c(C(N)=O)c(F)cc3[nH]nc(C4CC4)c23)ccc1S(C)(=O)=O]

3-Cyclopropyl-6-fluoro-4-(3-methyl-4-(methylsulfonyl)phenyl)-1H-indazole-5-carbonitrile (Example 87) (20 mg, 54 μmol) was suspended in sodium hydroxide (3 ml, 3M in water, 9 mmol) and heated to 150° C. in a microwave for 4.5 h. The reaction was acidified with 6 N hydrochloric acid and extracted with ethyl acetate, the combined organic was dried ($Na_2SO_4$) and concentrated to afford crude mixture (1:1) of 3-cyclopropyl-4-(4-cyclopropylsulfonyl-3-methyl-phenyl)-N-methyl-1H-pyrazolo[3,4-c]pyridine-5-carboxamide and 3-cyclopropyl-4-(4-cyclopropylsulfonyl-3-methyl-phenyl)-N-methyl-1H-pyrazolo[3,4-c]pyridine-5-carboxylic acid. Reaction with methylamine hydrochloride prepared in analogy to Example 72 followed by reversed phase preparative HPLC afforded the two title compounds. ([M+H]$^+$402.3 & 388.2).

Example 90: 6-chloro-3-cyclopropyl-4-(3-methyl-4-methylsulfonylphenyl)-1H-indazole-5-carbonitrile

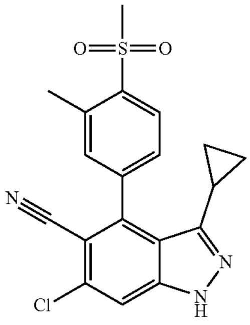 [SMILES: Cc1cc(-c2c(C#N)c(Cl)cc3[nH]nc(C4CC4)c23)ccc1S(C)(=O)=O]

Step 1: 2,6-dichloro-3-(cyclopropyl(hydroxy)methyl)-4-fluorobenzonitrile 2,6-dichloro-4-fluorobenzonitrile was reacted with LDA (1.0 eq) for 1 h before addition of cyclopropanecarbaldehyde (1.2 eq) in accordance with General procedure A to afford the title compound. ([M−$H_2O$, 2Cl]$^+$242.1).

Step 2: 2,6-dichloro-3-(cyclopropanecarbonyl)-4-fluorobenzonitrile 2,6-dichloro-3-(cyclopropyl(hydroxy)methyl)-4-fluorobenzonitrile (step 1) was oxidised using General procedure B1 to afford the title compound. ([M+H, 2Cl]$^+$258.1).

Step 3: 3-chloro-6-(cyclopropanecarbonyl)-5-fluoro-3'-methyl-4'-(methylsulfonyl)-[1,1'-biphenyl]-2-carbonitrile The title compound ([M+H,Cl]$^+$392.2) was prepared from Suzuki coupling of 2-chloro-32,6-dichloro-3-(cyclopropanecarbonyl)-4-fluorobenzonitrile (step 2) and (3-methyl-4-(methylsulfonyl)phenyl)boronic acid with cesium carbonate at 100° C. in accordance with General procedure D.

Step 4: 6-chloro-3-cyclopropyl-4-(3-methyl-4-methylsulfonylphenyl)-1H-indazole-5-carbonitrile 3-chloro-6-(cyclopropanecarbonyl)-5-fluoro-3'-methyl-4'-(methylsulfonyl)-[1,1'-biphenyl]-2-carbonitrile (step 3) was reacted with hydrazine hydrate (15 eq) in THF at ambient temperature in accordance with General procedure C to afford the title compound. ([M+H,Cl]$^+$386.2).

Example 91: 4-(3-methyl-4-methylsulfonyl-phenyl)-3-(trifluoromethoxy)-1H-pyrazolo[4,3-b]pyridin-5-one

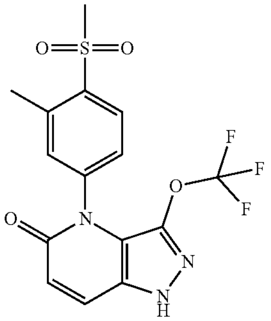 [SMILES: Cc1cc(-n2c(=O)ccc3[nH]nc(OC(F)(F)F)c32)ccc1S(C)(=O)=O]

Step 1: 5-methoxy-3-(trifluoromethoxy)-1-trityl-pyrazolo[4,3-b]pyridine

To a solution of 5-methoxy-1-trityl-pyrazolo[4,3-b]pyridin-3-ol (Example 78, step 2) (430 mg, 1.1 mmol) in DMF (16 mL) was added potassium carbonate (438 mg, 3.2 mmol) and 1-trifluoromethyl-1,2-benziodoxol-3-(1H)-one (1001 mg, 3.2 mmol). The mixture was stirred at 25° C. for 16 h, after which time a second portion of potassium carbonate (438 mg, 3.2 mmol) and 1-trifluoromethyl-1,2-benziodoxol-3-(1H)-one (1001 mg, 3.2 mmol)was added and the reaction stirred for a further 12 h. The reaction was diluted with water and repeatedly extracted with ethyl acetate. The combined organic was washed with brine, dried ($Na_2SO_4$) and concentrated. Purification by preparative TLC (heptane: ethyl acetate 1:10) afforded the title compound (110 mg, 21%) as a white solid. ([M+H]$^+$476.1).

Step 2: 3-(trifluoromethoxy)-1-trityl-4H-pyrazolo[4,3-b]pyridin-5-one

A solution of 5-methoxy-3-(trifluoromethoxy)-1-trityl-pyrazolo[4,3-b]pyridine (step 1) (110 mg, 0.2 mmol) in 4 M HCl in dioxane (20.0 mL, 80 mmol) was stirred at 80° C. for 24 h. The reaction was concentrated and purification by preparative TLC (heptane: ethyl acetate 1:1 afforded the title compound (60 mg, 53%) as a white solid. ([M+H]$^+$462.1).

Step 3: 4-(3-methyl-4-methylsulfonyl-phenyl)-3-(trifluoromethoxy)-1-trityl-pyrazolo[4,3-b]pyridin-5-one To a solution of 3-(trifluoromethoxy)-1-trityl-4H-pyrazolo[4,3-b]pyridin-5-one (step 2) (55 mg, 0.1 mmol) in DCM (4 mL) was added (3-methyl-4-methylsulfonyl-phenyl)boronic acid (51 mg, 0.2 mmol), pyridine (0.02 mL, 0.2 mmol), triethylamine (0.03 mL, 0.2 mmol) and copper (II) acetate (43 mg, 0.2 mmol) and the reaction was stirred at ambient temperature under oxygen atmosphere (balloon). After 12 h a further portion of (3-methyl-4-methylsulfonyl-phenyl)boronic acid (51 mg, 0.2 mmol) pyridine (0.02 mL, 0.2 mmol), triethylamine (0.03 mL, 0.2 mmol) was added and the mixture stirred for a further 12 h before the reaction was diluted with ethyl acetate and filtered Purification by preparative TLC afforded the title compound (90 mg, 63%) as a white solid. ([M+H]$^+$630.1).

Step 4: 4-(3-methyl-4-methylsulfonyl-phenyl)-3-(trifluoromethoxy)-1H-pyrazolo[4,3-b]pyridin-5-one 4-(3-methyl-4-methylsulfonyl-phenyl)-3-(trifluoromethoxy)-1-trityl-pyrazolo[4,3-b]pyridin one was deprotected using General procedure I1 to afford the title compound. ([M+H]$^+$388.1).

Example 92: 3-cyclopropyl-4-(3-methyl-4-methylsulfonyl-phenyl)-1H-pyrrolo[3,2-b]pyridin-5-one

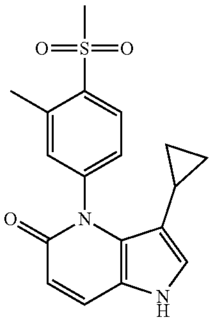 [SMILES: Cc1cc(-n2c(=O)ccc3[nH]cc(C4CC4)c32)ccc1S(C)(=O)=O]

Step 1: 3-bromo-5-methoxy-1H-pyrrolo[3,2-b]pyridine

To a solution of 5-methoxy-1H-pyrrolo[3,2-b]pyridine (1.0 g, 6.75 mmol, 1 eq) in DMF (20 mL) was added N-bromosuccinimide (1.4 g, 7.1 mmol) at 25° C. and the reaction mixture was stirred at ambient temperature for 16 h. The reaction was diluted with water and repeatedly extracted with ethyl acetate. The combined organic was washed with brine, dried ($Na_2SO_4$) and concentrated. Flash column chromatography (Ethyl acetate: n-Heptane=0:1-1:8) afforded the title compound (1.2 g, 76%) as a white solid. ([M+H, Br]$^+$227.0).

Step 2: 2-[(3-bromo-5-methoxy-pyrrolo[3,2-b]pyridin-1-yl)methoxy]ethyl-trimethyl-silane 3-Bromo-5-methoxy-1H-pyrrolo[3,2-b]pyridine (step 1) was converted to the title compound employing General procedure E1 in THF. ([M+H, Br]$^+$357.1)

Step 3: 2-[(3-cyclopropyl-5-methoxy-pyrrolo[3,2-b]pyridin-1-yl)methoxy]ethyl-trimethyl-silane The title compound ([M+Hl]$^+$319.2) was prepared from Suzuki coupling of 2-[(3-bromo-5-methoxy-pyrrolo[3,2-b]pyridin-1-yl)methoxy]ethyl-trimethyl-silane (step 2) and cylcopropyl boronic acid (10 eq) with potassium carbonate (8 eq) at 100° C. in accordance with General procedure D.

Step 4: 3-cyclopropyl-1-(methoxymethyl)-4H-pyrrolo[3,2-b]pyridin-5-one

A solution of 2-[(3-cyclopropyl-5-methoxy-pyrrolo[3,2-b]pyridin-1-yl)methoxy]ethyl-trimethyl-silane (step 3) (320 mg, 1 mmol) in 4M HCl in dioxane (20.0 mL, 80 mmol) was stirred at 90° C. for 5 h. The reaction was concentrated and purification by preparative TLC (Heptane: ethyl acetate 1:1) afforded the title compound (140 mg, 58%) as an off-white solid. ([M+H]$^+$219.1).

Step 5: 3-cyclopropyl-1-(methoxymethyl)-4-(3-methyl-4-methylsulfonyl-phenyl)pyrrolo[3,2-b]pyridin-5-one To a solution of 3-cyclopropyl-1-(methoxymethyl)-4H-pyrrolo[3,2-b]pyridin-5-one (step 4) (140 mg, 0.6 mmol) in dichloromethane (6 mL) was added (3-methyl-4-methylsulfonyl-phenyl)boronic acid (250 mg, 1.2 mmol), pyridine (0.09 mL, 1.2 mmol), triethylamine (0.16 mL, 1.2 mmol) and copper (II) acetate (212 mg, 1.2 mmol) and the reaction was stirred at ambient temperature under oxygen atmosphere (balloon). After 2 h a further portion of (3-methyl-4-methylsulfonyl-phenyl)boronic (3-methyl-4-methylsulfonyl-phenyl)boronic acid (250 mg, 1.2 mmol) and triethylamine (0.16 mL, 1.2 mmol) was added and the mixture stirred for a further 2 h before a third identical readdition of boronic acid and triethylamine added and the reaction stirred for a further 12 h. The reaction was then filtered and concentrated. Purification by preparative TLC (Heptane: ethyl acetate 1:1) afforded the title compound (170 mg, 68%) as a yellow solid. ([M+H]$^+$387.1).

Step 6: 3-cyclopropyl-4-(3-methyl-4-methylsulfonyl-phenyl)-1H-pyrrolo[3,2-b]pyridin-5-one 3-Cyclopropyl-1-(methoxymethyl)-4-(3-methyl-4-methylsulfonyl-phenyl)pyrrolo[3,2-b]pyridin-5-one (step 5) was deprotected using General procedure J to afford the title compound. ([M+H]$^+$343.2).

Example 93: 4-(3-methyl-4-(methylsulfonyl)phenyl)-5-(methylsulfonyl)-3-(trifluoromethoxy)-1H-indazole

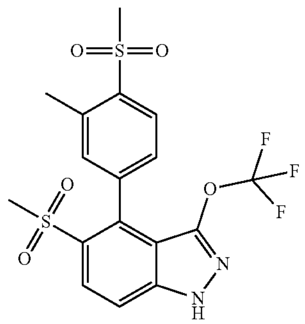 [SMILES: Cc1cc(-c2c(S(C)(=O)=O)ccc3[nH]nc(OC(F)(F)F)c23)ccc1S(C)(=O)=O]

Step 1: 4-(3-methyl-4-(methylsulfonyl)phenyl)-5-(methylsulfonyl)-1-trityl-1H-indazol-3-ol The title compound ([M−H]$^-$621.5) was prepared from Suzuki coupling of 4-bromo-5-(methylsulfonyl)-1-trityl-1H-indazol-3-ol (Intermediate 16, step 4) and (3-methyl-4-(methylsulfonyl)phenyl)boronic acid with potassium carbonate at 100° C. in accordance with General procedure D.

Step 2: 4-(3-methyl-4-(methylsulfonyl)phenyl)-5-(methylsulfonyl)-3-(trifluoromethoxy)-1-trityl-1H-indazole To a solution of 4-(3-methyl-4-(methylsulfonyl)phenyl)-5-(methylsulfonyl)-1-trityl-1H-indazol-3-ol (step 1) (206 mg, 0.3 mmol) in DMF (3 ml) was added potassium carbonate (137 mg, 1.0 mmol) and 1-(trifluoromethyl)-113- benzo[d][1,2]iodaoxol-3(1H)-one (165 mg, 0.5 mmol) and the mixture stirred 18 h at ambient temperature. The reaction was concentrated to dryness, suspended in ethyl acetate, washed with water, dried ($Na_2SO_4$) and concentrated. Flash column chromatography (heptane:ethyl acetate 1:9-0:1) afforded the title compound (46 mg, 20%) as a white solid. ($[M+NH_4^+]^+$708.5)

Step 3: 4-(3-methyl-4-(methylsulfonyl)phenyl)-5-(methylsulfonyl)-3-(trifluoromethoxy)-1H-indazole 4-(3-methyl-4-(methylsulfonyl)phenyl)-5-(methylsulfonyl)-3-(trifluoromethoxy)-1-trityl-1H-indazole (step 2) was deprotected using General procedure I1 to afford the title compound. ($[M+H]^+$449.2).

Example 94: 3-cyclopropyl-4-(3-(difluoromethyl)-4-(methylsulfonyl)phenyl)-5-(methylsulfonyl)-1H-indazole

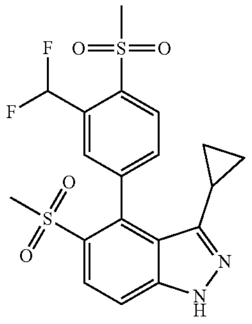 [SMILES: CS(=O)(=O)c1ccc(-c2c(S(C)(=O)=O)ccc3[nH]nc(C4CC4)c23)cc1C(F)F]

Step 1: cyclopropyl(3'-(difluoromethyl)-3-fluoro-4'-(methylsulfonyl)-6-(methylthio)-[1,1'-biphenyl]-2-yl)methanone The title compound ($[M+H]^+$415.2) was prepared from Suzuki coupling of (2-bromo-6-fluoro-3-(methylthio)phenyl)(cyclopropyl)methanone (Example 75, step 2) and 2-(3-(difluoromethyl)-4-(methylsulfonyl)phenyl)-4,4,5,5-tetramethyl-1,3,2-dioxaborolane (Intermediate 21) with potassium carbonate at 100° C. in accordance with General procedure D. Step 2: cyclopropyl(3'-(difluoromethyl)-3-fluoro-4',6-bis(methylsulfonyl)-[1,1'-biphenyl]-2-yl)methanone Cyclopropyl(3'-(difluoromethyl)-3-fluoro-4'-(methylsulfonyl)-6-(methylthio)-[1,1'-biphenyl]-2-yl)methanone (step 1) is converted to the title compound using General procedure G. ($[M+H]^+$447.3).

Step 3: 3-cyclopropyl-4-(3-(difluoromethyl)-4-(methylsulfonyl)phenyl)-5-(methylsulfonyl)-1H-indazole Cyclopropyl(3'-(difluoromethyl)-3-fluoro-4',6-bis(methylsulfonyl)-[1,1'-biphenyl]-2-yl)methanone (step 2) was reacted with hydrazine hydrate (2 eq) in THF at ambient temperature in accordance with General procedure C to afford the title compound. ($[M+H]^+$441.2).

Example 95: 3-(difluoromethoxy)-N-methyl-4-(3-methyl-4-methylsulfonyl-phenyl)-1H-pyrazolo[3,4-c]pyridine-5-carboxamide

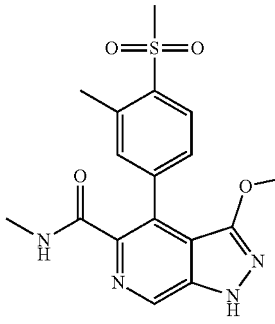

Step 1: 3-(difluoromethoxy)-4-(3-methyl-4-methylsulfonyl-phenyl)-1H-pyrazolo[3,4-c]pyridine-5-carboxylic acid A solution of 3-(difluoromethoxy)-4-(3-methyl-4-methylsulfonyl-phenyl)-1H-pyrazolo[3,4-c]pyridine-5-carbonitrile (Example 52) (100 mg, 0.3 mmol) in water (4 mL) was added sodium hydroxide (1.0 mL, 6 N, 6 mmol) and the reaction heated to 100° C. for 10 h. The reaction mixture was cooled to 0° C. and acidified with concentrated aqueous HCl, extracted repeatedly with ethyl acetate, the combined organic dried ($Na_2SO_4$) and concentrated to afford the title compound (100 mg, 95%) as yellow solid. ($[M+H]^+$398.0)

Step 2: 3-(difluoromethoxy)-N-methyl-4-(3-methyl-4-methylsulfonyl-phenyl)-1H-pyrazolo[3,4-c]pyridine-5-carboxamide The title compound ($[M+H]^+$411.1) was prepared in analogy to Example 72 from 3-(difluoromethoxy)-4-(3-methyl-4-methylsulfonyl-phenyl)-1H-pyrazolo[3,4-c]pyridine-5-carboxylic acid (step 4) and methylamine hydrochloride.

Example 96: 3-cyclopropyl-4-(4-cyclopropylsulfonyl-2-fluoro-5-methyl-phenyl)-N-methyl-1H-pyrazolo[3,4-c]pyridine-5-carboxamide

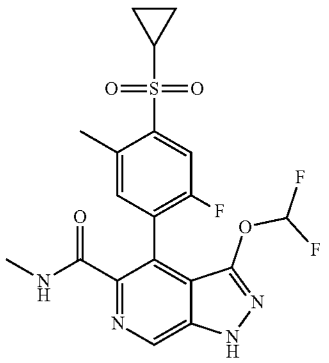 [SMILES: CNC(=O)c1ncc2[nH]nc(OC(F)F)c2c1-c1cc(C)c(S(=O)(=O)C2CC2)cc1F]

Step 1: 1-bromo-4-cyclopropylsulfanyl-2-fluoro-5-methyl-benzene

To a stirred suspension of potassium tert-butoxide (61 mg, 0.5 mmol) in DMSO (1 mL) was added 4-bromo-5-fluoro-2-methyl-benzenethiol (CAS: 1208077-77-3) (100 mg, 0.5 mmol) and cyclopropyl bromide (164 mg, 1.4 mmol) and the reaction was heated to 100° C. for 12 h. The reaction was extracted repeatedly with ethyl acetate, the combined organic dried ($Na_2SO_4$) and concentrated, Purification by preparative TLC (heptane) afforded the title compound (60 mg, 51%) as a colourless oil. 1H NMR (400 MHz, CHLOROFORM-d) δ=7.29 (d, J=9.5 Hz, 1H), 7.27-7.24 (m, 1H), 2.18 (s, 3H), 2.13-2.06 (m, 1H), 1.19-1.13 (m, 2H), 0.75-0.67 (m, 2H)

Step 2: 1-bromo-4-cyclopropylsulfonyl-2-fluoro-5-methyl-benzene

1-Bromo-4-cyclopropylsulfanyl-2-fluoro-5-methyl-benzene (step 1) is converted to the title compound using General procedure G. ($[M+H]^+$293.0).

Step 3: 2-(4-cyclopropylsulfonyl-2-fluoro-5-methyl-phenyl)-4,4,5,5-tetramethyl-1,3,2-dioxaborolane 1-bromo-4-cyclopropylsulfonyl-2-fluoro-5-methyl-benzene (step 2) is converted to the title compound employing General procedure F. ($[M+H]^+$258.9).

Step 4: 3-cyclopropyl-4-(4-cyclopropylsulfonyl-2-fluoro-5-methyl-phenyl)-1H-pyrazolo[3,4-c]pyridine-5-carbonitrile The title compound ($[M+H]^+$397.2) was prepared from Suzuki coupling of 4-bromo-3-(difluoromethoxy)-1-trityl-pyrazolo[3,4-c]pyridine-5-carbonitrile (Intermediate 17), 2-(4-cyclopropylsulfonyl-2-fluoro-5-methyl-phenyl)-4,4,5,5-tetramethyl-1,3,2-dioxaborolane (step 4) with potassium carbonate and, 1'-bis(diphenylphosphino)ferrocene-palladium(II) dichloride dichloromethane adduct (0.5 eq) at 120° C. in accordance with General procedure D.

Step 5: 3-cyclopropyl-4-(4-cyclopropylsulfonyl-2-fluoro-5-methyl-phenyl)-1H-pyrazolo[3,4-c]pyridine-5-carboxylic acid A solution of 3-cyclopropyl-4-(4-cyclopropylsulfonyl-2-fluoro-5-methyl-phenyl)-1H-pyrazolo[3,4-c]pyridine-5-carbonitrile (step 4) (20 mg, 0.1 mmol) in water (0.2 mL) was added sodium hydroxide (0.05 mL, 6 N, 0.3 mmol) and the reaction heated to 100° C. for 38 h. The reaction mixture was cooled to 0° C. and acidified with concentrated aqueous HCl, extracted repeatedly with ethyl acetate, the combined organic dried ($Na_2SO_4$) and concentrated to afford the title compound (20 mg, 95%). ($[M+H]^+$416.1)

Step 6: 3-cyclopropyl-4-(4-cyclopropylsulfonyl-2-fluoro-5-methyl-phenyl)-N-methyl-1H-pyrazolo[3,4-c]pyridine-5-carboxamide The title compound ($[M+H]^+$429.1) was prepared in analogy to Example 72 from 3-cyclopropyl-4-(4-cyclopropysulfonyl-2-fluoro-5-methyl-phenyl)-1H-pyrazolo[3,4-c] pyridine-5-carboxylic acid (step 5) and methylamine hydrochloride.

Example 97: 3-cyclopropyl-4-(2-fluoro-5-methyl-4-methylsulfonyl-phenyl)-N-methyl-1H-pyrazolo[3,4-c]pyridine-5-carboxamide

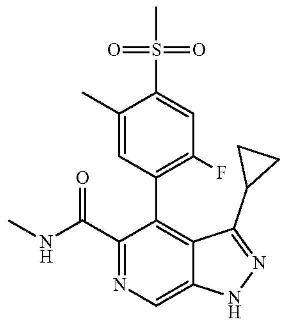 [SMILES: CNC(=O)c1ncc2[nH]nc(C3CC3)c2c1-c1cc(C)c(S(C)(=O)=O)cc1F]

Step 1: 3-cyclopropyl-4-(2-fluoro-5-methyl-4-methylsulfonyl-phenyl)-1H-pyrazolo[3,4-c]pyridine-5-carboxylic acid To a suspension of of 3-cyclopropyl-4-(2-fluoro-5-methyl-4-methylsulfonyl-phenyl)-1H-pyrazolo[3,4-c]pyridine-5-carbonitrile (Example 47) (50 mg, 0.1 mmol) in water (0.6 mL) was added sodium hydroxide (0.1 mL, 0.8 mmol). The reaction mixture was stirred at 100° C. for 18 h. The reaction mixture was cooled to 0° C. and acidified with concentrated aqueous HCl, extracted repeatedly with ethyl acetate, the combined organic dried ($Na_2SO_4$) and concentrated. Purification by reversed phase preparative HPLC afforded the title compound (20 mg, 34%) as a grey foam. ($[M+H]^+$390.0)

Step 2: 3-cyclopropyl-4-(2-fluoro-5-methyl-4-methylsulfonyl-phenyl)-N-methyl-1H-pyrazolo[3,4-c] pyridine-5-carboxamide The title compound ($[M+H]^+$403.1) was prepared in analogy to Example 72 from 3-cyclopropyl-4-(2-fluoro-5-methyl-4-methylsulfonyl-phenyl)-1H-pyrazolo[3,4-c]pyridine-5-carboxylic acid (step 1) and methylamine hydrochloride.

Example 98: 3-(difluoromethoxy)-4-(3-methyl-4-methylsulfonyl-phenyl)-1H-pyrazolo[3,4-c]pyridine-5-carboxamide

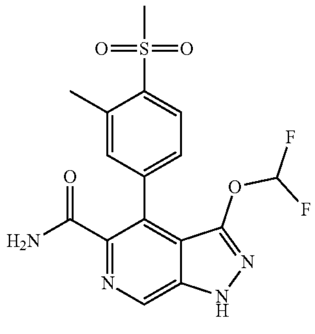 [SMILES: Cc1cc(-c2c(C(N)=O)ncc3[nH]nc(OC(F)F)c23)ccc1S(C)(=O)=O]

A solution of 3-(difluoromethoxy)-4-(3-methyl-4-methylsulfonyl-phenyl)-1H-pyrazolo [3,4-c]pyridine-5-carbonitrile (Example 52) (100 mg, 0.3 mmol) in ethanol (4 mL) was added sodium hydroxide (0.7 mL, 6 N, 0.3 mmol) and the reaction heated to 100° C. for 12 h. The reaction mixture was concentrated and the residue purified by reversed phase preparative HPLC to afford the title compound (28 mg, 26%) as white solid. ([M+H]+397.1)

Example 99: N-[2-[2-[[3-cyclopropyl-4-(3-methyl-4-methylsulfonyl-phenyl)-1H-pyrazolo[4,3-c]pyridin-7-yl]amino]ethoxy]ethyl]acetamide; Formic Acid Salt

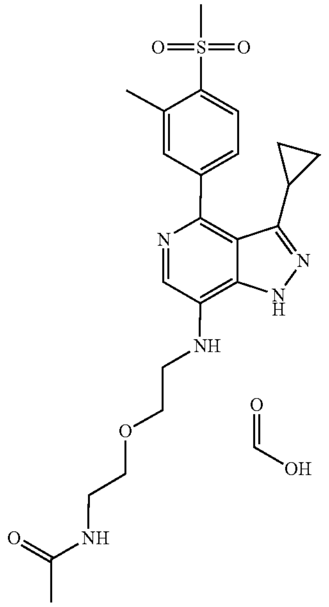 [SMILES: CC(=O)NCCOCCNc1cnc(-c2ccc(S(C)(=O)=O)c(C)c2)c2c(C3CC3)n[nH]c12 ; O=CO]

Step 1: 7-bromo-3-cyclopropyl-4-(3-methyl-4-methylsulfonyl-phenyl)-1-tetrahydropyran-2-yl-pyrazolo[4,3-c]pyridine To a solution of 7-bromo-3-cyclopropyl-4-(3-methyl-4-methylsulfonyl-phenyl)-1H-pyrazolo[4,3-c]pyridine (Example 64, step 1) (100 mg, 0.3 mmol) in THF (1 mL) was added p-toluenesulfonic acid monohydrate (13 mg, 0.1 mmol) and dihydropyran (0.07 mL, 0.7 mmol) and the reaction solution was stirred at 60° C. for 12 h. To the reaction mixture was added saturated sodium hydrogen carbonate solution and the mixture extracted with ethyl acetate, the combined organic was dried ($Na_2SO_4$) and concentrated. Purification by preparative TLC (heptane: ethyl acetate 1:1) afforded the title compound (60 mg, 50%) as a yellow oil. ([M+H, Br]+490.0)

Step 2: N-[2-[2-[[3-cyclopropyl-4-(3-methyl-4-methylsulfonyl-phenyl)-1-tetrahydropyran-2-yl-pyrazolo[4,3-c]pyridin-7-yl]amino]ethoxy]ethyl]acetamide To a mixture of 7-bromo-3-cyclopropyl-4-(3-methyl-4-methylsulfonyl-phenyl)-1-tetrahydropyran-2-yl-pyrazolo[4,3-c]pyridine (step 1) (100 mg, 0.2 mmol) in 1,4-dioxane (5 mL) was added cesium carbonate (332 mg, 1.0 mmol), N-[2-(2-aminoethoxy)ethyl]acetamide (179 mg, 1.2 mmol), xantphos (14 mg, 0.02 mmol) and $Pd(OAc)_2$ (4.6 mg, 0.02 mmol) was stirred at 80° C. for 12 h under a nitrogen atmosphere. The reaction mixture was filtered and concentrated. Purification by reversed phase preparative HPLC afforded the title compound (40 mg, 34%) as a yellow solid. ([M+H]+556.2)

Step 3: N-[2-[2-[[3-cyclopropyl-4-(3-methyl-4-methylsulfonyl-phenyl)-1H-pyrazolo[4,3-c]pyridin-7-yl]amino]ethoxy]ethyl]acetamide; formic acid salt N-[2-[2-[[3-cyclopropyl-4-(3-methyl-4-methylsulfonyl-phenyl)-1-tetrahydropyran-2-yl-pyrazolo[4,3-c]pyridin-7-yl]amino]ethoxy]ethyl]acetamide (step 2) was deprotected using General procedure I1 to afford the title compound. ([M+H]+472.3).

Example 100: N-[3-[[3-cyclopropyl-4-(3-methyl-4-methylsulfonyl-phenyl)-1H-pyrazolo[4,3-c]pyridin-7-yl]amino]propyl]acetamide; Formic Acid Salt

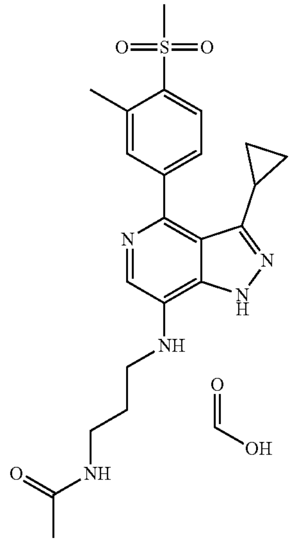 [SMILES: CC(=O)NCCCNc1cnc(-c2ccc(S(C)(=O)=O)c(C)c2)c2c(C3CC3)n[nH]c12 ; O=CO]

Step 1: N-[3-[[3-cyclopropyl-4-(3-methyl-4-methylsulfonyl-phenyl)-1-tetrahydropyran-2-yl-pyrazolo[4,3-c]pyridin-7-yl]amino]propyl]acetamide To a mixture of 7-bromo-3-cyclopropyl-4-(3-methyl-4-methylsulfonyl-phenyl-1-tetrahydropyran-2-yl-pyrazolo[4,3-c]pyridine (Example 99, step 1) (100 mg, 0.2 mmol) in 1,4-dioxane (3 mL) was added cesium carbonate (332 mg, 1.0 mmol), N-(3-aminopropyl)acetamide (118 mg, 1.0 mmol), xantphos (14 mg, 0.02 mmol) and $Pd(OAc)_2$ (5 mg, 0.02 mmol) was stirred at 80° C. for 12 h under a nitrogen atmosphere. The reaction mixture was filtered and concentrated. Purification by reversed phase preparative HPLC afforded the title compound (60 mg, 56%) as a yellow solid. ([M+H]+526.0)

Step 2: N-[3-[[3-cyclopropyl-4-(3-methyl-4-methylsulfonyl-phenyl)-1H-pyrazolo[4,3-c]pyridin-7-yl]amino]propyl]acetamide; formic acid N-[3-[[3-cyclopropyl-4-(3-methyl-4-methylsulfonyl-phenyl)-1-tetrahydropyran-2-yl-pyrazolo[4,3-c]pyridin-7-yl]

amino]propyl]acetamide (step 1) was deprotected using General procedure I1 to afford the title compound. ([M+H]$^+$ 441.9).

Example 101: N-[2-(2-aminoethoxy)ethyl]-3-cyclopropyl-4-(3-methyl-4-methylsulfonyl-phenyl)-1H-pyrazolo[4,3-c]pyridin-7-amine; Formic Acid

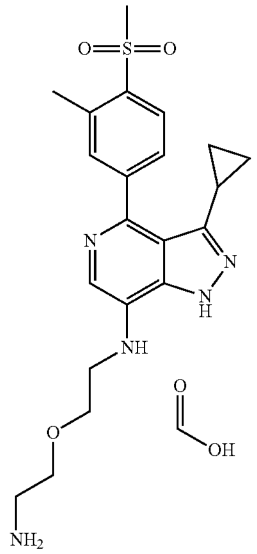 [SMILES: Cc1cc(-c2ncc(NCCOCCN)c3[nH]nc(C4CC4)c23)ccc1S(C)(=O)=O ; O=CO]

Step 1: tert-butyl N-[2-[2-[[3-cyclopropyl-4-(3-methyl-4-methylsulfonyl-phenyl)-1-tetrahydropyran-2-yl-pyrazolo[4,3-c]pyridin-7-yl]amino]ethoxy]ethyl]carbamate To a mixture of 7-bromo-3-cyclopropyl-4-(3-methyl-4-methylsulfonyl-phenyl)-1-tetrahydropyran-2-yl-pyrazolo[4,3-c]pyridine (Example 99, step 1) (120 mg, 0.2 mmol) in 1,4-dioxane (4 mL) was added cesium carbonate (399 mg, 1.2 mmol), N-Boc-2-(2-amino-ethoxy)-ethylamine (150 mg, 0.7 mmol), xantphos (17 mg, 0.03 mmol) and Pd(OAc)$_2$ (5 mg, 0.02 mmol) was stirred at 80° C. for 12 h under a nitrogen atmosphere. The reaction mixture was filtered and concentrated. Purification by reversed phase preparative HPLC afforded the title compound (98 mg, 62%) as a yellow solid. ([M+H]$^+$614.2)

Step 2: N-[2-(2-aminoethoxy)ethyl]-3-cyclopropyl-4-(3-methyl-4-methylsulfonyl-phenyl)-1H-pyrazolo[4,3-c]pyridin-7-amine; formic acid salt tert-butyl N-[2-[2-[[3-cyclopropyl-4-(3-methyl-4-methylsulfonyl-phenyl)-1-tetrahydropyran-2-yl-pyrazolo[4,3-c]pyridin-7-yl]amino]ethoxy]ethyl]carbamate (step 1) was deprotected using General procedure I1 to afford the title compound. ([M+H]$^+$430.1).

Example 102: N'-[3-cyclopropyl-4-(3-methyl-4-methylsulfonyl-phenyl)-1H-pyrazolo[4,3-c]pyridin-7-yl]butane-1,4-diamine

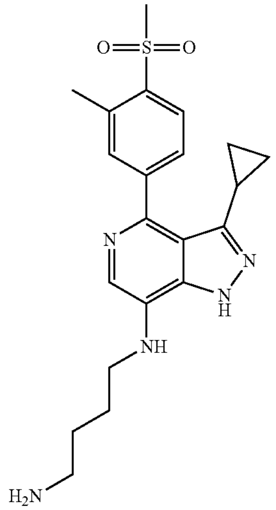 [SMILES: Cc1cc(-c2ncc(NCCCCN)c3[nH]nc(C4CC4)c23)ccc1S(C)(=O)=O]

Step 1: tert-butyl N-[4-[[3-cyclopropyl-4-(3-methyl-4-methylsulfonyl-phenyl)-1-tetrahydropyran-2-yl-pyrazolo[4,3-c]pyridin-7-yl]amino]butyl]carbamate To a mixture of 7-bromo-3-cyclopropyl-4-(3-methyl-4-methylsulfonyl-phenyl)-1-tetrahydropyran-2-yl-pyrazolo[4,3-c]pyridine (Example 99, step 1) (130 mg, 0.3 mmol) in 1,4-dioxane (4 mL) was added cesium carbonate (432 mg, 1.3 mmol), N-Boc-1,4-diaminobutane (150 mg, 0.8 mmol), xantphos (18 mg, 0.03 mmol) and Pd(OAc)$_2$ (6 mg, 0.03 mmol) was stirred at 80° C. for 12 h under a nitrogen atmosphere. The reaction mixture was filtered and concentrated. Purification by reversed phase preparative HPLC afforded the title compound (90 mg, 56%) as a yellow solid. ([M+H]$^+$598.2)

Step 2: N'-[3-cyclopropyl-4-(3-methyl-4-methylsulfonyl-phenyl)-1H-pyrazolo[4,3-c]pyridin-7-yl]butane-1,4-diamine tert-butyl N-[4-[[3-cyclopropyl-4-(3-methyl-4-methylsulfonyl-phenyl)-1-tetrahydropyran-2-yl-pyrazolo[4,3-c]pyridin-7-yl]amino]butyl]carbamate (step 1) was deprotected using General procedure I1 to afford the title compound. ([M+H]$^+$414.1).

Example 103: N-[4-[[3-cyclopropyl-4-(3-methyl-4-methylsulfonyl-phenyl)-1H-pyrazolo[4,3-c]pyridin-7-yl]amino]butyl]acetamide

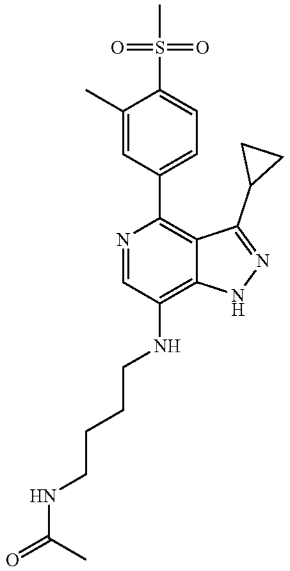 [SMILES: CC(=O)NCCCCNc1cnc(-c2ccc(S(C)(=O)=O)c(C)c2)c2c(C3CC3)n[nH]c12]

Step 1: N-[4-[[3-cyclopropyl-4-(3-methyl-4-methylsulfonyl-phenyl)-1-tetrahydropyran-2-yl-pyrazolo[4,3-c]pyridin-7-yl]amino]butyl]acetamide To a mixture of 7-bromo-3-cyclopropyl-4-(3-methyl-4-methylsulfonyl-phenyl)-1-tetrahydropyran-2-yl-pyrazolo[4,3-c]pyridine (Example 99, step 1) (80 mg, 0.2 mmol) in 1,4-dioxane (2 mL) was added cesium carbonate (266 mg, 0.8 mmol), N-(4-aminobutyl)acetamide (106 mg, 0.8 mmol), xantphos (11 mg, 0.02 mmol) and $Pd(OAc)_2$ (4 mg, 0.02 mmol) was stirred at 80° C. for 12 h under a nitrogen atmosphere. The reaction mixture was filtered and concentrated. Purification by reversed phase preparative HPLC afforded the title compound (60 mg, 68%) as a yellow solid. ($[M+H]^+$540.1)

Step 2: N-[4-[[3-cyclopropyl-4-(3-methyl-4-methylsulfonyl-phenyl)-1H-pyrazolo[4,3-c]pyridin-7-yl]amino]butyl]acetamide N-[4-[[3-cyclopropyl-4-(3-methyl-4-methylsulfonyl-phenyl)-1-tetrahydropyran-2-yl-pyrazolo[4,3-c]pyridin-7-yl]amino]butyl]acetamide (step 1) was deprotected using General procedure I1 to afford the title compound. ($[M+H]^+$ 499.9).

Example 104: N'-[3-cyclopropyl-4-(3-methyl-4-methylsulfonyl-phenyl)-1H-pyrazolo[4,3-c]pyridin-7-yl]propane-1,3-diamine

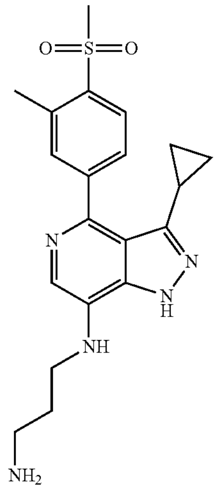 [SMILES: Cc1cc(-c2ncc(NCCCN)c3[nH]nc(C4CC4)c23)ccc1S(C)(=O)=O]

Step 1: tert-butyl N-[3-[[3-cyclopropyl-4-(3-methyl-4-methylsulfonyl-phenyl)-1-tetrahydropyran-2-yl-pyrazolo[4,3-c]pyridin-7-yl]amino]propyl]carbamate To a mixture of 7-bromo-3-cyclopropyl-4-(3-methyl-4-methylsulfonyl-phenyl)-1-tetrahydropyran-2-yl-pyrazolo[4,3-c]pyridine (Example 99, step 1) (100 mg, 0.2 mmol) in 1,4-dioxane (4 mL) was added cesium carbonate (332 mg, 1.0 mmol), N-Boc-1,3-diaminopropane (107 mg, 0.6 mmol), xantphos (14 mg, 0.02 mmol) and $Pd(OAc)_2$ (5 mg, 0.02 mmol) was stirred at 80° C. for 12 h under a nitrogen atmosphere. The reaction mixture was filtered and concentrated. Purification by reversed phase preparative HPLC afforded the title compound (50 mg, 42%) as a brown oil. ($[M+H]^+$584.4)

Step 2: N'-[3-cyclopropyl-4-(3-methyl-4-methylsulfonyl-phenyl)-1H-pyrazolo[4,3-c]pyridin-7-yl]propane-1,3-diamine N tert-butyl N-[3-[[3-cyclopropyl-4-(3-methyl-4-methylsulfonyl-phenyl)-1-tetrahydropyran-2-yl-pyrazolo[4,3-c]pyridin-7-yl]amino]propyl]carbamate (step 1) was deprotected using General procedure I1 to afford the title compound. ($[M+H]^+$399.9).

Example 105: 3-(difluoromethoxy)-4-(4-((difluoromethyl)sulfonyl)-3-methylphenyl)-1H-pyrazolo[3,4-c]pyridine-5-carbonitrile

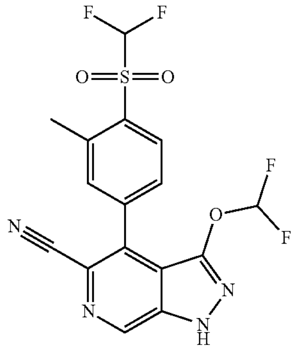 [SMILES: Cc1cc(-c2c(C#N)ncc3[nH]nc(OC(F)F)c23)ccc1S(=O)(=O)C(F)F]

Step 1: 3-(difluoromethoxy)-4-(4-((difluoromethyl)sulfonyl)-3-methylphenyl)-1-trityl-1H-pyrazolo[3,4-c]pyridine-5-carbonitrile The title compound ([M+formate]$^-$701.3) was prepared from Suzuki coupling of 4-bromo-3-(difluoromethoxy)-1-trityl-pyrazolo[3,4-c]pyridine-5-carbonitrile (Intermediate 17), 2-(4-cyclopropylsulfonyl-2-fluoro-5-methyl-phenyl)-4,4,5,5-tetramethyl-1,3,2-dioxaborolane (step 4) with potassium carbonate and 1,1'-bis(diphenylphosphino)ferrocene-palladium(II) dichloride dichloromethane adduct (0.05 eq) at 100° C. in accordance with General procedure D.

Step 2: 3-(difluoromethoxy)-4-(4-((difluoromethyl)sulfonyl)-3-methylphenyl)-1H-pyrazolo[3,4-c]pyridine-5-carbonitrile 3-(difluoromethoxy)-4-(4-((difluoromethyl)sulfonyl)-3-methylphenyl)-1-trityl-1H-pyrazolo[3,4-c]pyridine-5-carbonitrile is deprotected using General procedure H to afford the titled compound ([M+H]$^+$415.2) after flash column chromatography.

Example 106: 3-(difluoromethoxy)-4-[4-(difluoromethylsulfonyl)-3-methyl-phenyl]-1H-pyrazolo[3,4-c]pyridine-5-carboxamide

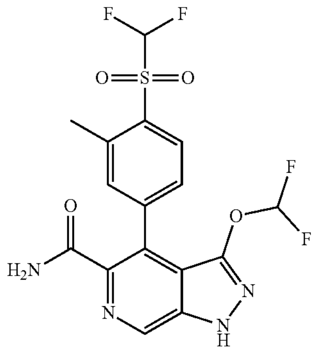 [SMILES: Cc1cc(-c2c(C(N)=O)ncc3[nH]nc(OC(F)F)c23)ccc1S(=O)(=O)C(F)F]

Step 1: 3-(difluoromethoxy)-4-[4-(difluoromethylsulfonyl)-3-methyl-phenyl]-1-trityl-pyrazolo[3,4-c]pyridine-5-carboxamide To a solution of 3-(difluoromethoxy)-4-[4-(difluoromethylsulfonyl)-3-methyl-phenyl]-1-trityl-pyrazolo[3,4-c]pyridine-5-carbonitrile (Example 105, step 1) (295 mg, 0.45 mmol) in dimethyl sulfoxide (3.5 mL) was added potassium carbonate (12.4 mg, 0.09 mmol) followed by dropwise addition of 35% aqueous hydrogen peroxide (153 μL, 10.23 mmol). The reaction was stirred for 16 h after which time it was diluted with water resulting in precipitation of product. The suspension was aged, filtered, the filter cake washed with water and dried to afford the title product compound (325 mg, quant) as an off-white powder. ([M+H]$^+$675.3)

Step 2: 3-(difluoromethoxy)-4-[4-(difluoromethylsulfonyl)-3-methyl-phenyl]-1H-pyrazolo[3,4-c]pyridine-5-carboxamide 3-(difluoromethoxy)-4-[4-(difluoromethylsulfonyl)-3-methyl-phenyl]-1-trityl-pyrazolo[3,4-c]pyridine-5-carboxamide is deprotected using General procedure H to afford the titled compound ([M+H]+433.2) after flash column chromatography.

Example 107: 3-(difluoromethoxy)-4-[4-(difluoromethylsulfonyl)-3-methyl-phenyl]-N-(oxetan-3-yl)-1H-pyrazolo[3,4-c]pyridine-5-carboxamide

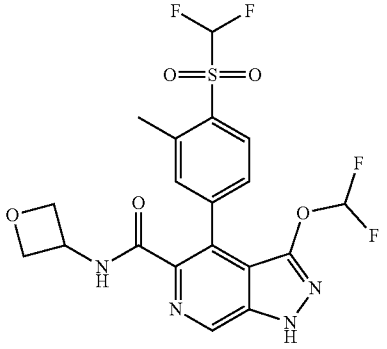 [SMILES: Cc1cc(-c2c(C(=O)NC3COC3)ncc3[nH]nc(OC(F)F)c23)ccc1S(=O)(=O)C(F)F]

Step 1: 3-(difluoromethoxy)-4-[4-(difluoromethylsulfonyl)-3-methyl-phenyl]-1H-pyrazolo[3,4-c]pyridine-5-carboxylic acid 3-(difluoromethoxy)-4-[4-(difluoromethylsulfonyl)-3-methyl-phenyl]-1-trityl-pyrazolo[3,4-c]pyridine-5-carboxamide (150 mg, 0.22 mmol) was dissolved in acetonitrile (5 mL) and heated to 80° C. tert-Butyl nitrite (132 μL, 1.11 mmol) was added and the mixture was stirred for 4 hr after which time the mixture was evaporated to dryness to afford the crude titled product (208 mg) as an orange foam, used in the next step without further purification. ([M+H]+434.2)

Step 2: 3-(difluoromethoxy)-4-[4-(difluoromethylsulfonyl)-3-methyl-phenyl]-N-(oxetan-3-yl)-1H-pyrazolo[3,4-c]pyridine-5-carboxamide The title compound ([M+H]$^+$489.2) was prepared in analogy to Example 72 from 3-(difluoromethoxy)-4-[4-(difluoromethylsulfonyl)-3-methyl-phenyl]-1H-pyrazolo[3,4-c]pyridine-5-carboxylic acid (step 1) and oxetan-3-ylamine.

Example 108: 3-(difluoromethoxy)-4-[4-(difluoromethylsulfonyl)-3-methyl-phenyl]-N-(oxetan-3-yl)-1H-pyrazolo[3,4-c]pyridine-5-carboxamide

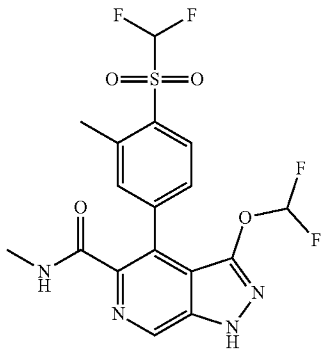 [SMILES: CNC(=O)c1ncc2[nH]nc(OC(F)F)c2c1-c1ccc(S(=O)(=O)C(F)F)c(C)c1]

The title compound ([M+H]+447.1) was prepared in analogy to Example 72 from 3-(difluoromethoxy)-4-[4-(difluoromethylsulfonyl)-3-methyl-phenyl]-1H-pyrazolo[3,4-c]pyridine-5-carboxylic acid (Example, 107 step 1) and methylamine hydrochloride.

Example 109: 3-(difluoromethoxy)-4-[4-(difluoromethylsulfonyl)-3-methyl-phenyl]-N-(2-methoxyethyl)-1H-pyrazolo[3,4-c]pyridine-5-carboxamide

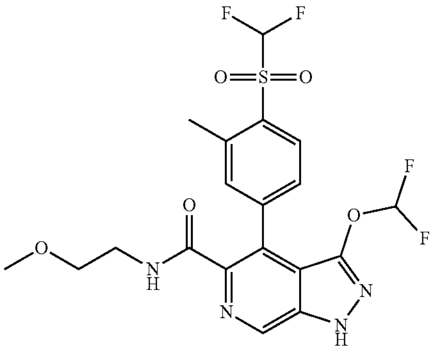 [SMILES: COCCNC(=O)c1ncc2[nH]nc(OC(F)F)c2c1-c1ccc(S(=O)(=O)C(F)F)c(C)c1]

The title compound ([M+H]+447.1) was prepared in analogy to Example 72 from 3-(difluoromethoxy)-4-[4-(difluoromethylsulfonyl)-3-methyl-phenyl]-1H-pyrazolo[3,4-c]pyridine-5-carboxylic acid (Example 107, step 1) and 2-methoxyethylamine.

Example 110: 3-(difluoromethoxy)-N-methyl-4-(3-methyl-4-methylsulfonyl-phenyl)-1H-pyrazolo[3,4-c]pyridine-5-carboxamide

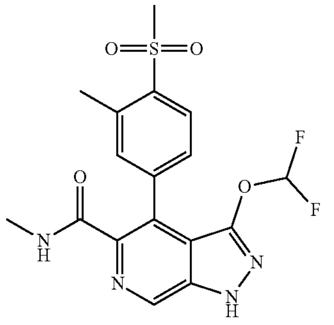 [SMILES: CNC(=O)c1ncc2[nH]nc(OC(F)F)c2c1-c1ccc(S(C)(=O)=O)c(C)c1]

Step 1: 3-(difluoromethoxy)-4-(3-methyl-4-(methylsulfonyl)phenyl)-1H-pyrazolo[3,4-c]pyridine-5-carboxylic acid To 3-(difluoromethoxy)-4-(3-methyl-4-methylsulfonyl-phenyl)-1H-pyrazolo[3,4-c]pyridine-5-carbonitrile (Example 52) (238 mg, 0.6 mmol) was added 6 N sodium hydroxide (2.5 mL) and the reaction heated to 100° C. for 2.5 h after which time it was diluted with water (9 ml) and the heating continued for 36 h at 90° C. The reaction was cooled to 0° C. and acidifed with 25% hydrochloric acid and the product isolated by filtration to afford the title compound (92 mg, 30%) as a light brown solid. ([M+H]+398.2)

Step 2: 3-(difluoromethoxy)-N-methyl-4-(3-methyl-4-methylsulfonyl-phenyl)-1H-pyrazolo[3,4-c]pyridine-5-carboxamide The title compound ([M+H]+411.3) was prepared in analogy to Example 72 from 3-(difluoromethoxy)-4-(3-methyl-4-(methylsulfonyl)phenyl)-1H-pyrazolo[3,4-c]pyridine-5-carboxylic acid (step 1) and methylamine hydrochloride.

Example 111: 3-(difluoromethoxy)-4-(3-methyl-4-methylsulfonyl-phenyl)-5-(oxetan-3-ylsulfonyl)-1H-indazole

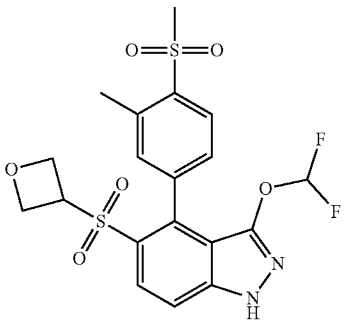 [SMILES: Cc1cc(-c2c(S(=O)(=O)C3COC3)ccc3[nH]nc(OC(F)F)c23)ccc1S(C)(=O)=O]

Step 1: 3-(2-bromo-4-fluoro-phenyl)sulfanyloxetane

To a stirred suspension of 3-iodooxetane (10.4 g, 56.5 mmol) in DMF (30 mL) was added 2-bromo-4-fluorothiophenol (3.9 g, 18.8 mmol) and potassium tert-butoxide (2.5 g, 22.6 mmol) and the reaction heated to 100° C. for 5 h. The reaction was diluted with ethyl acetate washed with water, brine, dried ($Na_2SO_4$) and concentrated. Flash column chromatography (Ethyl acetate: n-Heptane 1:10-1:3) afforded the title compound (4.1 g, 83%) as a yellow oil. 1H NMR (400 MHz, CHLOROFORM-d) δ=7.37 (dd, J=2.7, 8.1 Hz, 1H), 7.12-7.07 (m, 1H), 7.05-6.98 (m, 1H), 5.06 (t, J=7.1 Hz, 2H), 4.68 (t, J=6.6 Hz, 2H), 4.49-4.41 (m, 1H)

Step 2: ethyl 2-bromo-6-fluoro-3-(oxetan-3-ylsulfanyl)benzoate 3-(2-bromo-4-fluoro-phenyl)sulfanyloxetane (Step 1) was deprotonated with LDA (1.1 eq) for 30 minutes and reacted with ethyl chloroformate (1.2 eq) in accordance with General procedure A to afford the title compound. 1H NMR (400 MHz, CHLOROFORM-d) δ=7.12-7.05 (m, 2H), 5.07 (t, J=7.1 Hz, 2H), 4.67 (t, J=6.6 Hz, 2H), 4.50-4.42 (m, 3H), 1.42 (t, J=7.1 Hz, 3H)

Step 3: ethyl 2-bromo-6-fluoro-3-(oxetan-3-ylsulfonyl)benzoate

To a solution of ethyl 2-bromo-6-fluoro-3-(oxetan-3-ylsulfanyl)benzoate (step 2) (4.1 g, 12.2 mmol) in dichloromethane (100 ml) was added mCPBA (6.2 g, 30.6 mmol) and the reaction stirred at ambient temperature for 16 h. The reaction was then diluted with DCM, washed with 1 aq.sat. sodium hydrogencarbonate solution, dried ($Na_2SO_4$) and concentrated. Flash column chromatography (Ethyl acetate: n-Heptane 3:1-1:1) afforded the title compound (4.6 g, 87%) as a yellow solid. 1H NMR (400 MHz, CHLOROFORM-d) δ=8.31 (dd, J=5.6, 8.9 Hz, 1H), 7.33 (dd, J=7.6, 8.9 Hz, 1H), 5.03-4.96 (m, 3H), 4.89-4.83 (m, 2H), 4.49 (q, J=7.1 Hz, 2H), 1.42 (t, J=7.2 Hz, 3H)

Step 4: 4-bromo-5-(oxetan-3-ylsulfonyl)-1,2-dihydroindazol-3-one

To an ice-cold solution of ethyl 2-bromo-6-fluoro-3-(oxetan-3-ylsulfonyl)benzoate (step 3) (4.6 g, 12.5 mmol) in ethanol (40 ml) was added hydrazine monohydrate (689 µL, 13.9 mmol) followed by triethylamine (2.1 ml, 15.0 mmol) and the reaction brought to ambient temperature. It was then heated to 80° C. for 2 h after which time the reaction was concentrated to dryness. Reversed phase preparative HPLC afforded the title compound (2.8 g, 67%) was obtained as a light yellow solid. ([M+H, Br]$^+$335.0).

Step 5: 4-bromo-5-(oxetan-3-ylsulfonyl)-1-trityl-indazol-3-ol

To an ice cold solution of 4-bromo-5-(oxetan-3-ylsulfonyl)-1,2-dihydroindazol-3-one (step 4) (2.7 g, 8.1 mmol) in DMF (30 ml) was added trityl chloride (2.5 g, 8.9 mmol) followed by sodium hydride (389 mg, 60% dispersion in mineral oil, 9.7 mmol), the cooling bath was removed and the reaction stirred at ambient temperature for 1 h. The reaction was then diluted with ethyl acetate, washed with water, dried ($Na_2SO_4$) and concentrated. Flash column chromatography (Ethyl acetate: n-Heptane 1:3-1:0) afforded the title compound (4.1 g, 65%) as a colourless solid. ([M+Na+, Br]+599.1).

Step 6: 4-bromo-3-(difluoromethoxy)-5-(oxetan-3-ylsulfonyl)-1-trityl-indazole

A mixture of 4-bromo-5-(oxetan-3-ylsulfonyl)-1-trityl-indazol-3-ol (step 5) (4.0 g, 5.21 mmol) in DMF (40 mL) was added sodium chlorofluoroacetate (1.6 g, 10.4 mmol) and potassium carbonate (2.1 g, 15.6 mmol) was heated to 80° C. for 0.5 h. The reaction was diluted with ethyl acetate washed with water, brine, dried ($Na_2SO_4$) and concentrated. Flash column chromatography (Ethyl acetate: n-Heptane 1:3-1:0) afforded the title compound (2.8 g, 86%) as a white solid. ([M+Na]$^+$649.1).

Step 7: 3-(difluoromethoxy)-4-(3-methyl-4-methylsulfonyl-phenyl)-5-(oxetan-3-ylsulfonyl)-1-trityl-indazole The title compound ([M+Na+]$^+$737.4) was prepared from Suzuki coupling of 4-bromo-3-(difluoromethoxy)-5-(oxetan-3-ylsulfonyl)-1-trityl-indazole (step 6), (3-methyl-4-(methylsulfonyl)phenyl)boronic acid with potassium carbonate and 1,1'-bis(diphenylphosphino)ferrocene-palladium (II) dichloride dichloromethane adduct (0.1 eq) at 100° C. in accordance with General procedure D.

Step 8: 3-(difluoromethoxy)-4-(3-methyl-4-methylsulfonyl-phenyl)-5-(oxetan-3-ylsulfonyl)-1H-indazole 3-(difluoromethoxy)-4-(3-methyl-4-methylsulfonyl-phenyl)-5-(oxetan-3-ylsulfonyl)-1-trityl-indazole (step 7) is deprotected using General procedure H to afford the titled compound ([M+H]+495.2) after flash column chromatography.

Example 112: p-cyclopropyl-4-(3-methyl-4-methylsulfonylphenyl)-1H-indazol-5-yl]-imino-methyl-oxo-sulfane

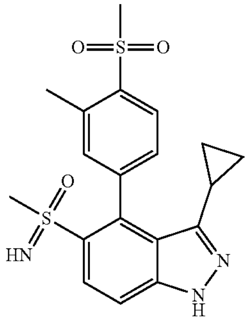 [SMILES: Cc1cc(-c2c(S(C)(=N)=O)ccc3[nH]nc(C4CC4)c23)ccc1S(C)(=O)=O]

Step 1: (6-(cyclopropanecarbonyl)-5-fluoro-3'-methyl-4'-(methylsulfonyl)-[1,1'-biphenyl]-2-yl)(imino)(methyl)-16-sulfanone To a solution of yclopropyl(3-fluoro-3'-methyl-4'-(methylsulfonyl)-6-(methylthio)-[1,1'-biphenyl]-2-yl)methanone (Example 75, step 3) (250 mg, 661 µmol) in MeOH (3 ml) was added ammonium carbonate (95 mg, 991 µmol) and (diacetoxyiodo)benzene (532 mg, 1.65 mmol) The and the mixture stirred at ambient temperature for 1 h. The reaction was diluted with ethyl acetate washed with water, dried ($Na_2SO_4$) and concentrated. Flash column chromatography (dichloromethane:MeOH 1:0-9:1) afforded the title compound (199 mg, 72%) as a white solid. ([M+H]$^+$410.2).

Step 2: [3-cyclopropyl-4-(3-methyl-4-methylsulfonylphenyl)-1H-indazol-5-yl]-imino-methyl-oxo-sulfane To an solution of (6-(cyclopropanecarbonyl)-5-fluoro-3'-methyl-4'-(methylsulfonyl)-[1,1'-biphenyl]-2-yl)(imino)(methyl)-16-sulfanone (step 1) (15 mg, 36.6 μmol) in methanol (1 ml) was added hydrazine monohydrate (28 μL, 366 μmol) and the reaction heated to 65° C. for 16 h after which time the reaction was concentrated to dryness. Flash column chromatography (dichloromethane:MeOH 9:1) afforded the title compound (10 mg, 67%) as a white solid. ([M+H]$^+$ 404.1).

Example 113: [3-cyclopropyl-4-(3-methyl-4-methylsulfonyl-phenyl)-1H-indazol-5-yl]-methyl-methylimino-oxo-λ$^6$-sulfane

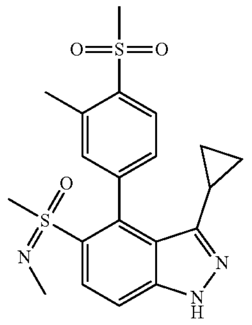 [SMILES: CN=S(C)(=O)c1ccc2[nH]nc(C3CC3)c2c1-c1ccc(S(C)(=O)=O)c(C)c1]

Step 1: (6-(cyclopropanecarbonyl)-5-fluoro-3'-methyl-4'-(methylsulfonyl)-[1,1'-biphenyl]-2-yl)(methyl)(methylimino)-16-sulfanone To a solution of (6-(cyclopropanecarbonyl)-5-fluoro-3'-methyl-4'-(methylsulfonyl)-[1,1'-biphenyl]-2-yl)(imino)(methyl)-16-sulfanone (50 mg, 122 μmol) in DMF (1 ml) was added sodium hydride (7.3 mg, 183 μmol) and iodomethane (10 μl, 159 μmol) and the reaction mixture was stirred at ambient temperature for 16 h. The reaction was diluted with ethyl acetate washed with water, dried ($Na_2SO_4$) and concentrated. Reversed phase preparative HPLC afforded the title compound (22 mg, 37%) as a white solid. ([M+H]$^+$424.2).

Step 2: [3-cyclopropyl-4-(3-methyl-4-methylsulfonyl-phenyl)-1H-indazol-5-yl]-methyl-methylimino-oxo-λ$^6$-sulfane To a solution of (6-(cyclopropanecarbonyl)-5-fluoro-3'-methyl-4'-(methylsulfonyl)-[1,1'-biphenyl]-2-yl)(methyl)(methylimino)-16-sulfanone (step 1) (22 mg, 52.7 μmol) in ethanol (0.4 ml) was added hydrazine monohydrate (156 μl, 316 μmol) followed by triethylamine (11 μl, 79 μmol) and the reaction stirred at ambient temperature for 16 h after which time the reaction was concentrated to dryness. Flash column chromatography (dichloromethane: MeOH 9:1) afforded the title compound (19 mg, 85%) as a white solid. ([M+H]$^+$418.2).

Example 114: 3-cyclopropyl-N,N-dimethyl-4-(3-methyl-4-methylsulfonyl-phenyl)-1H-indazole-5-sulfonamide

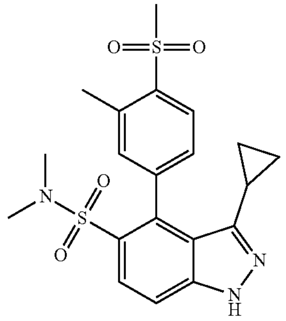 [SMILES: Cc1cc(-c2c(S(=O)(=O)N(C)C)ccc3[nH]nc(C4CC4)c23)ccc1S(C)(=O)=O]

Step 1: 2-bromo-4-fluoro-N,N-dimethyl-benzenesulfonamide

To a solution of 2-bromo-4-fluorobenzenesulfonyl chloride (2.0 g, 7.31 mmol) in dichloromethane (20 mL) was added diisopropylethylamine (2.8 mL, 21.9 mmol) and dimethylamine hydrochloride (1.1 g, 14.6 mmol) and the reaction mixture stirred for 2 h at ambient temperature. The reaction was diluted with ethyl acetate, washed with 1M HCl and concentrated. Flash column chromatography (Ethyl acetate: n-Heptane 1:10-3:1) afforded the title compound (1.8 g, 83%) as a white solid. ([M+H, Br]$^+$282.0).

Step 2: 2-bromo-3-[cyclopropyl(hydroxy)methyl]-4-fluoro-N,N-dimethyl-benzenesulfonamide 2-bromo-4-fluoro-N,N-dimethyl-benzenesulfonamide (step 1) was deprotonated with LDA (1.2 eq) for 0.5 h and reacted with cyclopropanecarboxaldehyde (1.5 eq) for 1 h in accordance with General procedure A to afford the title compound ([M+H (—OH), Br]$^+$334.0.

Step 3: 2-bromo-3-(cyclopropanecarbonyl)-4-fluoro-N,N-dimethyl-benzenesulfonamide 2-bromo-3-[cyclopropyl(hydroxy)methyl]-4-fluoro-N,N-dimethyl-benzenesulfonamide (step 2) was oxidised using General procedure B2 to afford the title compound. ([M+H, Br]$^+$350.0.

Step 4: 4-bromo-3-cyclopropyl-N,N-dimethyl-1H-indazole-5-sulfonamide

To a solution of 2-bromo-3-(cyclopropanecarbonyl)-4-fluoro-N,N-dimethyl-benzenesulfonamide (step 3) (60 mg, 170 μmol) in ethanol (2 ml) was added hydrazine monohydrate (170 μl, 316 μmol) followed by triethylamine (30 μl, 210 μmol) and the reaction heated to 80° C. for 16 h after which time the reaction was concentrated to dryness. Reversed phase preparative HPLC afforded the title compound (40 mg, 67%) as a light yellow solid. ([M+H, Br]$^+$346.1).

Step 5: 3-cyclopropyl-N,N-dimethyl-4-(3-methyl-4-methylsulfonyl-phenyl)-1H-indazole-5-sulfonamide The title compound ([M+Na$^+$]$^+$434.2) was prepared from Suzuki coupling of 4-bromo-3-cyclopropyl-N,N-dimethyl- 1H-indazole-5-sulfonamide (step 4), (3-methyl-4-(methylsulfonyl)phenyl)boronic acid with potassium carbonate and 1,1'-bis(diphenylphosphino)ferrocene-palladium(II) dichloride dichloromethane adduct (0.1 eq) at 100° C. in accordance with General procedure D.

Example 115: 3-cyclopropyl-N-methyl-4-(3-methyl-4-methylsulfonyl-phenyl)-1H-indazole-5-sulfonamide

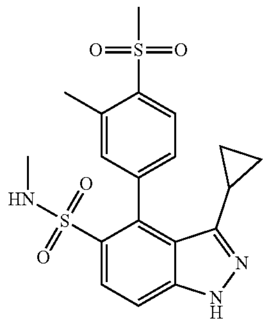 [SMILES: CNS(=O)(=O)c1ccc2[nH]nc(C3CC3)c2c1-c1ccc(S(C)(=O)=O)c(C)c1]

Step 1: 2-bromo-4-fluoro-N-[(4-methoxyphenyl)methyl]-N-methyl-benzenesulfonamide To a solution of 2-bromo-4-fluorobenzenesulfonyl chloride (2.0 g, 7.31 mmol) in dichloromethane (20 mL) was added diisopropylethylamine (1.6 mL, 14.6 mmol) and 4-methoxy-N-methylbenzylamine (1.7 g, 11.0 mmol) and the reaction mixture stirred for 2 h at ambient temperature. The reaction was diluted with ethyl acetate, washed with 1M HCl and concentrated. Flash column chromatography afforded the title compound (2.6 g, 92%) as a white solid. ([M+H, Br]$^+$412.1).

Step 2: 2-bromo-3-[cyclopropyl(hydroxy)methyl]-4-fluoro-N-[(4-methoxyphenyl)methyl]-N-methyl-benzenesulfonamide 2-bromo-4-fluoro-N-[(4-methoxyphenyl)methyl]-N-methyl-benzenesulfonamide (step 1) was deprotonated with LDA (1.2 eq) for 0.5 h and reacted with cyclopropanecarboxaldehyde (1.5 eq) for 1 h in accordance with General procedure A to afford the title compound ([M+Na, Br]$^+$ 482.1.

Step 3: 2-bromo-3-(cyclopropanecarbonyl)-4-fluoro-N-[(4-methoxyphenyl)methyl]-N-methyl-benzenesulfonamide 2-bromo-3-[cyclopropyl(hydroxy)methyl]-4-fluoro-N,N-dimethyl-benzenesulfonamide (step 2) was oxidised using General procedure B2 to afford the title compound. ([M+H, Br]$^+$480.2.

Step 4: 4-bromo-3-cyclopropyl-N-[(4-methoxyphenyl)methyl]-N-methyl-1H-indazole-5-sulfonamide To a solution of 2-bromo-3-(cyclopropanecarbonyl)-4-fluoro-N-[(4-methoxyphenyl)methyl]-N-methyl-benzenesulfonamide (step 3) (200 mg, 440 μmol) in ethanol (4 ml) was added hydrazine monohydrate (44 μl, 880 μmol) followed by triethylamine (70 μl, 530 μmol) and the reaction heated to 80° C. for 2 h after which time the reaction was concentrated to dryness. Reversed phase preparative HPLC afforded the title compound (200 mg, quant.) as a white solid. ([M+H, Br]$^+$450.0).

Step 5: 3-cyclopropyl-N-[(4-methoxyphenyl)methyl]-N-methyl-4-(3-methyl-4-methylsulfonyl-phenyl)-1H-indazole-5-sulfonamide The title compound ([M+Na$^+$]$^+$5402) was prepared from Suzuki coupling of 44-bromo-3-cyclopropyl-N-[(4-methoxyphenyl)methyl]-N-methyl-1H-indazole-5-sulfonamide (step 4), (3-methyl-4-(methylsulfonyl)phenyl)boronic acid with potassium carbonate and 1,1'-bis(diphenylphosphino)ferrocene-palladium(II) dichloride dichloromethane adduct (0.1 eq) at 100° C. in accordance with General procedure D.

Step 6: 3-cyclopropyl-N-methyl-4-(3-methyl-4-methylsulfonyl-phenyl)-1H-indazole-5-sulfonamide 3-cyclopropyl-N-[(4-methoxyphenyl)methyl]-N-methyl-4-(3-methyl-4-methylsulfonyl-phenyl)-1H-indazole-5-sulfonamide (step 5) is deprotected using General procedure H to afford the titled compound ([M+H]+420.0) after flash column chromatography.

Example 116: 4-(4-cyclopropylsulfonyl-3-methyl-phenyl)-3-(difluoromethoxy)-1H-pyrazolo[3,4-c]pyridine-5-carboxamide

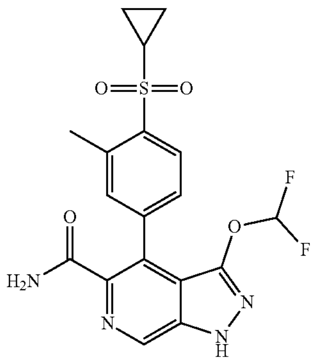 [SMILES: Cc1cc(-c2c(C(N)=O)ncc3[nH]nc(OC(F)F)c23)ccc1S(=O)(=O)C1CC1]

Step 1: 3-(difluoromethoxy)-4-(4-((difluoromethyl)sulfonyl)-3-methylphenyl)-1-trityl-1H-pyrazolo[3,4-c]pyridine-5-carbonitrile The title compound ([M+Na]$^+$669.3) was prepared from Suzuki coupling of 4-bromo-3-(difluoromethoxy)-1-trityl-pyrazolo[3,4-c]pyridine-5-carbonitrile (Intermediate 17) and 2-(4-(cyclopropylsulfonyl)-3-methylphenyl)-4,4,5,5-tetramethyl-1,3,2-dioxaborolane (Intermediate 8) with potassium carbonate and 1,1'-bis(diphenylphosphino)ferrocene-palladium(II) dichloride dichloromethane adduct (0.05 eq) at 100° C. in accordance with General procedure D.

Step 2: 4-(4-cyclopropylsulfonyl-3-methyl-phenyl)-3-(difluoromethoxy)-1-trityl-pyrazolo[3,4-c]pyridine-5-carboxamide To the solution of 4-(4-cyclopropylsulfonyl-3-methyl-phenyl)-3-(difluoromethoxy)-1-trityl-pyrazolo[3,4-c]pyridine-5-carbonitrile (step 1) (220.0 mg, 0.34 mmol) in ethanol (5 mL) was added 2 N aq. NaOH (0.85 mL, 1.7 mmol) ad the reaction heated to 100° C. for 6 h. The reaction was acidified by addition of 1N HCl, extracted with ethyl acetate and concentrated. Preparative tlc ((Ethyl acetate: n-Heptane 1:2) afforded the title compound (150 mg, 66%) as a yellow solid.

Step 3: 4-(4-cyclopropylsulfonyl-3-methyl-phenyl)-3-(difluoromethoxy)-1H-pyrazolo[3,4-c]pyridine-5-carboxamide 4-(4-cyclopropylsulfonyl-3-methyl-phenyl)-3-(difluoromethoxy)-1-trityl-pyrazolo[3,4-c]pyridine-5-carboxamide (step 2) is deprotected using General procedure H to afford the titled compound ([M+H]+423.2) after flash column chromatography.

Example 117: 3-(difluoromethoxy)-4-(4-((difluoromethyl)sulfonyl)-3-methylphenyl)-5-(methylsulfonyl)-1H-indazole

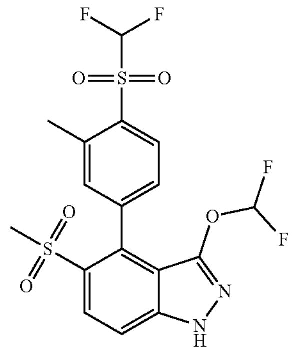 [SMILES: Cc1cc(-c2c(S(C)(=O)=O)ccc3[nH]nc(OC(F)F)c23)ccc1S(=O)(=O)C(F)F]

The title compound ([M+Na]$^+$465.1) could be prepared in analogy to Example 49 by Suzuki coupling of 4-bromo-3-(difluoromethoxy)-5-(methylsulfonyl)-1-trityl-1H-indazole (intermediate 6) and 2-[4-(difluoromethylsulfonyl)-3-methyl-phenyl]-4,4,5,5-tetramethyl-1,3,2-dioxaborolane (Intermediate 27) followed by deprotection using General procedure H.

Example 118: 5-cyclopropylsulfonyl-3-(difluoromethoxy)-4-(3-methyl-4-methylsulfonyl-phenyl)-1H-indazole

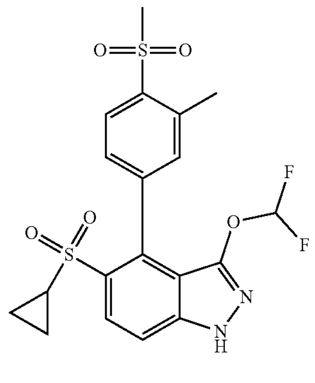 [SMILES: Cc1cc(-c2c(S(=O)(=O)C3CC3)ccc3[nH]nc(OC(F)F)c23)ccc1S(C)(=O)=O]

Step 1: 2-bromo-1-cyclopropylsulfanyl-4-fluoro-benzene

To a stirred suspension of cyclopropyl bromide (6.1 g, 50.71 mmol) in DMF (50 mL) was added 2-bromo-4-fluorothiophenol (3.5 g, 16.9 mmol) and potassium tert-butoxide (2.2 g, 20.3 mmol) and the reaction heated to 100° C. for 12 h. The reaction was diluted with ethyl acetate washed with water, brine, dried ($Na_2SO_4$) and concentrated. Flash column chromatography (n-Heptane) afforded the title compound (1.7 g, 41%) as a colourless oil. 1H NMR (400 MHz, CHLOROFORM-d) δ=7.50 (dd, J=5.6, 8.4 Hz, 1H), 7.30 (dd, J=2.0, 8.1 Hz, 1H), 7.06 (dt, J=1.9, 8.4 Hz, 1H), 2.20-2.11 (m, 1H), 1.16-1.10 (m, 2H), 0.79-0.71 (m, 2H)

Step 2: ethyl 2-bromo-3-cyclopropylsulfanyl-6-fluoro-benzoate 2-bromo-1-cyclopropylsulfanyl-4-fluoro-benzene (Step 1) was deprotonated with LDA (1.1 eq) for 30 minutes and reacted with ethyl chloroformate (1.2 eq) in accordance with General procedure A to afford the title compound. 1H NMR (400 MHz, CHLOROFORM-d) δ=7.56 (dd, J=5.5, 8.9 Hz, 1H), 7.12 (t, J=8.6 Hz, 1H), 4.45 (q, J=7.2 Hz, 2H), 2.14 (tt, J=4.4, 7.3 Hz, 1H), 1.41 (t, J=7.2 Hz, 3H), 1.18-1.13 (m, 2H), 0.77-0.71 (m, 2H)

Step 3: ethyl 2-bromo-3-cyclopropylsulfonyl-6-fluoro-benzoate

To a solution of ethyl 2-bromo-3-cyclopropylsulfanyl-6-fluoro-benzoate (step 2) (1.9 g, 5.95 mmol) in dichloromethane (40 ml) was added mCPBA (3.6 g, 17.9 mmol) and the reaction stirred at ambient temperature for 12 h. The reaction was then diluted with DCM, washed with 1 aq.sat. sodium hydrogencarbonate solution, dried ($Na_2SO_4$) and concentrated. Flash column chromatography (Ethyl acetate: n-Heptane 1:5-1:3) afforded the title compound (2.0 g, 84%) as a white solid. ([M+H, Br]+353.0)

Step 4: 4-bromo-5-cyclopropylsulfonyl-1,2-dihydroindazol-3-one

To an ice-cold solution of ethyl 2-bromo-3-cyclopropylsulfonyl-6-fluoro-benzoate (step 3) (2.0 g, 5.69 mmol) in ethanol (20 ml) was added hydrazine monohydrate (1130 μL, 22.6 mmol) followed by triethylamine (0.79 ml, 5.69 mmol) and the reaction brought to ambient temperature. It was then heated to 80° C. for 2 h after which time the reaction was concentrated to dryness. Reversed phase preparative HPLC afforded the title compound (1.1 g, 58%) was obtained as an off-white solid. ([M+H, Br]$^+$316.8).

Step 5: 4-bromo-5-cyclopropylsulfonyl-1-trityl-indazol-3-ol

To an ice cold solution of 4-bromo-5-cyclopropylsulfonyl-1,2-dihydroindazol-3-one (step 4) (1.0 g, 3.15 mmol) in DMF (20 ml) was added trityl chloride (0.97 g, 3.47 mmol) followed by sodium hydride (151 mg, 60% dispersion in mineral oil, 3.78 mmol), the cooling bath was removed and the reaction stirred at ambient temperature for 2 h. The reaction was then diluted with ethyl acetate, washed with water, dried ($Na_2SO_4$) and concentrated. Flash column chromatography (Ethyl acetate: n-Heptane 1:3-1:1) afforded the title compound (1.1 g, 52%) as a yellow solid. ([M+Na, Br]$^+$583.1).

Step 6: 4-bromo-5-cyclopropylsulfonyl-3-(difluoromethoxy)-1-trityl-indazole

A mixture of 4-bromo-5-cyclopropylsulfonyl-1-trityl-indazol-3-ol (step 5) (1.2 g, 2.06 mmol) in DMF (30 mL) was added sodium chlorofluoroacetate (0.63 g, 4.11 mmol) and potassium carbonate (0.85 g, 6.17 mmol) was heated to 80° C. for 0.5 h. The reaction was diluted with ethyl acetate washed with water, brine, dried ($Na_2SO_4$) and concentrated. Flash column chromatography (Ethyl acetate: n-Heptane 1:5-1:3) afforded the title compound (1.1 g, 83%) as a light yellow solid. ($[M+Na]^+633.0$).

Step 7: 5-cyclopropylsulfonyl-3-(difluoromethoxy)-4-(3-methyl-4-methylsulfonyl-phenyl)-1-trityl-indazole The title compound ($[M+Na^+]^+721.1$) was prepared from Suzuki coupling of 4-bromo-5-cyclopropylsulfonyl-3-(difluoromethoxy)-1-trityl-indazole (step 6), (3-methyl-4-(methylsulfonyl)phenyl)boronic acid with potassium carbonate and 1,1'-bis(diphenylphosphino)ferrocene-palladium (II) dichloride dichloromethane adduct (0.1 eq) at 100° C. in accordance with General procedure D.

Step 8: 5-cyclopropylsulfonyl-3-(difluoromethoxy)-4-(3-methyl-4-methylsulfonyl-phenyl)-1H-indazole 5-cyclopropylsulfonyl-3-(difluoromethoxy)-4-(3-methyl-4-methylsulfonyl-phenyl)-1-trityl-indazole (step 7) is deprotected using General procedure H to afford the titled compound ([M+H]+457.2) after flash column chromatography.

Example 119: 3-(difluoromethoxy)-4-(2-fluoro-5-methyl-4-methylsulfonyl-phenyl)-5-methylsulfonyl-1H-indazole

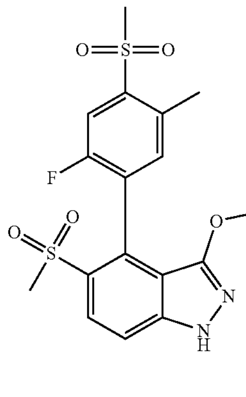

Step 1: 3-(difluoromethoxy)-4-(2-fluoro-5-methyl-4-methylsulfonyl-phenyl)-5-methylsulfonyl-1-trityl-indazole The title compound ([M+Na+]+713.2) was prepared from Suzuki coupling of 4-bromo-3-(difluoromethoxy)-5-methylsulfonyl-1-trityl-indazole (Intermediate 36), (2-(2-fluoro-5-methyl-4-methylsulfonyl-phenyl)-4,4,5,5-tetramethyl-1,3,2-dioxaborolane (Intermediate 25) with potassium carbonate and SPhos Pd G3 (0.1 eq) at 100° C. in accordance with General procedure D.

Step 2: 3-(difluoromethoxy)-4-(2-fluoro-5-methyl-4-methylsulfonyl-phenyl)-5-methylsulfonyl-1H-indazole 3-(difluoromethoxy)-4-(2-fluoro-5-methyl-4-methylsulfonyl-phenyl)-5-methylsulfonyl-1-trityl-indazole (step 1) is deprotected using General procedure H to afford the titled compound ([M+H]+448.0) after flash column chromatography.

Example 120: 4-(4-cyclopropylsulfonyl-3-methyl-phenyl)-3-(difluoromethoxy)-1H-pyrazolo[3,4-c]pyridine-5-carboxamide

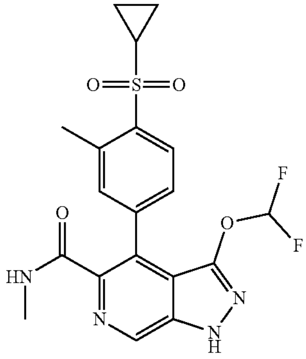 [SMILES: CNC(=O)c1ncc2[nH]nc(OC(F)F)c2c1-c1ccc(S(=O)(=O)C2CC2)c(C)c1]

Step 1: 4-(4-cyclopropylsulfonyl-3-methyl-phenyl)-3-(difluoromethoxy)-1-trityl-pyrazolo[3,4-c]pyridine-5-carboxamide To a solution of 4-(4-cyclopropylsulfonyl-3-methyl-phenyl)-3-(difluoromethoxy)-1-trityl-pyrazolo[3,4-c]pyridine-5-carboxamide (Example 116, step 2) (150.0 mg, 0.23 mmol) in DMF (1 mL) was added NaH (5.4 mg, 0.23 mmol) at 0° C. and the rection allowed to come to ambient temperature after which time iodomethane (32 mg, 0.23 mmol) was added and the mixture stirred for a further 2 h. The reaction was diluted with ethyl acetate washed with water, brine, dried ($Na_2SO_4$) and concentrated. Preparative tlc (Ethyl acetate: n-Heptane 1:3) afforded the title compound (110 mg, 73%) as a white solid. ($[M+H]^+679.2$).

The invention claimed is:

1. A compound of formula 1:

(I)

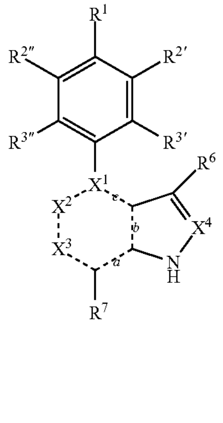

wherein $X^1$ is either N or C;

$X^2$ is either N or $CR^4$;

$X^3$ is either N or $CR^5$;

$X^4$ is either N or CH;

provided that no more than two of $X^1$, $X^2$ and $X^3$ represent N;

the dotted lines represent a single or double bond, to enable the six membered rings to be aromatic with the proviso that when $X^1$ is N and $X^2$ is C═O then the bond between $X^1$ and $X^2$, the bond between $X^2$ and $X^3$, the bonds a and c are single bonds and the bond between $X^3$ and $CR^7$ and b are double bonds; and with the proviso that when $X^1$ is N and $X^2$ is not C═O then the bond between $X^1$ and $X^2$, the bond between $X^3$ and $CR^7$, the bonds b and c are single bonds and the bond between $X^2$ and $X^3$ and the bond a are double bonds;

$R^1$ is —$SO_2R^{1a}$ or —$SOR^{1b}$;

$R^{1a}$ and $R^{1b}$ are independently selected from ($C_1$-$C_6$)alkyl, ($C_3$-$C_6$)cycloalkyl, ($C_3$-$C_6$)cycloalkyl-($C_1$-$C_6$)alkyl, halo($C_1$-$C_6$)alkyl, halo($C_1$-$C_6$)alkoxy, hydroxy($C_1$-$C_6$)alkyl, ($C_1$-$C_6$)alkoxy-($C_1$-$C_6$)alkyl, $NR^{1'a}$ $R^{1'b}$, oxetanyl, furanyl and pyranyl, wherein at least one of $R^{1'a}$ and $R^{1'b}$ is ($C_1$-$C_6$)alkyl and the other is H or ($C_1$-$C_6$)alkyl;

$R^{2'}$ is hydrogen, halogen, —$NH_2$, ($C_1$-$C_6$)alkyl, ($C_1$-$C_6$)alkoxy, halo($C_1$-$C_6$)alkyl or halo($C_1$-$C_6$)alkoxy;

$R^{2''}$ is hydrogen, halogen, —$NH_2$, ($C_1$-$C_6$)alkyl, ($C_1$-$C_6$)alkoxy, halo($C_1$-$C_6$)alkyl or halo($C_1$-$C_6$)alkoxy;

$R^{3'}$ is hydrogen, halogen, —$NH_2$, ($C_1$-$C_6$)alkyl, ($C_1$-$C_6$)alkoxy, halo($C_1$-$C_6$)alkyl or halo($C_1$-$C_6$)alkoxy;

$R^{3''}$ hydrogen, halogen, —$NH_2$, ($C_1$-$C_6$)alkyl, ($C_1$-$C_6$)alkoxy, halo($C_1$-$C_6$)alkyl or halo($C_1$-$C_6$)alkoxy;

$R^4$ is hydrogen, cyano, oxo, hydroxy, halogen, —$NH_2$, ($C_1$-$C_6$)alkyl, ($C_1$-$C_6$)alkoxy, halo($C_1$-$C_6$)alkyl, halo($C_1$-$C_6$)alkoxy, ($C_1$-$C_6$)alkoxy-($C_1$-$C_6$)alkyl, ($C_3$-$C_3$)cycloalkyl, ($C_3$-$C_6$)cycloalkyl-($C_1$-$C_6$)alkyl, —$CO_2R^{4a}$, —$CONR^{4b}R^{4c}$, —$SO_2R^{4d}$, —$SOR^{4c}$, —$SR^{4f}$, —$SO(NR^{4h})R^{4g}$ or —$SO_2(NR^{4i})R^{4j}$;

$R^{4a}$, $R^{4b}$ and $R^{4c}$ are independently selected from hydrogen, ($C_1$-$C_6$)alkyl, ($C_3$-$C_6$)cycloalkyl, ($C_3$-$C_6$)cycloalkyl-($C_1$-$C_6$)alkyl, halo($C_1$-$C_6$)alkyl and oxetanyl;

$R^{4d}$, $R^{4e}$ and $R^{4f}$ are independently selected from ($C_1$-$C_6$)alkyl, ($C_3$-$C_6$)cycloalkyl, ($C_3$-$C_6$)cycloalkyl-($C_1$-$C_6$)alkyl, halo($C_1$-$C_6$)alkyl and oxetanyl;

$R^{4h}$ and $R^{4g}$ are independently selected from hydrogen, ($C_1$-$C_6$)alkyl, ($C_3$ $C_6$)cycloalkyl, ($C_3$-$C_6$)cycloalkyl-($C_1$-$C_4$)alkyl, halo($C_1$-$C_6$)alkyl and oxetanyl;

$R^{4i}$ and $R^{4j}$ are independently selected from hydrogen, ($C_1$-$C_6$)alkyl, ($C_3$-$C_6$)cycloalkyl, ($C_3$-$C_6$)cycloalkyl-($C_1$-$C_6$)alkyl, halo($C_1$-$C_6$)alkyl and oxetanyl;

$R^5$ is hydrogen, halogen, ($C_1$-$C_6$)alkyl, ($C_3$-$C_6$)cycloalkyl, ($C_1$-$C_6$)alkoxy, halo($C_1$-$C_6$)alkyl or halo($C_1$-$C_6$)alkoxy;

$R^6$ is halogen, ($C_1$-$C_6$)alkyl, ($C_1$-$C_6$)alkoxy, cyano, halo($C_1$-$C_6$)alkyl, halo($C_1$-$C_6$)alkoxy, ($C_3$-$C_6$)cycloalkyl, oxetanyl or thiophenyl or —$SO_2R^{6a}$;

$R^{6a}$ is ($C_1$-$C_6$)alkyl, ($C_3$-$C_6$)cycloalkyl or halo($C_1$-$C_6$)alkyl; and $R^7$ is hydrogen, halogen, hydroxy, ($C_1$-$C_6$)alkyl, ($C_1$-$C_6$)alkoxy, halo-($C_1$-$C_6$)alkyl, halo-($C_1$-$C_6$)alkoxy or $NR^{7'a}R^{7'b}$, wherein one of $R^{7'a}$ and $R^{7'b}$ is hydrogen and the other is hydrogen, ($C_1$-$C_6$)alkyl, ($C_1$-$C_6$)alkoxy, —($C_1$-$C_6$)alkyl-O—($C_1$-$C_6$)alkyl-NHCO—($C_1$-$C_6$)alkyl, —($C_1$-$C_6$)alkyl-O—($C_1$-$C_6$)alkyl-$NH_2$, —($C_1$-$C_6$)alkyl-NHCO—($C_1$-$C_6$)alkyl or —($C_1$-$C_6$)alkyl-$NH_2$;

or pharmaceutically acceptable salts thereof.

2. A compound according to claim 1, wherein the compound is of formula Ia;

(Ia)

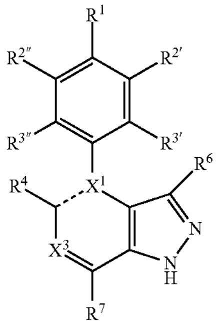

wherein $X^1$ is either N or C;

$X^3$ is either N or $CR^5$;

the dotted line represents a double bond to enable the six membered rings to be aromatic with the proviso that when $X^1$ is N and $R^4$ is oxo then the bond is a single bond;

$R^1$ is —$SO_2R^{1a}$ or —$SOR^{1b}$;

$R^{1a}$ and $R^{1b}$ are independently selected from ($C_1$-$C_6$)alkyl, ($C_3$-$C_6$)cycloalkyl, ($C_3$-$C_6$)cycloalkyl-($C_1$-$C_6$)alkyl, halo($C_1$-$C_6$)alkyl, halo($C_1$-$C_6$)alkoxy, hydroxy($C_1$-$C_6$)alkyl, ($C_1$-$C_6$)alkoxy($C_1$-$C_6$)alkyl, $NR^{1'a}$ $R^{1'b}$, oxetanyl, furanyl and pyranyl, wherein at least one of $R^{1'a}$ and $R^{1'b}$ is ($C_1$-$C_6$)alkyl and the other is H or ($C_1$-$C_6$)alkyl;

$R^{2'}$ is hydrogen, halogen, —$NH_2$, ($C_1$-$C_6$)alkyl, ($C_1$-$C_6$)alkoxy, halo($C_1$-$C_6$)alkyl or halo($C_1$-$C_6$)alkoxy;

$R^{2''}$ is hydrogen, halogen, —$NH_2$, ($C_1$-$C_6$)alkyl, ($C_1$-$C_6$)alkoxy, halo($C_1$-$C_6$)alkyl or halo($C_1$-$C_6$)alkoxy;

$R^{3'}$ is hydrogen, halogen, —$NH_2$, ($C_1$-$C_6$)alkyl, ($C_1$-$C_6$)alkoxy, halo($C_1$-$C_6$)alkyl or halo($C_1$-$C_6$)alkoxy;

$R^{3''}$ is hydrogen, halogen, —$NH_2$, ($C_1$-$C_6$)alkyl, ($C_1$-$C_6$)alkoxy, halo($C_1$-$C_6$)alkyl or halo($C_1$-$C_6$)alkoxy;

$R^4$ is hydrogen, cyano, oxo, hydroxy, halogen, —$NH_2$, ($C_1$-$C_6$)alkyl, ($C_1$-$C_6$)alkoxy, halo($C_1$-$C_6$)alkyl, halo($C_1$-$C_6$)alkoxy, ($C_1$-$C_6$)alkoxy-($C_1$-$C_6$)alkyl, ($C_3$-$C_6$)cycloalkyl, ($C_3$-$C_6$)cycloalkyl-($C_1$-$C_6$)alkyl, —$CO_2R^{4a}$, —$CONR^{4b}R^{4c}$, —$SO_2R^{4d}$, —$SOR^{4e}$, —$SR^{4f}$, —$SO(NR^{4h})R^{4g}$ or —$SO_2NR^{4i})R^{4j}$;

$R^{4a}$, $R^{4b}$ and $R^{4c}$ are independently selected from hydrogen, ($C_1$-$C_4$)alkyl, ($C_3$-$C_6$)cycloalkyl, ($C_3$-$C_6$)cycloalkyl-($C_1$-$C_6$)alkyl, halo($C_1$-$C_6$)alkyl and oxetanyl;

$R^{4d}$, $R^{4e}$ and $R^{4f}$ rare independently selected from ($C_1$-$C_6$)alkyl, ($C_3$-$C_6$)cycloalkyl, ($C_3$-$C_6$)cycloalkyl-($C_1$-$C_6$)alkyl, halo($C_1$-$C_6$)alkyl and oxetanyl;

$R^{4h}$ and $R^{4g}$ are independently selected from hydrogen, ($C_1$-$C_6$)alkyl, ($C_3$-$C_6$)cycloalkyl, ($C_3$-$C_6$)cycloalkyl-($C_1$-$C_6$)alkyl, halo($C_1$-$C_6$)alkyl and oxetanyl;

$R^{4i}$ and $R^{4j}$ are independently selected from hydrogen, ($C_1$-$C_6$)alkyl, ($C_3$-$C_6$)cycloalkyl, ($C_3$-$C_6$)cycloalkyl-($C_1$-$C_6$)alkyl, halo($C_1$-$C_6$)alkyl and oxetanyl;

$R^6$ is halogen, ($C_1$-$C_6$)alkyl, ($C_1$-$C_6$)alkoxy, cyano, halo($C_1$-$C_6$)alkyl, halo($C_1$-$C_6$)alkoxy, ($C_3$-$C_6$)cycloalkyl, oxetanyl or thiophenyl or —$SO_2R^{6a}$;

$R^{6a}$ is ($C_1$-$C_6$)alkyl, ($C_3$-$C_6$)cycloalkyl or halo($C_1$-$C_6$)alkyl; and $R^7$ is hydrogen, halogen, hydroxy, ($C_1$-$C_6$)alkyl, ($C_1$-$C_6$)alkoxy, halo-($C_1$-$C_6$)alkyl, halo-($C_1$-$C_6$)alkoxy or $NR^{7'a}R^{7'b}$, wherein one of $R^{7'a}$ and $R^{7'b}$ is hydrogen and the other is hydrogen, $(C_1\text{-}C_6)$alkyl, $(C_1\text{-}C_6)$alkoxy, —$(C_1\text{-}C_6)$alkyl-O—$(C_1\text{-}C_6)$alkyl-NHCO—$(C_1\text{-}C_6)$alkyl, —$(C_1\text{-}C_6)$alkyl-O—$(C_1\text{-}C_6)$alkyl-$NH_2$, —$(C_1\text{-}C_6)$alkyl-NHCO—$(C_1\text{-}C_6)$alkyl or —$(C_1\text{-}C_6)$alkyl-$NH_2$;

or pharmaceutically acceptable salts thereof.

3. The compound according to claim 1, wherein the compound is of formula Ib:

(Ib)

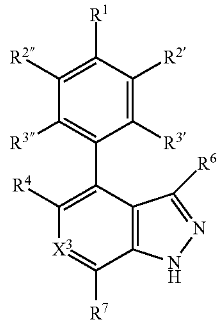

wherein $X^3$ is either N or CR $R^1$ is —$SO_2R^{1a}$ or —$SOR^{1b}$;

$R^{1a}$ and $R^{1b}$ are independently selected from $(C_1\text{-}C_6)$alkyl, $(C_3\text{-}C_6)$cycloalkyl, $(C_3\text{-}C_6)$cycloalkyl-$(C_1\text{-}C_6)$alkyl, halo$(C_1\text{-}C_6)$alkyl, halo$(C_1\text{-}C_6)$alkoxy, hydroxy$(C_1\text{-}C_6)$alkyl, $(C_1\text{-}C_6)$alkoxy-$(C_1\text{-}C_6)$alkyl, $NR^{1'a}$ $R^{1'b}$, oxetanyl, furanyl and pyranyl, wherein at least one of $R^{1'a}$ and $R^{1'b}$ is $(C_1\text{-}C_6)$alkyl and the other is H or $(C_1\text{-}C_6)$alkyl;

$R^{2'}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^{2'}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^{2''}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^{3'}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy, $R^4$ is hydrogen, cyano, oxo, hydroxy, halogen, —$NH_2$, $(C_1\text{-}C_4)$alkyl, $(C_1\text{-}C_6)$alkoxy, halo$(C_1\text{-}C_6)$alkyl, halo$(C_1\text{-}C_6)$alkoxy, $(C_1\text{-}C_6$alkoxy$(C_1\text{-}C_6)$alkyl, $(C_3\text{-}C_6)$cycloalkyl, $(C_3\text{-}C_6)$cycloalkyl-$(C_1\text{-}C_6)$alkyl, —$CO_2R^{4a}$, —$CONR^{4b}R^{4c}$, —$SO_2R^{4d}$, —$SOR^{4c}$, —$SR^{4f}$, —SO$(NR^{4h})R^{4g}$ or —$SO_2(NR^{4i})R^{4j}$;

$R^{4a}$, $R^{4b}$ and $R^{4c}$ are independently selected from hydrogen, $(C_1\text{-}C_6)$alkyl, $(C_3\text{-}C_6)$cycloalkyl, $(C_3\text{-}C_6)$cycloalkyl-$(C_1\text{-}C_6)$alkyl, halo$(C_1\text{-}C_6)$alkyl and oxetanyl;

$R^{4d}$, $R^{4e}$ and $R^{4f}$ are independently selected from $(C_1\text{-}C_6)$alkyl, $(C_3\text{-}C_6)$cycloalkyl, $(C_3\text{-}C_6)$cycloalkyl-$(C_1\text{-}C_6)$alkyl, halo$(C_1\text{-}C_6)$alkyl and oxetanyl;

$R^{4h}$ and $R^{4g}$ are independently selected from hydrogen, $(C_1\text{-}C_6)$alkyl, $(C_3\text{-}C_6)$cycloalkyl, $(C_3\text{-}C_6)$cycloalkyl-$(C_1\text{-}C_6)$alkyl, halo$(C_1\text{-}C_6)$alkyl and oxetanyl;

$R^{4i}$ and $R^{4j}$ are independently selected from hydrogen, $(C_1\text{-}C_6)$alkyl, $(C_3\text{-}C_6)$cycloalkyl, $(C_3\text{-}C_6)$cycloalkyl-$(C_1\text{-}C_6)$alkyl, halo$(C_1\text{-}C_6)$alkyl and oxetanyl;

$R^5$ is hydrogen, halogen, $(C_1\text{-}C_6)$alkyl, $(C_3\text{-}C_6)$cycloalkyl, $(C_1\text{-}C_6)$alkoxy, halo$(C_1\text{-}C_6)$alkyl or halo$(C_1\text{-}C_6)$alkoxy;

$R^6$ is halogen, $(C_1\text{-}C_6)$alkyl, $(C_1\text{-}C_6)$alkoxy, cyano, halo$(C_1\text{-}C_6)$alkyl, halo$(C_1\text{-}C_6)$alkoxy, $(C_3\text{-}C_6)$cycloalkyi, oxetanyl or thiophenyl or —$SO_2R^{6a}$;

$R^{6a}$ is $(C_1\text{-}C_6)$alkyl, $(C_3\text{-}C_6)$cycloalkyl or halo$(C_1\text{-}C_6)$alkyl; and $R^7$ is hydrogen, halogen, hydroxy, $(C_1\text{-}C_6)$alkyl, $(C_1\text{-}C_6)$alkoxy, halo-$(C_1\text{-}C_6)$alkyl, halo-$(C_1\text{-}C_6)$alkoxy or $NR^{7'a}R^{7'b}$, wherein one of $R^{7'a}$ and $R^{7'b}$ is hydrogen and the other is hydrogen, $(C_1\text{-}C_6)$alkyl, $(C_1\text{-}C_6)$alkoxy, —$(C_1\text{-}C_6)$alkyl-O—$(C_1\text{-}C_6)$alkyl-NHCO—$(C_1\text{-}C_6)$alkyl, —$(C_1\text{-}C_6)$alkyl-O—$(C_1\text{-}C_6)$alkyl-$NH_2$, —$(C_1\text{-}C_6)$alkyl-NHCO—$(C_1\text{-}C_6)$alkyl or —$(C_1\text{-}C_6)$alkyl-$NH_2$;

or pharmaceutically acceptable salts thereof.

4. The compound according to claim 1, wherein the compound is of formula Ic:

(Ic)

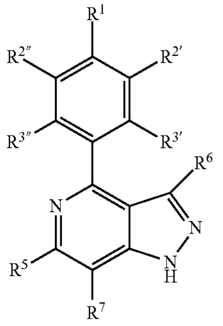

wherein $R^1$ is —$SO_2R^{1a}$ or —$SOR^{1b}$;

$R^{1a}$ and $R^{1b}$ are independently selected from $(C_1\text{-}C_6)$alkyl, $(C_3\text{-}C_6)$cycloalkyl, $(C_3\text{-}C_6)$cycloalkyl-$(C_1\text{-}C_6)$alkyl, halo$(C_1\text{-}C_6)$alkyl, halo$(C_1\text{-}C_6)$alkoxy, hydroxy$(C_1\text{-}C_6)$alkyl, $(C_1\text{-}C_6)$alkoxy-$(C_1\text{-}C_6)$alkyl, $NR^{1'a}$ $R^{1'b}$, oxetanyl, furanyl and pyranyl, wherein at least one of $R^{1'a}$ and $R^{1'b}$ is $(C_1\text{-}C_6)$alkyl and the other is H or $(C_1\text{-}C_6)$alkyl;

$R^{2'}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^{2''}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^{3'}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^{3''}$ is hydrogen, halogen, —$NH_2$, $(C_1\text{-}C_6)$alkyl, $(C_1\text{-}C_6)$alkoxy, halo$(C_1\text{-}C_6)$alkyl or halo$(C_1\text{-}C_6)$alkoxy;

$R^5$ is hydrogen, halogen, $(C_1\text{-}C_6)$alkyl, $(C_3\text{-}C_6)$cycloalkyl, $(C_1\text{-}C_6)$alkoxy, halo$(C_1\text{-}C_6)$alkyl or halo$(C_1\text{-}C_6)$alkoxy;

$R^6$ is halogen, $(C_1\text{-}C_6)$alkyl, $(C_1\text{-}C_6)$alkoxy, cyano, halo$(C_1\text{-}C_6)$alkyl, halo$(C_1\text{-}C_6)$alkoxy, $(C_3\text{-}C_6)$cycloalkyl, oxetanyl or thiophenyl or —$SO_2R^{6a}$;

$R^{6a}$ is $(C_1\text{-}C_6)$alkyl, $(C_3\text{-}C_6)$cycloalkyl or halo$(C_1\text{-}C_6)$alkyl; and $R^7$ is hydrogen, halogen, hydroxy, $(C_1\text{-}C_6)$alkyl, $(C_1\text{-}C_6)$alkoxy, halo-$(C_1\text{-}C_6)$alkyl, halo-$(C_1\text{-}C_6)$alkoxy or $NR^{7'a}R^{7'b}$, wherein one of $R^{7'a}$ and $R^{7'b}$ is hydrogen and the other is hydrogen, $(C_1\text{-}C_6)$alkyl, $(C_1\text{-}C_6)$alkoxy, —$(C_1\text{-}C_6)$alkyl-O—$(C_1\text{-}C_6)$alkyl-NHCO—$(C_1\text{-}C_6)$alkyl, —$(C_1\text{-}C_6)$alkyl-O—$(C_1\text{-}C_6)$alkyl-$NH_2$, —$(C_1\text{-}C_6)$alkyl-NHCO—$(C_1\text{-}C_6)$alkyl or —$(C_1\text{-}C_6)$alkyl-$NH_2$;

or pharmaceutically acceptable salts thereof.

5. The compound according to claim 1, wherein the compound is of formula Id;

(Id)

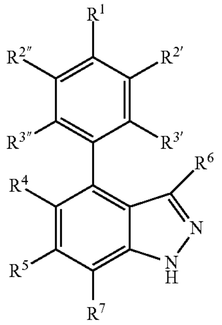

wherein $R^1$ is —$SO_2R^{1a}$ or —$SOR^{1b}$;

$R^{1a}$ and $R^{1b}$ are independently selected from $(C_1-C_6)$alkyl, $(C_3-C_6)$cycloalkyl, $(C_3-C_6)$cycloalkyl-$(C_1-C_6)$alkyl, halo$(C_1-C_6)$alkyl, halo$(C_1-C_6)$alkoxy, hydroxy$(C_1-C_6)$alkyl, $(C_1-C_6)$alkoxy-$(C_1-C_6)$alkyl, -, $NR^{1'a}$ $R^{1'b}$, oxetanyl, furanyl and pyranyl, wherein at least one of $R^{1'a}$ and $R^{1'b}$ is $(C_1-C_6)$alkyl and the other is H or $(C_1-C_6)$alkyl;

$R^{2'}$ is hydrogen, halogen, —$NH_2$, $(C_1-C_6)$alkyl, $(C_1-C_6)$alkoxy, halo$(C_1-C_6)$alkyl or halo$(C_1-C_6)$alkoxy;

$R^{2''}$ is hydrogen, halogen, —$NH_2$, $(C_1-C_6)$alkyl, $(C_1-C_6)$alkoxy, halo$(C_1-C_6)$alkyl or halo$(C_1-C_6)$alkoxy;

$R^{3'}$ is hydrogen, halogen, —$NH_2$, $(C_1-C_6)$alkyl, $(C_1-C_6)$alkoxy, halo$(C_1-C_6)$alkyl or halo$(C_1-C_6)$alkoxy;

$R^{3''}$ is hydrogen, halogen, —$NH_2$, $(C_1-C_6)$alkyl, $(C_1-C_6)$alkoxy, halo$(C_1-C_6)$alkyl or halo$(C_1-C_6)$alkoxy;

$R^4$ is hydrogen, cyano, oxo, hydroxy, halogen, —$NH_2$, $(C_1-C_6)$alkyl, $(C_1-C_6)$alkoxy, halo$(C_1-C_6)$alkyl, halo $(C_1-C_6)$alkoxy, $(C_1-C_6)$alkoxy-$(C_1-C_6)$alkyl, $(C_1-C_6)$ cycloalkyl, $(C_3-C_6)$cycloalkyl-$(C_1-C_6)$alkyl, —$CO_2R^{4a}$, —$CONR^{4b}R^{4c}$, —$SO_2R^{4d}$, —$SOR^{4e}$, —$SR^{4f}$, —$SO(NR^{4h})R^{4g}$ or —$SO_2(NR^{4i})R^{4j}$;

$R^{4a}$, $R^{4b}$ and $R^{4c}$ are independently selected from hydrogen, $(C_1-C_6)$alkyl, $(C_3-C_6)$cycloalkyl, $(C_3-C_6)$cycloalkyl-$(C_1-C_6)$alkyl, halo$(C_1-C_6)$alkyl and oxetanyl;

$R^{4d}$, $R^{4e}$ and $R^{4f}$ are independently selected from $(C_1-C_6)$alkyl, $(C_3-C_6)$cycloalkyl, $(C_3-C_6)$cycloalkyl-$(C_1-C_6)$alkyl, halo$(C_1-C_6)$alkyl and oxetanyl;

$R^{4h}$ and $R^{4g}$ are independently selected from hydrogen, $(C_1-C_6)$alkyl, $(C_3-C_6)$cycloalkyl, $(C_3-C_6)$cycloalkyl-$(C_1-C_6)$alkyl, halo$(C_1-C_6)$alkyl and oxetanyl;

$R^{4i}$ and $R^{4j}$ are independently selected from hydrogen, $(C_1-C_6)$alkyl, $(C_3-C_6)$cycloalkyl, $(C_3-C_6)$cycloalkyl-$(C_1-C_6)$alkyl, halo$(C_1-C_6)$alkyl and oxetanyl;

$R^5$ is hydrogen, halogen, $(C_1-C_6)$alkyl, $(C_3-C_6)$cycloalkyl, $(C_1-C_6)$alkoxy, halo$(C_1-C_6)$alkyl or halo$(C_1-C_6)$alkoxy;

$R^6$ is halogen, $(C_1-C_6)$alkyl, $(C_1-C_6)$alkoxy, cyano, halo $(C_1-C_6)$alkyl, halo$(C_1-C_6)$alkoxy, $(C_3-C_6)$cycloalkyl, oxetanyl or thiophenyl or —$SO_2R^{6a}$;

$R^{6a}$ is $(C_1-C_6)$alkyl, $(C_3-C_6)$cycloalkyl or halo$(C_1-C_6)$alkyl; and $R^7$ is hydrogen, halogen, hydroxy, $(C_1-C_6)$alkyl, $(C_1-C_6)$alkoxy, halo-$(C_1-C_6)$alkyl, halo-$(C_1-C_6)$alkoxy or $NR^{7'a}R^{7'b}$, wherein one of $R^{7'a}$ and $R^{7'b}$ is hydrogen and the other is hydrogen, $(C_1-C_6)$alkyl, $(C_1-C_6)$alkoxy, —$(C_1-C_6)$alkyl-O—$(C_1-C_6)$alkyl-NHCO—$(C_1-C_6)$alkyl, —$(C_1-C_6)$alkyl-O—$(C_1-C_6)$alkyl-$NH_2$, —$(C_1-C_6)$alkyl-NHCO—$(C_1-C_6)$alkyl or —$(C_1-C_6)$alkyl-$NH_2$;

or pharmaceutically acceptable salts thereof.

6. The compound according to claim 1, wherein the compound is of formula Ie:

(Ie)

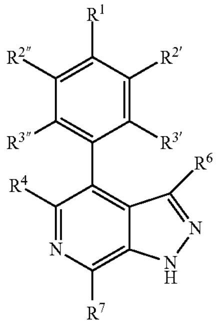

wherein $R^1$ is —$SO_2R^{1a}$ or —$SOR^{1b}$;

$R^{1a}$ and $R^{1b}$ are independently selected from $(C_1-C_6)$alkyl, $(C_3-C_6)$cycloalkyl, $(C_3-C_6)$cycloalkyl-$(C_1-C_6)$alkyl, halo$(C_1-C_6)$alkyl, halo$(C_1-C_6)$alkoxy, hydroxy$(C_1-C_6)$alkyl, $(C_1-C_6)$alkoxy-$(C_1-C_6)$alkyl, $NR^{1'a}$ $R^{1'b}$, oxetanyl, furanyl and pyranyl, wherein at least one of $R^{1'a}$ and $R^{1'b}$ is $(C_1-C_6)$alkyl and the other is H or $(C_1-C_6)$alkyl;

$R^{2'}$ is hydrogen, halogen, —$NH_2$, $(C_1-C_6)$alkyl, $(C_1-C_6)$alkoxy, halo$(C_1-C_6)$alkyl or halo$(C_1-C_6)$alkoxy;

$R^{2''}$ is hydrogen, halogen, —$NH_2$, $(C_1-C_6)$alkyl, $(C_1-C_6)$alkoxy, halo$(C_1-C_6)$alkyl or halo$(C_1-C_6)$alkoxy;

$R^{3'}$ is hydrogen, halogen, —$NH_2$, $(C_1-C_6)$alkyl, $(C_1-C_6)$alkoxy, halo$(C_1-C_6)$alkyl or halo$(C_1-C_6)$alkoxy;

$R^{3''}$ is hydrogen, halogen, —$NH_2$, $(C_1-C_6)$alkyl, $(C_1-C_6)$alkoxy, halo$(C_1-C_6)$alkyl or halo$(C_1-C_6)$alkoxy;

$R^4$ is hydrogen, cyano, oxo, hydroxy, halogen, —$NH_2$, $(C_1-C_6)$alkyl, $(C_1-C_6)$alkoxy, halo$(C_1-C_6)$alkyl, halo $(C_1-C_6)$alkoxy, $(C_1-C_6)$alkoxy-$(C_1-C_6)$alkyl, $(C_3-C_6)$cycloalkyl, $(C_3-C_6)$cycloalkyl$(C_1-C_6)$alkyl, —$CO_2R^{4a}$, —$CONR^{4b}R^{4c}$, —$SO_2R^{4d}$, —$SOR^{4e}$, —$SO(NR^{4h})^{4g}$ or —$SO_2(NR^{4i})R^{4j}$;

$R^{4a}$, $R^{4b}$ and $R^{4c}$ are independently selected from hydrogen, $(C_1-C_6)$alkyl, $(C_3-C_6)$cycloalkyl, $(C_3-C_6)$cycloalkyl-$(C_1-C_6)$alkyl, halo$(C_1-C_6)$alkyl and oxetanyl;

$R^{4d}$, $R^{4e}$ and $R^{4f}$ are independently selected from $(C_1-C_6)$alkyl, $(C_3-C_6)$cycloalkyl, $(C_3-C_6)$cycloalkyl-$(C_1-C_6)$alkyl, halo$(C_1-C_6)$alkyl and oxetanyl;

$R^{4h}$ and $R^{4g}$ are independently selected from hydrogen, $(C_1-C_6)$alkyl, $(C_3-C_6)$cycloalkyl, $(C_3-C_6)$cycloalkyl-$(C_1-C_6)$alkyl, halo$(C_1-C_6)$alkyl and oxetanyl;

$R^{4i}$ and $R^{4j}$ are independently selected from hydrogen, $(C_1-C_6)$alkyl, $(C_3-C_6)$cycloalkyl, $(C_3-C_6)$cycloalkyl-$(C_1-C_6)$alkyl, halo$(C_1-C_6)$alkyl and oxetanyl;

$R^6$ is halogen, $(C_1-C_6)$alkyl, $(C_1-C_6)$alkoxy, cyano, halo $(C_1-C_6)$alkyl, halo$(C_1-C_6)$alkoxy, $(C_3-C_6)$cycloalkyl, oxetanyl or thiophenyl or —$SO_2R^{6a}$;

$R^{6a}$ is $(C_1-C_6)$alkyl, $(C_3-C_6)$cycloalkyl or halo$(C_1-C_6)$alkyl; and $R^7$ is hydrogen, halogen, hydroxy, $(C_1-C_6)$alkyl, $(C_1-C_6)$alkoxy, halo-$(C_1-C_6)$alkyl, halo-$(C_1-C_6)$alkoxy or $NR^{7'a}R^{7'b}$, wherein one of $R^{7'a}$ and $R^{7'b}$ is hydrogen and the other is hydrogen, $(C_1-C_6)$alkyl, $(C_1-C_6)$alkoxy, —$(C_1-C_6)$alkyl-O—$(C_1-C_6)$alkyl-NHCO—$(C_1-C_6)$alkyl, —$(C_1-C_6)$alkyl-O—$(C_1-C_6)$alkyl-$NH_2$, —$(C_1-C_6)$alkyl-NHCO—$(C_1-C_6)$alkyl or —$(C_1-C_6)$alkyl-$NH_2$;

or pharmaceutically acceptable salts thereof.

7. The compound according to claim 1, wherein $X^4$ is N.

8. The compound according to claim 1, wherein $X^1$ is N or C, $X^2$ is N or $CR^4$ and $X^3$ is N or $CR^5$.

9. The compound according to claim 1, wherein $R^1$ is —$SO_2R^{1a}$.

10. The compound according to claim 1, wherein $R^{4a}$ and $R^{4b}$ are independently selected from $(C_1\text{-}C_6)$alkyl, $(C_3\text{-}C_6)$cycloalkyl,$(C_3\text{-}C_6)$cycloalkyl-$(C_1\text{-}C_6)$alkyl, halo$(C_1\text{-}C_6)$alkyl, halo$(C_1\text{-}C_6)$alkoxy, hydroxy$(C_1\text{-}C_6)$alkyl, $(C_1\text{-}C_6)$alkoxy-$(C_1\text{-}C_6)$alkyl, $NR^{1'a}$ $R^{1'b}$, oxetanyl, furanyl and pyranyl, wherein at least one of $R^{1'a}$ and $R^{1'b}$ is $(C_1\text{-}C_6)$alkyl and the other is H or $(C_1\text{-}C_6)$alkyl.

11. The compound according to claim 1, wherein $R^{1a}$ is selected from methyl, ethyl, propyl, i-propyl, i-butyl, cyclopropyl,

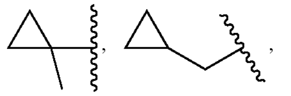

fluoromethyl, difluoromethyl, fluoro-ethanyl, difluoro-ethanyl, 1,2 difluoroethanyl, 1,1,2-trifluoroethanyl, 1,2,2-trifluoroethanyl, Hydroxymethyl, hydroxyethyl, metoxymethyl, methylaminyl (—$NHCH_3$), dimethylaminyl (—$N(CH_3)_2$) and oxetanyl.

12. The compound according to claim 1, wherein $R^{1b}$ is $(C_1\text{-}C_6)$alkyl.

13. The compound according to claim 1, wherein if $R^{2'}$ is other than hydrogen as defined according to claim 1, then $R^{3'}$ is hydrogen, $R^{2''}$ is hydrogen and $R^{3''}$ is as defined according to claim 1.

14. The compound according to claim 1, wherein one of $R^{2'}$ and $R^{2''}$ is hydrogen, halogen, —$NH_2$, $(C_1\text{-}C_2)$alkyl, $(C_1\text{-}C_2)$alkoxy or halo$(C_1\text{-}C_2)$alkyl, while the other one is hydrogen.

15. The compound according to claim 1, wherein one of $R^{3'}$ and $R^{3''}$ is hydrogen, halogen, —$NH_2$, $(C_1\text{-}C_3)$alkyl, $(C_1\text{-}C_3)$alkoxy or halo$(C_1\text{-}C_3)$alkyl, while the other one is hydrogen.

16. The compound according to claim 1, wherein both $R^{3'}$ and $R^{3''}$ are hydrogen.

17. The compound according to claim 1, wherein $R^4$ is cyano, oxo, hydroxy, $(C_1\text{-}C_3)$alkyl, $(C_1\text{-}C_3)$alkoxy, halo$(C_1\text{-}C_3)$alkyl, halo$(C_1\text{-}C_6)$alkoxy, $(C_1\text{-}C_3)$alkoxy-$(C_1\text{-}C_3)$alkyl, $(C_3\text{-}C_4)$cycloalkyl, —$CO_2R^{4a}$, —$CONR^{4b}R^{4c}$, —$SO_2R^{4d}$, —$SOR^{4e}$, —$SR^{4f}$ or —$SO(NR^{4h})R^{4g}$.

18. The compound according to claim 1, wherein $R^{4a}$, $R^{4b}$ and $R^{4c}$ are independently selected from hydrogen, $(C_1\text{-}C_3)$alkyl, $(C_3\text{-}C_4)$cycloalkyl, and oxetanyl.

19. The compound according to claim 1, wherein $R^{4a}$ is hydrogen.

20. The compound according to claim 1, wherein $R^{4d}$, $R^{4c}$ and $R^{4f}$ are independently selected from $(C_1\text{-}C_3)$alkyl, $(C_3\text{-}C_4)$cycloalkyl, and oxetanyl.

21. The compound according to claim 1, wherein $R^{4d}$ is methyl.

22. The compound according to claim 1, wherein $R^{4h}$ and $R^{4g}$ are independently selected from hydrogen and $(C_1\text{-}C_6)$alkyl.

23. The compound according to claim 1, wherein $R^{4i}$ and $R^{4j}$ are independently selected from hydrogen and $(C1\text{-}C_6)$alkyl.

24. The compound according to claim 1, wherein $R^5$ is hydrogen, halogen, $(C1\text{-}C_6)$alkyl, $(C1\text{-}C_6)$alkoxy or $(C3\text{-}C_6)$cycloalkyl.

25. The compound according to claim 1, wherein $R^5$ is hydrogen.

26. The compound according to claim 1, wherein $R^6$is halogen, $(C1\text{-}C_6)$alkyl, $(C1\text{-}C_6)$alkoxy, cyano, halo$(C1\text{-}C_6)$alkyl, halo$(C1\text{-}C_6)$alkoxy, $(C3\text{-}C_6)$cycloalkyl, thiophenyl, oxetanyl or —$SO_2R^{6a}$.

27. The compound according to claim 1, wherein $R^{6a}$ is $(C1\text{-}C_6)$alkyl.

28. The compound according to claim 1, wherein $R^7$ is hydrogen, halogen, hydroxy or $(C1\text{-}C_6)$alkyl.

29. The compound according to claim 1, wherein one of $R^{7'a}$ and $R^{7'b}$ is hydrogen and the other is hydrogen, $(C_1\text{-}C_6)$alkyl, $(C_1\text{-}C6)$alkoxy, -$(C1\text{-}C_3)$alkyl-O—$(C_1\text{-}C_3)$alkyl-NHCO—$(C_1\text{-}C_3)$alkyl, —$(C_1\text{-}C_3)$alkyl-O—$(C_1\text{-}C_3)$alkyl-$NH_2$, —$(C_1\text{-}C_3)$alkyl-NHCO—$(C_1\text{-}C_3)$alkyl or —$(C_1\text{-}C_3)$alkyl-$NH_2$.

30. The compound according to claim 1, wherein $R^{1b}$ is $(C_1\text{-}C_3)$alkyl.

31. The compound according to claim 1, wherein $R^{1b}$ is methyl.

32. The compound according to claim 1, selected from the group consisting of:

3-cyclopropyl-4-(3-methyl-4-(methylsulfonyl)phenyl)-1H-pyrazolo[4,3-c]pyridine;

3-cyclopropyl-4-(3-methoxy-4-(methylsulfonyl)phenyl)-1H-pyrazolo[4,3-c]pyridine;

4-(3-chloro-4-(methylsulfonyl)phenyl)-3-cyclopropyl-1H-pyrazolo[4,3-c]pyridine;

3-cyclopropyl-4-(4-(methylsulfonyl)-3-(trifluoromethyl)phenyl)-1H-pyrazolo(4,3-c]pyridine;

4-(3-cyclopropyl-1 H-pyrazolo[4,3-c]pyridin-4-yl)-N,N,2-trimethylbenzenesulfonamide;

3-cyclopropyl-5-methoxy-4-(4-methylsulfonylphenyl)-1H-pyrazolo[3,4-c]pyridine;

3-cyclopropyl-4-(4-(cyclopropylsulfonyl)-3-methylphenyl)-1H-pyrazolo[4,3-c]pyridine;

4-(3-chloro-4-(cyclopropylsulfonyl)phenyl)-3-cyclopropyl-1H-pyrazolo[4,3-c]pyridine;

2-chloro-4-(3-cyclopropyl-1H-pyrazolo[4,3-c]pyridin-4-yl)-N,N-dimethylbenzenesulfonamide;

4-(3-methyl-4-(methylsulfonyl)phenyl)-3-(trifluoromethyl)-1H-pyrazolo[3,4-b]pyridine;

4-(4-(methylsulfonyl)phenyl)-3-(trifluoromethyl)-1H-pyrazolo[4,3-c]pyridine;

3-cyclopropyl-4-(3-(difluoromethyl)-4-(methylsulfonyl)phenyl)-1H-pyrazolo[4,3-c]pyridine;

3-cyclopropyl-4-(3-(fluoromethyl)-4-(methylsulfonyl)phenyl)-1H-pyrazolo[4,3-c]pyridine;

3-bromo-4-(3-methyl-4-(methylsulfonyl)phenyl)-1H-pyrazolo[4,3-c]pyridine;

3-cyclopropyl-4-(3-methyl-4-(methylsulfonyl)phenyl)-1 H-pyrrolo[3,2-c]pyridine;

3-cyclopropyl-4-(3-methyl-4-(oxetan-3-ylsulfonyl)phenyl)-1H-pyrazolo[4,3-c]pyridine;

3-(difluoromethoxy)-4-(3-methyl-4-(methylsulfonyl)phenyl)-1H-pyrazolo[4,3-c]pyridine;

3-methoxy-4-(3-methyl-4-(methylsulfonyl)phenyl)-1H-pyrazolo[4,3-c]pyridine;

5-(3-cyclopropyl-1H-pyrazolo[4,3-c]pyridin-4-yl)-2-(methylsulfonyl)aniline;

4-(3-methyl-4-(methylsulfonyl)phenyl)-3-(methylsulfonyl)-1H-pyrazolo[4,3-c]pyridine;

3-cyclopropyl-4-(3-methyl-4-(methylsulfonyl)phenyl)-1H-pyrazolo[3,4-c]pyridine-5-carbonitrile;

3-(1,1-difluoroethyl)-4-(3-methyl-4-(methylsulfonyl)phenyl)-1H-pyrazolo[4,3-c]pyridine;

4-(3-methyl-4-(methylsulfonyl)phenyl)-1H-pyrazolo[4,3-c]pyridine-3-carbonitrile;
3-(difluoromethyl)-4-(3-methyl-4-methylsulfonylphenyl)-1H-pyrazolo[4,3-c]pyridine;
3-isopropyl-4-(3-methyl-4-(methylsulfonyl)phenyl)-1H-pyrazolo[4,3-c]pyridine;
3-cyclopropyl-4-(4-ethylsulfonyl-3-methyl-phenyl)-1H-pyrazolo[4,3-c]pyridine;
3-cyclopropyl-4-(2-fluoro-5-methyl-4-methylsulfonyl-phenyl)-1H-pyrazolo[4,3-c]pyridine;
3-cyclopropyl-4-(2,5-dimethyl-4-methylsulfonyl-phenyl)-1H-pyrazolo[4,3-c]pyridine hydrochloride;
3-cyclopropyl-4-(3-methyl-4-(methylsulfonyl)phenyl)-1H-pyrazolo[3,4-c]pyridine-5-carboxylic acid;
3-cyclopropyl-4-(3-methyl-4-methylsulfonylphenyl)-1H-indazole-5-carbonitrile;
3-cyclopropyl-4-(3-methyl-4-methylsulfinyl-phenyl)-1H-pyrazolo[4,3-c]pyridine hydrochloride;
3-cyclopropyl-4-(3-methyl-4-methylsulfonyl-phenyl)-1H-pyrazolo[4,3-c]pyridin-7-ol;
4-(3-methyl-4-(methylsulfonyl)phenyl)-3-(thiophen-3-yl)-1H-pyrazolo[4,3-c]pyridine;
3-cyclopropyl-5-methoxy-4-(3-methyl-4-(methylsulfonyl)phenyl)-1H-pyrazolo[3,4-c]pyridine;
3-ethoxy-4-(3-methyl-4-methylsulfonyl-phenyl)-1 H-pyrazolo[4,3-c]pyridine;
3-(difluoromethoxy)-4-[4-(difluoromethylsulfonyl)-3-methyl-phenyl]-1H-pyrazolo[4,3-c]pyridine;
4-(4-cyclopropylsulfonyl-3-methyl-phenyl)-3-(difluoromethoxy)-1 H-pyrazolo[4,3-c]pyridine;
3-cyclopropyl-7-fluoro-4-(3-methyl-4-methylsulfonyl-phenyl)-1H-pyrazolo[4,3-c]pyridine;
3-(difluoromethoxy)-4-(4-ethylsulfonyl-3-methyl-phenyl)-1H-pyrazolo[4,3-c]pyridine;
4-(3-methyl-4-methylsulfonyl-phenyl)-3-(oxetan-3-yl)-1H-pyrazolo[4,3-c]pyridine;
4-[4-(cyclopropylmethylsulfonyl)-3-methyl-phenyl]-3-(difluoromethoxy)-1H-pyrazolo[4,3-c]pyridine;
3-(difluoromethoxy)-4-(3-methyl-4-propylsulfonyl-phenyl)-1H-pyrazolo[4,3-c]pyridine;
3-(difluoromethoxy)-4-[3-(difluoromethyl)-4-methylsulfonyl-phenyl]-1H-pyrazolo[4,3-c]pyridine;
3-(difluoromethoxy)-4-(4-isopropylsulfonyl-3-methyl-phenyl)-1H-pyrazolo[4,3-c]pyridine;
4-[3-(difluoromethoxy)-1H-pyrazolo[4,3-c]pyridin-4-yl]-N,2-dimethyl-benzenesulfonamide;
3-methoxy-4-(3-methyl-4-(methylsulfonyl)phenyl)-1H-indazole-5-carbonitrile;
3-(difluoromethoxy)-4-(3-methyl-4-(methylsulfonyl)phenyl)-1H-indazole-5-carbonitrile;
6-chloro-3-cyclopropyl-4-(3-methyl-4-methylsulfonylphenyl)-1H-pyrazolo[4,3-c]pyridine;
3-(difluoromethoxy)-4-[3-methyl-4-(oxetan-3-ylsulfonyl)phenyl]-1H-pyrazolo[4,3-c]pyridine;
2-[4-[3-(difluoromethoxy)-1H-pyrazolo[4,3-c]pyridin-4-yl]-2-methyl-phenyl]sulfanylethanol;
3-cyclopropyl-6-methoxy-4-(3-methyl-4-methylsulfonylphenyl)-1H-pyrazolo[4,3-c]pyridine 2,2,2-trifluoroacetic acid;
3-(difluoromethoxy)-4-[3-methyl-4-(1-methylcyclopropyl)sulfonyl-phenyl]-1H-pyrazolo[4,3-c]pyridine;
4-(3-methyl-4-(methylsulfonyl)phenyl)-3-(trifluoromethoxy)-1 H-pyrazolo[4,3-c]pyridine,
3-cyclopropyl-4-(3-methyl-4-(methylsulfonyl)phenyl)-1H-pyrazolo[3,4-c]pyridine-5-carboxamide;
3-cyclopropyl-N-methyl-4-(3-methyl-4-methylsulfonyl)phenyl)-1 H-pyrazolo[3,4-c]pyridine-5-carboxamide;
3-cyclopropyl-4-(3-methyl-4-(methylsulfonyl)phenyl)-1H-pyrazolo[3,4-d]pyridazine;
3-cyclopropyl-4-(3-methyl-4-(methylsulfonyl)phenyl)-5-(methylthio)-1H-indazole;
3-cyclopropyl-4-(3-methyl-4-(methylsulfonyl)phenyl)-5-(methylsulfinyl)-1H-indazole;
3-cyclopropyl-4-(3-methyl-4-(methylsulfonyl)phenyl)-5-(methylsulfonyl)-1H-indazole;
3-(difluoromethoxy)-4-[4-(methoxymethylsulfonyl)-3-methyl-phenyl)-1 H-pyrazolo[4,3-c]pyridine formic acid;
5-methoxy-4-(3-methyl-4-(methylsulfonyl)phenyl)-3-(trifluoromethyl)-1H-pyrazolo[3,4-c]pyridine;
4-(3-methyl-4-(methylsulfonyl)phenyl)-3-(trifluoromethyl)-1H-pyrrolo[3,2-c]pyridine,
3-(difluoromethoxy)-4-(3-methyl-4-methylsulfonyl-phenyl)-1H-pyrazolo[4,3-b]pyridin-5-one;
3-cyclopropyl-4-(3-methyl-4-methylsulfonylphenyl)-5-(trifluoromethyl)-1 H-pyrazolo(3,4-c]pyridine;
3-cyclopropyl-6-methyl-4-(3-methyl-4-methylsulfonyl-phenyl)-1H-pyrazolo[4,3-b]pyridin-5-one;
3,6-dicyclopropyl-4-(3-methyl-4-methylsulfonyl-phenyl)-1H-pyrazolo[4,3-b]pyridin-5-one;
3-cyclopropyl-5-(difluoromethoxy)-4-(3-methyl-4-(methylsulfonyl)phenyl)-1H-pyrazolo[3,4-c]pyridine;
3-cyclopropyl-N,N-dimethyl-4-(3-methyl-4-(methylsulfonyl)phenyl)-1H-pyrazolo[3,4-c]pyridine-5-carboxamide;
3-cyclopropyl-5-(methoxymethyl)-4-(3-methyl-4-(methylsulfonyl)phenyl)-1H-pyrazolo[3,4-c]pyridine;
3-cyclopropyl-4-(3-methyl-4-(methylsulfonyl)phenyl)-N-(oxetan-3-yl)-1H-pyrazolo[3,4-c]pyridine-5-carboxamide;
3,5-dicyclopropyl-4-(3-methyl-4-methylsulfonylphenyl)-1H-pyrazolo[3,4-c]pyridine;
N,3-dicyclopropyl-4-(3-methyl-4-(methylsulfonyl)phenyl)-1H-pyrazolo[3,4-c]pyridine-5-carboxamide;
3-cyclopropyl-6-fluoro-4-(3-methyl-4-(methylsulfonyl) phenyl)-1H-indazole-5-carbonitrile;
3-cyclopropyl-4-(4-ethylsulfonyl-3-methyl-phenyl)-1H-pyrazolo[3,4-c]pyridine-5-carbonitrile;
3-cyclopropyl-4-(4-cyclopropylsulfonyl-3-methyl-phenyl)-1H-pyrazolo[3,4-c]pyridine-5-carbonitrile;
4-(3-methyl-4-(methylsulfonyl)phenyl)-5-(methylsulfonyl)-3-(trifluoromethyl)-1H-indazole;
3-cyclopropyl-4-(3-methyl-4-methylsulfonylphenyl)-1H-indole-5-carbonitrile;
3-cyclopropyl-4-(4-cyclopropylsulfonyl-3-methyl-phenyl)-N-methyl-1H-pyrazolo[3,4-c]pyridine-5-carboxamide;
3-cyclopropyl-6-fluoro-N-methyl-4-(3-methyl-4-(methylsulfonyl)phenyl)-1H-indazole-5-carboxamide;
3-cyclopropyl-6-fluoro-4-(3-methyl-4-(methylsulfonyl) phenyl)-1H-indazole-5-carboxamide;
6-chloro-3-cyclopropyl-4-(3-methyl-4-methylsulfonylphenyl)-1#H!-indazole-5-carbonitrile;
3-cyclopropyl-4-(2-fluoro-5-methyl-4-methylsulfonyl-phenyl)-1H-pyrazolo[3,4-c]pyridine-5-carbonitrile;
4-(3-methyl-4-methylsulfonyl-phenyl)-3-(trifluoromethoxy)-1H-pyrazolo[4,3-b]pyridin-5-one;
3-cyclopropyl-4-(3-methyl-4-methylsulfonyl-phenyl)-1H-pyrrolo(3,2-b]pyridin-5-one;
4-[3-(difluoromethoxy)-1H-pyrazolo[4,3-c]pyridin-4-yl]-2-(difluoromethyl)-N,N-dimethyl-benzenesulfonamide;
3-(difluoromethoxy)-4-(3-methyl-4-(methylsulfonyl)phenyl)-5-(methylsulfonyl)-1H-indazole;

3-cyclopropyl-4-[4-(difluoromethylsulfonyl)-3-methyl-phenyl]-1H-pyrazolo[3,4-c]pyridine-5-carbonitrile;

4-(3-methyl-4-(methylsulfonyl)phenyl)-5-(methylsulfonyl)-3-(trifluoromethoxy)-1H-indazole;

3-cyclopropyl-4-[3-(difluoromethyl)-4-methylsulfonyl-phenyl]-N-methyl-1H-pyrazolo[3,4-c]pyridine-5-carboxamide;

3-(difluoromethoxy)-4-(3-methyl-4-methylsulfonyl-phenyl)-1H-pyrazolo[3,4-c]pyridine-5-carbonitrile;

3-(difluoromethoxy)-4-[5-(difluoromethyl)-2-methyl-4-methylsulfinyl-phenyl]-1 H-pyrazolo[3,4-c]pyridine-5-carbonitrile;

4-[3-(difluoromethyl)-4-methylsulfonyl-phenyl]-5-methoxy-3-(trifluoromethyl)-1H-pyrazolo[3,4-c]pyridine;

3-cyclopropyl-4-(3-(difluoromethyl)-4-(methylsulfonyl)phenyl)-5-(methylsulfonyl)-1H-indazole;

3-(difluoromethoxy)-N-methyl-4-(3-methyl-4-methylsulfonyl-phenyl)-1H-pyrazolo[3,4-c]pyridine-5-carboxamide;

3-cyclopropyl-4-(4-cyclopropylsulfonyl-2-fluoro-5-methyl-phenyl)-N-methyl-1H-pyrazolo[3,4-c]pyridine-5-carboxamide;

4-(4-cyclopropylsulfonyl-3-methyl-phenyl)-3-(difluoromethoxy)-5-methylsulfonyl-1H-indazole;

3-cyclopropyl-4-(2-fluoro-5-methyl-4-methylsulfonyl-phenyl)-N-methyl-1H-pyrazolo(3,4-c]pyridine-5-carboxamide;

3-(difluoromethoxy)-4-(3-methyl-4-methylsulfonyl-phenyl)-1H-pyrazolo[3,4-c]pyridine-5-carboxamide;

3-(difluoromethoxy)-4-(4-((difluoromethyl)sulfonyl)-3-methylphenyl)-1H-pyrazolo[3,4-c]pyridine-5-carbonitrile;

3-(difluoromethoxy)-4-[4-(difluoromethylsulfonyl)-3-methyl-phenyl]-1H-pyrazolo[3,4-c]pyridine-5-carboxamide;

3-(difluoromethoxy)-4-[4-(difluoromethylsulfonyl)-3-methyl-phenyl]-N-(oxetan-3-yl)-1H-pyrazolo[3,4-c]pyridine-5-carboxamide;

3-(difluoromethoxy)-4-[4-(difluoromethylsulfonyl)-3-methyl-phenyl]-N-methyl-1H-pyrazolo[3,4-c]pyridine-5-carboxamide;

3-(difluoromethoxy)-4-[4-(difluoromethylsulfonyl)-3-methyl-phenyl]-N-(2-methoxyethyl)-1H-pyrazolo[3,4-c]pyridine-5-carboxamide;

3-(difluoromethoxy)-N-methyl-4-(3-methyl-4-methylsulfonyl-phenyl)-1H-pyrazolo[3,4-c]pyridine-5-carboxamide, 3-(difluoromethoxy)-4-(3-methyl-4-methylsulfonyl-phenyl)-5-(oxetan-3-ylsulfonyl)-1H-indazole;

[3-cyclopropyl-4-(3-methyl-4-methylsulfonylphenyl)-1H-indazol-5-yl]-imino-methyl-oxo-sulfane;

[3-cyclopropyl-4-(3-methyl-4-methylsulfonyl-phenyl)-1H-indazol-5-yl]-methyl-methylimino-oxo-$\lambda^6$-sulfane;

3-cyclopropyl-N,N-dimethyl-4-(3-methyl-4-methylsulfonyl-phenyl)-1H-indazole-5-sulfonamide;

3-cyclopropyl-N-methyl-4-(3-methyl-4-methylsulfonyl-phenyl)-1H-indazole-5-sulfonamide;

4-(4-cyclopropylsulfonyl-3-methyl-phenyl)-3-(difluoromethoxy)-1H-pyrazolo[3,4-c]pyridine-5-carboxamide;

3-(difluoromethoxy)-4-(4-((difluoromethyl)sulfonyl)-3-methylphenyl)-5-(methylsulfonyl)-1H-indazole;

5-cyclopropylsulfonyl-3-(difluoromethoxy)-4-(3-methyl-4-methylsulfonyl-phenyl)-1H-indazole;

3-(difluoromethoxy)-4-(2-fluoro-5-methyl-4-methylsulfonyl-phenyl)-5-methylsulfonyl-1H-indazole; and 4-(4-cyclopropylsulfonyl-3-methyl-phenyl)-3-(difluoromethoxy)-N-methyl-1H-pyrazolo[3,4-c]pyridine-5-carboxamide or pharmaceutically acceptable salts thereof.

33. The compound according to claim 1, selected from the group consisting of:

3-(difluoromethoxy)-4-(3-methyl-4-(methylsulfonyl)phenyl)-1H-indazole-5-carbonitrile;

3-(difluoromethoxy)-4-(3-methyl-4-methylsulfonyl-phenyl)-1H-pyrazolo[4,3-b]pyridin-5-one;

3-cyclopropyl-4-(4-ethylsulfonyl-3-methyl-phenyl)-1H-pyrazolo[3,4-c]pyridine-5-carbonitrile;

4-(3-methyl-4-(methylsulfonyl)phenyl)-5-(methylsulfonyl)-3-(trifluoromethyl)-1 H-indazole;

3-(difluoromethoxy)-4-(3-methyl-4-(methylsulfonyl)phenyl)-5-(methylsulfonyl)-1H-indazole;

3-cyclopropyl-4-[4-(difluoromethylsulfonyl)-3-methyl-phenyl]-1H-pyrazolo[3,4-c]pyridine-5-carbonitrile;

4-(3-methyl-4-(methylsulfonyl)phenyl)-5-(methylsulfonyl)-3-(trifluoromethoxy)-1H-indazole;

3-cyclopropyl-4-[3-(difluoromethyl)-4-methylsulfonyl-phenyl]-N-methyl-1H-pyrazolo[3,4-c]pyridine-5-carboxamide;

3-(difluoromethoxy)-4-(3-methyl-4-methylsulfonyl-phenyl)-1H-pyrazolo[3,4-c]pyridine-5-carbonitrile;

3-(difluoromethoxy)-N-methyl-4-(3-methyl-4-methylsulfonyl-phenyl)-1H-pyrazolo[3,4-c]pyridine-5-carboxamide;

3-(difluoromethoxy)-4-(3-methyl-4-methylsulfonyl-phenyl)-1H-pyrazolo[3,4-c]pyridine-5-carboxamide; and 3-(difluoromethoxy)-4-[4-(difluoromethylsulfonyl)-3-methyl-phenyl]-1H-pyrazolo[3,4-c]pyridine-5-carboxamide or pharmaceutically acceptable salts thereof.

34. A pharmaceutical composition comprising at least one compound of formula I according to claim 1 or its pharmaceutically acceptable salts and one or more pharmaceutically acceptable excipients.

35. A method for the treatment of Lung Adenocarcinoma, Melanoma, Pancreatic Adenocarcinoma, Head and Neck Squamous Cell Carcinoma, Lung Squamous Cell Carcinoma, Esophageal Carcinoma, Glioblastmoa Multiforme, Mesothelioma, or a combination thereof, which method comprises administering at least one compound of formula 1 according to claim 1 or its pharmaceutically acceptable salts to a subject.

36. A method for delaying the progression of Lung Adenocarcinoma, Melanoma, Pancreatic Adenocarcinoma, Head and Neck Squamous Cell Carcinoma, Lung Squamous Cell Carcinoma, Esophageal Carcinoma, Glioblastmoa Multiforme, Mesothelioma, or a combination thereof, which method comprises administering at least one compound of formula I according to claim 1 or its pharmaceutically acceptable salts to a subject.

* * * * *